(12) United States Patent  
Page et al.

(10) Patent No.: US 10,562,880 B2  
(45) Date of Patent: Feb. 18, 2020

(54) METHODS FOR TREATING PROTOZOAN INFECTIONS

(71) Applicant: Neoculi Pty Ltd., Burwood, Victoria (AU)

(72) Inventors: Stephen Page, Newton (AU); Andrew Stevens, Farrer (AU); Adam McCluskey, Charlestown (AU); Martine Keenan, Murdoch (AU); Rebecca Abraham, Adelaide (AU)

(73) Assignee: NEOCULI PTY LTD., Burwood, Victoria (AU)

( * ) Notice: Subject to any disclaimer, the term of this patent is extended or adjusted under 35 U.S.C. 154(b) by 0 days.

(21) Appl. No.: 16/505,049

(22) Filed: Jul. 8, 2019

(65) Prior Publication Data

US 2019/0330178 A1 Oct. 31, 2019

Related U.S. Application Data

(62) Division of application No. 15/508,266, filed as application No. PCT/AU2015/000527 on Aug. 28, 2015, now Pat. No. 10,392,363.

(30) Foreign Application Priority Data

Sep. 2, 2014 (AU) .................. 2014903503

(51) Int. Cl.
| | | |
|---|---|---|
| *C07D 333/50* | (2006.01) | |
| *A61K 9/00* | (2006.01) | |
| *A61K 31/155* | (2006.01) | |
| *A61K 31/341* | (2006.01) | |
| *A61K 31/44* | (2006.01) | |
| *A61K 31/505* | (2006.01) | |
| *C07D 333/58* | (2006.01) | |
| *A61K 45/06* | (2006.01) | |
| *C07D 209/08* | (2006.01) | |
| *C07C 335/40* | (2006.01) | |
| *A61K 31/496* | (2006.01) | |
| *C07C 47/565* | (2006.01) | |
| *C07D 209/14* | (2006.01) | |
| *C07D 239/50* | (2006.01) | |
| *C07C 211/29* | (2006.01) | |
| *C07D 401/14* | (2006.01) | |
| *C07C 251/24* | (2006.01) | |
| *C07D 241/20* | (2006.01) | |
| *C07C 281/18* | (2006.01) | |
| *A61K 31/498* | (2006.01) | |
| *A61K 31/4192* | (2006.01) | |
| *A61K 31/4045* | (2006.01) | |
| *A61K 31/381* | (2006.01) | |
| *C07D 307/56* | (2006.01) | |
| *C07D 295/135* | (2006.01) | |

(Continued)

(52) U.S. Cl.
CPC .......... *C07D 333/58* (2013.01); *A61K 9/0014* (2013.01); *A61K 9/0019* (2013.01); *A61K 9/0053* (2013.01); *A61K 31/155* (2013.01); *A61K 31/17* (2013.01); *A61K 31/341* (2013.01); *A61K 31/381* (2013.01); *A61K 31/404* (2013.01); *A61K 31/4045* (2013.01); *A61K 31/4192* (2013.01); *A61K 31/44* (2013.01); *A61K 31/496* (2013.01); *A61K 31/498* (2013.01); *A61K 31/505* (2013.01); *A61K 45/06* (2013.01); *C07C 47/565* (2013.01); *C07C 211/29* (2013.01); *C07C 251/24* (2013.01); *C07C 281/18* (2013.01); *C07C 335/40* (2013.01); *C07D 209/08* (2013.01); *C07D 209/14* (2013.01); *C07D 239/48* (2013.01); *C07D 239/50* (2013.01); *C07D 241/20* (2013.01); *C07D 249/14* (2013.01); *C07D 251/54* (2013.01); *C07D 295/135* (2013.01); *C07D 307/56* (2013.01); *C07D 311/58* (2013.01); *C07D 401/14* (2013.01); *C07C 2601/08* (2017.05); *C07C 2601/14* (2017.05)

(58) Field of Classification Search
None
See application file for complete search history.

(56) References Cited

U.S. PATENT DOCUMENTS

| | | | |
|---|---|---|---|
| 3,795,692 | A | 3/1974 | Kulsa et al. |
| 3,897,563 | A | 7/1975 | Kulsa et al. |

(Continued)

FOREIGN PATENT DOCUMENTS

| | | |
|---|---|---|
| GB | 12568723 A | 12/1971 |
| GB | 1304164 A | 1/1973 |
| WO | 1994/006280 A1 | 3/1994 |

OTHER PUBLICATIONS

International Search Report and Written Opinion dated Nov. 17, 2015 issued from the Australian Patent Office for International Application No. PCT/AU2015/000527, 20 pages.

(Continued)

*Primary Examiner* — Savitha M Rao
*Assistant Examiner* — Gregg Polansky
(74) *Attorney, Agent, or Firm* — MH2 Technology Law Group, LLP

(57) ABSTRACT

The invention provides compounds of Formula (I), and their use in methods for treating or preventing a protozoan infection in a subject using a compound of Formula (I). The invention also provides the use of a compound of Formula (I) in the manufacture of a medicament for the treatment of a protozoan infection in a subject. The invention further provides a medical device when used in a method of treating or preventing a protozoan infection in a subject and to a medical device comprising the composition of the invention.

9 Claims, 35 Drawing Sheets

(51) Int. Cl.
*C07D 251/54* (2006.01)
*C07D 249/14* (2006.01)
*C07D 239/48* (2006.01)
*C07D 311/58* (2006.01)
*A61K 31/404* (2006.01)
*A61K 31/17* (2006.01)

(56) References Cited

U.S. PATENT DOCUMENTS

| | | |
|---|---|---|
| 3,992,446 A | 11/1976 | Tomcufcik |
| 4,015,016 A | 3/1977 | Livak et al. |
| 4,310,541 A | 1/1982 | Wang et al. |

OTHER PUBLICATIONS

CAS Registry No. 936347-46-5, STN Entry Date Jun. 1, 2007.
CAS Registry No. 7147-21-9, STN Entry Date Nov. 16, 1984.
Karabay et al., "Albendazole versus metronidazole treatment of adult giardiasis: An open randomized clinical study", World Journal of Gastroenterology, 2004, vol. 10, No. 8, pp. 1215-1217.
Messeder et al., "Aromatic Guanyl Hydrazones: Synthesis, Structural Studies and in vitro Activity against Trypanosoma cruzi", Bioorganic & Medicinal Chemistry Letters, 1995, vol. 4, No. 24, pp. 3079-3084.

Figure 1

| NCL COMPOUND CODE | COMPOUND NAME | STRUCTURE |
|---|---|---|
| NCL812 | 2,2'-bis[(4-chlorophenyl)methylene]carbonimidic dihydrazide hydrochloride | 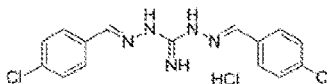 |
| NCL001 | 2,2'-bis[(4-chlorophenyl)methylene]carbonic dihydrazide | 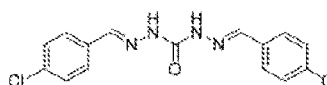 |
| NCL002 | 2,2'-bis[(2-chlorophenyl)methylene]carbonic dihydrazide | 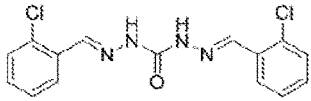 |
| NCL003 | 2,2'-bis[(4-fluorophenyl)methylene]carbonic dihydrazide | 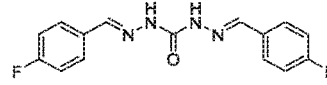 |
| NCL004 | 2,2'-bis[(3-fluorophenyl)methylene]carbonic dihydrazide | 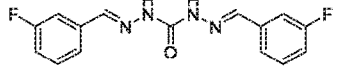 |
| NCL005 | 2,2'-bis[(2-fluorophenyl)methylene]carbonic dihydrazide | 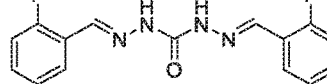 |
| NCL006 | 2,2'-bis[(4-methoxyphenyl)methylene]carbonic dihydrazide | 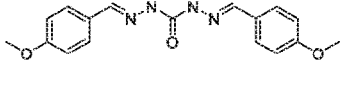 |
| NCL007 | 2,2'-bis[(4-cyanophenyl)methylene]carbonic dihydrazide | 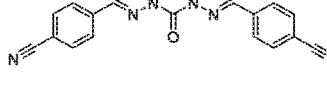 |
| NCL008 | 2,2'-bis[(2-cyanophenyl)methylene]carbonic dihydrazide | 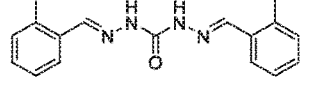 |

| | | |
|---|---|---|
| NCL009 | 2,2'-bis[(3-cyanophenyl)methylene]carbonic dihydrazide | 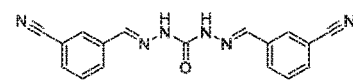 |
| NCL010 | 2,2'-bis[(3-methoxyphenyl)methylene]carbonic dihydrazide | 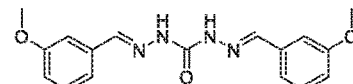 |
| NCL011 | 2,2'-bis{[3-(trifluoromethyl)phenyl]methylene}carbonic dihydrazide | 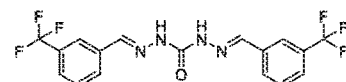 |
| NCL012 | 2,2'-bis{[4-(trifluoromethyl)phenyl]methylene}carbonic dihydrazide | 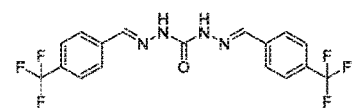 |
| NCL013 | 2,2'-bis{[2-(trifluoromethyl)phenyl]methylene}carbonic dihydrazide | 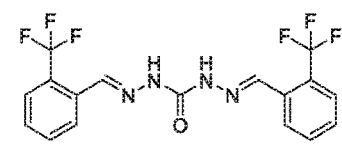 |
| NCL014 | 2-[(4-chlorophenyl)methylene]hydrazinecarboxamide | 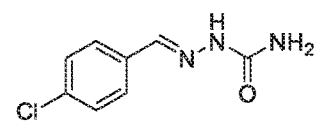 |
| NCL015 | 2-[(2-chlorophenyl)methylene]hydrazinecarboximidamide hydrochloride | 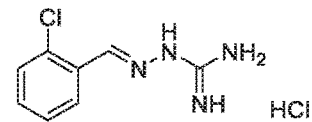 |
| NCL016 | 2-[(2-fluorophenyl)methylene]hydrazinecarboximidamide hydrochloride | 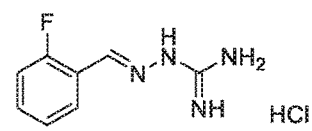 |
| NCL017 | 2-[(3-fluorophenyl)methylene]hydrazinecarboximidamide hydrochloride | 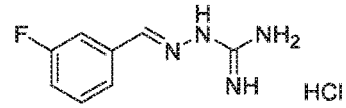 |
| NCL018 | 2,2'-bis[(2-methylphenyl)methylene]carbonic dihydrazide | 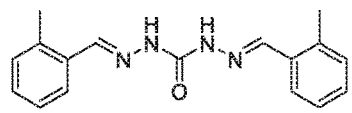 |
| NCL019 | 2,2'-bis[(3-methylphenyl)methylene]carbonic dihydrazide | 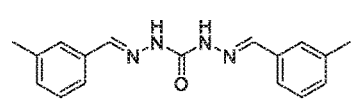 |

Figure 1 (cont.)

| | | |
|---|---|---|
| NCL020 | 2,2'-bis[(2-chlorophenyl)methylene]carbonimidic dihydrazide hydrochloride | 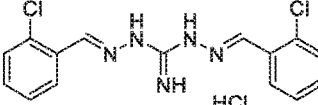 |
| NCL021 | 2,2'-bis[(4-fluorophenyl)methylene]carbonimidic dihydrazide hydrochloride | 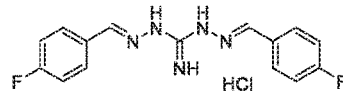 |
| NCL022 | 2,2'-bis[(2-fluorophenyl)methylene]carbonimidic dihydrazide hydrochloride | 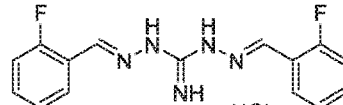 |
| NCL023 | 2,2'-bis[(3-fluorophenyl)methylene]carbonimidic dihydrazide hydrochloride | 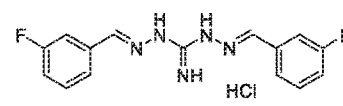 |
| NCL024 | 2,2'-bis[(4-cyanophenyl)methylene]carbonimidic dihydrazide hydrochloride | 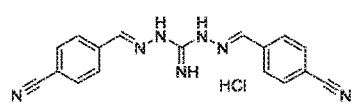 |
| NCL025 | 2,2'-bis[(2-cyanophenyl)methylene]carbonimidic dihydrazide hydrochloride | 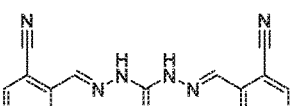 |
| NCL026 | 2,2'-bis[(3-cyanophenyl)methylene]carbonimidic dihydrazide hydrochloride | 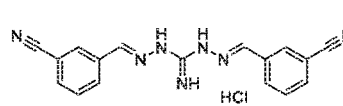 |
| NCL027 | 2,2'-bis[(4-methoxyphenyl)methylene]carbonimidic dihydrazide hydrochloride | 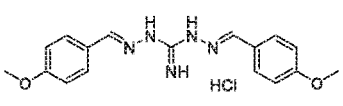 |
| NCL028 | 2,2'-bis[(2-methoxyphenyl)methylene]carbonimidic dihydrazide hydrochloride | 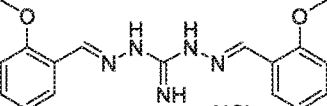 |
| NCL029 | 2,2'-bis[(3-methoxyphenyl)methylene]carbonimidic dihydrazide hydrochloride | 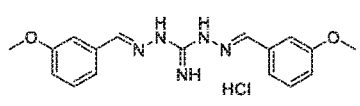 |
| NCL030 | 2-[(4-chlorophenyl)methylene]hydrazinecarboximidamide hydrochloride | 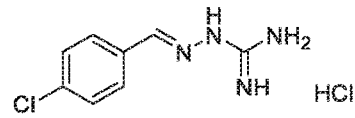 |

Figure 1 (cont.)

| | | |
|---|---|---|
| NCL031 | 2-[(4-cyanophenyl)methylene]hydrazinecarboximidamide hydrochloride | 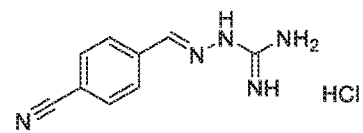 |
| NCL032 | 2-[(2-cyanophenyl)methylene]hydrazinecarboximidamide hydrochloride | 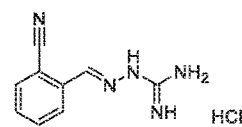 |
| NCL033 | 2-[(3-cyanophenyl)methylene]hydrazinecarboximidamide hydrochloride | 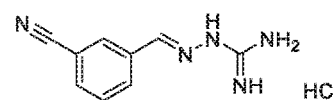 |
| NCL034 | 2-[(2-methoxyphenyl)methylene]hydrazinecarboximidamide hydrochloride | 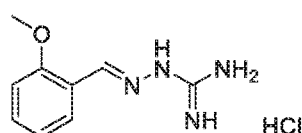 |
| NCL035 | 2,2'-bis{[4-(trifluoromethyl)phenyl]methylene}carbonimidic dihydrazide hydrochloride | 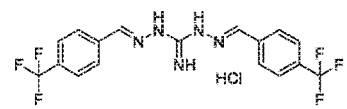 |
| NCL036 | 2,2'-bis{[2-(trifluoromethyl)phenyl]methylene}carbonimidic dihydrazide hydrochloride | 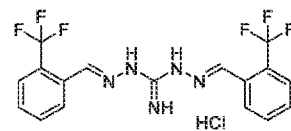 |
| NCL037 | 2,2'-bis{[3-(trifluoromethyl)phenyl]methylene}carbonimidic dihydrazide hydrochloride | 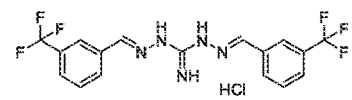 |
| NCL038 | 2,2'-bis[(4-methylphenyl)methylene]carbonimidic dihydrazide hydrochloride | 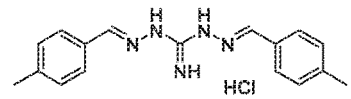 |
| NCL039 | 2,2'-bis[(2-methylphenyl)methylene]carbonimidic dihydrazide hydrochloride | 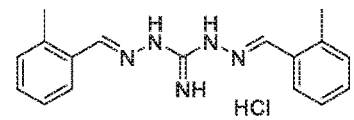 |
| NCL040 | 2,2'-bis[(3-methylphenyl)methylene]carbonimidic dihydrazide hydrochloride | 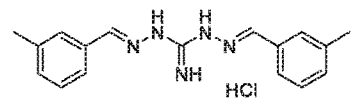 |
| NCL041 | 2-{[4-(trifluoromethyl)phenyl]methylene}hydrazinecarboximidamide hydrochloride | 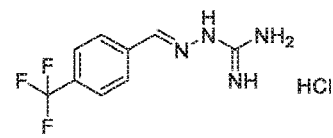 |

Figure 1 (cont.)

| | | |
|---|---|---|
| NCL042 | 2-{[2-(trifluoromethyl)phenyl]methylene}hydrazinecarboximidamide hydrochloride | 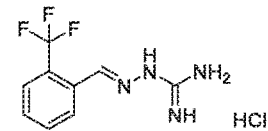 |
| NCL043 | 2-{[3-(trifluoromethyl)phenyl]methylene}hydrazinecarboximidamide hydrochloride | 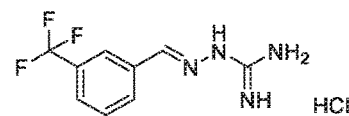 |
| NCL044 | 2-[(4-methylphenyl)methylene]hydrazinecarboximidamide hydrochloride | 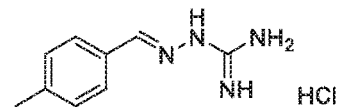 |
| NCL045 | 2-[(2-methylphenyl)methylene]hydrazinecarboximidamide hydrochloride | 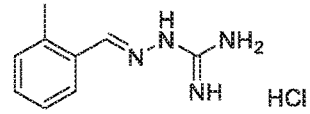 |
| NCL046 | 2-[(3-methylphenyl)methylene]hydrazinecarboximidamide hydrochloride | 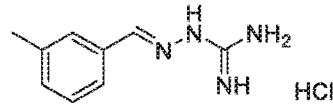 |
| NCL047 | 2-[(2-chlorophenyl)methylene]hydrazinecarboxamide | 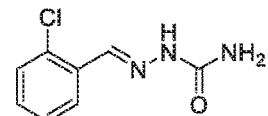 |
| NCL048 | 2-[(2-fluorophenyl)methylene]hydrazinecarboxamide | 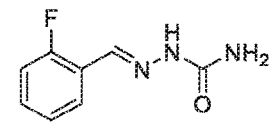 |
| NCL049 | 2-[(4-cyanophenyl)methylene]hydrazinecarboxamide | 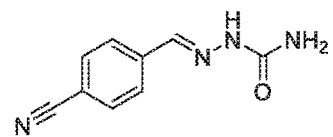 |
| NCL050 | 2-[(2-cyanophenyl)methylene]hydrazinecarboxamide | 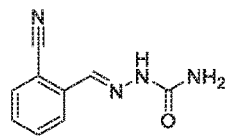 |
| NCL051 | 2-[(3-cyanophenyl)methylene]hydrazinecarboxamide | 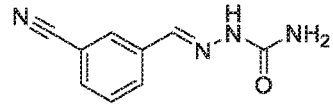 |
| NCL052 | 2-[(3-chlorophenyl)methylene]hydrazinecarboximidamide hydrochloride | 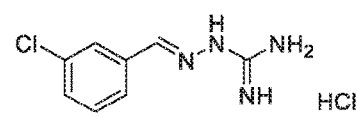 |

Figure 1 (cont.)

| | | |
|---|---|---|
| NCL053 | 2-[(4-fluorophenyl)methylene]hydrazinecarboximidamide hydrochloride | |
| NCL054 | 2,2'-bis[(3-chlorophenyl)methylene]carbonimidic dihydrazide hydrochloride | |
| NCL055 | 2-[(3-chlorophenyl)methylene]hydrazinecarboxamide | |
| NCL056 | 2-[(4-fluorophenyl)methylene]hydrazinecarboxamide | |
| NCL057 | 2-[(3-fluorophenyl)methylene]hydrazinecarboxamide | |
| NCL058 | 2-[(4-methoxyphenyl)methylene]hydrazinecarboxamide | |
| NCL059 | 2-[(3-methoxyphenyl)methylene]hydrazinecarboxamide | |
| NCL060 | 2-{[(2-trifluoromethyl)phenyl]methylene}hydrazinecarboxamide | |
| NCL061 | 2,2'-bis{1-[4-(trifluoromethyl)phenyl]ethylidene}carbonimidic dihydrazide hydrochloride | |
| NCL062 | 2,2'-bis[1-(4-chlorophenyl)ethylidene]carbonimidic dihydrazide hydrochloride | |
| NCL063 | 2,2'-bis{[4-(trifluoromethyl)phenyl]methylene}carbonothioic dihydrazide | |

Figure 1 (cont.)

| | | |
|---|---|---|
| NCL064 | 2,2'-bis[(2-cyanophenyl)methylene]carbonothioic dihydrazide | 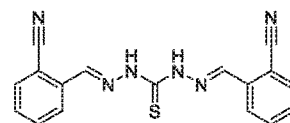 |
| NCL065 | 2,2'-bis[(3-cyanophenyl)methylene]carbonothioic dihydrazide | 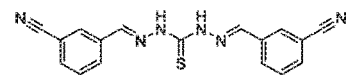 |
| NCL066 | 2,2'-bis[(3-fluorophenyl)methylene]carbonothioic dihydrazide | 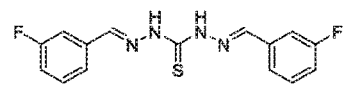 |
| NCL067 | 2-{[(3-trifluoromethyl)phenyl]methylene}hydrazinecarboxamide | 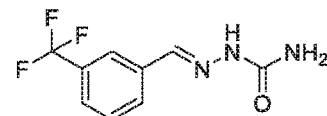 |
| NCL068 | 2-[1-(4-chlorophenyl)ethylidene]-2'-{1-[4-(trifluoromethyl)phenyl]methylene}carbonimidic dihydrazide hydrochloride | 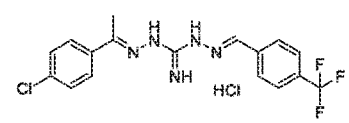 |
| NCL069 | 2-[1-(4-chlorophenyl)ethylidene]carbonimidic dihydrazide hydrochloride | 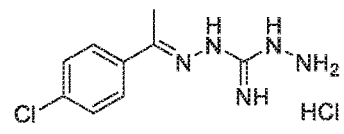 |
| NCL070 | 2,2'-bis[(3-chlorophenyl)methylene]carbonothioic dihydrazide | 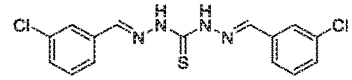 |
| NCL071 | 2-[(2-methoxyphenyl)methylene]hydrazinecarbothioamide | 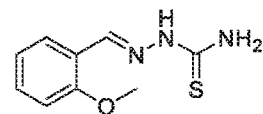 |
| NCL072 | 2-[(4-chlorophenyl)methylene]carbonimidic dihydrazide hydrochloride | 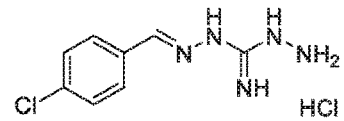 |
| NCL073 | 2-{[1-(4-trifluoromethyl)phenyl]ethylidene}carbonimidic dihydrazide hydrochloride | 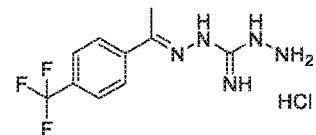 |
| NCL074 | 2-[(2,4-dichlorophenyl)methylene]-2'-[(4-chlorophenyl)methylene]carbonimidic dihydrazide hydrochloride | 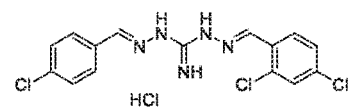 |

Figure 1 (cont.)

| | | |
|---|---|---|
| NCL075 | 2-{1-[4-(trifluoromethyl)phenyl]ethylidene}-2'-{[4-(trifluoromethyl)phenyl]methylene}carbonimidic dihydrazide hydrochloride | 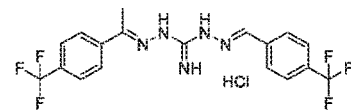 |
| NCL076 | 2-[(4-chlorophenyl)methylene]-2'-[(4-methylphenyl)methylene]carbonimidic dihydrazide hydrochloride | 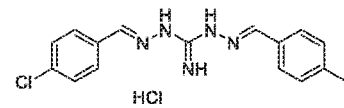 |
| NCL077 | 2-[(4-chlorophenyl)methylene]-2'-{[4-(trifluoromethyl)phenyl]methylene}carbonimidic dihydrazide hydrochloride | 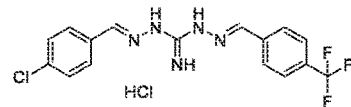 |
| NCL078 | 2-{[2-fluoro-4-(trifluoromethyl)phenyl]methylene}-2'-[(4-chlorophenyl)methylene]carbonimidic dihydrazide hydrochloride | 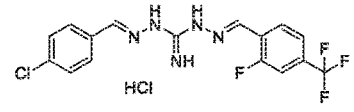 |
| NCL079 | 2-[(4-chlorophenyl)methylene]-2'-[(4-fluorophenyl)methylene]carbonimidic dihydrazide hydrochloride | 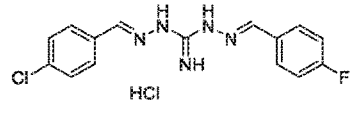 |
| NCL080 | 2-{1-[4-(trifluoromethyl)phenyl]ethylidene}-2'-[(4-chlorophenyl)methylene]carbonimidic dihydrazide hydrochloride | 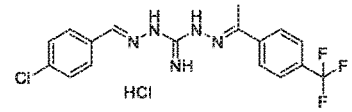 |
| NCL081 | 2-[1-(4-chlorophenyl)ethylidene]-2'-[(4-chlorophenyl)methylene]carbonimidic dihydrazide hydrochloride | 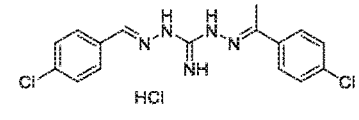 |
| NCL082 | 2-[(2-chlorophenyl)methylene]-2'-[(4-chlorophenyl)methylene]carbonimidic dihydrazide hydrochloride | 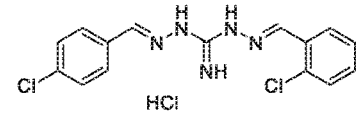 |
| NCL083 | 2-[(3-chlorophenyl)methylene]-2'-[(4-chlorophenyl)methylene]carbonimidic dihydrazide hydrochloride | 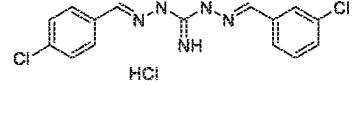 |
| NCL084 | 2-[(2-fluoro-4-chlorophenyl)methylene]-2'-[(4-chlorophenyl)methylene]carbonimidic dihydrazide hydrochloride | 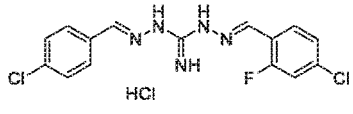 |
| NCL085 | 2-[(2-cyanophenyl)methylene]-2'-[(4-chlorophenyl)methylene]carbonimidic dihydrazide hydrochloride | 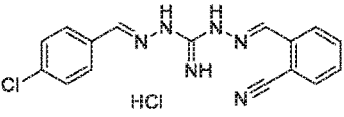 |

Figure 1 (cont.)

| | | |
|---|---|---|
| NCL086 | 2-[(3-cyanophenyl)methylene]-2'-[(4-chlorophenyl)methylene]carbonimidic dihydrazide hydrochloride | 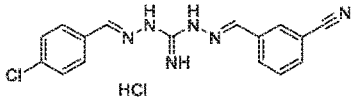 |
| NCL087 | 2-[(4-chlorophenyl)methylene]-2'-[(4-cyanophenyl)methylene]carbonimidic dihydrazide hydrochloride | 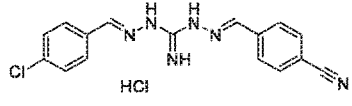 |
| NCL088 | 2-[(2-fluorophenyl)methylene]-2'-[(4-chlorophenyl)methylene]carbonimidic dihydrazide hydrochloride | 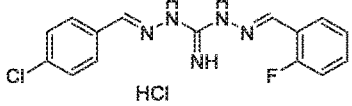 |
| NCL089 | 2-[1-(4-chlorophenyl)ethylidene]-2'-{1-[4-(trifluoromethyl)phenyl]ethylidene}carbonimidic dihydrazide hydrochloride | 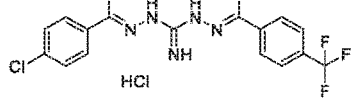 |
| NCL090 | N-benzoyl-1-benzoyl-2-[(2-chlorophenyl)methylene]hydrazinecarboximidamide hydrochloride | 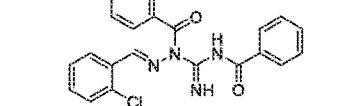 |
| NCL091 | N-(4-chlorophenyl)-3-[4-(trifluoromethyl)phenyl]-1H-1,2,4-triazol-5-amine | 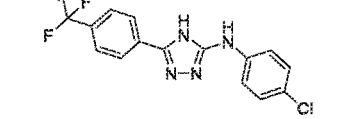 |
| NCL092 | N-(4-chlorobenzyl)-3-(4-chlorophenyl)-1H-1,2,4-triazol-5-amine | 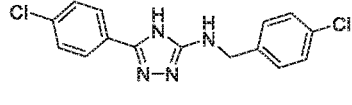 |
| NCL093 | 2,2'-bis(2-naphthalenylmethylene)carbonimidic dihydrazide hydrochloride | 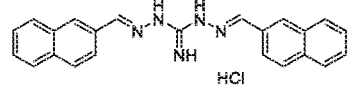 |
| NCL094 | 2,2'-bis(cyclohexylmethylene)carbonimidic dihydrazide hydrochloride | 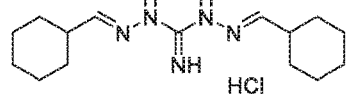 |
| NCL095 | 2,2'-bis(3-furanylmethylene)carbonimidic dihydrazide hydrochloride | 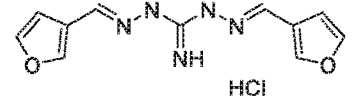 |
| NCL096 | 2,2'-bis(3-phenyl-2-propenylidene)carbonimidic dihydrazide hydrochloride | 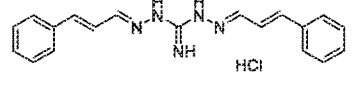 |

Figure 1 (cont.)

| | | |
|---|---|---|
| NCL097 | 2,2'-bis[(3,4,5-trihydroxyphenyl)methylene]carbonimidic dihydrazide hydrochloride | 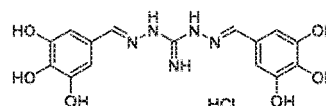 |
| NCL098 | 2,2'-bis[(3-carboxyphenyl)methylene]carbonimidic dihydrazide hydrochloride | 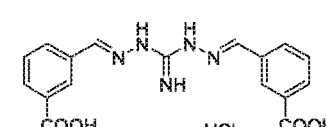 |
| NCL099 | 2,2'-bis{[4-(1,1-dimethylethyl)phenyl]methylene}carbonimidic dihydrazide hydrochloride | 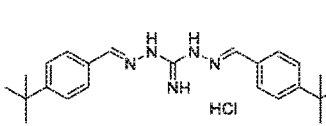 |
| NCL100 | 2,2'-bis(phenylmethylene)carbonimidic dihydrazide hydrochloride | 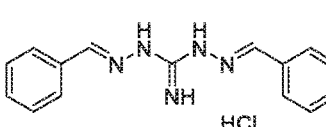 |
| NCL101 | 2,2'-bis[(2,3-dihydroxyphenyl)methylene]carbonimidic dihydrazide hydrochloride | 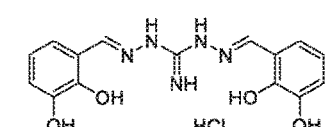 |
| NCL102 | 2,2'-bis[(2-nitrophenyl)methylene]carbonimidic dihydrazide hydrochloride | 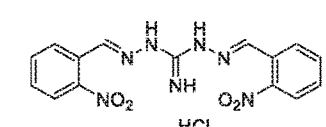 |
| NCL103 | 2,2'-bis[(2,4-dihydroxyphenyl)methylene]carbonimidic dihydrazide hydrochloride | 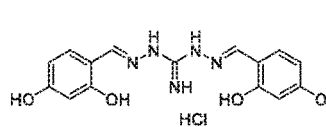 |
| NCL104 | 2,2'-bis[(2,4,5-trihydroxyphenyl)methylene]carbonimidic dihydrazide hydrochloride | 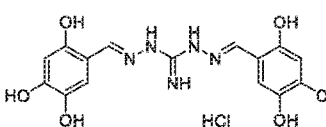 |
| NCL105 | 2,2'-bis[(2,3,4-trihydroxyphenyl)methylene]carbonimidic dihydrazide hydrochloride | 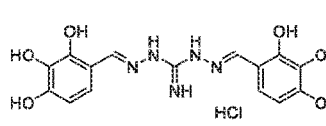 |
| NCL106 | 2,2'-bis[(4,5-dihydroxy-3-methoxyphenyl)methylene]carbonimidic dihydrazide hydrochloride | 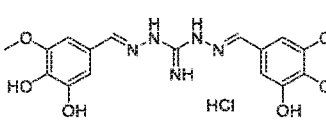 |
| NCL107 | 2,2'-bis[(2-hydroxyphenyl)methylene]carbonimidic dihydrazide hydrochloride | 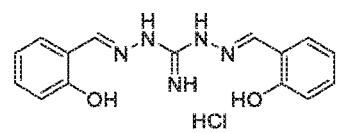 |

Figure 1 (cont.)

| | | |
|---|---|---|
| NCL108 | 2,2'-bis[(3-hydroxyphenyl)methylene]carbonimidic dihydrazide hydrochloride | 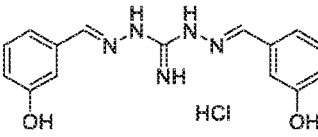 |
| NCL109 | 2,2'-bis[(3-nitrophenyl)methylene]carbonimidic dihydrazide hydrochloride | 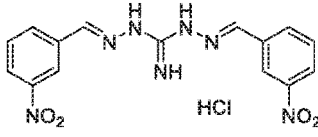 |
| NCL110 | 2,2'-bis[(4-nitrophenyl)methylene]carbonimidic dihydrazide hydrochloride | 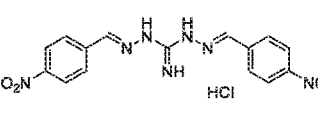 |
| NCL111 | 2,2'-bis[(3,4-dihydroxyphenyl)methylene]carbonimidic dihydrazide hydrochloride | 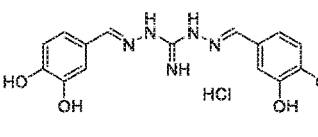 |
| NCL112 | 2,2'-bis([1,1'-biphenyl]-4-ylmethylene)carbonimidic dihydrazide hydrochloride | 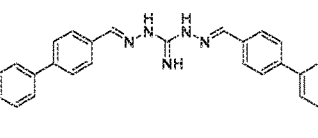 |
| NCL113 | 2,2'-bis{4-(dimethylamino)phenyl]methylene}carbonimidic dihydrazide hydrochloride | 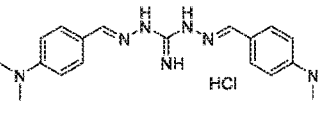 |
| NCL114 | 2,2'-bis[(3,5-dichlorophenyl)methylene]carbonimidic dihydrazide hydrochloride | 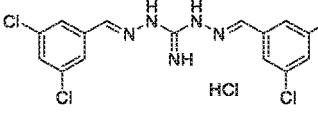 |
| NCL 115 | 2,2'-bis[(3,4-dimethoxyphenyl)methylene]carbonimidic dihydrazide hydrochloride | 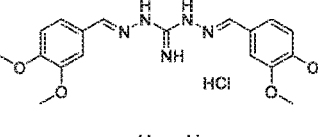 |
| NCL 116 | 2,2'-bis([1,1'-biphenyl]-2-ylmethylene)carbonimidic dihydrazide hydrochloride | 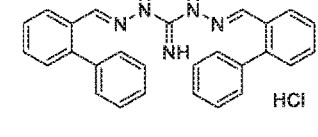 |
| NCL 117 | 2,2'-bis[(4-hydroxy-3-methoxyphenyl)methylene]carbonimidic dihydrazide hydrochloride | 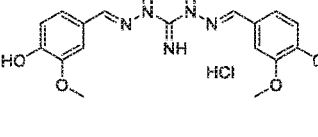 |
| NCL 118 | 2,2'-bis[(2,5-difluorophenyl)methylene]carbonimidic dihydrazide hydrochloride | 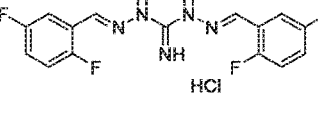 |

Figure 1 (cont.)

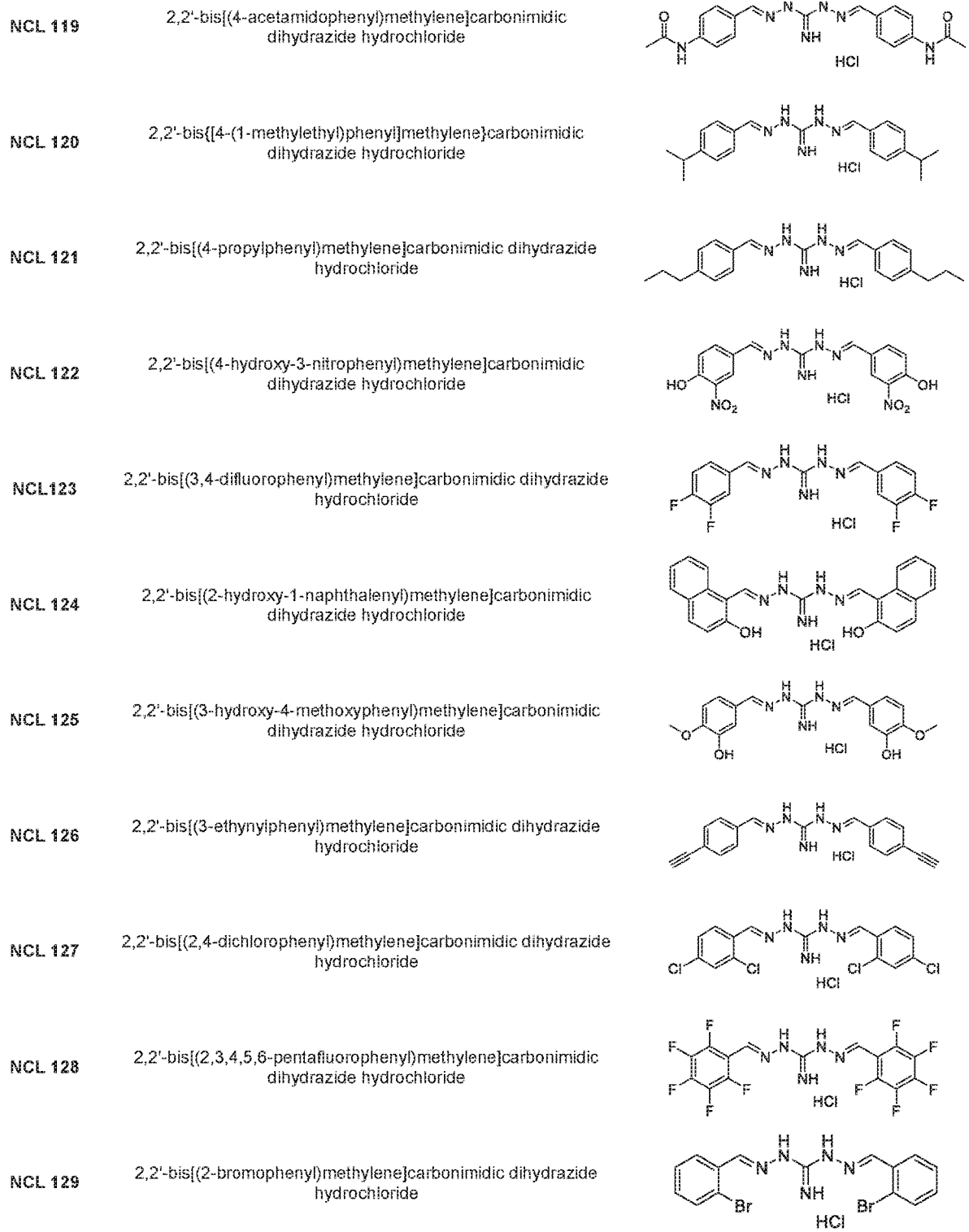

| NCL 119 | 2,2'-bis[(4-acetamidophenyl)methylene]carbonimidic dihydrazide hydrochloride |
| NCL 120 | 2,2'-bis{[4-(1-methylethyl)phenyl]methylene}carbonimidic dihydrazide hydrochloride |
| NCL 121 | 2,2'-bis[(4-propylphenyl)methylene]carbonimidic dihydrazide hydrochloride |
| NCL 122 | 2,2'-bis[(4-hydroxy-3-nitrophenyl)methylene]carbonimidic dihydrazide hydrochloride |
| NCL 123 | 2,2'-bis[(3,4-difluorophenyl)methylene]carbonimidic dihydrazide hydrochloride |
| NCL 124 | 2,2'-bis[(2-hydroxy-1-naphthalenyl)methylene]carbonimidic dihydrazide hydrochloride |
| NCL 125 | 2,2'-bis[(3-hydroxy-4-methoxyphenyl)methylene]carbonimidic dihydrazide hydrochloride |
| NCL 126 | 2,2'-bis[(3-ethynylphenyl)methylene]carbonimidic dihydrazide hydrochloride |
| NCL 127 | 2,2'-bis[(2,4-dichlorophenyl)methylene]carbonimidic dihydrazide hydrochloride |
| NCL 128 | 2,2'-bis[(2,3,4,5,6-pentafluorophenyl)methylene]carbonimidic dihydrazide hydrochloride |
| NCL 129 | 2,2'-bis[(2-bromophenyl)methylene]carbonimidic dihydrazide hydrochloride |

Figure 1 (cont.)

| | | |
|---|---|---|
| NCL 130 | 2,2'-bis[(3-bromo-4,5-dimethoxyphenyl)methylene]carbonimidic dihydrazide hydrochloride | |
| NCL 131 | 2,2'-bis[(3-bromophenyl)methylene]carbonimidic dihydrazide hydrochloride | |
| NCL 132 | 2,2'-bis[(4-chloro-6-fluoro-2H-1-benzopyran-3-yl)methylene]carbonimidic dihydrazide hydrochloride | |
| NCL 133 | 2,2'-bis[(4-bromo-2-furanyl)methylene]carbonimidic dihydrazide hydrochloride | |
| NCL 134 | 2,2'-bis[(4-bromophenyl)methylene]carbonimidic dihydrazide hydrochloride | |
| NCL 135 | 2,2'-bis[(2-bromo-4,5-dimethoxyphenyl)methylene]carbonimidic dihydrazide hydrochloride | |
| NCL 136 | 2,2'-bis[(4-butylphenyl)methylene]carbonimidic dihydrazide hydrochloride | |
| NCL 137 | 2,2'-bis[(2,6-dichlorophenyl)methylene]carbonimidic dihydrazide hydrochloride | |
| NCL 138 | 2,2'-bis(2,3-diphenyl-2-propenylidene)carbonimidic dihydrazide hydrochloride | |
| NCL139 | 2,2'-bis(3-quinolinylmethylene)carbonimidic dihydrazide hydrochloride | |
| NCL 140 | 2,2'-bis{[4-(methylsulfanyl)phenyl]methylene}carbonimidic dihydrazide hydrochloride | |

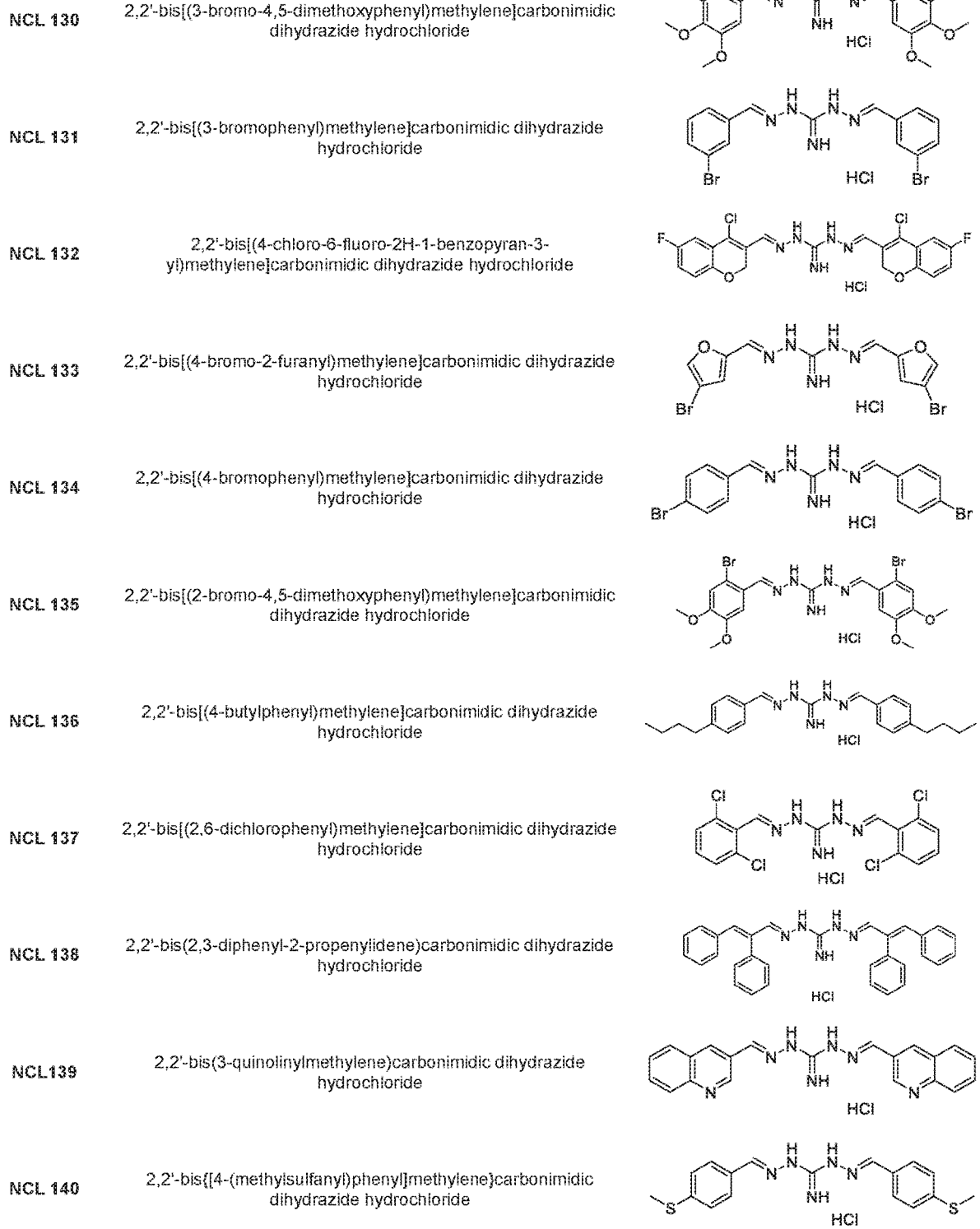

Figure 1 (cont.)

| | | |
|---|---|---|
| NCL 141 | 2,2'-bis[(5-chlorobenzo[b]thien-3-yl)methylene]carbonimidic dihydrazide hydrochloride | 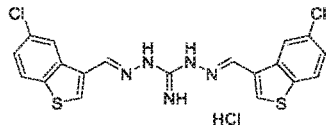 |
| NCL 142 | 1,3-bis(benzylamino)guanidine hydrochloride | 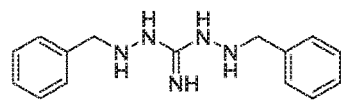 |
| NCL 143 | 2,2'-bis[1-phenylethylidene]carbonimidic dihydrazide hydrochloride | 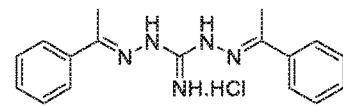 |
| NCL 144 | 2,2'-bis[(5-bromo-2-furanyl)methylene]carbonimidic dihydrazide hydrochloride | 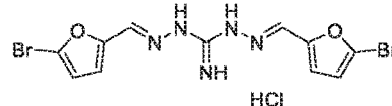 |
| NCL 145 | 2,2'-bis[(5-chloro-2-furanyl)methylene]carbonimidic dihydrazide hydrochloride | 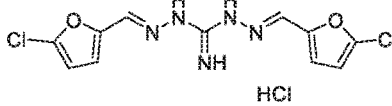 |
| NCL 146 | 2,2'-bis(1H-indol-5-ylmethylene)carbonimidic dihydrazide hydrochloride | 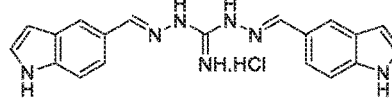 |
| NCL 147 | 2,2'-bis(2-quinoxalinylmethylene)carbonimidic dihydrazide hydrochloride | 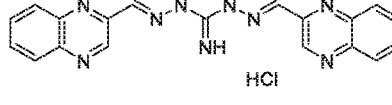 |
| NCL 148 | 2,2'-bis{[4-(carboxypropenyl)phenyl]methylene}carbonimidic dihydrazide hydrochloride | 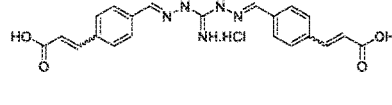 |
| NCL 149 | 2,2'-Bis(4-pyridinylmethylene)Carbonimidic dihydrazide hydrochloride | 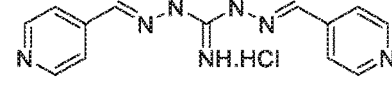 |
| NCL 150 | 2,2'-bis[3-(4-methoxylphenyl)-2-propenylidene]carbonimidic dihydrazide hydrochloride | 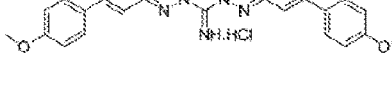 |
| NCL 151 | 2,2'-bis[(4-hydroxyphenyl)methylene]carbonimidic dihydrazide hydrochloride | 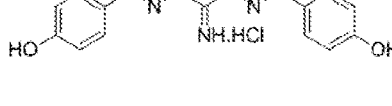 |

Figure 1 (cont.)

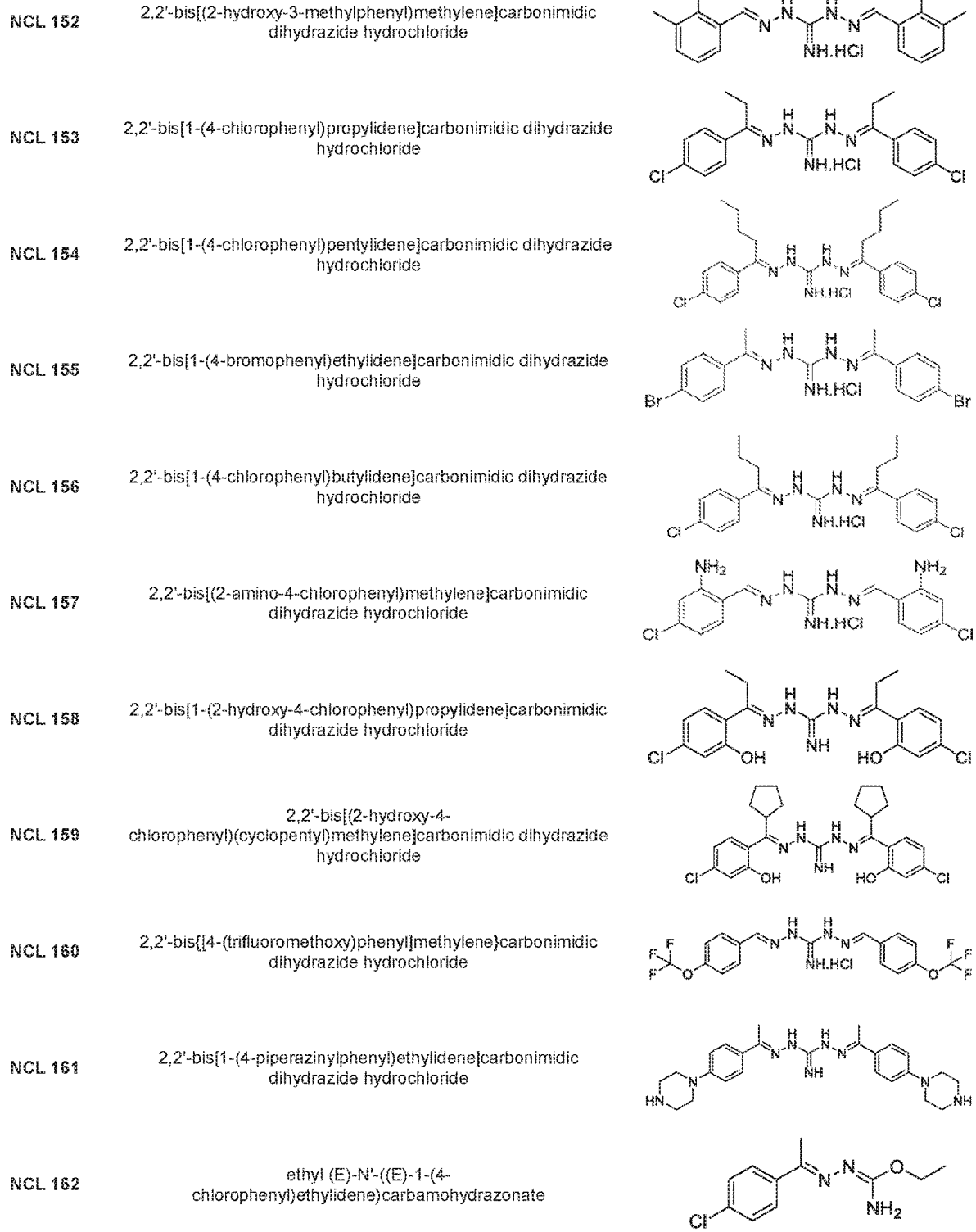

| NCL 152 | 2,2'-bis[(2-hydroxy-3-methylphenyl)methylene]carbonimidic dihydrazide hydrochloride |
| NCL 153 | 2,2'-bis[1-(4-chlorophenyl)propylidene]carbonimidic dihydrazide hydrochloride |
| NCL 154 | 2,2'-bis[1-(4-chlorophenyl)pentylidene]carbonimidic dihydrazide hydrochloride |
| NCL 155 | 2,2'-bis[1-(4-bromophenyl)ethylidene]carbonimidic dihydrazide hydrochloride |
| NCL 156 | 2,2'-bis[1-(4-chlorophenyl)butylidene]carbonimidic dihydrazide hydrochloride |
| NCL 157 | 2,2'-bis[(2-amino-4-chlorophenyl)methylene]carbonimidic dihydrazide hydrochloride |
| NCL 158 | 2,2'-bis[1-(2-hydroxy-4-chlorophenyl)propylidene]carbonimidic dihydrazide hydrochloride |
| NCL 159 | 2,2'-bis[(2-hydroxy-4-chlorophenyl)(cyclopentyl)methylene]carbonimidic dihydrazide hydrochloride |
| NCL 160 | 2,2'-bis{[4-(trifluoromethoxy)phenyl]methylene}carbonimidic dihydrazide hydrochloride |
| NCL 161 | 2,2'-bis[1-(4-piperazinylphenyl)ethylidene]carbonimidic dihydrazide hydrochloride |
| NCL 162 | ethyl (E)-N'-((E)-1-(4-chlorophenyl)ethylidene)carbamohydrazonate |

Figure 1 (cont.)

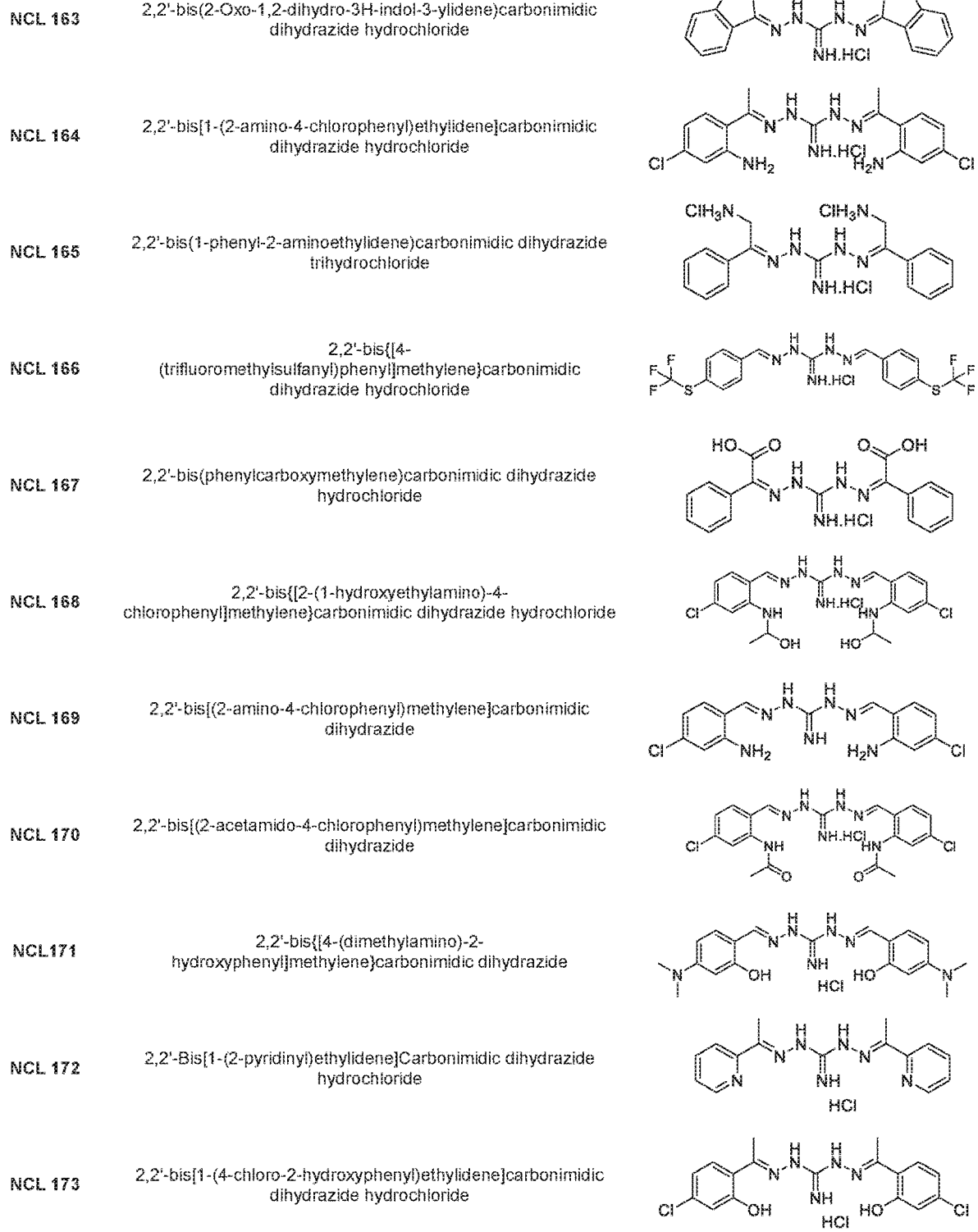

| | | |
|---|---|---|
| NCL 163 | 2,2'-bis(2-Oxo-1,2-dihydro-3H-indol-3-ylidene)carbonimidic dihydrazide hydrochloride | |
| NCL 164 | 2,2'-bis[1-(2-amino-4-chlorophenyl)ethylidene]carbonimidic dihydrazide hydrochloride | |
| NCL 165 | 2,2'-bis(1-phenyl-2-aminoethylidene)carbonimidic dihydrazide trihydrochloride | |
| NCL 166 | 2,2'-bis{[4-(trifluoromethylsulfanyl)phenyl]methylene}carbonimidic dihydrazide hydrochloride | |
| NCL 167 | 2,2'-bis(phenylcarboxymethylene)carbonimidic dihydrazide hydrochloride | |
| NCL 168 | 2,2'-bis{[2-(1-hydroxyethylamino)-4-chlorophenyl]methylene}carbonimidic dihydrazide hydrochloride | |
| NCL 169 | 2,2'-bis[(2-amino-4-chlorophenyl)methylene]carbonimidic dihydrazide | |
| NCL 170 | 2,2'-bis[(2-acetamido-4-chlorophenyl)methylene]carbonimidic dihydrazide | |
| NCL171 | 2,2'-bis{[4-(dimethylamino)-2-hydroxyphenyl]methylene}carbonimidic dihydrazide | |
| NCL 172 | 2,2'-Bis[1-(2-pyridinyl)ethylidene]Carbonimidic dihydrazide hydrochloride | |
| NCL 173 | 2,2'-bis[1-(4-chloro-2-hydroxyphenyl)ethylidene]carbonimidic dihydrazide hydrochloride | |

Figure 1 (cont.)

| | | |
|---|---|---|
| NCL 174 | 2,2'-bis(4-chloro-2-hydroxyphenylmethylene)carbonimidic dihydrazide hydrochloride | 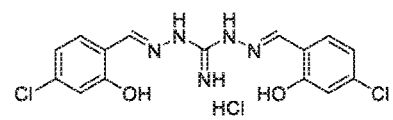 |
| NCL 175 | 2,2'-Bis(4-chloropyridin-3-ylmethylene)Carbonimidic dihydrazide hydrochloride | 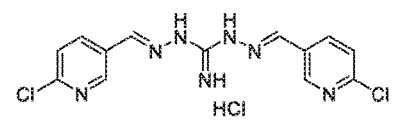 |
| NCL 176 | 2,2'-Bis(2-aminopyridin-3-ylmethylene)Carbonimidic dihydrazide hydrochloride | 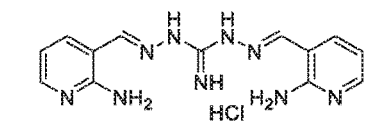 |
| NCL 177 | 2,2'-bis[1-(4-chlorophenyl)-2-hydroxyethylidene]carbonimidic dihydrazide hydrochloride | 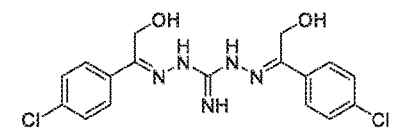 |
| NCL 178 | 4,6-bis(2-((E)-1-(4-chlorophenyl)ethylidene)hydrazinyl)pyrimidine | 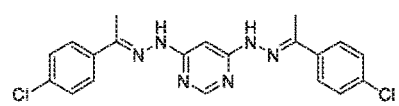 |
| NCL 179 | 4,6-bis(2-((E)-4-chlorobenzylidene)hydrazinyl)pyrimidin-2-amine | 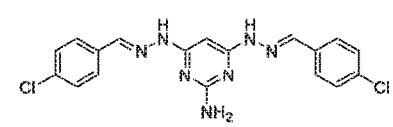 |
| NCL 180 | (2Z,2'Z)-2,2'-(pyrimidine-4,6-diylbis(hydrazin-2-yl-1-ylidene))bis(2-(4-chlorophenyl)ethan-1-ol) | 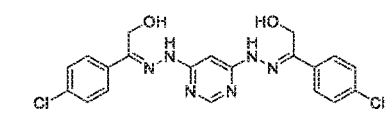 |
| NCL 181 | 4,6-bis(2-((E)-4-chlorobenzylidene)hydrazinyl)pyrimidine | 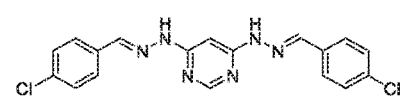 |
| NCL 182 | 6-chloro-$N^4$-(1-phenylethyl)pyrimidine-2,4-diamine | 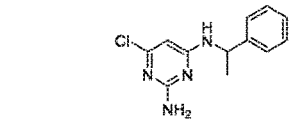 |
| NCL 183 | $N^4,N^6$-bis(1-phenylethyl)pyrimidine-4,6-diamine | 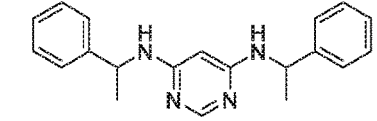 |
| NCL 184 | $N^4,N^6$-bis(1-phenylethyl)pyrimidine-2,4,6-triamine | 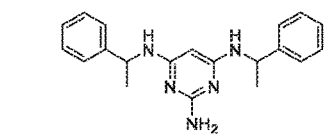 |

Figure 1 (cont.)

| | | |
|---|---|---|
| NCL 185 | 4,6-bis(2-((E)-1-(4-chlorophenyl)ethylidene)hydrazinyl)pyrimidine hydrochloride | 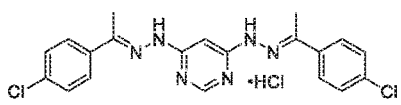 |
| NCL 186 | N²,N⁵-bis(1-(4-chlorophenyl)ethyl)pyrazine-2,5-diamine | 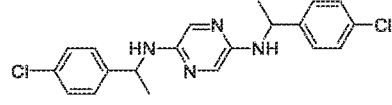 |
| NCL 187 | 4,6-bis(2-((E)-4-chlorobenzylidene)hydrazinyl)pyrimidine hydrochloride | 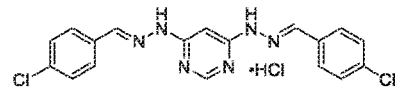 |
| NCL 188 | (E)-2-(1-(4-chlorophenyl)pentylidene)hydrazine-1-carboximidamide hydrochloride | 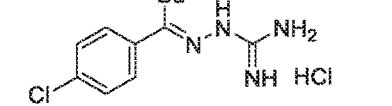 |
| NCL 189 | (2Z,2'Z)-2,2'-(pyrimidine-4,6-diylbis(hydrazin-2-yl-1-ylidene))bis(2-(4-chlorophenyl)ethan-1-ol) hydrochloride | 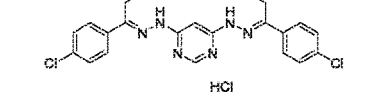 |
| NCL 190 | (Z)-2-(1-(4-chlorophenyl)-2-hydrazinylethylidene)hydrazine-1-carboximidamide hydrochloride | 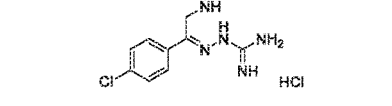 |
| NCL 191 | (E)-2-(1-(4-chlorophenyl)ethylidene)hydrazine-1-carboximidamide hydrochloride | 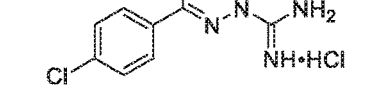 |
| NCL 192 | (Z)-2-(2-carbamimidoylhydrazono)-2-phenylacetic acid hydrochloride | 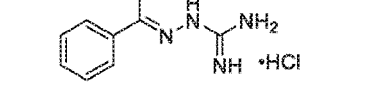 |
| NCL193 | 4,6-bis(2-((E)-4-bromobenzylidene)hydrazinyl)pyrimidin-2-amine | 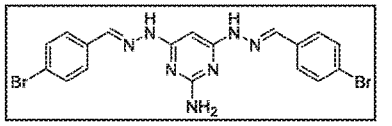 |
| NCL194 | N',N'''-(2-aminopyrimidine-4,6-diyl)di(benzohydrazide) | 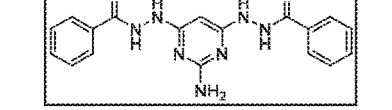 |

Figure 1 (cont.)

| | | |
|---|---|---|
| NCL195 | 4,6-bis(2-((E)-4-methylbenzylidene)hydrazinyl)pyrimidin-2-amine | 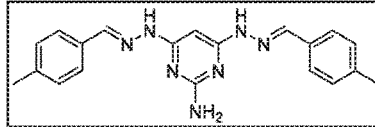 |
| NCL196 | 4,4'-((1E,1'E)-((2-aminopyrimidine-4,6-diyl)bis(hydrazin-2-yl-1-ylidene))bis(methanylylidene))diphenol | 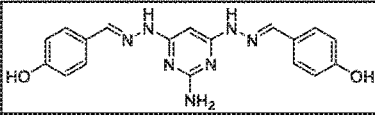 |
| NCL197 | 3,3'-((1E,1'E)-((2-aminopyrimidine-4,6-diyl)bis(hydrazin-2-yl-1-ylidene))bis(methanylylidene))diphenol | 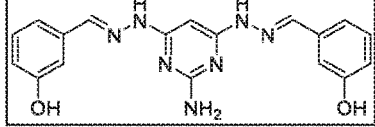 |
| NCL198 | 4,6-bis(2-((E)-4-(tert-butyl)benzylidene)hydrazinyl)pyrimidin-2-amine dihydrochloride | 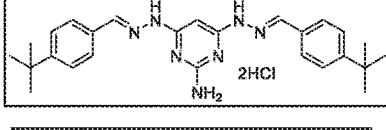 |
| NCL199 | 4,6-bis(2-((E)-benzylidene)hydrazinyl)pyrimidin-2-amine | 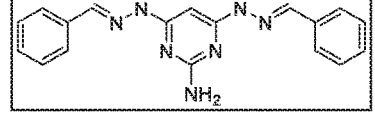 |
| NCL200 | 4,6-bis(2-((E)-4-(tert-butyl)benzylidene)hydrazinyl)pyrimidin-2-amine | 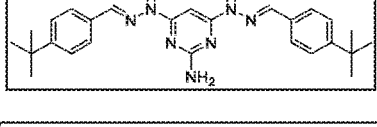 |
| NCL201 | 4,4'-((1E,1'E)-((2-aminopyrimidine-4,6-diyl)bis(hydrazin-2-yl-1-ylidene))bis(methanylylidene))bis(N,N-dimethylaniline) | 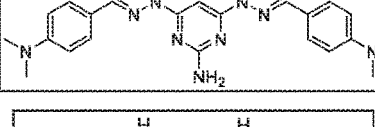 |
| NCL202 | 2,2'-((1E,1'E)-((2-aminopyrimidine-4,6-diyl)bis(hydrazin-2-yl-1-ylidene))bis(methanylylidene))diphenol | 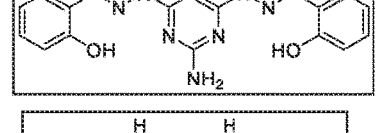 |
| NCL203 | 4,6-bis(2-((E)-cyclohexylmethylene)hydrazinyl)pyrimidin-2-amine dihydrochloride | 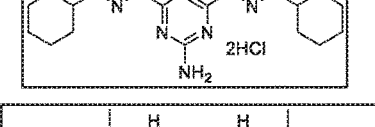 |
| NCL204 | 4,6-bis(2-((E)-1-(4-chlorophenyl)ethylidene)hydrazinyl)pyrimidin-2-amine | 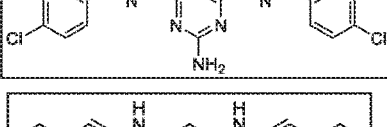 |
| NCL205 | 4,6-bis(2-((E)-2-chlorobenzylidene)hydrazinyl)pyrimidin-2-amine | 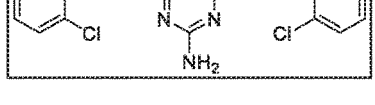 |

Figure 1 (cont.)

| | | |
|---|---|---|
| NCL206 | 4,6-bis(2-((E)-4-methylbenzylidene)hydrazinyl)-1,3,5-triazin-2-amine | |
| NCL207 | 2,2'-((1E,1'E)-((6-amino-1,3,5-triazine-2,4-diyl)bis(hydrazin-2-yl-1-ylidene))bis(methanylylidene))diphenol | |
| NCL208 | 4,6-bis(2-((E)-1-(4-chlorophenyl)ethylidene)hydrazinyl)-1,3,5-triazin-2-amine | |
| NCL209 | 3,3'-((1E,1'E)-((6-amino-1,3,5-triazine-2,4-diyl)bis(hydrazin-2-yl-1-ylidene))bis(methanylylidene))diphenol | |
| NCL210 | 4,6-bis(2-((E)-4-(trifluoromethyl)benzylidene)hydrazinyl)-1,3,5-triazin-2-amine | |
| NCL211 | 4,4'-((1E,1'E)-((6-amino-1,3,5-triazine-2,4-diyl)bis(hydrazin-2-yl-1-ylidene))bis(methanylylidene))diphenol | |
| NCL212 | 4,6-bis(2-((E)-4-bromobenzylidene)hydrazinyl)-1,3,5-triazin-2-amine | |
| NCL213 | 4,6-bis(2-((E)-cyclohexylmethylene)hydrazinyl)-1,3,5-triazin-2-amine | |
| NCL214 | 4,6-bis(2-((E)-benzylidene)hydrazinyl)-1,3,5-triazin-2-amine | |
| NCL215 | 2,2'-bis[1-(4-chloro-2-fluorophenyl)ethylidene]carbonimidic dihydrazide hydrochloride | |
| NCL216 | N',2-bis((E)-4-chloro-2-fluorobenzylidene)hydrazine-1-carboximidhydrazide hydrochloride | |

Figure 1 (cont.)

| | | |
|---|---|---|
| NCL217 | N',2-bis((E)-1-(p-tolyl)ethylidene)hydrazine-1-carboximidhydrazide hydrochloride | 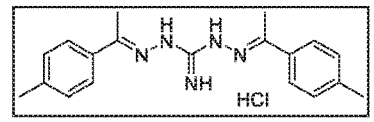 |
| NCL812FB | As Previous | 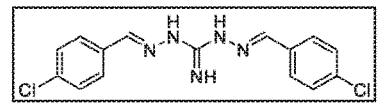 |
| NCL062FB | As Previous | 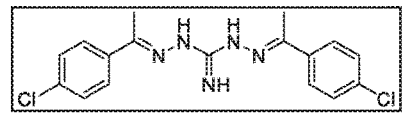 |
| NCL218 | 4-((E)-(2-(2-amino-6-(2-((E)-4-((diethoxyphosphoryl)oxy)benzylidene)hydrazinyl)pyrimidin-4-yl)hydrazono)methyl)phenyl diethyl phosphate | 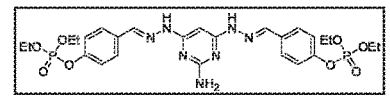 |
| NCL219 | 2,2'-bis{1-[4-(t-butyl)phenyl]ethylidene}carbonimidic dihydrazide hydrochloride | 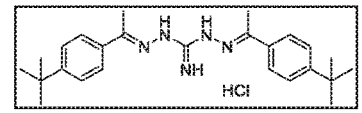 |
| NCL220 | 4,6-bis(2-((E)-4-fluorobenzylidene)hydrazinyl)pyrimidin-2-amine | 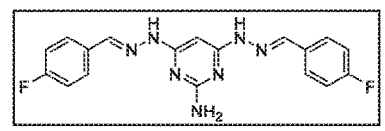 |
| NCL221 | 4,6-bis(2-((E)-4-(trifluoromethyl)benzylidene)hydrazinyl)pyrimidin-2-amine | 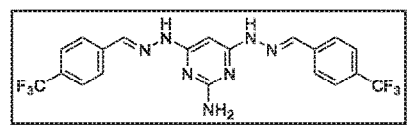 |
| NCL222 | 4,6-bis(2-((E)-3,4-difluorobenzylidene)hydrazinyl)pyrimidin-2-amine | 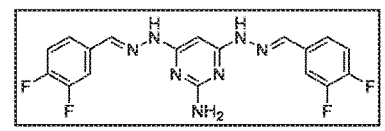 |
| NCL223 | N,N'-(((1E,1'E)-((2-aminopyrimidine-4,6-diyl)bis(hydrazin-2-yl-1-ylidene))bis(methanylylidene))bis(4,1-phenylene))diacetamide | 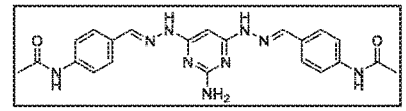 |
| NCL224 | ethyl 2-((E)-4-chlorobenzylidene)-1-((E)-N'-((E)-4-chlorobenzylidene)carbamohydrazonoyl)hydrazine-1-carboxylate | 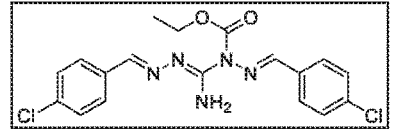 |
| NCL225 | isobutyl 2-((E)-4-chlorobenzylidene)-1-((E)-N'-((E)-4-chlorobenzylidene)carbamohydrazonoyl)hydrazine-1-carboxylate | 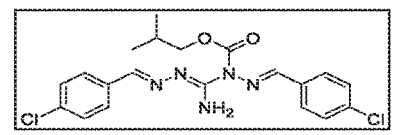 |

Figure 1 (cont.)

| | | |
|---|---|---|
| NCL226 | 2-((E)-4-chlorobenzylidene)-1-((E)-N'-((E)-4-chlorobenzylidene)carbamohydrazonoyl)-N-ethylhydrazine-1-carboxamide | 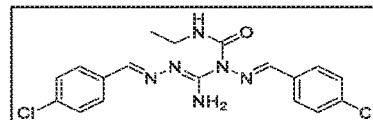 |
| NCL227 | N-benzyl-2-((E)-4-chlorobenzylidene)-1-((E)-N'-((E)-4-chlorobenzylidene)carbamohydrazonoyl)hydrazine-1-carboxamide | 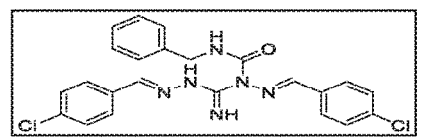 |
| NCL228 | 2-((E)-4-chlorobenzylidene)-1-((E)-N'-((E)-4-chlorobenzylidene)carbamohydrazonoyl)-N-hexylhydrazine-1-carboxamide | 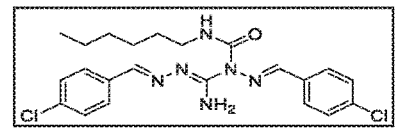 |
| NCL229 | 2-((E)-4-chlorobenzylidene)-1-((E)-N'-((E)-4-chlorobenzylidene)carbamohydrazonoyl)-N-(furan-2-ylmethyl)hydrazine-1-carboxamide | 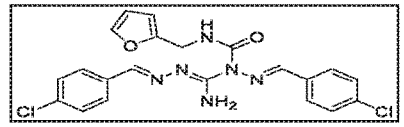 |
| NCL230 | 4,6-bis(2-((E)-4-methoxybenzylidene)hydrazinyl)pyrimidin-2-amine | 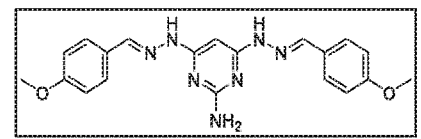 |
| NCL231 | (E)-2-(1-(4-(tert-butyl)phenyl)ethylideneamino)guanidine | 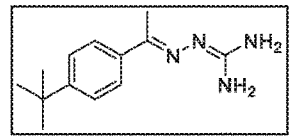 |
| NCL232 | (E)-2-(4-(tert-butyl)benzylideneamino)guanidine | 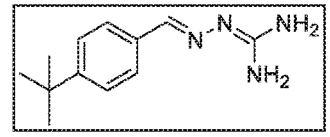 |
| NCL233 | (E)-2-(1-(4-chlorophenyl)butylidene)hydrazine-1-carboximidamide hydrochloride | 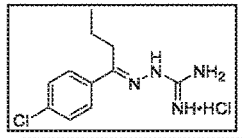 |
| NCL234 | (E)-2-(1-(4-chlorophenyl)propylidene)hydrazine-1-carboximidamide | 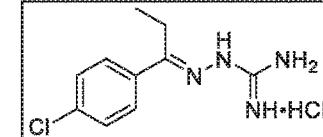 |
| NCL235 | (E)-2-(4-chloro-2-fluorobenzylidene)hydrazine-1-carboximidamide | 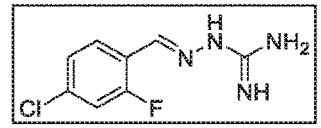 |

Figure 1 (cont.)

| | | |
|---|---|---|
| NCL236 | (E)-2-(1-(4-chloro-2-fluorophenyl)ethylidene)hydrazine-1-carboximidamide | 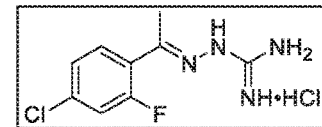 |
| NCL237 | (E)-2-(1-(4-chloro-2-hydroxyphenyl)-2-cyclohexylethylideneamino)guanidine | 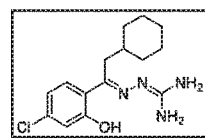 |
| NCL238 | 4,6-bis(2-((E)-(6-chloropyridin-3-yl)methylene)hydrazinyl)pyrimidin-2-amine | 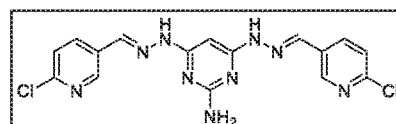 |
| NCL239 | 4,6-bis(2-((E)-pyridin-3-ylmethylene)hydrazinyl)pyrimidin-2-amine | 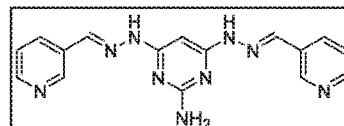 |
| NCL240 | 4,6-bis(2-((E)-pyridin-2-ylmethylene)hydrazinyl)pyrimidin-2-amine | 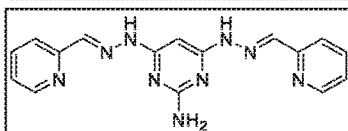 |
| NCL241 | 4,6-bis(2-((E)-pyridin-4-ylmethylene)hydrazinyl)pyrimidin-2-amine | 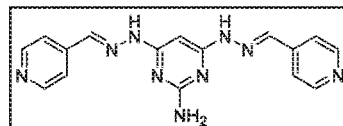 |
| NCL242 | 4,6-bis(2-((E)-2,5-dihydroxybenzylidene)hydrazinyl)pyrimidin-2-aminium 2-formyl-4-hydroxyphenolate | 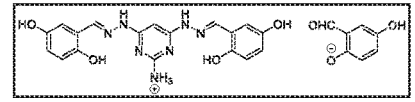 |
| NCL243 | 4,6-bis(2-((E)-3,4-dihydroxybenzylidene)hydrazinyl)pyrimidin-2-amine | 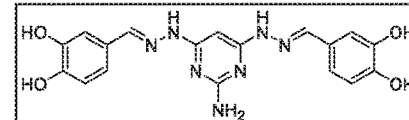 |
| NCL244 | 4,6-bis(2-((E)-2,3-dihydroxybenzylidene)hydrazinyl)pyrimidin-2-aminium 2-formyl-6-hydroxyphenolate | 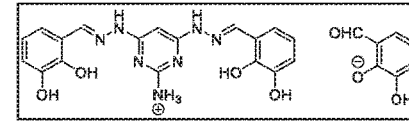 |
| NCL245 | 4,6-bis(2-((E)-naphthalen-1-ylmethylene)hydrazinyl)pyrimidin-2-amine | 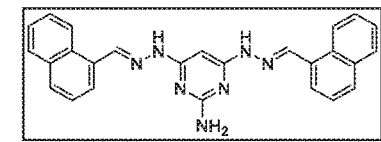 |
| NCL246 | 4,6-bis(2-((1E,2E)-3-phenylallylidene)hydrazinyl)pyrimidin-2-amine | 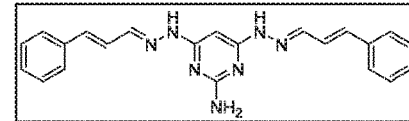 |

Figure 1 (cont.)

| | | |
|---|---|---|
| NCL247 | 4,6-bis(2-((E)-3,4,5-trihydroxybenzylidene)hydrazinyl)pyrimidin-2-amine | 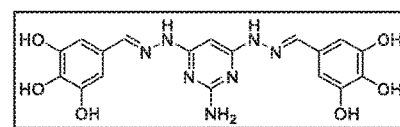 |
| NCL248 | (E)-2-(naphthalen-1-ylmethylideneamino)guanidine | 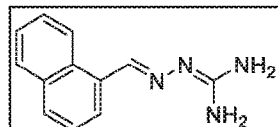 |
| NCL249 | (E)-2-((E)-3-phenylallylideneamino)guanidine | 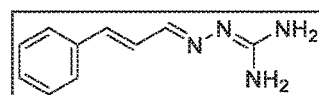 |
| NCL250 | (1E,1'E)-N,N'-(ethane-1,2-diyl)bis(1-(4-chlorophenyl)methanimine) | 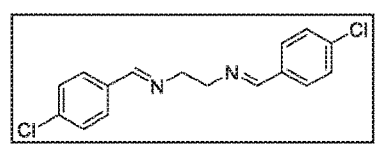 |
| NCL251 | (1E,1'E)-N,N'-(butane-1,4-diyl)bis(1-(4-chlorophenyl)methanimine) | 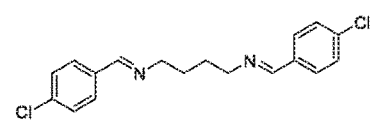 |
| NCL252 | (1E,1'E)-N,N'-(propane-1,3-diyl)bis(1-(4-chlorophenyl)methanimine) | 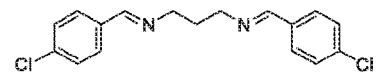 |
| NCL253 | (E)-2-(4-(dimethylamino)benzylideneamino)guanidine | 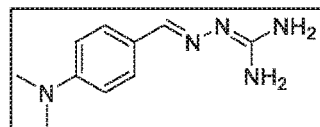 |
| NCL254 | (E)-2-(1-(4-chlorophenyl)hexylidene)hydrazine-1-carboximidamide hydrochloride | 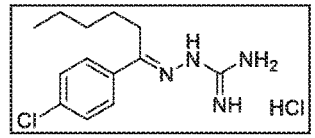 |
| NCL255 | 4,6-bis(2-((E)-[1,1'-biphenyl]-4-ylmethylene)hydrazinyl)pyrimidin-2-amine | 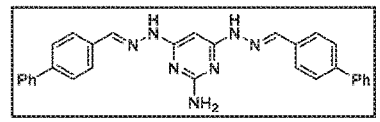 |
| NCL256 | 4,6-bis(2-((E)-2,4-dihydroxybenzylidene)hydrazinyl)pyrimidin-2-amine | 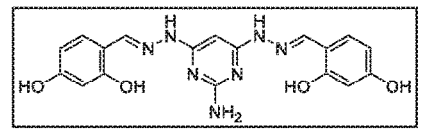 |
| NCL257 | (E)-2-((2-hydroxynaphthalen-1-yl)methylene)hydrazine-1-carboximidamide hydrochloride | 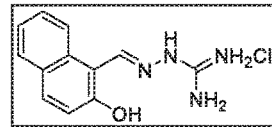 |

Figure 1 (cont.)

| | | |
|---|---|---|
| NCL258 | N1,N4-bis(4-chlorobenzyl)butane-1,4-diamine | 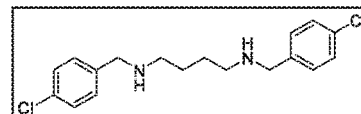 |
| NCL259 | (E)-2-(1-(4-chlorophenyl)-2-cyclohexylethylidene)hydrazine-1-carboximidamide hydrochloride | 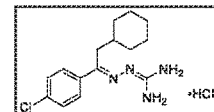 |
| NCL260 | N1,N2-bis(4-chlorobenzyl)ethane-1,2-diamine | 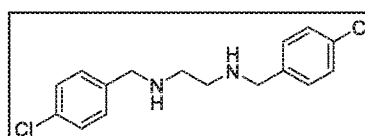 |
| NCL261 | (E)-2-(naphthalen-2-ylmethylene)hydrazine-1-carboximidamide hydrochloride | 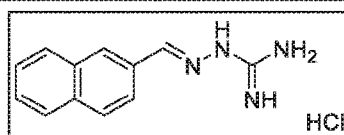 |
| NCL262 | 4,6-bis(2-((E)-3-phenylpropylidene)hydrazinyl)pyrimidin-2-amine | 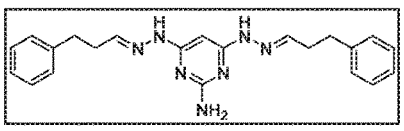 |
| NCL263 | (E)-2-(2-fluoro-4-(trifluoromethyl)benzylidene)hydrazine-1-carboximidamide hydrochloride | 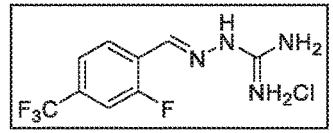 |
| NCL264 | 4,6-bis(2-((E)-naphthalen-2-ylmethylene)hydrazinyl)pyrimidin-2-amine | 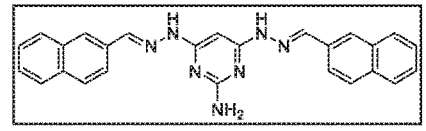 |
| NCL265 | (E)-2-(1-(4-chlorophenyl)-octylideneamino)guanidine | 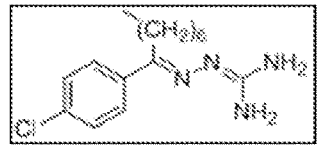 |
| NCL266 | (E)-2-(1-(4-chlorophenyl)-3-cyclopentylpropylideneamino)guanidine | 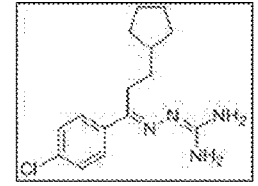 |

Figure 1 (cont.)

| | | |
|---|---|---|
| NCL267 | (E)-4-chloro-6-(2-(4-chlorobenzylidene)hydrazinyl)pyrimidin-2-amine | 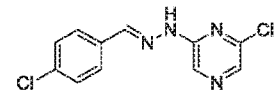 |
| NCL268 | (E)-4-chloro-6-(2-(4-methylbenzylidene)hydrazinyl)pyrimidin-2-amine | 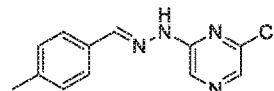 |
| NCL269 | (Z)-2-(1-(1H-indol-3-yl)ethylidene)hydrazinecarboximidamide | 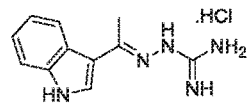 |
| NCL270 | 2,2'-Bis(1-(1H-indol-3-yl)ethylidine)hydrazidecarboximidamide | 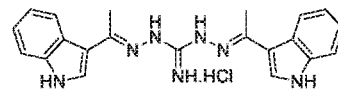 |
| NCL271 | 2,2'-Bis(1-(4-chlorophenyl)hexylidene)hydrazidecarboximidamide | 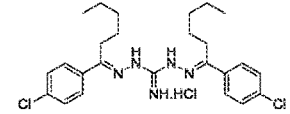 |
| NCL272 | 2,2'-Bis(1-(4-chlorophenyl)octylidene)hydrazidecarboximidamide | 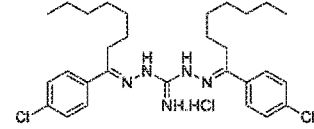 |
| NCL273 | 2,2'-Bis(1-(4-chlorophenyl)-3-cyclopentylpropylidene)hydrazidecarboximidamide | 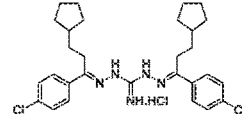 |
| NLC274 | 2,2'-Bis((1H-indol-3-yl)methylene)hydrazine carboximidamide | 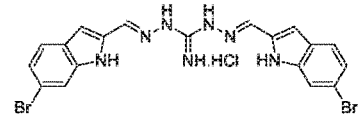 |
| NCL275 | 2,2'-Bis(1-(4-chlorophenyl)-2-ethoxyethylidene)hydrazidecarboximidamide | 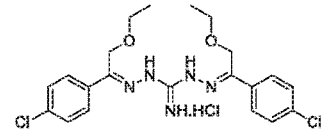 |

| Compound Details | | | Physicochemical Parameters | | | | | | | | | Metabolism Parameters | | | |
|---|---|---|---|---|---|---|---|---|---|---|---|---|---|---|---|
| Compound | Batch | Structure | MW | PSA (Å²) | FRB | # H-Bond Don | # H-Bond Acc | pKa | LogD pH 3.0 | LogD pH 7.4 | Solubility (µg/mL) pH 3.0 | Solubility (µg/mL) pH 6.5 | Species | T₁/₂ (min) | CL_int (µL/min/mg protein) | E_H |
| NCL026 | AS5099 | [structure] | 315.33 | 120.2 | 4 | 3 | 7 | 4.8 – imine (bold); 1.2 – amine (italic) | 2.8 | 3.6 | 1.6 – 3.1 | <1.6 | Human | >247 | <7 | <0.22 |
| | | | | | | | | | | | | | Mouse | 98 | 18 | 0.28 |
| NCL028 | AS5098 | [structure] | 325.37 | 91.1 | 6 | 3 | 9 | 5.2 – imine (bold); 1.5 – amine (italic) | 3.3 | 4.2 | 12.5 – 25 | 1.6 – 3.1 | Human | 234 | 7 | 0.23 |
| | | | | | | | | | | | | | Mouse | 6 | 276 | 0.86 |
| NCL099 | AS5096 | [structure] | 377.53 | 72.6 | 6 | 3 | 5 | 5.1 – imine (bold); 2.4 – amine (italic) | 4.9 | >5.3 | <1.6 | <1.6 | Human | 20 | 89 | 0.79 |
| | | | | | | | | | | | | | Mouse | 25 | 70 | 0.60 |

| Compound Details | | | | Physicochemical Parameters | | | | | | | | | Metabolism Parameters | | | |
|---|---|---|---|---|---|---|---|---|---|---|---|---|---|---|---|---|
| Compound | Batch | Structure | MW | PSA (Å²) | FRB | #H-Bond Don | #H-Bond Acc | pKa | LogD pH 2.0 | LogD pH 7.4 | Solubility (µg/mL) pH 2.0 | Solubility (µg/mL) pH 6.5 | Species | T₁/₂ (min) | CL_int (µL/min/mg protein) | E_H |
| NCL171 | AS2102 | | 383.45 | 119.6 | 6 | 5 | 11 | 6.6/6.0 – dimethyl amines 4.0 – imine (bold) | 3.2 | 4.0 | ND* | | Human | 9 | 188 | 0.88 |
| | | | | | | | | | | | | | Mouse | 19 | 92 | 0.66 |
| NCL177 | AS5088 | | 394.26 | 113.1 | 6 | 5 | 9 | 8.6/9.2 – phenols (acidic) 5.1 – imine (bold) | 3.2 | 4.0 | 25 – 50 | <1.6 | Human | >247 | <7 | <0.22 |
| | | | | | | | | | | | | | Mouse | 131 | 13 | 0.22 |
| NCL195 | AS5087 | | 359.43 | 100.6 | 6 | 4 | 7 | 4.9/4.3 – amines (bold) 2.2 – pyrimidine (italic) | 3.7 | 4.3 | 3.1 – 6.3 | <1.6 | Human | >247 | <7 | <0.22 |
| | | | | | | | | | | | | | Mouse | >247 | <7 | <0.13 |
| NCL217 | AS5073 | | 321.42 | 72.6 | 4 | 3 | 5 | 5.5 – imine (bold) 2.1 – amine (italic) | 3.9 | 5.1 | 3.1 – 6.3 | <1.6 | Human | 71 | 24 | 0.49 |
| | | | | | | | | | | | | | Mouse | 14 | 122 | 0.72 |

Figure 11 (cont.)

| Compound Details | | | Physicochemical Parameters | | | | | | | | | Metabolism Parameters | | | |
|---|---|---|---|---|---|---|---|---|---|---|---|---|---|---|---|
| Compound | Batch | Structure | MW | PSA (Å²) | FRB | # H-Bond | | pKa | LogD | | Solubility (μg/mL) | | Species | T₁/₂ (min) | CL_int (μL/min/mg protein) | E_h |
| | | | | | | Don | Acc | | pH 3.0 | pH 7.4 | pH 2.0 | pH 6.5 | | | | |
| NCL259 | A55072 | | 292.81 | 76.0 | 4 | 4 | 4 | 8.6 – imine (bold) 1.4 – amine (italic) | 3.4 | 4.6 | >100 | 6.3 - 12.5 | Human | >247 | <7 | <0.22 |
| | | | | | | | | | | | | | Mouse | 87 | 20 | 0.30 |
| NCL812 | A55086 | | 334.20 | 72.6 | 4 | 3 | 5 | 5.0 – imine (bold) 1.2 – amine (italic) | 3.7 | 4.5 | 6.3 - 12.5 | <1.6 | Human | >247 | <7 | <0.22 |
| | | | | | | | | | | | | | Mouse | >247 | <7 | <0.13 |

ᵃ Solubility value could not be determined, as the nephelometry results were inconclusive.

Figure 11 (cont.)

METHODS FOR TREATING PROTOZOAN INFECTIONS

CROSS REFERENCE TO RELATED APPLICATIONS

This application is a divisional of U.S. application Ser. No. 15/508,266 (Allowed), filed 2 Mar. 2017, which is a U.S. National Stage application of PCT/AU2015/000527, filed 28 Aug. 2015, which claims priority to Australia application No. 2014903503, filed 2 Sep. 2014, the contents of all of which are hereby incorporated by reference in their entirety.

TECHNICAL FIELD

This invention relates to compounds of Formula I and their use in methods for treating or preventing a protozoan infection in a subject using a compound of Formula I, the use of a compound of Formula I in the manufacture of a medicament for the treatment of a protozoan infection in a subject, and medical devices when used in a method of treating or preventing a protozoan infection in a subject.

BACKGROUND ART

Giardiasis, amoebiasis and cryptosporidiosis are the most common protozoal parasitic diseases of the human intestinal tract and common causes of enteric disease in non-human animal species as well. Different drugs have been used for the management of these diseases, but many have a significant failure rate in clearing parasites from the intestine and many are associated with a high incidence of undesirable side effects, which often leads to use being contraindicated in certain circumstances. There is a need in the art for an improved treatment which would require one or very few dosings, would be associated with a very high level of clearance of the target protozoal agent, would kill intestinal cysts (to reduce environmental contamination and the reservoir of reinfection), be associated with no or only mild and well tolerated adverse effects, have no pre-existing resistance, be safe for use in pregnant and lactating humans and other species and/or be suitable for use as a preventive medication.

Many existing antiprotozoal agents, especially those for the treatment of giardiasis, have suboptimal intrinsic efficacy. For metronidazole *Giardia* curative rates may be high, but have also been reported as low as 60% (measured by clearance of the protozoan) in human adult and paediatric patients when it is administered for 5-10 days. Both metronidazole and tinidazole have been reported to have a median efficacy of approximately 89%. The newer antigiardial agent, nitazoxanide has demonstrated an overall response rate of 75% (measured by clearance of the protozoan), ranging between 64 and 94%.

To improve compliance it is highly desirable that the dosage regimen is simple and of short duration. As outlined above, the duration of dosing with metronidazole is most commonly 5-10 days, leaving many opportunities for missed treatments, poor compliance and reduced efficacy or treatment failure.

Acquired resistance by *Giardia* to the available treatments is widely experienced and an increasing cause of treatment failure. This is not surprising as the majority of currently recommended antiprotozoal agents have been in use for many decades. A review of antiprotozoal agents approved by the FDA between 1987 and 2013 (Kesselheim, A. S. and J. J. Darrow (2014). "Drug Development and FDA Approval, 1938-2013." New England Journal of Medicine 370(26): e39) discloses only 7 new agents for all protozoan diseases (mefloquine in 1989, eflornithine in 1990, halofantrine and atovaquone in 1992, nitazoxanide in 2002, tinidazole in 2004 and the combination of artemether and lumefantrine in 2009). Amongst these agents, only nitazoxanide and tinidazole are used for *Giardia* treatment, and both have median efficacies less than 90%.

Frequently it is the profile of adverse effects that limits the use of antiprotozoal agents. There is a diversity of adverse effects of currently available antiprotozoal agents. For example, side effects for the widely used metronidazole include metallic taste, nausea, headache, vertigo, leukopenia, insomnia and irritability. Less frequently, CNS toxicity has been reported especially with high doses, and alcohol consumption is not recommended when taking metronidazole because of the possibility of developing a reaction similar to that of disulfiram. Metronidazole has been shown to be mutagenic in bacteria; based on animal studies, the drug has been carcinogenic at high doses and over long periods. For quinacrine adverse effects include headache, nausea, vomiting and a bitter taste, resulting in poor compliance. Yellow discolouration of the skin, urine and sclerae may also follow its administration. Blue or black pigmentation of the nails, urticaria and exfoliative dermatitis can also occur. Other side effects reported are haemolysis in patients with glucose-6-phosphate dehydrogenase (G6PD)-deficiency, toxic psychosis and exacerbation of psoriasis. Quinacrine, in common with other antiprotozoal agents, is able to cross the placenta and reach the foetus, contraindicating its use during pregnancy due to a possible link with birth deformities. Other serious side effects described have included psychiatric disturbances.

For the treatment of cryptosporidia and amoebiasis caused by *Entamoeba histolytica* the limitations on available treatments are even more limited than with *Giardia*, with no consistently effective and specific treatment for cryptosporidia (Cabada, M. M. and A. C. White, Jr. (2010). "Treatment of cryptosporidiosis: do we know what we think we know?" Curr Opin Infect Dis 23(5): 494-499).

There is an unmet clinical need for antiprotozoan agents with novel mechanisms of action to supplement and/or replace currently available antiprotozoan agents, the efficacy of which is increasingly undermined by antiprotozoan resistance mechanisms. There additionally remains a need for alternative antiprotozoan agents in the treatment of infection by multi-resistant protozoa. However, as reported by the Pharmaceutical Research and Manufacturers of America in their 2013 report "Medicines in Development for Infectious Diseases" no novel antiprotozoan agents and few line extensions are being developed that offer promising results over existing treatments.

It is an object of the present invention to overcome at least one of the failings of the prior art.

The discussion of the background art set out above is intended to facilitate an understanding of the present invention only. The discussion is not an acknowledgement or admission that any of the material referred to is or was part of the common general knowledge as at the priority date of the application.

SUMMARY OF INVENTION

According to one aspect of the invention, there is a method of treating or preventing a protozoan colonisation or infection in a subject, the method including the step of administering a therapeutically effective amount of a compound of Formula I or stereoisomer, tautomer, pharmaceutically acceptable salt, or prodrug thereof to the subject, wherein the protozoan infection is caused by a protozoan agent.

In one embodiment of the invention, the compound of Formula I, is:

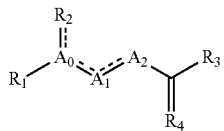

Formula I

In another embodiment of the invention, $R_1$ is H, cycloalkyl, Formula II, or Formula III;

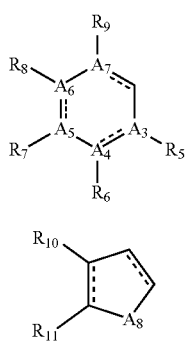

Formula II

Formula III

In another embodiment of the invention, $R_3$ is selected from the group consisting of: H; $NH_2$; $NHNH_2$; O—$CH_2$—$CH_3$; NH—C(O)-phenyl; N—CH-chlorophenyl; NH-chlorophenyl; NH—$CH_2$-chlorophenyl; NH—N—CH-cycloalkyl; N and $R_4$ is CH—N—CH—CCl— and $R_4$ is bonded to $R_3$; Formula IV; Formula V; and Formula VI;

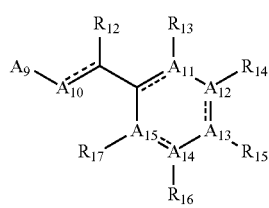

Formula IV

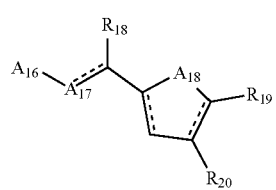

Formula V

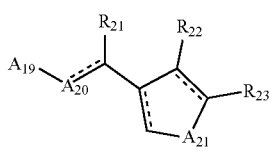

Formula VI

In another embodiment of the invention, $A_0$ is N, C, CH, or $A_0$ is C and $A_0$ is bonded to $R_4$ to form a triazole ring.

In another embodiment, $R_4$ is CH—N—CH—CCl—. Preferably, $R_4$ is bonded to $R_3$ when $R_3$ is N.

In another embodiment of the invention, $A_1$ is N, C, NH, —$(CH)_2$—N—, —$(C_6H_5)$C—CH—N—, or Formula VII;

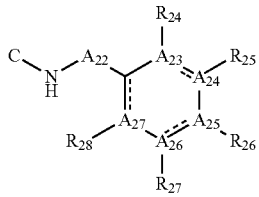

Formula VII

In another embodiment of the invention, $A_2$ is N, C, NH, N—C(O)-phenyl or Formula VII, or $(CH_2)_n$, wherein n is an integer between 1 and 3, inclusive.

In another embodiment of the invention, $A_3$, $A_4$, $A_5$, $A_6$, $A_7$, $A_8$, $A_{11}$, $A_{12}$, $A_{13}$, $A_{14}$, $A_{15}$, $A_{16}$, $A_{17}$, $A_{18}$, $A_{19}$, $A_{20}$, $A_{21}$ $A_{23}$, $A_{24}$, $A_{25}$, $A_{26}$ and $A_{27}$ are independently C, O, N, NH, S.

In another embodiment of the invention, $A_9$ is C, O, N, NH, N—C(O)—O—$CH_2$—$CH_3$, N—C(O)—O—$CH(CH_3)_2$, N—C(O)—NH—$CH_2$—$CH_3$, N—C(O)—NH—$CH_2$-phenyl, N—C(O)—$CH_2$—$H_2$—$CH_2$—$CH_2$—$CH_2$—$CH_3$, N—C(O)—$CH_2$-furan-2-yl.

In another embodiment of the invention, $A_{10}$ is C, NH, —N—$(CH)_2$—, —N—CH—C$(C_6H_5)$—.

In another embodiment of the invention, $A_{22}$ is —CH$(CH_3)$—, —N—CH—, —N—C$(CH_3)$—, N—C$(CH_2OH)$—.

In another embodiment of the invention, $R_2$ is H, COOH, $CH_2NH_2$, $CH_2OH$, $CH_2NHNH_2$, methyl, ethyl, propyl, butyl, pentyl, heptyl, cyclopentyl, $CH_2$(Cyclohexyl), $(CH_2)_2$(cyclopentyl), or Formula VII and $R_2$ are $R_4$ are bonded together to form a pyrimidine, pyrazine or triazine ring, or $R_2$ and $R_9$ are bonded together to form a pyrrolidinyl oxindole ring.

In another embodiment of the invention, $R_4$ is $H_2$, N, NH, O, S, or $R_4$ and $A_0$ are bonded together to form a triazole ring, or $R_4$ is N and $R_4$ and $R_2$ are bonded together to form a pyrimidine ring.

In another embodiment of the invention, $R_7$ is H, Cl, Br, F, OH, $CH_3$, $OCH_3$, $SCH_3$, CN, CCH, $CF_3$, $OCF_3$, $SCF_3$, $NO_2$, butyl, t-butyl, dimethylamino, phenyl, n-propyl, i-propyl, —NH—C(O)—$CH_3$, —$(CH)_2$—COOH, piperazin-1-yl, or $R_7$ and $R_8$ are bonded together to form a substituted or unsubstituted, saturated or unsaturated aliphatic ring, heterocyclic ring or benzene ring.

In another embodiment of the invention, $R_6$, $R_8$, $R_{14}$, $R_{16}$, $R_{25}$ and $R_{27}$ are independently H, OH, Cl, F, Br, $CH_3$, CN, $OCH_3$, COOH, $NO_2$, $CF_3$, $R_8$ and $R_7$ bond together to form a substituted or unsubstituted, saturated or unsaturated aliphatic ring, heterocyclic ring, or benzene ring, $R_{14}$ and $R_{15}$ are bonded together to form a substituted or unsubstituted, saturated or unsaturated aliphatic ring, heterocyclic ring or benzene ring, $R_8$ and $R_9$ are bonded together to form a substituted or unsubstituted, saturated or unsaturated aliphatic ring, heterocyclic ring or benzene ring, or $R_{14}$ and $R_{13}$ are bonded together to form a substituted or unsubstituted saturated or unsaturated aliphatic ring, heterocyclic ring or benzene ring.

In another embodiment of the invention, $R_5$, $R_9$, $R_{17}$, $R_{24}$ and $R_{28}$ are independently H, O, OH, Cl, F, Br, $NH_2$, $CH_3$, $CF_3$, $OCH_3$, CN, $NO_2$, phenyl, —NH—CH(OH)—$CH_3$, —NH—C(O)—$CH_3$, or $R_9$ and $R_8$ are bonded together to form a substituted or unsubstituted, saturated or unsaturated aliphatic ring, heterocyclic ring or benzene ring, or $R_{13}$ and $R_{14}$ are bonded together to form a substituted or unsubstituted saturated or unsaturated aliphatic ring, heterocyclic ring or benzene ring.

In another embodiment of the invention, $R_{10}$, $R_{11}$, $R_{19}$, $R_{20}$, $R_{22}$ and $R_{23}$ are independently H, Cl, or Br, or $R_{10}$ and $R_{11}$ are bonded together to form a substituted or unsubstituted, saturated or unsaturated aliphatic ring, heterocyclic ring or benzene ring, or $R_{19}$ and $R_{20}$ are bonded together to form a substituted or unsubstituted, saturated or unsaturated aliphatic ring, heterocyclic ring or benzene ring, or $R_{22}$ and $R_{23}$ are bonded together to form a substituted or unsubstituted, saturated or unsaturated aliphatic ring, heterocyclic ring or benzene ring In another embodiment of the invention, $R_{12}$, $R_{18}$ and $R_{21}$ are independently H, COOH, $CH_2NH_2$, $CH_2OH$, methyl, ethyl, propyl, butyl, cyclopentyl, or $R_{12}$ and $R_{13}$ are bonded together to form a pyrrolidinyl oxindole ring.

In another embodiment of the invention, $R_{15}$ and $R_{26}$ are independently H, Cl, Br, F, OH, $CH_3$, $OCH_3$, $SCH_3$, CN, $CF_3$, $OCF_3$, $SCF_3$, $NO_2$, CCH, n-butyl, t-butyl, dimethylamino, phenyl, n-propyl, i-propyl, —NH—C(O)—$CH_3$, —(CH)$_2$—COOH, piperazin-1-yl, or $R_{15}$ and $R_{14}$ are bonded together to form a substituted or unsubstituted, saturated or unsaturated aliphatic ring, heterocyclic ring or benzene ring, and In another embodiment of the invention, "----" is a double bond or a single bond.

In another embodiment of the invention, the compound of Formula I, or a stereoisomer, tautomer, pharmaceutically acceptable salt, or prodrug thereof, is selected from the compounds presented in FIG. 1.

In another embodiment of the invention, the compound of Formula I, or a stereoisomer, tautomer, pharmaceutically acceptable salt, or prodrug thereof comprises the following features:

wherein $A_0$ is C;
wherein $A_1$ is N; or Formula VII;
wherein $A_2$ is N; or NH;
wherein $A_3$, $A_4$, $A_6$, $A_7$, $A_{11}$, $A_{12}$, $A_{14}$, $A_{15}$, are N; or C;
wherein $A_5$, $A_{13}$, $A_{23}$, $A_{24}$, $A_{25}$, $A_{26}$ and $A_{27}$ are C;
wherein $A_8$ and $A_{21}$ are S;
wherein $A_9$ is NH;
wherein $A_{10}$ is N;
wherein $A_{22}$ is —N—CH—; —N—C($CH_3$)—; or —N—C($CH_2OH$)—;
wherein $R_1$ is H; Formula II; Formula III; cycloalkyl;
wherein $R_2$ is H; methyl; ethyl; $CH_2NHNH_2$; $CH_2OH$; butyl; cyclopentyl; or Formula VII and $R_2$ is bonded to $R_4$, to form a pyrimidine ring;
wherein $R_3$ is $NH_2$; Formula IV; Formula V; Formula VI; $NH_2$, NH—N—CH-cycloalkyl; or O—$CH_2$—$CH_3$;
wherein $R_4$ is NH; O; S; or $R_4$ is N and $R_4$ and $R_2$ are bonded together to form a pyrimidine ring;
wherein $R_7$ is H; F; Cl; $CF_3$; methyl; $R_7$ and $R_8$ are bonded together to form an unsubstituted, benzene ring; OH; t-butyl; phenyl; dimethylamino; i-propyl; n-propyl; CN; CCH; n-butyl; $SCH_3$; $R_7$ and $R_8$ are bonded together to form an unsubstituted, unsaturated heterocyclic ring; $OCH_3$; Br; $OCF_3$; piperazin-1-yl; or $SCF_3$;
wherein $R_6$, $R_8$, $R_{14}$, and $R_{16}$ are independently H; OH; F; $OCH_3$; $CF_3$; methyl; Cl; CN; Br; $R_8$ and $R_7$ are bonded together to form an unsubstituted, benzene ring; $R_8$ and $R_7$ are bonded together to form an unsubstituted, unsaturated heterocyclic ring; $R_{14}$ and $R_{15}$ are bonded together to form an unsubstituted, benzene ring; or $R_{14}$ and $R_{15}$ are bonded together to form an unsubstituted, unsaturated heterocyclic ring;
wherein $R_5$, $R_9$, $R_{13}$, and $R_{17}$ are independently H; OH; $NH_2$; Cl; F; $OCH_3$; OH; —NH—CH(OH)—$CH_3$;
wherein $R_{12}$ is H; methyl; ethyl; $CH_2OH$; or cyclopentyl;
wherein $R_{15}$ is H; F; Cl; $CF_3$; methyl; $R_7$ and $R_8$ are bonded together to form an unsubstituted, benzene ring; OH; t-butyl; phenyl; dimethylamino; i-propyl; n-propyl; CN; CCH; n-butyl; $SCH_3$; $R_{15}$ and $R_{14}$ are bonded together to form an unsubstituted, unsaturated heterocyclic ring; $OCH_3$; Br; $OCF_3$; piperazin-1-yl; or $SCF_3$;
wherein $R_{24}$ and $R_{28}$ are independently H; OH; or Cl;
wherein $R_{25}$ and $R_{27}$ are independently H; or OH;
wherein $R_{26}$ is H; $CH_3$; Br; Cl; OH; dimethylamino; —O—P(O)(OEt)$_2$; $CF_3$; or F; and
wherein "----" is independently a single or a double bond.

In another embodiment of the invention, the compound is selected from the group comprising: NCL008; NCL009; NCL023; NCL025; NCL026; NCL028; NCL029; NCL036; NCL037; NCL039; NCL040; NCL050; NCL061; NCL062; NCL064; NCL065; NCL068; NCL075; NCL076; NCL078; NCL079; NCL080; NCL081; NCL084; NCL085; NCL086; NCL088; NCL089; NCL090; NCL092; NCL094; NCL095; NCL097; NCL098; NCL099; NCL101; NCL104; NCL105; NCL106; NCL108; NCL111; NCL112; NCL114; NCL115; NCL116; NCL118; NCL119; NCL121; NCL122; NCL123; NCL124; NCL125; NCL126; NCL130; NCL131; NCL132; NCL133; NCL135; NCL136; NCL137; NCL138; NCL139; NCL140; NCL141; NCL144; NCL145; NCL146; NCL147; NCL148; NCL150; NCL152; NCL153; NCL154; NCL156; NCL157; NCL158; NCL159; NCL161; NCL162; NCL164; NCL165; NCL166; NCL167; NCL168; NCL169; NCL170; NCL171; NCL172; NCL173; NCL174; NCL176; NCL177; NCL178; NCL179; NCL180; NCL181; NCL183; NCL184; NCL185; NCL186; NCL187; NCL188; NCL189; NCL190; NCL193; NCL194; NCL195; NCL196; NCL197; NCL198; NCL199; NCL200; NCL201; NCL202; NCL203; NCL204; NCL205; NCL206; NCL207; NCL208; NCL209; NCL210; NCL211; NCL212; NCL213; NCL215; NCL216; NCL217; NCL218; NCL219; NCL220; NCL221; NCL222; NCL223; NCL223; NCL224; NCL225; NCL226; NCL227; NCL228; NCL229; NCL230; NCL231; NCL232; NCL233; NCL234; NCL235; NCL236; NCL237; NCL238; NCL239; NCL240; NCL241; NCL242; NCL243; NCL244; NCL245; NCL246; NCL247; NCL248; NCL249; NCL250; NCL251; NCL252; NCL253; NCL254; NCL255; NCL256; NCL257; NCL258; NCL259; NCL260; NCL261; NCL262; NCL263; NCL264; NCL265; NCL266; NCL267; NCL268; NCL269; NCL270; NCL271; NCL272; NCL273; NCL274; and NCL275.

In another embodiment of the invention, the compound is selected from the group comprising: NCL028; NCL040; NCL062; NCL078; NCL079; NCL080; NCL081; NCL084; NCL088; NCL089; NCL097; NCL099; NCL123; NCL146; NCL157; NCL158; NCL177; NCL179; NCL188; NCL193; NCL195; NCL196; NCL197; NCL199; NCL202; NCL204; NCL205; NCL215; NCL216; NCL217; NCL219; NCL221; NCL245 and NCL246.

In a preferred embodiment of the invention, the compound is selected from the group comprising: NCL062; NCL078; NCL079; NCL080; NCL081; NCL084; NCL089; NCL097; NCL099; NCL157; NCL158; NCL179; NCL188;

NCL193; NCL195; NCL196; NCL199; NCL204; NCL216; NCL217; NCL219; NCL221; NCL245 and NCL246.

In an even more preferred embodiment of the invention, the compound is selected from the group comprising: NCL062; NCL089; NCL097; NCL099; NCL157; NCL179; NCL188; NCL193; NCL195; NCL196; NCL216; NCL219; and NCL221.

In an even more preferred embodiment of the invention, the compound is selected from the group comprising: NCL062; NCL097; NCL099; NCL157; NCL179; NCL188; NCL195; and NCL196.

In another embodiment of the invention, the compound is a chloride salt.

In another embodiment of the invention, the compound is a compound selected from the group comprising: NCL812 and NCL062. In another embodiment of the invention, the compound is not a compound selected from the group comprising: NCL812 and NCL062. For example, the compound is NCL099.

In another embodiment of the invention, the compound is a compound selected from the group comprising: NCL020, NCL021, NCL024, NCL035, NCL072, NCL077, NCL107, NCL109, NCL134, NCL143, NCL143, NCL151, NCL155 and NCL160. In another embodiment of the invention, the compound is not a compound selected from the group comprising: NCL020, NCL021, NCL024, NCL035, NCL072, NCL077, NCL107, NCL109, NCL134, NCL143, NCL143, NCL151, NCL155 and NCL160. For example, the compound is NCL099.

In another embodiment of the invention, the subject is an animal most preferably selected from the group comprising: human, canine, feline, bovine, ovine, caprine, porcine, avian, piscine and equine species.

In another embodiment of the invention, the compound is administered to the subject in a dose in the range of 0.1 mg/kg to 250 mg/kg bodyweight.

In another embodiment of the invention, the protozoan agent is selected from the group of protozoa genera comprising: *Acanthamoeba, Babesia, Balamuthia, Balantidium, Besnoitia, Blastocystis, Chilomastix, Cochlosoma, Cryptosporidium, Cyclospora, Cystoisospora, Cytauxzoon, Dientamoeba, Eimeria, Endolimax, Entamoeba, Giardia, Haemoproteus, Hammondia Hartmannella, Hepatozoon, Hexamita, Histomonas, Isospora, Leishmania* (including subgenus *Viannia*), *Leucocytozoon, Naegleria, Neospora, Pentatrichomonas, Plasmodium* (including subgenera *Plasmodium (Bennettinia)* (birds); *Plasmodium (Giovannolaia)* (birds); *Plasmodium (Haemamoeba)* (birds); *Plasmodium (Huffia)* (birds); *Plasmodium (Laverania)* (higher primates, includes *Plasmodium falciparum*); *Plasmodium (Novyella)* (birds); *Plasmodium (Paraplasmodium)* (lizards); *Plasmodium (Plasmodium)* (higher primates, includes *Plasmodium brasilianum, cynomolgi, inui, knowlesi, malariae*]; *Plasmodium (Sauramoeba)* (lizards); *Plasmodium (Vinckeia)), Sappinia, Sarcocystis, Tetratrichomonas, Theileria, Toxoplasma, Trichomonas, Tritrichomonas, Trypanosoma* (Subgenera *Duttonella, Herpetosoma, Nannomonas, Schizotrypanum, Trypanozoon), Tyzzeria* and *Wenyonella*.

In another embodiment of the invention, the protozoan agent is selected from the group of protozoa listed in Table 1 (see below).

In another embodiment of the invention, the protozoan agent is a resistant protozoa.

In another embodiment of the invention, the infection or colonisation is caused by a mixture of at least two protozoan agents.

In another embodiment of the invention, the protozoan agent is resistant to one or more compounds selected from the group listed in Table 2 (see below).

In another embodiment of the invention, the protozoan agent is resistant to the compound when the protozoan agent is exposed to the compound at a concentration range selected from the following: 0.001 µg/mL-10,000 µg/mL; 0.01 µg/mL-1000 µg/mL; 0.10 µg/mL-100 µg/mL; and 1 µg/mL-50 µg/mL.

In another embodiment of the invention, the protozoan infection or colonisation in the subject is a zoonosis.

In another embodiment of the invention, the protozoan infection or colonisation in the subject substantially causes an indication selected from the group comprising: Trypanosomosis (caused by the order, Kinestoplastorida of the family, Trypanosamidae); Amboebiasis (caused by the subphylum, Sarcodina, of the order, Amoebidorida, of the family Endamoebidae); Babesiosis (caused by the class, Piroplasmida, of the family, Babesiidae); Balantidiosis (caused by the phylum, Ciliphora, of the order, Trichostomatorida, of the family Balantidiidae); Chagas Disease (caused by the order, Kinestoplastorida, of the family, Trypanosomatidae); Cryptosporidiosis (caused by the subclass, Coccidea, of the family, Cryptosporidiidae); Giardiosis (caused by the class, Zoomastigophora, of the order, Diplomonadida, of the family, Diplomonadida, including *Giardia lamblia*); Leishmaniasis (caused by the class, Zoomastigophora, of the family, Trypanosomatidae, of the genus, *Leishmania*); Malaria (caused by the genus, *Plasmodium*, including *P. falciparum, P. vivax, P. ovale*, and *P. malariae*) Sarcocystosis (caused by the subclass, Coccidia, of the order Eucoccidiorida, of the family Sarcocystidae); Toxoplasmosis (cause by the subclass, Coccidia, of the order, Eucoccidiorida, of the family, Sarcocystidae, including *Toxoplasma gondii*); Cyclosporiasis (caused by the species, *Cyclospora cayetanensis*); Infections caused by free-living Amoebae (caused by *Naegleria, Acanthamoeba* and/or *Balamuthia*); Malaria in Non-human Primates (caused by the genus, *Plasmodium*); Microsporidiosis (caused by *Enterocytozzon bieneusi, Encephalitizoon intestinalis* and/or *E. cuniculi*); Atypical Human Trypanosomosis (*T. lewisi, T. evansi, T. brucei, T. vivax*, and/or *T. congolense*); Trichomoniasis (caused by *Trichomonas vaginalis*); Amoebic dysentery (caused by *Entamoeba histolyticum*); and Acanthamoebiasis (caused by *Acanthamoeba*).

In another embodiment of the invention, the therapeutically effective amount of compound of Formula I, or a therapeutically acceptable salt thereof, is administered to the subject by oral administration.

In another embodiment of the invention, the therapeutically effective amount of compound of Formula I, or a therapeutically acceptable salt thereof, is administered to the subject together with a second antimicrobial agent selected from the group consisting of compounds listed in Table 2 (see below).

In another embodiment of the invention, the therapeutically effective amount of compound of Formula I, or a therapeutically acceptable salt thereof, is administered to the subject by parenteral administration.

In another embodiment of the invention, the therapeutically effective amount of compound of Formula I, or a therapeutically acceptable salt thereof, is administered to the subject by topical administration.

In a further aspect of the invention, the invention is a antiprotozoan pharmaceutical composition comprising a therapeutically effective amount of a compound of Formula I, or a therapeutically acceptable salt thereof, and optionally a pharmaceutically acceptable excipient or carrier.

In a further aspect of the invention, the invention is a antiprotozoan veterinary composition comprising a therapeutically effective amount of a compound of Formula I, or a therapeutically acceptable salt thereof, and optionally a veterinary acceptable excipient or carrier.

In another embodiment of the invention, the composition comprises a further antimicrobial agent selected from the group listed in Table 2 (see below).

In another embodiment of the invention, the composition is adapted for oral administration.

In another embodiment of the invention, the composition is adapted for parenteral administration.

In another embodiment of the invention, the composition is adapted for topical administration.

In a further aspect of the invention, the invention is the use of a compound of Formula I, or a therapeutically acceptable salt thereof, in the manufacture of a medicament for the treatment of a protozoan colonisation or infection in a subject. In another embodiment of the invention, the use comprises administering a therapeutically effective amount of compound of Formula I, or a therapeutically acceptable salt thereof, to the subject. In another embodiment of the invention, the compound of Formula I is administered to the subject in a dose in the range of 0.1 mg/kg to 250 mg/kg body weight. In one preferred embodiment, the compound is administered to the subject in a dose in the range selected from the group consisting of: 0.1 mg/kg to 100 mg/kg body weight; 0.1 mg/kg to 50 mg/kg body weight; 1 mg/kg to 20 mg/kg body weight; 1 mg/kg to 10 mg/kg body weight; and 2 mg/kg to 5 mg/kg body weight. In one preferred embodiment, the compound is administered to the subject at a dose that achieves within 1 hour a compound plasma concentration range selected from the group consisting of: 0.01 µg/ml-100 µg/ml; 0.1 µg/ml-10 µg/ml; 1 µg/ml-8 µg/ml. Preferably, after 1 hour, the dose achieves a compound plasma concentration above 8 µg/ml. Preferably, after 7 hours, the dose achieves a compound plasma concentration above 8 µg/ml. Preferably, after 24 hours, the dose achieves a compound plasma concentration above 8 µg/ml.

In one preferred embodiment, the compound is administered to the subject at a frequency selected from the group consisting of: every 30 minutes; every hour; every 2 hours; every 3 hours; every 4 hours; every 5 hours; every 6 hours; every 8 hours; every 12 hours; once daily; every 2 days; once weekly; twice weekly; once every 2 weeks; once monthly; once every 2 months; once every 3 months; once every 4 months; once every 5 months; once every 6 months; once every year; once every 2 years; and once.

In another embodiment of the invention, the medicament is administered to the subject by oral administration. In another embodiment of the invention, the medicament is administered to the subject by parenteral administration. In another embodiment of the invention, the medicament is administered to the subject by topical administration.

In a further aspect of the invention, the invention is a medical device when used in a method of treating or preventing a protozoan colonisation or infection in the subject, wherein the medical device comprises the composition of the invention. In another embodiment of the invention, the medical device is in a form selected from the group comprising: a plaster, a bandage, a dressing or implant applied to a protozoan colonisation or infection in a subject.

In a further aspect of the invention, the invention is a method of killing protozoa, the method including the step of contacting the protozoa with a compound of Formula I, or a therapeutically acceptable salt thereof.

In a further aspect of the invention, the invention is the use of a compound of Formula I, or a therapeutically acceptable salt thereof, to kill protozoa, said use comprising the step of contacting the protozoa with a compound of Formula I, or a therapeutically acceptable salt thereof.

In a further aspect of the invention, the invention is a method, a composition, device or a use, substantially as described herein with reference to the accompanying Examples and Figures.

In a preferred aspect of the invention, the compound of Formula I is robenidine (also referenced in this specification as NCL812 and also known as 1,3-bis[(E)-(4-chlorophenyl)methyleneamino]guanidine), which has a structure as follows:

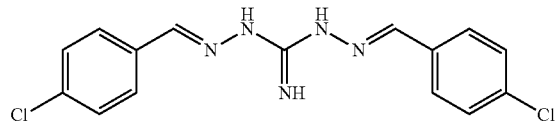 [SMILES: N=C(N/N=C/c1ccc(Cl)cc1)N/N=C/c1ccc(Cl)cc1]

In one preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{13}$, $R_{15}$, $R_{16}$, $R_{17}$ are H; $R_4$ is O; $R_8$ and $R_{14}$ are $CF_3$; and "----" in Formula I between $A_0$ and $A_1$, all Formula II and all Formula IV "----" are double bonds. An example of a compound of this embodiment of the invention includes (NCL101):

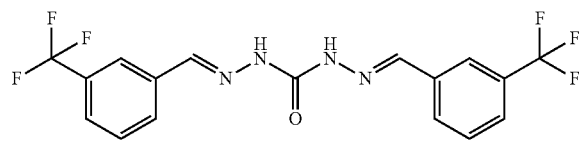 [SMILES: O=C(N/N=C/c1cccc(C(F)(F)F)c1)N/N=C/c1cccc(C(F)(F)F)c1]

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N and $A_2$ is NH; $A_0$, $A_3$, $A_4$, $A_5$, $A_6$, and $A_7$ are C; $R_2$, $R_5$, $R_6$, $R_7$, and $R_8$ are H; $R_4$ is NH; $R_9$ is Cl; and "----" in Formula I between $A_0$ and $A_1$ and all Formula II "----" are double bonds. An example of a compound of this embodiment of the invention includes (NCL015):

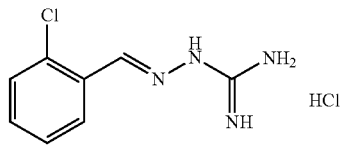 [SMILES: N=C(N)N/N=C/c1ccccc1Cl ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, $R_{17}$ are H; $R_4$ is NH; $R_7$ and $R_{15}$ are F; and "----" in Formula I between $A_0$ and $A_1$, all Formula II and all Formula IV "----" are double bonds. An example of a compound of this embodiment of the invention includes (NCL021):

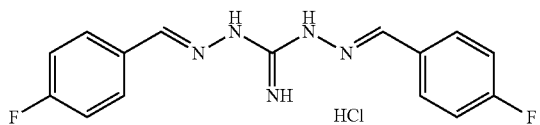 [SMILES: N=C(N/N=C/c1ccc(F)cc1)N/N=C/c1ccc(F)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{13}$, $R_{15}$, $R_{16}$, $R_{17}$ are H; $R_4$ is NH; $R_8$ and $R_{14}$ are F; and "----" in Formula I between $A_0$ and $A_1$, all Formula II and all Formula IV "----" are double bonds. An example of a compound of this embodiment of the invention includes (NCL023):

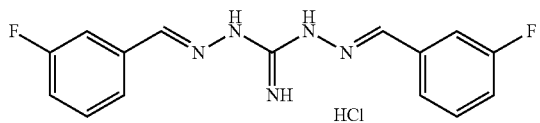 [SMILES: N=C(N/N=C/c1cccc(F)c1)N/N=C/c1cccc(F)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_8$, $R_{12}$, $R_{14}$, $R_{15}$, $R_{16}$, $R_{17}$ are H; $R_4$ is NH; $R_9$ and $R_{13}$ are $OCH_3$; and "----" in Formula I between $A_0$ and $A_1$, all Formula II and all Formula IV "----" are double bonds. An example of a compound of this embodiment of the invention includes (NCL028):

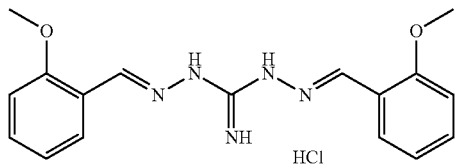 [SMILES: COc1ccccc1/C=N/NC(=N)N/N=C/c1ccccc1OC ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{13}$, $R_{15}$, $R_{16}$, $R_{17}$ are H; $R_4$ is NH; $R_8$ and $R_{14}$ are $OCH_3$; and "----" in Formula I between $A_0$ and $A_1$, all Formula II and all Formula IV "----" are double bonds. An example of a compound of this embodiment of the invention includes (NCL029):

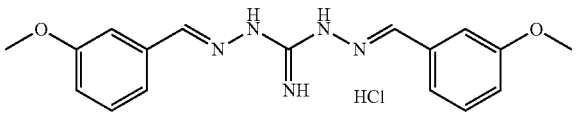

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_8$ and $R_9$ are H; $R_4$ is NH; $R_7$ is Cl; and "----" in Formula I between $A_0$ and $A_1$, and all Formula II "----" are double bonds. An example of a compound of this embodiment of the invention includes (NCL030):

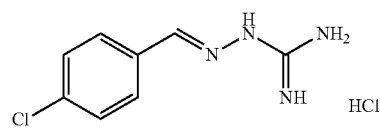 [SMILES: N=C(N)N/N=C/c1ccc(Cl)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, $R_{17}$ are H; $R_4$ is NH; $R_7$ and $R_{15}$ are $CF_3$; and "----" in Formula I between $A_0$ and $A_1$, all Formula II and Formula IV "----" are double bonds. An example of a compound of this embodiment of the invention includes (NCL035):

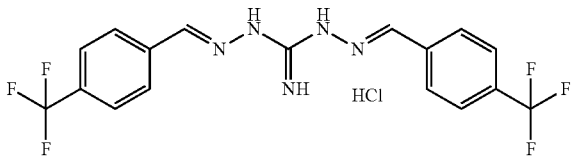 [SMILES: N=C(N/N=C/c1ccc(C(F)(F)F)cc1)N/N=C/c1ccc(C(F)(F)F)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, $R_{17}$ are H; $R_4$ is NH; $R_7$ and $R_{15}$ are methyl; and "----" in Formula I between $A_0$ and $A_1$, all Formula II and Formula IV "----" are double bonds. An example of a compound of this embodiment of the invention includes (NCL038):

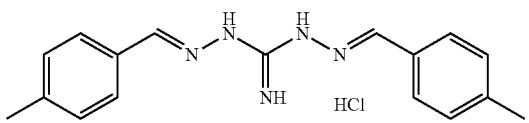

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_8$, $R_{12}$, $R_{14}$, $R_{15}$, $R_{16}$, $R_{17}$ are H; $R_4$ is NH; $R_9$ and $R_{13}$ are methyl; and "----" in Formula I between $A_0$ and $A_1$, all Formula II and Formula IV "----" are double bonds. An example of a compound of this embodiment of the invention includes (NCL039):

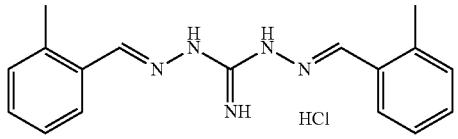 [SMILES: Cc1ccccc1/C=N/NC(=N)N/N=C/c1ccccc1C ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{13}$, $R_{15}$, $R_{16}$ and $R_{17}$ are H; $R_4$ is NH; $R_8$ and $R_{14}$ are methyl; and "----" in Formula I between $A_0$ and $A_1$, all Formula II and Formula IV "----" are double bonds. An example of a compound of this embodiment of the invention includes (NCL040):

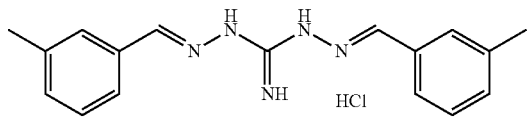

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_8$, and $R_9$ are H; $R_4$ is NH; $R_7$ is $CF_3$; and "----" in Formula I between $A_0$ and $A_1$, and all Formula II "----" are double bonds. An example of a compound of this embodiment of the invention includes (NCL041):

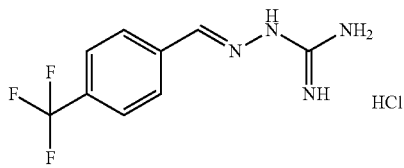 [SMILES: N=C(N)N/N=C/c1ccc(C(F)(F)F)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_7$, and $R_9$ are H; $R_4$ is NH; $R_8$ is $CF_3$; and "----" in Formula I between $A_0$ and $A_1$, and all Formula II "----" are double bonds. An example of a compound of this embodiment of the invention includes (NCL043):

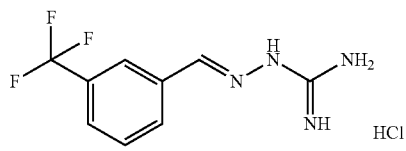 [SMILES: N=C(N)N/N=C/c1cccc(C(F)(F)F)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_8$, and $R_9$ are H; $R_4$ is NH; $R_7$ is methyl; and "----" in Formula I between $A_0$ and $A_1$, and all Formula II "----" are double bonds. An example of a compound of this embodiment of the invention includes (NCL044):

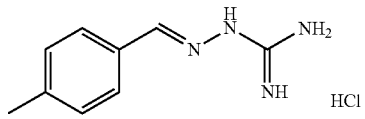

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ is NH; $A_0$, $A_3$, $A_4$, $A_5$, $A_6$, and $A_7$ are C; $R_2$, $R_5$, $R_6$, $R_7$, and $R_9$ are H; $R_4$ is NH; $R_8$ is Cl; and "----" in Formula I between $A_0$ and $A_1$, and all Formula II "----" are double bonds. An example of a compound of this embodiment of the invention includes (NCL052):

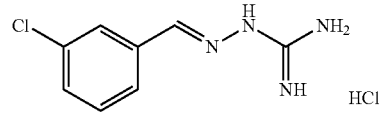 [SMILES: N=C(N)N/N=C/c1cccc(Cl)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{13}$, $R_{15}$, $R_{16}$, $R_{17}$ are H; $R_4$ is NH; $R_8$ and $R_{14}$ are Cl; and "----" in Formula I between $A_0$ and $A_1$, all Formula II and Formula IV "----" are double bonds. An example of a compound of this embodiment of the invention includes (NCL054):

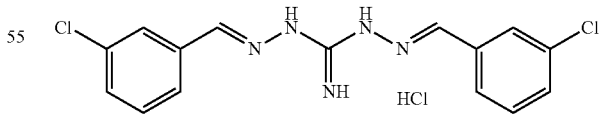

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$, $R_{17}$ are H; $R_4$ is NH; $R_7$ and $R_{15}$ are $CF_3$; and "----" in Formula I between $A_0$ and $A_1$, all Formula II and Formula IV "----" are double bonds. An example of a compound of this embodiment of the invention includes (NCL061):

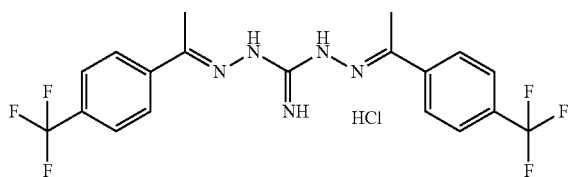 [SMILES: C/C(=N\NC(=N)N/N=C(\C)c1ccc(C(F)(F)F)cc1)c1ccc(C(F)(F)F)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$ and $R_{17}$ are H; $R_4$ is NH; $R_7$ and $R_{15}$ are Cl; and "----" in Formula I between $A_0$ and $A_1$, all Formula II and Formula IV "----" are double bonds. An example of a compound of this embodiment of the invention includes (NCL062):

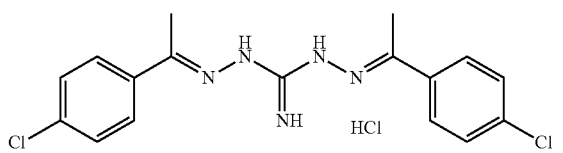 [SMILES: C/C(=N\NC(=N)N/N=C(\C)c1ccc(Cl)cc1)c1ccc(Cl)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is NHNH$_2$; $A_1$ is N; $A_2$ is NH; $A_0$, $A_3$, $A_4$, $A_5$, $A_6$, and $A_7$ are C; $R_2$ is methyl, $R_5$, $R_6$, $R_8$ and $R_9$ are H; $R_4$ is NH; $R_7$ is Cl; and "----" in Formula I between $A_0$ and $A_1$, and all Formula II "----" are double bonds. An example of a compound of this embodiment of the invention includes (NCL069):

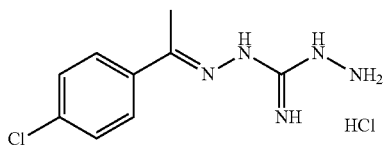

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_9$, $R_{12}$, $R_{13}$, $R_{15}$, $R_{16}$, and $R_{17}$ are H; $R_4$ is S; $R_8$ and $R_{14}$ are Cl; and "----" in Formula I between $A_0$ and $A_1$, all Formula II and Formula IV "----" are double bonds. An example of a compound of this embodiment of the invention includes (NCL070):

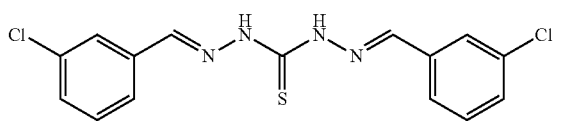 [SMILES: S=C(N/N=C/c1cccc(Cl)c1)N/N=C/c1cccc(Cl)c1]

In another preferred embodiment of the invention, the compound is a compound of Formula I, or a stereoisomer, tautomer, pharmaceutically acceptable salt, or prodrug thereof, wherein $R_1$ is Formula II; $R_3$ is NH$_2$; $A_1$ is N; $A_2$ is NH; $A_0$, $A_3$, $A_4$, $A_5$, $A_6$, and $A_7$ are C; $R_2$, $R_5$, $R_6$, $R_8$, and $R_9$ are H; $R_4$ is NH; $R_7$ is Cl; and "----" in Formula I between $A_0$ and $A_1$, and all Formula II "----" are double bonds. An example of a compound of this embodiment of the invention includes (NCL072):

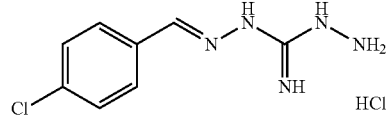 [SMILES: N=C(NN)N/N=C/c1ccc(Cl)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is NHNH$_2$; $A_1$ is N; $A_2$ is NH; $A_0$, $A_3$, $A_4$, $A_5$, $A_6$, and $A_7$ are C; $R_2$ is methyl; $R_5$, $R_6$, $R_8$, and $R_9$ are H; $R_4$ is NH; $R_7$ is CF$_3$; and "----" in Formula I between $A_0$ and $A_1$, and all Formula II "----" are double bonds. An example of a compound of this embodiment of the invention includes (NCL073):

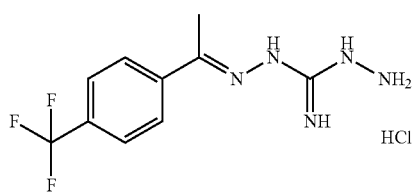 [SMILES: C/C(=N\NC(=N)NN)c1ccc(C(F)(F)F)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, and $R_{16}$ are H; $R_4$ is NH; $R_7$, $R_{15}$ and $R_{17}$ are Cl; and "----" in Formula I between $A_0$ and $A_1$, all Formula II and Formula IV "----" are double bonds. An example of a compound of this embodiment of the invention includes (NCL074):

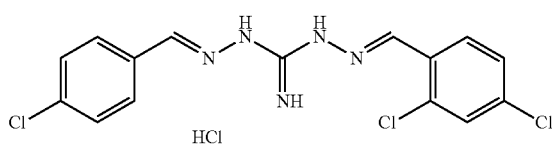 [SMILES: N=C(N/N=C/c1ccc(Cl)cc1)N/N=C/c1ccc(Cl)cc1Cl ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, and $R_{16}$ are H; $R_4$ is NH; $R_7$ is Cl; $R_{15}$ is CF$_3$; $R_{17}$ is F; and "----" in Formula I between $A_0$ and $A_1$, all Formula II and Formula IV "----" are double bonds. An example of a compound of this embodiment of the invention includes (NCL078):

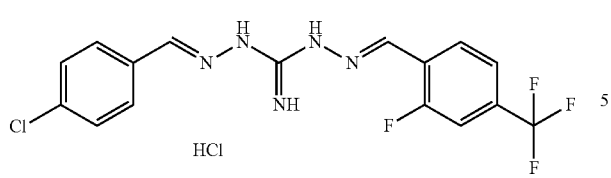

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$ and $R_{17}$ are H; $R_4$ is NH; $R_7$ is Cl; $R_{15}$ is F; and "----" in Formula I between $A_0$ and $A_1$, all Formula II and Formula IV "----" are double bonds. An example of a compound of this embodiment of the invention includes (NCL079):

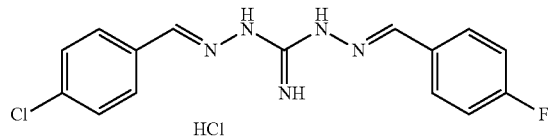 [SMILES: N=C(N/N=C/c1ccc(F)cc1)N/N=C/c1ccc(Cl)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{13}$, $R_{14}$, $R_{16}$ and $R_{17}$ are H; $R_4$ is NH; $R_7$ is Cl; $R_{12}$ is methyl; $R_{15}$ is $CF_3$; and "----" in Formula I between $A_0$ and $A_1$, all Formula II and Formula IV "----" are double bonds. An example of a compound of this embodiment of the invention includes (NCL080):

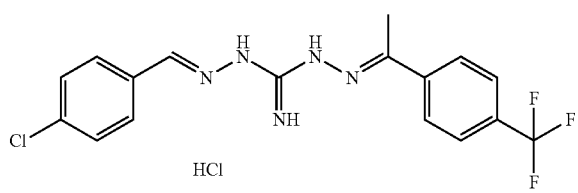 [SMILES: C/C(=N\NC(=N)N/N=C/c1ccc(Cl)cc1)c1ccc(C(F)(F)F)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{13}$, $R_{14}$, $R_{16}$ and $R_{17}$ are H; $R_4$ is NH; $R_7$ and $R_{15}$ are Cl; $R_{12}$ is methyl; and "----" in Formula I $A_0$ and $A_1$, all Formula II and Formula IV "----" are double bonds. An example of a compound of this embodiment of the invention includes (NCL081):

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{15}$, and $R_{16}$ are H; $R_4$ is NH; $R_7$ and $R_{17}$ are Cl; and "----" in Formula I between $A_0$ and $A_1$, all Formula II and Formula IV "----" are double bonds. An example of a compound of this embodiment of the invention includes (NCL082):

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, and $R_{16}$ are H; $R_4$ is NH; $R_7$ and $R_{15}$ are Cl; $R_{17}$ is F; and "----" in Formula I between $A_0$ and $A_1$, all Formula II and Formula IV "----" are double bonds. An example of a compound of this embodiment of the invention includes (NCL084):

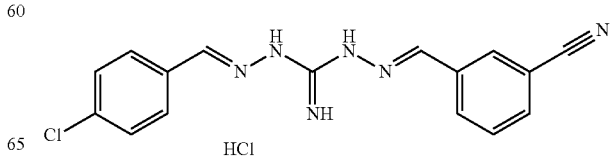

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{15}$, $R_{16}$, and $R_{17}$ are H; $R_4$ is NH; $R_7$ is Cl; $R_{14}$ is CN; and "----" in Formula I between $A_0$ and $A_1$, all Formula II and Formula IV "----" are double bonds. An example of a compound of this embodiment of the invention includes (NCL086):

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{15}$, and $R_{16}$ are H; $R_4$ is NH; $R_7$ is Cl; $R_{17}$ is F; and "----" in Formula I between $A_0$ and $A_1$, all Formula II and Formula IV "----" are double bonds. An example of a compound of this embodiment of the invention includes (NCL088):

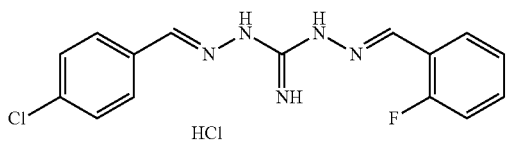 [SMILES: N=C(N/N=C/c1ccc(Cl)cc1)N/N=C/c1ccccc1F ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$, and $R_{17}$ are H; $R_4$ is NH; $R_7$ is Cl; $R_{15}$ is $CF_3$; and "----" in Formula I between $A_0$ and $A_1$, all Formula II and Formula IV "----" are double bonds. An example of a compound of this embodiment of the invention includes (NCL089):

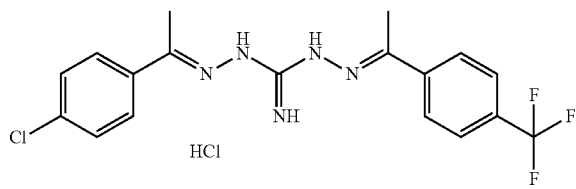 [SMILES: C/C(=N\NC(=N)N/N=C(\C)c1ccc(C(F)(F)F)cc1)c1ccc(Cl)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_9$, $R_{12}$, $R_{13}$, $R_{16}$, and $R_{17}$ are H; $R_4$ is NH; $R_7$ and $R_8$ are bonded together to form an unsubstituted, benzene ring; $R_{14}$ and $R_{15}$ are bonded together to form an unsubstituted, benzene ring; and "----" in Formula I between $A_0$ and $A_1$, all Formula II and Formula IV "----" are double bonds. An example of a compound of this embodiment of the invention includes (NCL093):

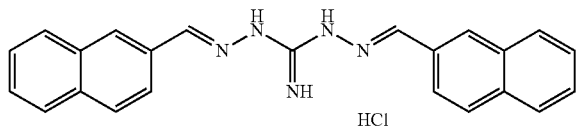 [SMILES: N=C(N/N=C/c1ccc2ccccc2c1)N/N=C/c1ccc2ccccc2c1 ; Cl]

In another preferred embodiment of the invention, the compound is a compound of Formula I, or a stereoisomer, tautomer, pharmaceutically acceptable salt, or prodrug thereof, wherein $A_0$ is C; $A_1$ is N; $A_2$ is NH; $R_1$ is cyclohexyl; $R_3$ is NH—N—CH-cyclohexyl; $R_4$ is NH; $R_2$ is H; and "----" in Formula I between $A_0$ and $A_1$ is a double bond. An example of a compound of this embodiment of the invention includes (NCL094):

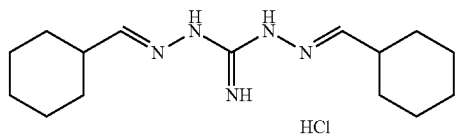 [SMILES: N=C(N/N=C/C1CCCCC1)N/N=C/C1CCCCC1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{12}$, $A_{13}$, $A_{14}$ and $A_{15}$, are C; $R_2$, $R_5$, $R_9$, $R_{12}$, $R_{13}$ and $R_{17}$ are H; $R_4$ is NH; $R_6$, $R_7$, $R_8$, $R_{14}$, $R_{15}$, and $R_{16}$ are OH; and "----" in Formula I between $A_0$ and $A_1$, all Formula II and Formula IV "----" are double bonds. An example of a compound of this embodiment of the invention includes (NCL097):

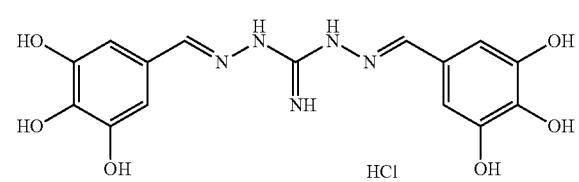 [SMILES: N=C(N/N=C/c1cc(O)c(O)c(O)c1)N/N=C/c1cc(O)c(O)c(O)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$ and $R_{17}$ are H; $R_4$ is NH; $R_7$ and $R_{15}$ are t-butyl; and "----" in Formula I between $A_0$ and $A_1$, all Formula II and Formula IV "----" are double bonds. An example of a compound of this embodiment of the invention includes (NCL099):

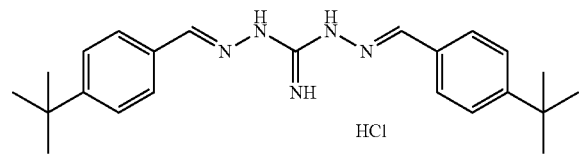 [SMILES: CC(C)(C)c1ccc(/C=N/NC(=N)N/N=C/c2ccc(C(C)(C)C)cc2)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_7$, $R_8$, $R_9$, $R_{12}$, $R_{13}$, $R_{14}$, and $R_{15}$ are H; $R_4$ is NH; $R_5$, $R_6$, $R_{16}$, and $R_{17}$ are OH; and "----" in Formula I between $A_0$ and $A_1$, all Formula II and Formula IV "----" are double bonds. An example of a compound of this embodiment of the invention includes (NCL101):

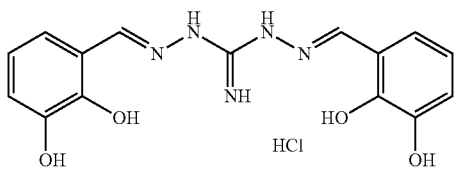 [SMILES: N=C(N/N=C/c1cccc(O)c1O)N/N=C/c1cccc(O)c1O ; Cl]

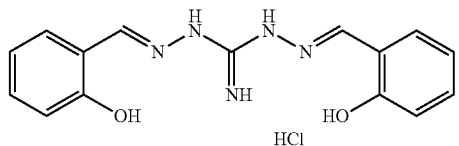

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_8$, $R_{12}$, $R_{14}$, and $R_{17}$ are H; $R_4$ is NH; $R_6$, $R_7$, $R_9$, $R_{13}$, $R_{15}$, and $R_{16}$ are OH; and "----" in Formula I between $A_0$ and $A_1$, all Formula II and Formula IV "----" are double bonds. An example of a compound of this embodiment of the invention includes (NCL104):

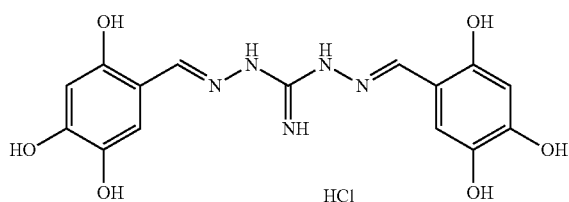 [SMILES: N=C(N/N=C/c1cc(O)c(O)cc1O)N/N=C/c1cc(O)c(O)cc1O ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_{12}$, $R_{16}$, and $R_{17}$ are H; $R_4$ is NH; $R_7$, $R_8$, $R_9$, $R_{13}$, $R_{14}$, and $R_{15}$ are OH; and "----" in Formula I between $A_0$ and $A_1$, all Formula II and Formula IV "----" are double bonds. An example of a compound of this embodiment of the invention includes (NCL097):

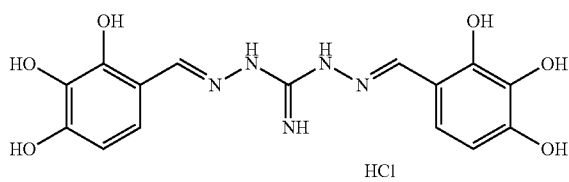 [SMILES: N=C(N/N=C/c1ccc(O)c(O)c1O)N/N=C/c1ccc(O)c(O)c1O ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_6$, $R_7$, $R_8$, $R_9$, $R_{12}$, $R_{13}$, $R_{14}$, $R_{15}$, and $R_{16}$ are H; $R_4$ is NH; $R_5$ and $R_{17}$ are OH; and "----" in Formula I between $A_0$ and $A_1$, all Formula II and Formula IV "----" are double bonds. An example of a compound of this embodiment of the invention includes (NCL107):

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_7$, $R_8$, $R_9$, $R_{12}$, $R_{13}$, $R_{14}$, $R_{15}$, and $R_{17}$ are H; $R_4$ is NH; $R_6$ and $R_{16}$ are OH; and "----" in Formula I between $A_0$ and $A_1$, all Formula II and Formula IV "----" are double bonds. An example of a compound of this embodiment of the invention includes (NCL108):

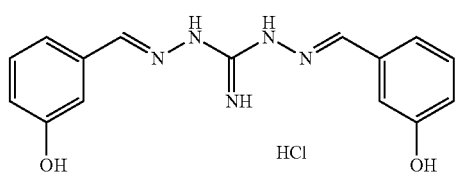 [SMILES: N=C(N/N=C/c1cccc(O)c1)N/N=C/c1cccc(O)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_8$, $R_9$, $R_{12}$, $R_{13}$, $R_{14}$, and $R_{17}$ are H; $R_4$ is NH; $R_6$, $R_7$, $R_{15}$, and $R_{16}$ are OH; and "----" in Formula I between $A_0$ and $A_1$, all Formula II and Formula IV "----" are double bonds. An example of a compound of this embodiment of the invention includes (NCL111):

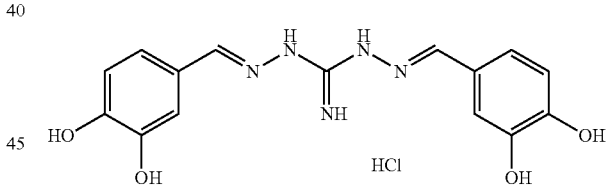

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are phenyl; and "----" in Formula I between $A_0$ and $A_1$, all Formula II and Formula IV "----" are double bonds. An example of a compound of this embodiment of the invention includes (NCL112):

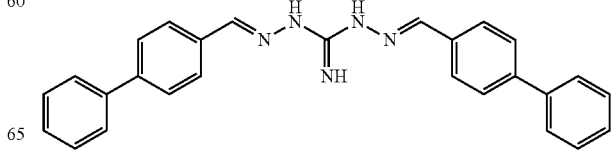

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are dimethylamino; and "----" in Formula I between $A_0$ and $A_1$, all Formula II and Formula IV "----" are double bonds. An example of a compound of this embodiment of the invention includes (NCL113):

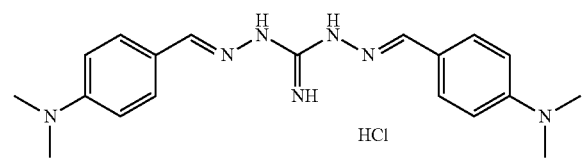

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_8$, $R_9$, $R_{12}$, $R_{13}$, $R_{14}$, and $R_{17}$ are H; $R_4$ is NH; $R_6$ and $R_{16}$ are $OCH_3$; $R_7$ and $R_{15}$ are OH; and "----" in Formula I between $A_0$ and $A_1$, all Formula II and Formula IV "----" are double bonds. An example of a compound of this embodiment of the invention includes (NCL117):

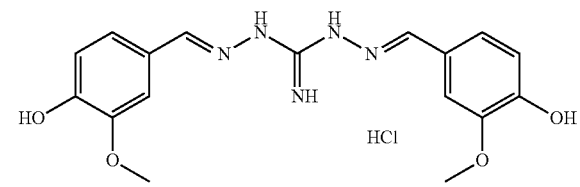 [SMILES: COc1cc(/C=N/NC(=N)N/N=C/c2ccc(O)c(OC)c2)ccc1O ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are i-propyl; and "----" in Formula I between $A_0$ and $A_1$, all Formula II and Formula IV "----" are double bonds. An example of a compound of this embodiment of the invention includes (NCL120):

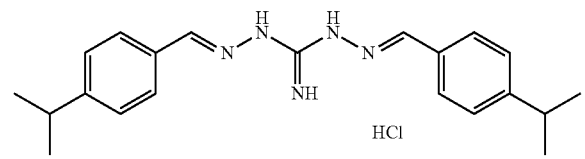 [SMILES: CC(C)c1ccc(/C=N/NC(=N)N/N=C/c2ccc(C(C)C)cc2)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are n-propyl; and "----" in Formula I between $A_0$ and $A_1$, all Formula II and Formula IV "----" are double bonds. An example of a compound of this embodiment of the invention includes (NCL121):

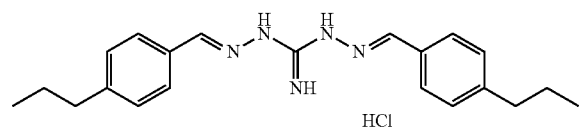 [SMILES: CCCc1ccc(/C=N/NC(=N)N/N=C/c2ccc(CCC)cc2)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_8$, $R_9$, $R_{12}$, $R_{13}$, $R_{14}$, and $R_{17}$ are H; $R_4$ is NH; $R_6$, $R_7$, $R_{15}$, and $R_{16}$ are F; and "----" in Formula I between $A_0$ and $A_1$, all Formula II and Formula IV "----" are double bonds. An example of a compound of this embodiment of the invention includes (NCL123):

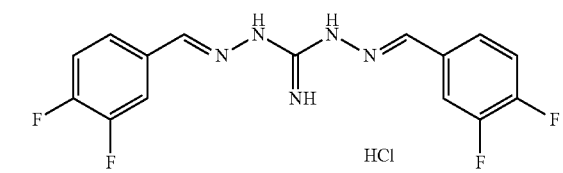 [SMILES: N=C(N/N=C/c1ccc(F)c(F)c1)N/N=C/c1ccc(F)c(F)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are CCH; and "----" in Formula I between $A_0$ and $A_1$, all Formula II and Formula IV "----" are double bonds. An example of a compound of this embodiment of the invention includes (NCL126):

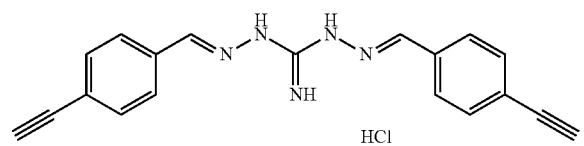 [SMILES: C#Cc1ccc(/C=N/NC(=N)N/N=C/c2ccc(C#C)cc2)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_7$, $R_8$, $R_9$, $R_{12}$, $R_{13}$, $R_{14}$, $R_{15}$, and $R_{17}$ are H; $R_4$ is NH; $R_6$ and $R_{16}$ are Br; and "----" in Formula I between $A_0$ and $A_1$, all Formula II and Formula IV "----" are double bonds. An example of a compound of this embodiment of the invention includes (NCL131):

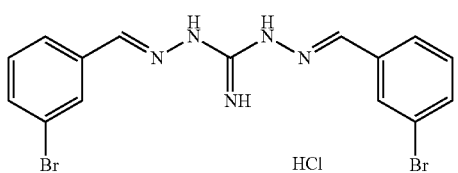 [SMILES: N=C(N/N=C/c1cccc(Br)c1)N/N=C/c1cccc(Br)c1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are butyl; and "----" in Formula I between $A_0$ and $A_1$, all Formula II and Formula IV "----" are double bonds. An example of a compound of this embodiment of the invention includes (NCL136):

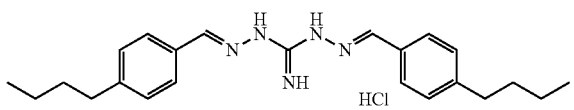 [SMILES: CCCCc1ccc(/C=N/NC(=N)N/N=C/c2ccc(CCCC)cc2)cc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ is —C($C_6H_5$)—CH—N— and $A_{10}$ is —N—CH—C($C_6H_5$)—; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_7$, $R_8$, $R_9$, $R_{12}$, $R_{13}$, $R_{14}$, $R_{15}$, $R_{16}$, and $R_{17}$ are H; $R_4$ is NH; and "----" in Formula I between $A_0$ and $A_1$, all Formula II and Formula IV "----" are double bonds. An example of a compound of this embodiment of the invention includes (NCL138):

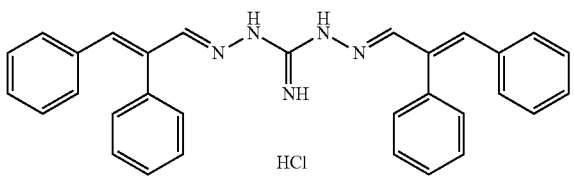 [SMILES: N=C(N/N=C/C(=C/c1ccccc1)c1ccccc1)N/N=C/C(=C/c1ccccc1)c1ccccc1 ; Cl]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$, and $R_{17}$ are H; $R_4$ is NH; $R_7$ and $R_{15}$ are $CH_3S$; and "----" in Formula I between $A_0$ and $A_1$, all Formula II and Formula IV "----" are double bonds. An example of a compound of this embodiment of the invention includes (NCL140):

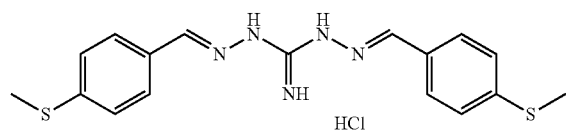

In another preferred embodiment of the invention, the compound is a compound of Formula I, or a stereoisomer, tautomer, pharmaceutically acceptable salt, or prodrug thereof, wherein $R_1$ is Formula III; $R_3$ is Formula VI; $A_0$ is C; $R_2$ and $R_{21}$ are H; $A_1$ and $A_{20}$ are N; $A_2$ and $A_{19}$ are NH; $A_8$ and $A_{21}$ are S; $R_4$ is NH; $R_{10}$ and $R_{11}$ are bonded together to form a substituted benzene ring; $R_{22}$ and $R_{23}$ are bonded together to form a substituted benzene ring; and "----" in Formula I between $A_0$ and $A_1$, and all Formula III and Formula VI "----" are double bonds. An example of a compound of this embodiment of the invention includes (NCL141):

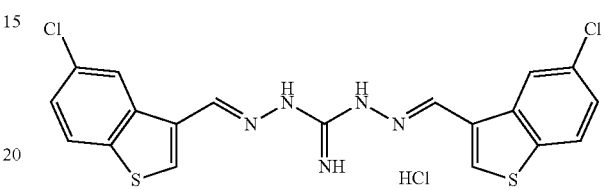

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_7$, $R_8$, $R_9$, $R_{13}$, $R_{14}$, $R_{15}$, $R_{16}$, and $R_{17}$ are H; $R_4$ is NH; and "----" in Formula I between $A_0$ and $A_1$, all Formula II and Formula IV "----" are double bonds. An example of a compound of this embodiment of the invention includes (NCL143):

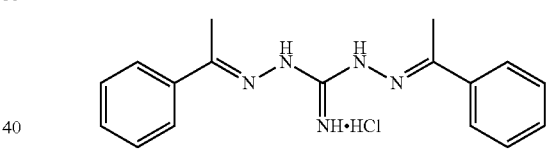

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_9$, $R_{12}$, $R_{13}$, $R_{16}$, and $R_{17}$ are H; $R_4$ is NH; $R_7$ and $R_8$ are bonded together to form an unsubstituted, heterocyclic ring; $R_{14}$ and $R_{15}$ are bonded together to form an unsubstituted, unsaturated heterocyclic ring; and "----" in Formula I between $A_0$ and $A_1$, all Formula II and Formula IV "----" are double bonds. An example of a compound of this embodiment of the invention includes (NCL146):

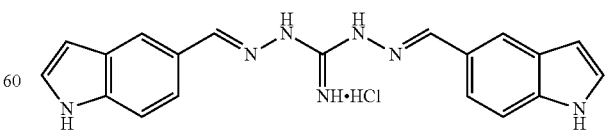

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ is —(CH)$_2$—N— and A$_0$ is —N—(CH)$_2$—; A$_2$ and A$_9$ are NH; A$_0$, A$_3$, A$_4$, A$_5$, A$_6$, A$_7$, A$_{11}$, A$_{12}$, A$_{13}$, A$_{14}$ and A$_{15}$, are C; R$_2$, R$_5$, R$_6$, R$_8$, R$_9$, R$_{12}$, R$_{13}$, R$_{14}$, R$_{16}$, and R$_{17}$ are H; R$_4$ is NH; R$_7$ and R$_{15}$ are OCH$_3$; and "----" in Formula I between A$_0$ and A$_1$, all Formula II and Formula IV "----" are double bonds. An example of a compound of this embodiment of the invention includes (NCL150):

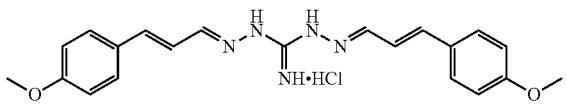

In another preferred embodiment of the invention, the compound is a compound of Formula I, or a stereoisomer, tautomer, pharmaceutically acceptable salt, or prodrug thereof, wherein R$_1$ is Formula II; R$_3$ is Formula IV; A$_1$ and A$_{10}$ are N; A$_2$ and A$_9$ are NH; A$_0$, A$_3$, A$_4$, A$_5$, A$_6$, A$_7$, A$_{11}$, A$_{12}$, A$_{13}$, A$_{14}$ and A$_{15}$, are C; R$_2$, R$_5$, R$_6$, R$_8$, R$_9$, R$_{12}$, R$_{13}$, R$_{14}$, R$_{16}$, and R$_{17}$ are H; R$_4$ is NH; R$_7$ and R$_{15}$ are OH; and "----" in Formula I between A$_0$ and A$_1$, all Formula II and Formula IV "----" are double bonds. An example of a compound of this embodiment of the invention includes (NCL151):

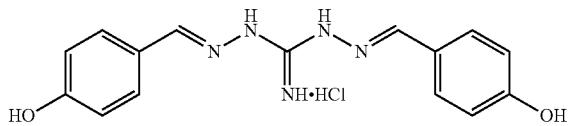

In another preferred embodiment of the invention, the compound is a compound of Formula I, or a stereoisomer, tautomer, pharmaceutically acceptable salt, or prodrug thereof, wherein R$_1$ is Formula II; R$_3$ is Formula IV; A$_1$ and A$_{10}$ are N; A$_2$ and A$_9$ are NH; A$_0$, A$_3$, A$_4$, A$_5$, A$_6$, A$_7$, A$_{11}$, A$_{12}$, A$_{13}$, A$_{14}$ and A$_{15}$, are C; R$_2$ and R$_{12}$ are ethyl; R$_5$, R$_6$, R$_8$, R$_9$, R$_{13}$, R$_{14}$, R$_{16}$, and R$_{17}$ are H; R$_4$ is NH; R$_7$ and R$_{15}$ are Cl; and "----" in Formula I between A$_0$ and A$_1$, all Formula II and Formula IV "----" are double bonds. An example of a compound of this embodiment of the invention includes (NCL153):

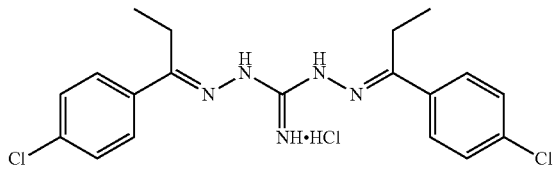

In another preferred embodiment of the invention, the compound is a compound of Formula I, or a stereoisomer, tautomer, pharmaceutically acceptable salt, or prodrug thereof, wherein R$_1$ is Formula II; R$_3$ is Formula IV; A$_1$ and A$_{10}$ are N; A$_2$ and A$_9$ are NH; A$_0$, A$_3$, A$_4$, A$_5$, A$_6$, A$_7$, A$_{11}$, A$_{12}$, A$_{13}$, A$_{14}$ and A$_{15}$, are C; R$_2$ and R$_{12}$ are methyl; R$_5$, R$_6$, R$_8$, R$_9$, R$_{13}$, R$_{14}$, R$_{16}$, and R$_{17}$ are H; R$_4$ is NH; R$_7$ and R$_{15}$ are Br; and "----" in Formula I between A$_0$ and A$_1$, all Formula II and Formula IV "----" are double bonds. An example of a compound of this embodiment of the invention includes (NCL155):

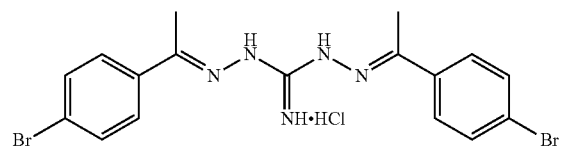

In another preferred embodiment of the invention, the compound is a compound of Formula I, or a stereoisomer, tautomer, pharmaceutically acceptable salt, or prodrug thereof, wherein R$_1$ is Formula II; R$_3$ is Formula IV; A$_1$ and A$_{10}$ are N; A$_2$ and A$_9$ are NH; A$_0$, A$_3$, A$_4$, A$_5$, A$_6$, A$_7$, A$_{11}$, A$_{12}$, A$_{13}$, A$_{14}$ and A$_{15}$, are C; R$_2$, R$_5$, R$_6$, R$_8$, R$_{12}$, R$_{14}$, R$_{16}$, and R$_{17}$ are H; R$_4$ is NH; R$_7$ and R$_{15}$ are Cl; R$_9$ and R$_{13}$ are NH$_2$; and "----" in Formula I between A$_0$ and A$_1$, all Formula II and Formula IV "----" are double bonds. An example of a compound of this embodiment of the invention includes (NCL157):

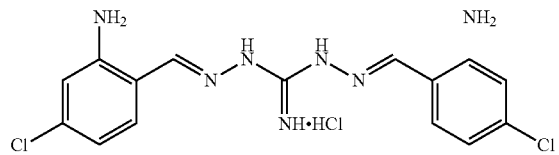

In another preferred embodiment of the invention, the compound is a compound of Formula I, or a stereoisomer, tautomer, pharmaceutically acceptable salt, or prodrug thereof, wherein R$_1$ is Formula II; R$_3$ is Formula IV; A$_1$ and A$_{10}$ are N; A$_2$ and A$_9$ are NH; A$_0$, A$_3$, A$_4$, A$_5$, A$_6$, A$_7$, A$_{11}$, A$_{12}$, A$_{13}$, A$_{14}$ and A$_{15}$, are C; R$_2$ and R$_{12}$ are ethyl; R$_5$ and R$_{17}$ are OH; R$_6$, R$_8$, R$_9$, R$_{13}$, R$_{14}$, and R$_{16}$ are H; R$_4$ is NH; R$_7$ and R$_{15}$ are Cl; and "----" in Formula I between A$_0$ and A$_1$, all Formula II and Formula IV "----" are double bonds. An example of a compound of this embodiment of the invention includes (NCL158):

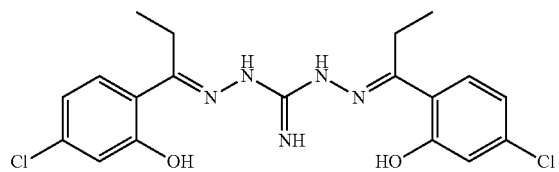 [SMILES: CC/C(=N\NC(=N)N/N=C(\CC)c1ccc(Cl)cc1O)c1ccc(Cl)cc1O]

In another preferred embodiment of the invention, the compound is a compound of Formula I, or a stereoisomer, tautomer, pharmaceutically acceptable salt, or prodrug thereof, wherein R$_1$ is Formula II; R$_3$ is Formula IV; A$_1$ and A$_{10}$ are N; A$_2$ and A$_9$ are NH; A$_0$, A$_3$, A$_4$, A$_5$, A$_6$, A$_7$, A$_1$, A$_{12}$, A$_{13}$, A$_{14}$ and A$_{15}$, are C; R$_2$ and R$_{12}$ are cyclopentyl; R$_5$ and R$_{17}$ are OH; R$_6$, R$_8$, R$_9$, R$_{13}$, R$_{14}$, and R$_{16}$ are H; R$_4$ is NH; R$_7$ and R$_{15}$ are Cl; and "----" in Formula I between A$_0$ and A$_1$, all Formula II and Formula IV "----" are double bonds. An example of a compound of this embodiment of the invention includes (NCL159):

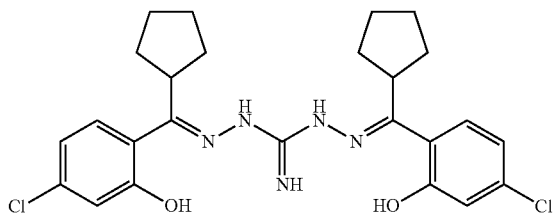 [SMILES: N=C(N/N=C(/c1ccc(Cl)cc1O)C1CCCC1)N/N=C(/c1ccc(Cl)cc1O)C1CCCC1]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$ and $R_{17}$ are H; $R_4$ is NH; $R_7$ and $R_{15}$ are $OCF_3$; and "----" in Formula I between $A_0$ and $A_1$, all Formula II and Formula IV "----" are double bonds. An example of a compound of this embodiment of the invention includes (NCL160):

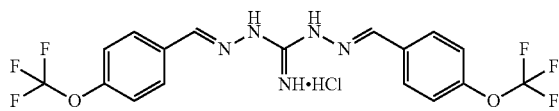

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$ and $R_{17}$ are H; $R_4$ is NH; $R_7$ and $R_{15}$ are piperazin-1-yl; and "----" in Formula I between $A_0$ and $A_1$, all Formula II and Formula IV "----" are double bonds. An example of a compound of this embodiment of the invention includes (NCL161):

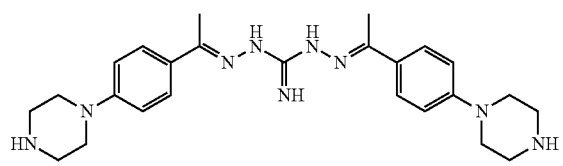 [SMILES: C/C(=N\NC(=N)N/N=C(\C)c1ccc(N2CCNCC2)cc1)c1ccc(N2CCNCC2)cc1]

In another preferred embodiment of the invention, the compound is a compound of Formula I, or a stereoisomer, tautomer, pharmaceutically acceptable salt, or prodrug thereof, wherein $R_1$ is Formula II; $R_3$ is O—$CH_2$—$CH_3$; $A_1$ is N; $A_2$ is NH; $A_0$, $A_3$, $A_4$, $A_5$, $A_6$ and $A_7$ are C; $R_2$ is methyl; $R_5$, $R_6$, $R_8$, and $R_9$ are H; $R_4$ is NH; $R_7$ is Cl; and "----" in Formula I between $A_0$ and $A_1$, and all Formula II "----" are double bonds. An example of a compound of this embodiment of the invention includes (NCL162):

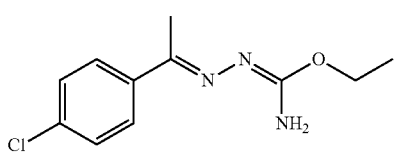 [SMILES: CCO/C(N)=N/N=C(\C)c1ccc(Cl)cc1]

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_5$, $R_6$, $R_8$, $R_9$, $R_{12}$, $R_{13}$, $R_{14}$, $R_{16}$ and $R_{17}$ are H; $R_4$ is NH; $R_7$ and $R_{15}$ are $SCF_3$; and "----" in Formula I between $A_0$ and $A_1$, all Formula II and Formula IV "----" are double bonds. An example of a compound of this embodiment of the invention includes (NCL166):

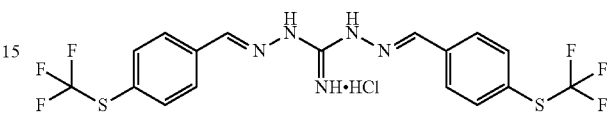

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_6$, $R_8$, $R_9$, $R_{12}$, $R_{13}$, $R_{14}$, and $R_{16}$ are H; $R_4$ is NH; $R_7$ and $R_{15}$ are Cl; $R_5$ and $R_{17}$ are —NH—CH(OH)—$CH_3$; and "----" in Formula I between $A_0$ and $A_1$, all Formula II and Formula IV "----" are double bonds. An example of a compound of this embodiment of the invention includes (NCL168):

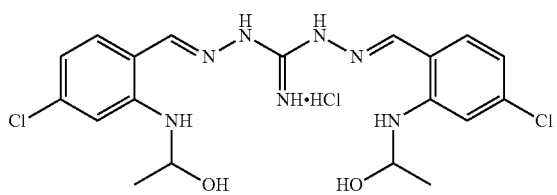

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is Cl. An example of a compound of this embodiment of the invention includes (NCL179):

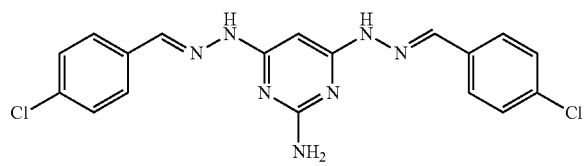 [SMILES: Nc1nc(N/N=C/c2ccc(Cl)cc2)cc(N/N=C/c2ccc(Cl)cc2)n1]

In another preferred embodiment of the invention, the compound is a compound of Formula I, or a stereoisomer, tautomer, pharmaceutically acceptable salt, or prodrug thereof, wherein $R_1$ is Formula II; $R_3$ is $NH_2$; $A_1$ is N; $A_2$ and $R_4$ are NH; $A_0$, $A_3$, $A_4$, $A_5$, $A_6$, and $A_7$ are C; $R_5$, $R_6$, $R_8$, and $R_9$ are H; $R_2$ is butyl; $R_7$ is Cl; and "----" in Formula I between $A_0$ and $A_1$, and all Formula II "----" are double bonds. An example of a compound of this embodiment of the invention includes (NCL188):

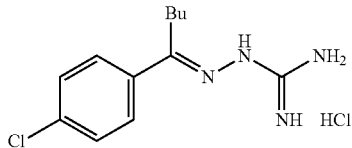

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is $CH_3$. An example of a compound of this embodiment of the invention includes (NCL195):

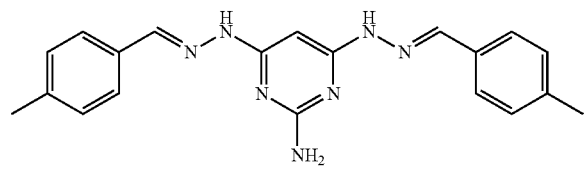

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is OH. An example of a compound of this embodiment of the invention includes (NCL196):

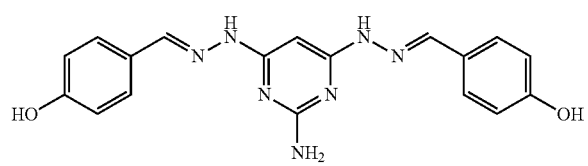 [SMILES: Nc1nc(N/N=C/c2ccc(O)cc2)cc(N/N=C/c2ccc(O)cc2)n1]

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is Br. An example of a compound of this embodiment of the invention includes (NCL193):

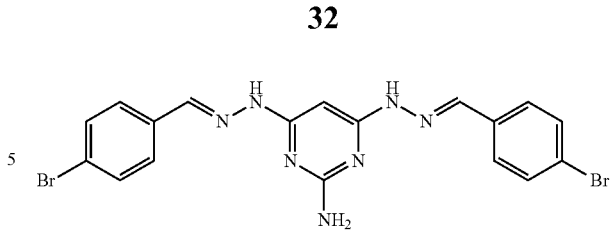

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{26}$, $R_{27}$ and $R_{28}$ are H; and $A_{23}$, $A_{24}$, $A_{25}$, $A_{26}$ and $A_{27}$ are C. An example of a compound of this embodiment of the invention includes (NCL199):

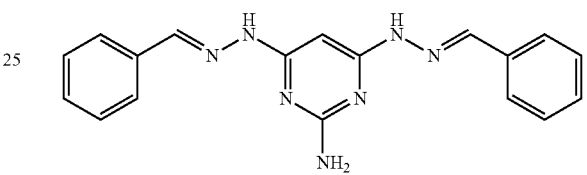

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—C($CH_3$)—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is Cl. An example of a compound of this embodiment of the invention includes (NCL204):

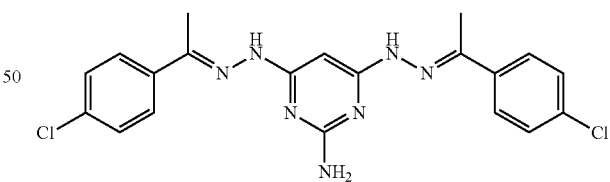

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$, $R_6$, $R_8$, $R_9$, $R_{12}$, $R_{13}$, $R_{14}$, and $R_{16}$ are H; $R_4$ is NH; $R_7$ and $R_{15}$ are Cl; $R_5$ and $R_{17}$ are F; and "----" in Formula I between $A_0$ and $A_1$, all Formula II and Formula IV "----" are double bonds. An example of a compound of this embodiment of the invention includes (NCL216):

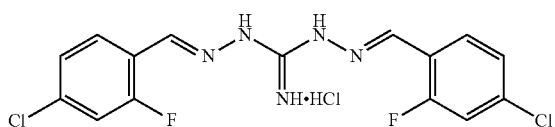

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$ and $R_{17}$ are H; $R_4$ is NH; $R_7$ and $R_{15}$ are $CH_3$; and "----" in Formula I between $A_0$ and $A_1$, all Formula II and Formula IV "----" are double bonds. An example of a compound of this embodiment of the invention includes (NCL217):

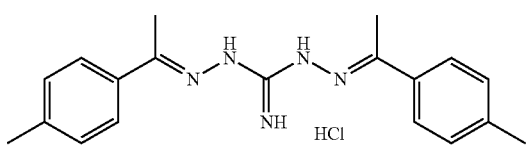

In another preferred embodiment of the invention, the compound is a compound of Formula I, or a stereoisomer, tautomer, pharmaceutically acceptable salt, or prodrug thereof, wherein $R_1$ is Formula II; $R_3$ is Formula IV; $A_1$ and $A_{10}$ are N; $A_2$ and $A_9$ are NH; $A_0$, $A_3$, $A_4$, $A_5$, $A_6$, $A_7$, $A_{11}$, $A_{12}$, $A_{13}$, $A_{14}$ and $A_{15}$, are C; $R_2$ and $R_{12}$ are methyl; $R_5$, $R_6$, $R_8$, $R_9$, $R_{13}$, $R_{14}$, $R_{16}$ and $R_{17}$ are H; $R_4$ is NH; $R_7$ and $R_{15}$ are t-butyl; and "----" in Formula I between $A_0$ and $A_1$, all Formula II and Formula IV "----" are double bonds. An example of a compound of this embodiment of the invention includes (NCL219):

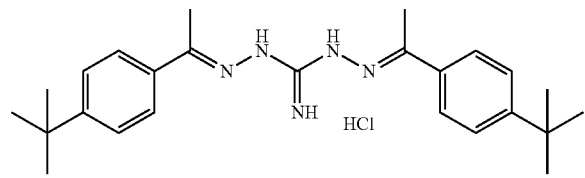 [SMILES: C/C(=N\NC(=N)N/N=C(\C)c1ccc(C(C)(C)C)cc1)c1ccc(C(C)(C)C)cc1 ; Cl]

In another preferred embodiment of the invention, the compound is a compound of Formula I, or a stereoisomer, tautomer, pharmaceutically acceptable salt, or prodrug thereof, wherein $A_0$ is C; $R_1$ is H; $A_2$ and $R_4$ are N; $R_3$ is $NH_2$; $A_1$ is Formula VII; $R_2$ is Formula VII and $R_2$ is bonded to $R_4$, forming a pyrimidine ring; "----" in Formula I between $R_2$ and $A_0$, and between $A_1$ and $A_2$ are double bonds; $A_{22}$ is —N—CH—; $R_{24}$, $R_{25}$, $R_{27}$ and $R_{28}$ are H; $A_{23}$, $A_{24}$, $A_{25}$, $A_{26}$ and $A_{27}$ are C; and $R_{26}$ is $CF_3$. An example of a compound of this embodiment of the invention includes (NCL221):

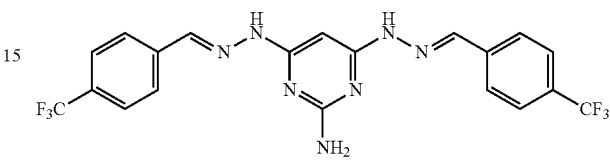

In another aspect of the invention, the invention is a compound selected from the list of compounds presented in FIG. 1. In one preferred embodiment, the compound is a compound selected from the following compounds: NCL231 to NCL275. In a further aspect, the invention is a composition comprising a compound of the invention. In yet a further aspect, the invention is a pharmaceutical composition comprising a compound of the invention together with an pharmaceutically acceptable excipient and/or carrier. In yet a further aspect, the invention is a veterinary composition comprising a compound of the invention together with an acceptable excipient and/or carrier.

Terms used herein will have their customary meanings in the art unless specified. As used herein, the term robenidine, NCL812 (also known as 1,3-bis[(E)-(4-chlorophenyl)methyleneamino]guanidine) refers to a compound having the following chemical structure:

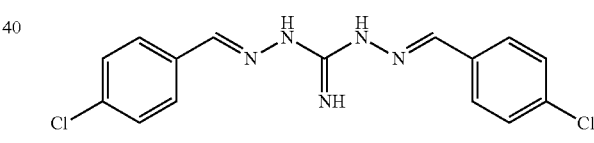

Preferably, the protozoan agent is selected from the group of genera, sub-genera and species listed in Table 1.

TABLE 1

*Acanthamoeba* (Scientific classification: Eukaryota; Amoebozoa; Discosea; Longamoebia; Centramoebida; Acanthamoebidae) including *Acanthamoeba astronyxis, Acanthamoeba castellanii, Acanthamoeba comandoni, Acanthamoeba culbertsoni, Acanthamoeba divionensis, Acanthamoeba echinulata, Acanthamoeba griffini, Acanthamoeba hatchetti, Acanthamoeba healyi, Acanthamoeba jacobsi, Acanthamoeba lenticulata, Acanthamoeba lugdunensis, Acanthamoeba mauritaniensis, Acanthamoeba palestinensis, Acanthamoeba paradivionensis, Acanthamoeba pearcei, Acanthamoeba polyphaga, Acanthamoeba pustulosa, Acanthamoeba quina, Acanthamoeba rhysodes, Acanthamoeba royreba, Acanthamoeba stevensoni, Acanthamoeba terricola, Acanthamoeba triangularis, Acanthamoeba tubiashi, Acanthamoeba* sp., and unclassified *Acanthamoeba*.
*Babesia* (Scientific classification: Eukaryota; Alveolata; Apicomplexa; Aconoidasida; Piroplasmida; Babesiidae) including *Babesia bennetti, Babesia bicornis, Babesia bigemina, Babesia* cf. *bigemina, Babesia bovis, Babesia* cf. *bovis, Babesia caballi, Babesia canis* (and subspecies *Babesia canis canis, Babesia canis rossi* and *Babesia canis vogeli*), *Babesia capreoli, Babesia conradae, Babesia crassa, Babesia* cf. *crassa* GU184, *Babesia divergens, Babesia* cf. *divergens, Babesia* cf. *divergens* AdL5, *Babesia duncani, Babesia equi, Babesia felis, Babesia* cf. *felis, Babesia gibsoni, Babesia hongkongensis, Babesia kiwiensis, Babesia lengau, Babesia leo, Babesia major, Babesia microti, Babesia* cf. *microti, Babesia* cf. *microti* MES-2012, *Babesia motasi, Babesia muratovi, Babesia occultans, Babesia odocoilei, Babesia* cf. *odocoilei, Babesia orientalis, Babesia* cf. *orientalis, Babesia ovata, Babesia ovis, Babesia poelea, Babesia rodhaini, Babesia vesperuginis, Babesia vitalii, Babesia* sp. 'venatorum', and unclassified *Babesia*.
*Balamuthia* (Scientific classification: Eukaryota; Amoebozoa; Discosea; Longamoebia; Centramoebida; Balamuthiidae) including *Balamuthia mandrillaris*

TABLE 1-continued

*Balantidium* (Scientific classification: Eukaryota; Alveolata; Ciliophora; Intramacronucleata; Litostomatea; Trichostomatia; Vestibuliferida; Balantidiidae) including *Balantidium* cf. *coli*, *Balantidium ctenopharyngodoni* and *Balantidium entozoon*.
*Besnoitia* (Scientific classification: Eukaryota; Alveolata; Apicomplexa; Conoidasida; Coccidia; Eucoccidiorida; Eimeriorina; Sarcocystidae) including, *Besnoitia akodoni*, *Besnoitia bennetti*, *Besnoitia besnoiti*, *Besnoitia caprae*, *Besnoitia darlingi*, *Besnoitia jellisoni*, *Besnoitia neotomofelis*, *Besnoitia oryctofelisi*, and *Besnoitia tarandi*.
*Blastocystis* (Scientific classification: Eukaryota; Stramenopiles) including *Blastocystis cycluri*, *Blastocystis geocheloni*, *Blastocystis hominis*, *Blastocystis lapemi*, *Blastocystis pythoni*, *Blastocystis ratti*, and *Blastocystis* sp. Subtypes.
*Chilomastix* (Scientific classification: Eukaryota; Fornicata; Retortamonadidae) including *Chilomastix caulleryi*, *Chilomastix mesnili* and *Chilomastix wenrichi*.
*Cochlosoma* (Scientific classification: Eukaryota; Parabasalia; Trichomonadida; Trichomonadidae) including *Cochlosoma anatis*.
*Cryptosporidium* (Scientific classification: Eukaryota; Alveolata; Apicomplexa; Conoidasida; Coccidia; Eucoccidiorida; Eimeriorina; Cryptosporidiidae) including *Cryptosporidium andersoni*, *Cryptosporidium baileyi*, *Cryptosporidium bovis*, *Cryptosporidium canis*, *Cryptosporidium* cf. *bovis* G2, *Cryptosporidium* cf. *bovis* G3, *Cryptosporidium* cf. *bovis* G4, *Cryptosporidium* cf. *bovis* G7, *Cryptosporidium* cf. *molnari*, *Cryptosporidium* cf. *parvum*, *Cryptosporidium* cf. *suis*, *Cryptosporidium cuniculus*, *Cryptosporidium erinacei*, *Cryptosporidium fayeri*, *Cryptosporidium felis*, *Cryptosporidium fragile*, *Cryptosporidium galli*, *Cryptosporidium hominis*, *Cryptosporidium macropodum*, *Cryptosporidium meleagridis*, *Cryptosporidium molnari*, *Cryptosporidium muris*, *Cryptosporidium parvum*, *Cryptosporidium parvum* mouse genotype, *Cryptosporidium ryanae*, *Cryptosporidium saurophilum*, *Cryptosporidium scrofarum*, *Cryptosporidium serpentis*, *Cryptosporidium struthionis*, *Cryptosporidium suis*, *Cryptosporidium tyzzeri*, *Cryptosporidium ubiquitum*, *Cryptosporidium viatorum*, *Cryptosporidium wrairi*, *Cryptosporidium xiaoi*, and unclassified *Cryptosporidium*.
*Cyclospora* (Scientific classification: Eukaryota; Alveolata; Apicomplexa; Conoidasida; Coccidia; Eucoccidiorida; Eimeriorina; Eimeriidae) including *Cyclospora cayetanensis*, *Cyclospora cercopitheci*, *Cyclospora colobi*, *Cyclospora papionis*, and *Cyclospora* sp.
*Cystoisospora* (Scientific classification: Eukaryota; Alveolata; Apicomplexa; Conoidasida; Coccidia; Eucoccidiorida; Eimeriorina; Sarcocystidae) including *Cystoisospora belli*, *Cystoisospora felis*, *Cystoisospora ohioensis*, *Cystoisospora* cf. *ohioensis*, *Cystoisospora rivolta*, *Cystoisospora suis*, and *Cystoisospora timoni*.
*Cytauxzoon* (Scientific classification: Eukaryota; Alveolata; Apicomplexa; Aconoidasida; Piroplasmida; Theileriidae) including *Cytauxzoon felis*, *Cytauxzoon manul* and unclassified *Cytauxzoon*.
*Dientamoeba* (Scientific classification: Eukaryota; Parabasalia; Tritrichomonadida; Dientamoebidae) including *Dientamoeba fragilis*.
*Eimeria* ( Scientific classification: Eukaryota; Alveolata; Apicomplexa; Conoidasida; Coccidia; Eucoccidiorida; Eimeriorina; Eimeriidae) including *Eimeria acervulina*, *Eimeria adenoeides*, *Eimeria ahsata*, *Eimeria alabamensis*, *Eimeria albigulae*, *Eimeria alorani*, *Eimeria anguillae*, *Eimeria anseris*, *Eimeria antrozoi*, *Eimeria apionodes*, *Eimeria arizonensis*, *Eimeria arloingi*, *Eimeria arnyi*, *Eimeria auburnensis*, *Eimeria auritusi*, *Eimeria banffensis*, *Eimeria bovis*, *Eimeria brunetti*, *Eimeria bukidnonensis*, *Eimeria burdai*, *Eimeria cahirinensis*, *Eimeria callospermophili*, *Eimeria canadensis*, *Eimeria catronensis*, *Eimeria caviae*, *Eimeria chaetodipi*, *Eimeria chinchillae*, *Eimeria chobotari*, *Eimeria coecicola*, *Eimeria crandallis*, *Eimeria cylindrica*, *Eimeria cylindrospora*, *Eimeria daviesae*, *Eimeria dipodomysis*, *Eimeria dispersa*, *Eimeria ellipsoidalis*, *Eimeria exigua*, *Eimeria falciformis*, *Eimeria faurei*, *Eimeria flavescens*, *Eimeria furonis*, *Eimeria gallopavonis*, *Eimeria gruis*, *Eimeria hermani*, *Eimeria hessei*, *Eimeria intestinalis*, *Eimeria irresidua*, *Eimeria krijgsmanni*, *Eimeria lamae*, *Eimeria lancasterensis*, *Eimeria langebarteli*, *Eimeria leucisci*, *Eimeria leucopi*, *Eimeria macropodis*, *Eimeria macusaniensis*, *Eimeria magna*, *Eimeria maxima*, *Eimeria media*, *Eimeria meleagrimitis*, *Eimeria mitis*, *Eimeria mivati*, *Eimeria* cf. *mivati*, *Eimeria myoxi*, *Eimeria nafuko*, *Eimeria necatrix*, *Eimeria nemethi*, *Eimeria nieschulzi*, *Eimeria ontarioensis*, *Eimeria onychomysis*, *Eimeria ovinoidalis*, *Eimeria papillata*, *Eimeria pavonina*, *Eimeria percae*, *Eimeria perforans*, *Eimeria peromysci*, *Eimeria phalacrocoraxae*, *Eimeria pilarensis*, *Eimeria piriformis*, *Eimeria polita*, *Eimeria porci*, *Eimeria praecox*, *Eimeria pragensis*, *Eimeria quokka*, *Eimeria ranae*, *Eimeria reedi*, *Eimeria reichenowi*, *Eimeria rioarribaensis*, *Eimeria rutili*, *Eimeria scabra*, *Eimeria scholtysecki*, *Eimeria separata*, *Eimeria setonicis*, *Eimeria sevilletensis*, *Eimeria siliculiformis*, *Eimeria sinensis*, *Eimeria stiedai*, *Eimeria subepithelialis*, *Eimeria subspherica*, *Eimeria telekii*, *Eimeria tenella*, *Eimeria* cf. *tenggilingi* L12_Ros, *Eimeria trichosuri*, *Eimeria tropidura*, *Eimeria variabilis*, *Eimeria vejdovskyi*, *Eimeria vermiformis*, *Eimeria vilasi*, *Eimeria weybridgensis*, *Eimeria wyomingensis*, *Eimeria zuernii*, and unclassified *Eimeria*.
*Endolimax* (Scientific classification: Eukaryota; Amoebozoa; Archamoebae; Entamoebidae) including *Endolimax nana* and *Endolimax piscium*.
*Entamoeba* (Scientific classification: Eukaryota; Amoebozoa; Archamoebae; Entamoebidae) including *Entamoeba bangladeshi*, *Entamoeba bovis*, *Entamoeba chattoni*, *Entamoeba coli*, *Entamoeba dispar*, *Entamoeba ecuadoriensis*, *Entamoeba equi*, *Entamoeba gingivalis*, *Entamoeba hartmanni*, *Entamoeba histolytica*, *Entamoeba insolita*, *Entamoeba invadens*, *Entamoeba moshkovskii*, *Entamoeba muris*, *Entamoeba nuttalli*, *Entamoeba polecki*, *Entamoeba ranarum*, *Entamoeba struthionis*, *Entamoeba suis*, and *Entamoeba terrapinae*.
*Giardia* (Scientific classification: Eukaryota; Fornicata; Diplomonadida; Hexamitidae; Giardiinae) including *Giardia ardeae*, *Giardia intestinalis* (synonyms *Giardia duodenalis* and *Giardia lamblia*) (and various assemblages), *Giardia microti*, *Giardia muris*, *Giardia psittaci* and unclassified *Giardia*.
*Haemoproteus* (Scientific classification: Eukaryota; Alveolata; Apicomplexa; Aconoidasida; Haemosporida) including *Haemoproteus balmorali*, *Haemoproteus belopolskyi*, *Haemoproteus chelodinae*, *Haemoproteus coatneyi*, *Haemoproteus columbae*, *Haemoproteus danilewskyii*, *Haemoproteus elani*, *Haemoproteus enucleator*, *Haemoproteus fringillae*, *Haemoproteus hirudinis*, *Haemoproteus homobelopolskyi*, *Haemoproteus iwa*, *Haemoproteus jenniae*, *Haemoproteus kopki*, *Haemoproteus lanii*, *Haemoproteus magnus*, *Haemoproteus majoris*, *Haemoproteus mesnili*, *Haemoproteus micronuclearis*, *Haemoproteus minutus*, *Haemoproteus motacillae*, *Haemoproteus multipigmentatus*, *Haemoproteus nucleofascialis*, *Haemoproteus pallidulus*, *Haemoproteus pallidus*, *Haemoproteus parabelopolskyi*, *Haemoproteus paranucleophilus*, *Haemoproteus passeris*, *Haemoproteus pastoris*, *Haemoproteus payevskyi*, *Haemoproteus picae*, *Haemoproteus ptyodactylii*, *Haemoproteus sacharovi*, *Haemoproteus sanguinis*, *Haemoproteus sylvae*, *Haemoproteus syrnii*, *Haemoproteus tartakovskyi*, *Haemoproteus turtur*, *Haemoproteus vacuolatus*, and unclassified *Haemoproteus*.
*Hammondia* (Scientific classification: Eukaryota; Alveolata; Apicomplexa; Conoidasida; Coccidia; Eucoccidiorida; Eimeriorina; Sarcocystidae) including *Hammondia hammondi*, *Hammondia heydorni*, *Hammondia triffittae* and *Hammondia* sp. Fox-2000.

TABLE 1-continued

*Hartmannella* (Scientific classification: Eukaryota; Amoebozoa; Tubulinea; Euamoebida; Tubulinida;
Hartmannellidae) including *Hartmannella abertawensis*, *Hartmannella cantabrigiensis*, *Hartmannella* cf. *vermiformis*
[now known at *Vermamoeba vermiformis*], and *Hartmanella* sp.
*Hepatozoon* (Scientific classification: Eukaryota; Alveolata; Apicomplexa; Conoidasida; Coccidia; Eucoccidiorida;
Adeleorina; Hepatozoidae) including *Hepatozoon americanum*, *Hepatozoon ayorgbor*, *Hepatozoon canis*,
*Hepatozoon catesbianae*, *Hepatozoon* cf. *catesbianae*, *Hepatozoon clamatae*, *Hepatozoon* cf. *clamatae*, *Hepatozoon
erhardovae*, *Hepatozoon felis*, *Hepatozoon seychellensis*, *Hepatozoon sipedon*, *Hepatozoon tuatarae*, *Hepatozoon
ursi*, and unclassified *Hepatozoon*.
*Hexamita* (Scientific classification: Eukaryota; Fornicata; Diplomonadida; Hexamitidae; Hexamitinae) including
*Hexamita inflata*, *Hexamita nelsoni* and *Hexamita* sp.
*Histomonas* (Scientific classification: Eukaryota; Parabasalia; Tritrichomonadida; Dientamoebidae) including
*Histomonas meleagridis* and *Histomonas* sp.
*Isospora* (Scientific classification: Eukaryota; Alveolata; Apicomplexa; Conoidasida; Coccidia; Eucoccidiorida;
Eimeriorina; Eimeriidae) including *Isospora anthochaerae*, *Isospora gryphoni*, *Isospora hypoleucae*, *Isospora
insularius*, *Isospora lesouefi*, *Isospora orlovi*, *Isospora peromysis*, and *Isospora robini*.
*Leishmania* (Scientific classification: Eukaryota; Euglenozoa; Kinetoplastida; Trypanosomatidae; Leishmaniinae)
including subgenus *Leishmania* (including *Leishmania aethiopica* species complex, *Leishmania aristidesi*,
*Leishmania deanei*, *Leishmania donovani* species complex, *Leishmania hertigi*, *Leishmania major* species complex,
*Leishmania major* x *donovani*, *Leishmania mexicana* species complex, *Leishmania tropica* species complex, lizard
*Leishmania* (*Leishmania adleri*, *Leishmania gymnodactyli*, *Leishmania hoogstraali*, *Leishmania tarentolae*,
*Leishmania* sp. NC29/Iran/2007), subgenus *Viannia* (including *Leishmania braziliensis* species complex, *Leishmania
garnhami*, *Leishmania guyanensis* species complex, *Leishmania lainsoni* species complex, *Leishmania lindenbergi*,
*Leishmania naiffi* species complex, *Leishmania utingensis*, and unclassified *Leishmania*).
*Leucocytozoon* (Scientific classification: Eukaryota; Alveolata; Apicomplexa; Aconoidasida; Haemosporida)
including *Leucocytozoon buteonis*, *Leucocytozoon caulleryi*, *Leucocytozoon dubreuili*, *Leucocytozoon fringillinarum*,
*Leucocytozoon gentili*, *Leucocytozoon lovati*, *Leucocytozoon macleani*, *Leucocytozoon majoris*, *Leucocytozoon
quynzae*, *Leucocytozoon sabrazesi*, *Leucocytozoon schoutedeni*, *Leucocytozoon simondi*, *Leucocytozoon
squamatus*, *Leucocytozoon toddi*, *Leucocytozoon ziemanni*, *Leucocytozoon* sp., and unclassified *Leucocytozoon*.
*Naegleria* (Scientific classification: Eukaryota; Heterolobosea; Schizopyrenida; Vahlkampfiidae) including *Naegleria
americana*, *Naegleria andersoni*, *Naegleria angularis*, *Naegleria antarctica*, *Naegleria arctica*, *Naegleria
australiensis*, *Naegleria* cf. *australiensis*, *Naegleria canariensis*, *Naegleria carteri*, *Naegleria chilensis*, *Naegleria
clarki*, *Naegleria dobsoni*, *Naegleria dunnebackei*, *Naegleria endoi*, *Naegleria fowleri*, *Naegleria fultoni*, *Naegleria
galeacystis*, *Naegleria gallica*, *Naegleria gruberi*, *Naegleria* cf. *gruberi*, *Naegleria indonesiensis*, *Naegleria italica*,
*Naegleria jadini*, *Naegleria jamiesoni*, *Naegleria laresi*, *Naegleria lovaniensis*, *Naegleria mexicana*, *Naegleria minor*,
*Naegleria morganensis*, *Naegleria neoantarctica*, *Naegleria neochilensis*, *Naegleria neodobsoni*, *Naegleria
neopolaris*, *Naegleria pagei*, *Naegleria paradobsoni*, *Naegleria peruana*, *Naegleria philippinensis*, *Naegleria polaris*,
*Naegleria pringsheimi*, *Naegleria pussardi*, *Naegleria robinsoni*, *Naegleria schusteri*, *Naegleria spitzbergeniensis*,
*Naegleria tenerifensis*, *Naegleria tihangensis*, *Naegleria* sp., and unclassified *Naegleria*.
*Neospora* (Scientific classification: Eukaryota; Alveolata; Apicomplexa; Conoidasida; Coccidia; Eucoccidiorida;
Eimeriorina; Sarcocystidae) including *Neospora caninum*, *Neospora hughesi* and *Neospora* sp.
*Pentatrichomonas* (Scientific classification: Eukaryota; Parabasalia; Trichomonadida; Trichomonadidae) including
*Pentatrichomonas hominis*.
*Plasmodium* (Scientific classification: Eukaryota; Alveolata; Apicomplexa; Aconoidasida; Haemosporida) including
*Plasmodium ovale*, *Plasmodium simiovale*, *Plasmodium simium*, *Plasmodium vivax*, and subgenera *Plasmodium
(Bennettinia)* (birds); *Plasmodium (Giovannolaia)* (birds); *Plasmodium (Haemamoeba)* (birds); *Plasmodium (Huffia)*
(birds); *Plasmodium (Laverania)* (higher primates, includes *Plasmodium falciparum*); *Plasmodium (Novyella)* (birds);
*Plasmodium (Paraplasmodium)* (lizards); *Plasmodium (Plasmodium)* (higher primates, includes *Plasmodium
brasilianum*, *Plasmodium cynomolgi*, *Plasmodium inui*, *Plasmodium knowlesi*, *Plasmodium malariae*]; *Plasmodium
(Sauramoeba)* (lizards); and *Plasmodium (Vinckeia)*.
*Sappinia* (Scientific classification: Eukaryota; Amoebozoa; Discosea; Longamoebia; Thecamoebida) including
*Sappinia diploidea*, *Sappinia pedata* and *Sappinia* sp.
*Sarcocystis* (Scientific classification: Eukaryota; Alveolata; Apicomplexa; Conoidasida; Coccidia; Eucoccidiorida;
Eimeriorina; Sarcocystidae) including *Sarcocystis albifronsi*, *Sarcocystis alces*, *Sarcocystis alceslatrans*, *Sarcocystis
anasi*, *Sarcocystis arctica*, *Sarcocystis arieticanis*, *Sarcocystis atheridis*, *Sarcocystis aucheniae*, *Sarcocystis
buffalonis*, *Sarcocystis calchasi*, *Sarcocystis campestris*, *Sarcocystis canis*, *Sarcocystis capracanis*, *Sarcocystis
capreolicanis*, *Sarcocystis* cf. *clethrionomyelaphis* JJH-2013, *Sarcocystis columbae*, *Sarcocystis cornixi*, *Sarcocystis
cruzi*, *Sarcocystis* cf. *cruzi*, *Sarcocystis dasypi*, *Sarcocystis dispersa*, *Sarcocystis elongata*, *Sarcocystis falcatula*,
*Sarcocystis* cf. *falcatula*, *Sarcocystis fayeri*, *Sarcocystis felis*, *Sarcocystis* cf. *felis* WACF-2013, *Sarcocystis fusiformis*,
*Sarcocystis gallotiae*, *Sarcocystis gigantea*, *Sarcocystis gracilis*, *Sarcocystis grueneri*, *Sarcocystis hardangeri*,
*Sarcocystis hirsuta*, *Sarcocystis hjorti*, *Sarcocystis hominis*, *Sarcocystis lacertae*, *Sarcocystis lamacanis*, *Sarcocystis
lindsayi*, *Sarcocystis miescheriana*, *Sarcocystis moulei*, *Sarcocystis mucosa*, *Sarcocystis muris*, *Sarcocystis nesbitti*,
*Sarcocystis neurona* [agent of equine protozoal myeloencephalitis (EPM)], *Sarcocystis* cf. *neurona*, *Sarcocystis*
neurona-like protozoan, *Sarcocystis ovalis*, *Sarcocystis oviformis*, *Sarcocystis ramphastosi*, *Sarcocystis rangi*,
*Sarcocystis rangiferi*, *Sarcocystis rileyi*, *Sarcocystis rodentifelis*, *Sarcocystis scandinavica*, *Sarcocystis silva*,
*Sarcocystis sinensis*, *Sarcocystis singaporensis*, *Sarcocystis suihominis*, *Sarcocystis taeniata*, *Sarcocystis tarandi*,
*Sarcocystis tarandivulpes*, *Sarcocystis tenella*, *Sarcocystis truncata*, *Sarcocystis turdusi*, *Sarcocystis wobeseri*,
*Sarcocystis zamani*, *Sarcocystis zuoi*, and unclassified *Sarcocystis*.
*Tetratrichomonas* (Scientific classification: Eukaryota; Parabasalia; Trichomonadida; Trichomonadidae) including
*Tetratrichomonas brumpti*, *Tetratrichomonas buttreyi*, *Tetratrichomonas gallinarum*, *Tetratrichomonas limacis*,
*Tetratrichomonas prowazeki*, *Tetratrichomonas undula*, and unclassified *Tetratrichomonas*.
*Theileria* (Scientific classification: Eukaryota; Alveolata; Apicomplexa; Aconoidasida; Piroplasmida; Theileriidae)
including *Theileria annae*, *Theileria annulata*, *Theileria annulata* strain Ankara, *Theileria bicornis*, *Theileria
brachyuri*, *Theileria buffeli*, *Theileria* cf. *buffeli* A MEC-2013, *Theileria* cf. *buffeli* B, *Theileria* cf. *buffeli* C, *Theileria*
cf. *buffeli* MC-2012, *Theileria capreoli*, *Theileria cervi*, *Theileria equi*, *Theileria fuliginosus*, *Theileria lestoquardi*,
*Theileria* cf. *lestoquardi* (Atbara), *Theileria* cf. *lestoquardi* G4, *Theileria* cf. *lestoquardi* G6, *Theileria luwenshuni*,
*Theileria mutans*, *Theileria* cf. *mutans* 3, *Theileria* cf. *mutans* A MEC-2013, *Theileria* cf. *mutans* B MEC-2013,
*Theileria* cf. *mutans* C MEC-2013, *Theileria orientalis*, *Theileria orientalis* complex isolate 9172, *Theileria orientalis*
complex isolate 9196, *Theileria orientalis* strain Shintoku, *Theileria ovis*, *Theileria* cf. *ovis* G4, *Theileria* cf. *ovis* G6,
*Theileria parva*, *Theileria parva bovis*, *Theileria parva lawrencei*, *Theileria parva parva*, *Theileria parva* strain
Muguga, *Theileria penicillata*, *Theileria separata*, *Theileria sergenti*, *Theileria sinensis*, *Theileria* cf. *sinensis*, TABLE 1-continued

*Theileria* cf. *sinensis* MC-2012, *Theileria taurotragi*, *Theileria uilenbergi*, *Theileria velifera*, *Theileria* cf. *velifera* A, *Theileria* cf. *velifera* A MEC-2013, *Theileria* cf. *velifera* B, *Theileria* cf. *velifera* B MEC-2013, *Theileria* cf. *velifera* (*Syncerus caffer*), *Theileriayoungi*, *Theileria* sp., and unclassified *Theileria*.
*Toxoplasma* (Scientific classification: Eukaryota; Alveolata; Apicomplexa; Conoidasida; Coccidia; Eucoccidiorida; Eimeriorina; Sarcocystidae) including *Toxoplasma gondii*.
*Trichomonas* (Scientific classification: Eukaryota; Parabasalia; Trichomonadida; Trichomonadidae) including *Trichomonas canistomae*, *Trichomonas equibuccalis*, *Trichomonas gallinae*, *Trichomonas stableri*, *Trichomonas tenax*, and *Trichomonas vaginalis*.
*Tritrichomonas* (Scientific classification: Eukaryota; Parabasalia; Tritrichomonadida; Tritrichomonadidae) including *Tritrichomonas augusta*, *Tritrichomonas foetus*, *Tritrichomonas mobilensis*, *Tritrichomonas muris*, *Tritrichomonas nonconforma*, and *Tritrichomonas suis*.
*Trypanosoma* (Scientific classification: Eukaryota; Euglenozoa; Kinetoplastida; Trypanosomatidae) including Subgenus *Duttonella* (*Trypanosoma vivax* and *Trypanosoma* sp. T78), Subgenus *Herpetosoma* (*Trypanosoma blanchardi*, *Trypanosoma lewisi*, *Trypanosoma rabinowitschae*, *Trypanosoma rangeli*, *Trypanosoma* sp. SJP-2011), Subgenus *Nannomonas* (*Trypanosoma congolense*, *Trypanosoma simiae*, *Trypanosoma simiae Tsavo*, *Trypanosoma* sp. Fly9), Subgenus *Schizotrypanum* (*Trypanosoma cruzi*, *Trypanosoma dionisii*, *Trypanosoma erneyi*, *Trypanosoma vespertilionis*), *Trypanosoma* with unspecified subgenus (*Trypanosoma avium*, *Trypanosoma* cf. *avium* TRM-2012, *Trypanosoma bennetti*, *Trypanosoma binneyi*, *Trypanosoma boissoni*, *Trypanosoma caninum*, *Trypanosoma carassii*, *Trypanosoma cascavelli*, *Trypanosoma cervi*, *Trypanosoma chattoni*, *Trypanosoma chelodinae*, *Trypanosoma cobitis*, *Trypanosoma conorhini*, *Trypanosoma copemani*, *Trypanosoma corvi*, *Trypanosoma culicavium*, *Trypanosoma cyclops*, *Trypanosoma danilewskyi*, *Trypanosoma desterrensis*, *Trypanosoma everetti*, *Trypanosoma evotomys*, *Trypanosoma fallisi*, *Trypanosoma gallinarum*, *Trypanosoma godfreyi*, *Trypanosoma granulosum*, *Trypanosoma grayi*, *Trypanosoma grosi*, *Trypanosoma hastatus*, *Trypanosoma irwini*, *Trypanosoma kuseli*, *Trypanosoma leeuwenhoeki*, *Trypanosoma livingstonei*, *Trypanosoma mega*, *Trypanosoma melophagium*, *Trypanosoma microti*, *Trypanosoma minasense*, *Trypanosoma murmanensis*, *Trypanosoma musculi*, *Trypanosoma nabiasi*, *Trypanosoma neveulemairei*, *Trypanosoma nudigobii*, *Trypanosoma ophiocephali*, *Trypanosoma otospermophili*, *Trypanosoma percae*, *Trypanosoma pestanai*, *Trypanosoma pleuronectidium*, *Trypanosoma ralphi*, *Trypanosoma ranarum*, *Trypanosoma rotatorium*, *Trypanosoma scelopori*, *Trypanosoma siniperca*, *Trypanosoma terrestris*, *Trypanosoma theileri*, *Trypanosoma therezieni*, *Trypanosoma triglae*, *Trypanosoma varani*), Subgenus *Trypanozoon* (*Trypanosoma brucei*, *Trypanosoma* cf. *brucei Msubugwe*, *Trypanosoma equiperdum*, *Trypanosoma evansi*, and unclassified *Trypanosoma*).
Tyzzeria (Scientific classification: Eukaryota; Alveolata; Apicomplexa; Conoidasida; Coccidia; Eucoccidiorida; Eimeriorina; Eimeriidae) species.
*Wenyonella* (Scientific classification: Eukaryota; Alveolata; Apicomplexa; Conoidasida; Coccidia; Eucoccidiorida; Eimeriorina; Eimeriidae) species.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which:

FIG. 1 presents the chemical name and chemical structure of the compounds NCL001 to NCL230;

FIG. 11 is a table illustrating the physicochemical and metabolic characteristics of nine NCL compounds;

DESCRIPTION OF EMBODIMENTS

General

Figure 2:
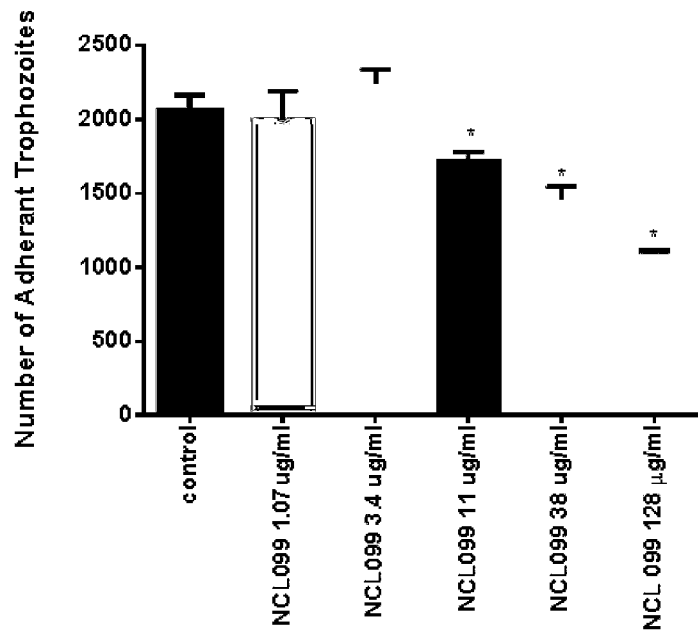
FIG. 2 is a graph illustrating the activity of NCL099 against *Giardia duodenalis*.

Before describing the present invention in detail, it is to be understood that the invention is not limited to particular exemplified methods or compositions disclosed herein. It is also to be understood that the terminology used herein is for the purpose of describing particular embodiments of the invention only, and is not intended to be limiting.

All publications referred to herein, including patents or patent applications, are incorporated by reference in their entirety. However, applications that are mentioned herein are referred to simply for the purpose of describing and disclosing the procedures, protocols, and reagents referred to in the publication which may have been used in connection with the invention. The citation of any publications referred to herein is not to be construed as an admission that the invention is not entitled to antedate such disclosure by virtue of prior invention.

In addition, the carrying out of the present invention makes use of, unless otherwise indicated, conventional microbiological techniques within the skill of the art. Such conventional techniques are known to the skilled worker.

As used herein, and in the appended claims, the singular forms "a", "an", and "the" include the plural unless the context clearly indicates otherwise.

Unless otherwise indicated, all technical and scientific terms used herein have the same meanings as commonly understood by one of ordinary skill in the art to which this invention belongs. Although any materials and methods similar to, or equivalent to, those described herein may be used to carry out the present invention, the preferred materials and methods are herein described.

The invention described herein may include one or more ranges of values (e.g. size, concentration, dose etc). A range of values will be understood to include all values within the range, including the values defining the range, and values adjacent to the range that lead to the same or substantially the same outcome as the values immediately adjacent to that value which define the boundary of the range.

The pharmaceutical or veterinary compositions of the invention may be administered in a variety of unit dosages depending on the method of administration, target site, physiological state of the patient, and other medicaments administered. For example, unit dosage form suitable for oral administration include solid dosage forms such as a powder, tablets, pills, and capsules, and liquid dosage forms, such as elixirs, syrups, solutions and suspensions. The active ingredients may also be administered parenterally in sterile liquid dosage forms. Gelatin capsules may contain the active ingredient and inactive ingredients such as powder carriers, glucose, lactose, sucrose, mannitol, starch, cellulose or cellulose derivatives, magnesium stearate, stearic acid, sodium saccharin, talcum, magnesium carbonate, and the like.

The phrase "therapeutically effective amount" as used herein refers to an amount sufficient to inhibit protozoan growth associated with a protozoan infection or colonisation. That is, reference to the administration of the therapeutically effective amount of a compound of Formula I according to the methods or compositions of the invention refers to a therapeutic effect in which substantial protozoacidal or protozoastatic activity causes a substantial inhibition of protozoan infection. The term "therapeutically effective amount" as used herein, refers to a sufficient amount of the composition to provide the desired biological, therapeutic, and/or prophylactic result. The desired results include elimination of protozoan infection or colonisation or reduction and/or alleviation of the signs, symptoms, or causes of a disease, or any other desired alteration of a biological system. An effective amount in any individual case may be determined by one of ordinary skill in the art using routine experimentation. In relation to a pharmaceutical or veterinary composition, effective amounts can be dosages that are recommended in the modulation of a diseased state or signs or symptoms thereof. Effective amounts differ depending on the composition used and the route of administration employed. Effective amounts are routinely optimized taking into consideration pharmacokinetic and pharmacodynamic characteristics as well as various factors of a particular patient, such as age, weight, gender, etc and the area affected by disease or disease causing microbes.

As referred to herein, the terms "treatment" or "treating" refers to the full or partial removal of the symptoms and signs of the condition. For example, in the treatment of a protozoan infection or colonisation, the treatment completely or partially removes the signs of the infection. Preferably in the treatment of infection, the treatment reduces or eliminates the infecting protozoan pathogen leading to microbial cure.

As referred to herein, the term "protozoa" refers to members of a large domain of eukaryotic unicellular microorganisms. Typically a few micrometres in length, protozoa have a number of shapes, ranging from spheres to rods and spirals and can be present as individual cells or present in linear chains or clusters of variable numbers and shape. Preferably the terms "protozoa" and its adjectives "protozoan" "protozoal" refer to protozoa. The terms may refer to an antiprotozoal-sensitive strain or an antiprotozoal-resistant strain.

Referred to herein, the term "resistant protozoa" refers a protozoa isolate that demonstrates resistance to anyone of the following antimicrobial agents listed in Table 2.

TABLE 2

Antimicrobial agents

| Chemical Class | Examples |
| --- | --- |
| 4-aminoquinoline | Amodiaquine, chloroquine, hydroxychloroquine, piperaquine (bis-4-aminoquinoline) |
| 8-aminoquinoline | Bulaquine, pamaquine, Primaquine, tafenoquine |
| Acetamide | Thiolutin |
| Acridine dye | Acriflavine, mepacrine (quinacrine) |
| Alkylphosphocholine | Miltefosine |
| Allylamine | Terbinafine |
| Aminoglycosides | Paromomycin |
| Aminophenanthridium | Homidium, isometamidium chloride, |
| Aminopyridine antimalarials | MMV390048 |
| Antimonials, pentavalent | Sodium stibogluconate, meglumine antimoniate |
| Arsenicals (trivalent & pentavalent) | Acetarsol (5+), arsthinol (3+), carbarsone (5+), difetarsone (5+), glycobiarsol (5+), melarsomine (3+), melarsoprol (3+), nitarsone (5+), oxophenarsine (3+), roxarsone (5+), tryparsamide (5+) |
| Arylaminoalcohol | Halofantrine, lumefantrine, quinine/quinidine |
| Azo naphthalene dyes | Trypan blue, trypan red |
| Azoles (triazoles and imidazoles) | Albaconazole, itraconazole, ketoconazole, posoconazole, ravuconazole |
| Benzamide | Zoxamide |
| Benzenediol | Resveratrol |
| Benzimidazoles and probenzimidazoles | Albendazole, fenbendazole, febantel, mebendazole, omeprazole |
| Bicyclohexylammonium | Fumagillin |
| Carbamate | Disulfiram |
| Cinnamamido adenosine | Puromycin |
| Coumarin | Flocoumafen |
| Diamidines | Amicarbalide, diminazene diaceturate, imidocarb dipropionate, pafuramidine, pentamidine isethionate, phenamidine isethionate, propamidine, stilbamidine |

TABLE 2-continued

Antimicrobial agents

| Chemical Class | Examples |
| --- | --- |
| Dichloroacetamide | Clefamide, Etofamide, Teclozan |
| Dichloroacetamide | Diloxanide furoate |
| Difluoromethylornithine | Eflornithine |
| Dihydrofolate reductase/thymidyate synthase inhibitors | Diaveridine, ormetoprim, pyrimethamine, trimethoprim |
| Dihydrooratate dehydrogenase (DHODH) inhibitors | |
| Dinitroaniline | Trifluralin, oryzalin |
| Dinitrocarbanilide + pyrimidinol | Nicarbazin |
| Dithiocarbamate | Thiram |
| Ethoxybenzoic acid | Ethopabate |
| Fluoroquinolones | Ciprofloxacin, enrofloxacin, marbofloxacin |
| Guanidines | Chloroproguanil, cycloguanil, lauroguadine, proguanil, Robenidine |
| Halogenated 8-hydroxyquinoline | Iodoquinol, chlorquinaldol, tilbroquinol, broxyquinoline, diiodohydroxyquinoline, clioquinol |
| Hydroxyoxo-cyclohexenecarbaldehyde oxime | Sethoxydim, tralkoxydim, alloxydim, clethodim and cycloxydim |
| Hydroxyquinolones | Buquinolate, decoquinate, nequinate |
| Imidazolopiperazine | Kaf156 |
| Isoquinoline | Emetine/dehydroemetine |
| Lincosamides | Clindamycin, lincomycin |
| Macrolides | Azithromycin, clarithromycin, erythromycin, roxithromycin, spiramycin |
| Methylquinolinium | Quinapyramine, quinuronium sulfate |
| Miscellaneous | Pyridaben |
| Naphthoquinones | Atovaquone, buparvaquone, parvaquone |
| Naphthyridine | Pyronaridine |
| Nitrobenzamides | Aklomide, dinitolmide |
| Nitrofurans | Nifurtimox, furaltodone, furazolidone, nifuratel, nifuroxime, nifursol |
| Nitroimidazoles | Azanidazole, benznidazole, carnidazole, dimetridazole, fexnidazole, ipronidazole, metronidazole, nimorazole, ornidazole, propenidazole, ronidazole, satranidazole, secnidazole, ternidazole, tinidazole |
| Nitrothiazoles | Nitazoxanide, aminitrozole (nithiamide), forminitrazole, niridazole, tenonitrozole |
| Organometallic antiprotozoal | Auranofin, ferroquine |
| Oxaborole (including benzoxaboroles) | SCYX-7158 |
| Phenoxyphenol | Triclosan |
| phenylsulfamide | Tolylfluanid |
| Phosphonic acid derivative | Fosmidomycin |
| Phosphonomethylglycine | Glyphosate |
| Phosphoramidothioic acid | Amiprofos-methyl |
| Polyene | Amphotericin B, mepartricin, hachimycin, Hamycin |
| Polyether ionophores | Laidlomycin, lasalocid, maduramicin, monensin, narasin, salinomycin, semduramicin |
| Polypeptide | Bacitracin (zinc, methylene disalicylate), cecropins, cyclosporins, dermaseptin, magainins, tachyplesin, thiostrepton |
| Polysulfonated naphthylamine | Suramin |
| Propylphosphonic acid | Fosmidomycin |
| Purinamine | Arprinocid |
| Pyrazolopyran | |
| Pyrazolopyrimidine | Allopurinol |
| Pyridinols | Clopidol |
| Pyrimidine | Fenarimol |
| Pyrrolidinediol | Anisomycin |
| Quinazolinone | Febrifugine, halofuginone |
| Quinoline | Mefloquine, nequinate (methyl benzoquate), quinfamide, tiliquinol |
| Quinoxaline | Carbadox |
| Rifamycin | Rifaximin |
| Spiroindolone | KAE609 (formerly NITD609), cipargamin |
| Strobilurin | Fluacrypyrim, azoxystrobin, trifloxystrobin, dimoxystrobin |
| Sulfonamides | Sulfadiazine, sulfadimethoxine, sulfadoxine, sulfaguanidine, sulfamethazine (sulfadimidine), sulfamethoxazole, sulfanitran, sulfaquinoxaline, sulfamethoxypyrazine, cyazofamid |
| Sulphone | Dapsone |
| Tetracyclines | Chlortetracycline, doxycycline, oxytetracycline, tetracycline, tigecycline |
| Tetraoxanes | |
| Thiamine analogs | Amprolium |
| Thiophenone | Thiolactomycin |
| Translation elongation factor 2 (eEF2) inhibitor | DDD107498 |

TABLE 2-continued

Antimicrobial agents

| Chemical Class | Examples |
| --- | --- |
| Triazine | Clazuril, diclazuril, ponazuril, toltrazuril |
| Triazole | Bitertanol |
| Trioxane (sesquiterpene lactones, artemisinins) | Artemether, artesunate, dihydroartemisinin, artemotil, artemisinin, arteether, artemisone |
| Trioxolane (including ozonides) | Arterolane, OZ277, OZ439 |

Pharmaceutically and veterinary acceptable salts include salts which retain the biological effectiveness and properties of the compounds of the present disclosure and which are not biologically or otherwise undesirable. In many cases, the compounds disclosed herein are capable of forming acid and/or base salts by virtue of the presence of amino and/or carboxyl groups or groups similar thereto. Acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as by way of example only, alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amines, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Pharmaceutically and veterinary acceptable acid addition salts may be prepared from inorganic and organic acids. The inorganic acids that can be used include, by way of example only, hydrochloric acid, hydrobromic acid, sulfuric acid, nitric acid, phosphoric acid, and the like. The organic acids that can be used include, by way of example only, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The pharmaceutically or veterinary acceptable salts of the compounds useful in the present disclosure can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences. 17th ed., Mack Publishing Company, Easton, Pa. (1985), p. 1418, the disclosure of which is hereby incorporated by reference. Examples of such acceptable salts are the iodide, acetate, phenyl acetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, γ-hydroxybutyrate, β-hydroxybutyrate, butyne-1,4-dioate, hexyne-1,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

The pharmaceutical or veterinary compositions of the invention may be formulated in conventional manner, together with other pharmaceutically acceptable excipients if desired, into forms suitable for oral, parenteral, or topical administration. The modes of administration may include parenteral, for example, intramuscular, subcutaneous and intravenous administration, oral administration, topical administration and direct administration to sites of infection such as intraocular, intraaural, intrauterine, intranasal, intramammary, intraperitoneal, intralesional, etc.

The pharmaceutical or veterinary compositions of the invention may be formulated for oral administration. Traditional inactive ingredients may be added to provide desirable colour, taste, stability, buffering capacity, dispersion, or other known desirable features. Examples include red iron oxide, silica gel, sodium laurel sulphate, titanium dioxide, edible white ink, and the like. Conventional diluents may be used to make compressed tablets. Both tablets and capsules may be manufactured as sustained-release compositions for the continual release of medication over a period of time. Compressed tablets may be in the form of sugar coated or film coated tablets, or enteric-coated tablets for selective disintegration in the gastrointestinal tract. Liquid dosage forms for oral administration may contain colouring and/or flavouring to increase patient compliance. As an example, the oral formulation comprising compounds of the invention may be a tablet comprising any one, or a combination of, the following excipients: calcium hydrogen phosphate dehydrate, microcrystalline cellulose, lactose, hydroxypropyl methyl cellulose, and talc.

The compositions described herein may be in the form of a liquid formulation. Examples of preferred liquid compositions include solutions, emulsions, injection solutions, solutions contained in capsules. The liquid formulation may comprise a solution that includes a therapeutic agent dissolved in a solvent. Generally, any solvent that has the desired effect may be used in which the therapeutic agent dissolves and which can be administered to a subject. Generally, any concentration of therapeutic agent that has the desired effect can be used. The formulation in some variations is a solution which is unsaturated, a saturated or a supersaturated solution. The solvent may be a pure solvent or may be a mixture of liquid solvent components. In some variations the solution formed is an in situ gelling formulation. Solvents and types of solutions that may be used are well known to those versed in such drug delivery technologies.

The composition described herein may be in the form of a liquid suspension. The liquid suspensions may be prepared according to standard procedures known in the art. Examples of liquid suspensions include micro-emulsions, the formation of complexing compounds, and stabilising suspensions. The liquid suspension may be in undiluted or concentrated form. Liquid suspensions for oral use may contain suitable preservatives, antioxidants, and other excipients known in the art functioning as one or more of dispersion agents, suspending agents, thickening agents, emulsifying agents, wetting agents, solubilising agents, stabilising agents, flavouring and sweetening agents, colouring agents, and the like. The liquid suspension may contain glycerol and water.

The composition described herein may be in the form of an oral paste. The oral paste may be prepared according to standard procedures known in the art.

The composition is described herein may be in the form of a liquid formulation for injection, such as intra-muscular injection, and prepared using methods known in the art. For example, the liquid formulation may contain polyvinylpyrrolidone K30 and water.

The composition is described herein may be in the form of topical preparations. The topical preparation may be in the form of a lotion or a cream, prepared using methods known in the art. For example, a lotion may be formulated with an aqueous or oily base and may include one or more excipients known in the art, functioning as viscosity enhancers, emulsifying agents, fragrances or perfumes, preservative agents, chelating agents, pH modifiers, antioxidants, and the like. For example, the topical formulation comprising one or more compounds of the invention may be a gel comprising anyone, or a combination of, the following excipients: PEG 8000, PEG 4000, PEG 200, glycerol, propylene glycol. The NCL812 compound may further be formulated into a solid dispersion using SoluPlus (BASF, www.soluplus.com) and formulated with anyone, or a combination of, the following excipients: PEG 8000, PEG 4000, PEG 200, glycerol, and propylene glycol.

For aerosol administration, the composition of the invention is provided in a finely divided form together with a non-toxic surfactant and a propellant. The surfactant is preferably soluble in the propellant. Such surfactants may include esters or partial esters of fatty acids.

The compositions of the invention may alternatively be formulated for delivery by injection. As an example, the compound is delivered by injection by any one of the following routes: intravenous, intramuscular, intradermal, intraperitoneal, and subcutaneous.

The compositions of the invention may alternatively be formulated using nanotechnology drug delivery techniques such as those known in the art. Nanotechnology-based drug delivery systems have the advantage of improving bioavailability, patient compliance and reducing side effects.

The formulation of the composition of the invention includes the preparation of nanoparticles in the form of nanosuspensions or nanoemulsions, based on compound solubility. Nanosuspensions are dispersions of nanosized drug particles prepared by bottom-up or top-down technology and stabilised with suitable excipients. This approach may be applied to the compounds of the invention which can have poor aqueous and lipid solubility, in order to enhance saturation solubility and improve dissolution characteristics. An example of this technique is set out in Sharma and Garg (2010) (Pure drug and polymer-based nanotechnologies for the improved solubility, stability, bioavailability, and targeting of anti-HIV drugs. *Advanced Drug Delivery Reviews*, 62: p. 491-502). Saturation solubility will be understood to be a compound-specific constant that depends on temperature, properties of the dissolution medium, and particle size (<1-2 µm).

The composition of the invention may be provided in the form of a nanosuspension. For nanosuspensions, the increase in the surface area may lead to an increase in saturation solubility. Nanosuspensions are colloidal drug delivery systems, consisting of particles below 1 µm. Compositions of the invention may be in the form of nanosuspensions including nanocrystalline suspensions, solid lipid nanoparticles (SLNs), polymeric nanoparticles, nanocapsules, polymeric micelles and dendrimers. Nanosuspensions may be prepared using a top-down approach where larger particles may be reduced to nanometre dimensions by a variety of techniques known in the art including wet-milling and high-pressure homogenisation. Alternatively, nanosuspensions may be prepared using a bottom-up technique where controlled precipitation of particles may be carried out from solution.

The composition of the invention may be provided in the form of a nanoemulsion. Nanoemulsions are typically clear oil-in-water or water-in-oil biphasic systems, with a droplet size in the range of 100-500 nm, and with compounds of interest present in the hydrophobic phase. The preparation of nanoemulsions may improve the solubility of the compounds of the invention described herein, leading to better bioavailability. Nanosized suspensions may include agents for electrostatic or steric stabilisation such as polymers and surfactants. Compositions in the form of SLNs may comprise biodegradable lipids such as triglycerides, steroids, waxes and emulsifiers such as soybean lecithin, egg lecithin, and poloxamers. The preparation of a SLN preparation may involve dissolving/dispersing drug in melted lipid followed by hot or cold homogenisation. If hot homogenisation is used, the melted lipidic phase may be dispersed in an aqueous phase and an emulsion prepared. This may be solidified by cooling to achieve SLNs. If cold homogenisation is used, the lipidic phase may be solidified in liquid nitrogen and ground to micron size. The resulting powder may be subjected to high-pressure homogenisation in an aqueous surfactant solution.

The Compounds of Formula I as described herein may be dissolved in oils/liquid lipids and stabilised into an emulsion formulation. Nanoemulsions may be prepared using high- and low-energy droplet reduction techniques. High-energy methods may include high-pressure homogenisation, ultrasonication and microfluidisation. If the low-energy method is used, solvent diffusion and phase inversion will generate a spontaneous nanoemulsion. Lipids used in nanoemulsions may be selected from the group comprising triglycerides, soybean oil, safflower oil, and sesame oil. Other components such as emulsifiers, antioxidants, pH modifiers and preservatives may also be added.

The composition may be in the form of a controlled-release formulation and may include a degradable or non-degradable polymer, hydrogel, organogel, or other physical construct that modifies the release of the compound. It is understood that such formulations may include additional inactive ingredients that are added to provide desirable colour, stability, buffering capacity, dispersion, or other known desirable features. Such formulations may further include liposomes, such as emulsions, foams, micelles, insoluble monolayers, liquid crystals, phospholipid dispersions, lamellar layers and the like. Liposomes for use in the invention may be formed from standard vesicle-forming lipids, generally including neutral and negatively charged phospholipids and a sterol, such as cholesterol.

The formulations of the invention may have the advantage of increased solubility and/or stability of the compounds, particularly for those formulations prepared using nanotechnology techniques. Such increased stability and/or stability of the compounds of Formula I may improve bioavailability and enhance drug exposure for oral and/or parenteral dosage forms.

Throughout this specification, unless the context requires otherwise, the word "comprise" or variations such as "comprises" or "comprising", will be understood to imply the inclusion of a stated integer or group of integers but not the exclusion of any other integer or group of integers.

EXAMPLES

Example 1: Preparation of NCL812 Analogues

Materials and Methods

NCL812

Analytical grade NCL812 with a defined potency of 960 mg/g (i.e. 96%) was obtained. The powder was stored in a sealed sample container out of direct sunlight and at room temperature at the study site. Aliquots (1 mL) of stock solution (containing 25.6 mg/mL of NCL812 in DMSO) were prepared and stored at −80° C. and defrosted immediately before use.

Synthesising and Testing of NCL812 Analogues

Analogues NCL001 to NCL275, as identified in FIG. 1, were synthesised using standard methods in the art. As an example, the methods used to manufacture compounds NCL097; NCL157; NCL179; NCL188; NCL195; and NCL196 are as follows:

NCL 097 (2,2'-bis[(3,4,5-trihydroxyphenyl)methylene]carbonimidic Dihydrazide Hydrochloride)

A suspension of 3,4,5-trihydroxybenzaldehyde (412.0 mg, 2.673 mmol, 2.21 eq.) and N,N'-diaminoguanidine hydrochloride (152.0 mg, 1.211 mmol) in EtOH (5 mL) was subjected to microwave irradiation (150 W) at 100° C. for 10 min. The reaction was then allowed to cool to ambient temperature. The resulting precipitate was collected and washed with chilled EtOH (5 mL) and Et$_2$O (5 mL) to afford the carbonimidicdihydrazide (369.0 mg, 77%) as a pale brown solid. M.P. 292° C. (Decomp.). $^1$H NMR (300 MHz, DMSO-d6) δ 9.06 (br s, 6H), 8.25-8.01 (m, 4H), 6.83 (s, 4H). $^{13}$C NMR (75 MHz, DMSO-d6) δ 152.2, 149.7, 146.2, 136.5, 123.7, 107.4. LRMS (ESI$^+$): 361.95 [M+1]$^+$.

NCL157 (2,2'-bis[(2-amino-4-chlorophenyl)methylene]carbonimidic Dihydrazide Hydrochloride)

Synthesis of 2-amino-4-chloro-N-methoxy-N-methylbenzamide

To a solution of 2-amino-4-chlorobenzoic acid (5.6691 g, 33.041 mmol), N,O-dimethylhydroxylamine hydrochloride (5.7504 g, 58.954 mmol, 1.78 eq.), N-(3-dimethylaminopropyl)-N'-ethylcarbodiimide hydrochloride (7.7925 g, 40.649 mmol, 1.23 eq.) and N-hydroxybenzotriazole hydrate (5.2371 g, 38.793 mmol (anhydrous basis), 1.17 eq.) in DMF (100 mL) was added diisopropylethylamine (18.0 mL, 13.4 g, 104 mmol, 3.15 eq.) and the brown solution stirred at ambient temperature for 7 h. The reaction was then concentrated in vacuo before dilution with 1M NaOH (100 mL) and extracting with CH$_2$Cl$_2$ (3×100 mL) The combined organic extracts were washed with 1M HCl (100 mL) before drying over MgSO$_4$ and concentrating in vacuo to afford a brown syrup. This oil was then further dried at 60° C. under high vacuum to afford the crude Weinreb amide (7.021 g, 99%) as a brown syrup that crystallised on standing. The crude material was used without further purification. $^1$H NMR (400 MHz, CDCl$_3$) δ 7.24 (d, J=8.4 Hz, 1H), 6.62 (d, J=18 Hz, 1H), 6.54 (dd, J=8.4, 1.9 Hz, 1H), 4.75 (s, 2H), 3.48 (s, 3H), 3.24 (s, 3H). $^{13}$C NMR (101 MHz, CDCl$_3$) δ 169.2, 148.4, 137.1, 130.6, 116.6, 116.1, 115.0, 61.1, 34.0.

Synthesis of 2-amino-4-chlorobenzaldehyde

Crude 2-amino-4-chloro-N-methoxy-N-methylbenzamide (751.1 mg, 3.532 mmol) was broken up into ca. 120 mg batches and each dissolved in THF (10 mL) and cooled to 0° C. before LiAlH$_4$ (2M in THF, 0.5 mL) was added to each and the solutions stirred for 16 h, allowing the reactions to achieve room temperature. The reactions were quenched with saturated NH$_4$Cl (1 mL) before being combined, diluted with saturated NaHCO$_3$ (160 mL) and extracted with CHCl$_3$ (2×150 mL, 1×75 mL). The combined organics were dried over MgSO$_4$ and concentrated in vacuo to afford the crude benzaldehyde (463.3 mg, 85%) as yellow/orange crystals. The material was used without further purification. $^1$H (400 MHz, CD$_3$OD) 9.77 (d, J=0.7 Hz, 1H), 7.46 (d, J=8.3 Hz, 1H), 6.83-6.71 (m, 1H), 6.63 (dd, J=8.4, 1.9 Hz, 1H). $^{13}$C NMR (101 MHz, CD$_3$OD) δ 194.6, 153.0, 142.5, 138.4, 118.3, 116.8, 116.1.

Synthesis of 2,2'-bis[(2-amino-4-chlorophenyl)methylene]carbonimidic Dihydrazide Hydrochloride A suspension of 2-amino-4-chlorobenzaldehyde (128.0 mg, 0.823 mmol, 1.78 eq.) and N,N'-diaminoguanidine hydrochloride (58.0 mg, 0.462 mmol) in EtOH (2 mL) was subjected to microwave irradiation (100 W) at 60° C. for 5 minutes. Most solvent was then removed in vacuo, EtOH (1 mL) was added and the flask was transferred to the freezer to effect crystallisation. The resulting precipitate was collected and washed with EtOH (1 mL) to afford the carbonimidicdihydrazide (21.0 mg, 13%) as a pale yellow solid. $^1$H NMR (400 MHz, DMSO-d$_6$) δ 11.71 (br s, 2H), 8.40 (s, 2H), 8.37 (s, 2H), 7.29 (d, J=8.4 Hz, 2H), 6.87 (d, J=2.0 Hz, 2H), 6.73 (br s, 4H), 6.59 (dd, J=8.3, 2.0 Hz, 2H). $^{13}$C NMR (101 MHz, DMSO-d$_6$) δ 152.1, 151.5, 148.9, 136.0, 134.7, 115.1, 114.5, 112.8.

NCL179 (4,6-bis(2-(4-chlorobenzylidene)hydrazinyl)pyrimidin-2-amine)

A suspension of 2-amino-4,6-dihydrazinylpyrimidine (67.3 mg, 0.434 mmol) and 4-chlorobenzaldehyde (198.8 mg, 1.414 mmol, 3.26 eq.) in EtOH (25 mL) was heated at reflux for 16 h. After this time, the condenser was removed and the solution concentrated to approximately 1 mL and the resulting precipitate filtered hot and washed with $Et_2O$ (10 mL) to afford the aminopyrimidine (42.8 mg, 25%) as an off-white amorphous powder. M.P. 275° C. (Decomp.). $^1$H NMR (400 MHz, DMSO) δ 10.70 (s, 2H), 8.02 (s, 2H), 7.67 (d, J=8.4 Hz, 4H), 7.52 (d, J=8.4 Hz, 4H), 6.28 (s, 1H), 5.85 (s, 2H). $^{13}$C NMR (101 MHz, DMSO) δ 162.8, 162.6, 138.8, 134.1, 133.1, 128.9, 127.6, 73.5.

NCL188 ((E)-2-(1-(4-chlorophenyl)pentylidene)hydrazine-1-carboximidamide Hydrochloride)

A suspension of 1-(4-chlorophenyl)pentanone (1.8319 g, 9.3146 mmol, 1.95 eq.) and aminoguanidine hydrochloride (527.6 mg, 4.773 mmol) in EtOH (15 mL) was heated at 65° C. for 16 h. The crude was cooled to ambient temperature before being diluted with $Et_2O$ (60 mL) and cooled to 0° C. to precipitate unreacted aminoguanidine hydrochloride (174.5 mg). The mother liquors were then concentrated in vacuo and the residue dissolved in $Et_2O$ (20 mL). The solution was then boiled and hexanes (10 mL) added to afford the carboximidamide as a cream solid. $^1$H NMR (400 MHz, DMSO) δ 11.54 (s, 1H), 7.99 (d, J=8.7 Hz, 2H), 7.90 (s, 3H), 7.47 (d, J=8.6 Hz, 2H), 2.91-2.82 (m, 2H), 1.48-1.32 (m, 4H), 0.89-0.84 (m, 3H). $^{13}$C NMR (101 MHz, DMSO) δ 156.2, 153.8, 134.8, 134.4, 128.7, 128.4, 28.1, 26.6, 22.0, 13.8

NCL195 (4,6-bis(2-((E)-4-methylbenzylidene)hydrazinyl)pyrimidin-2-amine)

A suspension of 2-amino-4,6-dihydrazinopyrimidine (58.9 mg, 0.380 mmol) and 4-methylbenzaldehyde (0.10 mL, 100 mg, 0.832 mmol, 2.19 eq.) in EtOH (4 mL) was heated at reflux for 16 h. The reaction mixture was cooled to ambient temperature before collecting the pellet-like precipitate, washing with $Et_2O$ (20 mL). The 'pellets' were then crushed and the solid further washed with $Et_2O$ (10 mL) to afford the pyrimidine (85.8 mg, 63%) as a white 'fluffy' powder. M.P. 274-276° C. $^1$H NMR (400 MHz, DMSO) δ 10.51 (s, 2H), 8.00 (s, 2H), 7.54 (d, J=8.0 Hz, 4H), 7.26 (d, J=7.9 Hz, 4H), 6.26 (s, 1H), 5.77 (s, 2H), 2.34 (s, 6H). $^{13}$C NMR (101 MHz, DMSO) δ 162.8, 162.6, 140.1, 138.4, 132.5, 129.4, 126.0, 73.3, 21.0.

NCL196 (4',4'-((1E,1'E)-((2-aminopyrimidine-4,6-diyl)bis(hydrazin-2-yl-1-ylidene))bis(methanylylidene))diphenol)

A suspension of 2-amino-4,6-dihydrazinopyrimidine (70.4 mg, 0.454 mmol) and 4-hydroxybenzaldehyde (140.3 mg, 1.149 mmol, 2.53 eq.) in EtOH (3 mL) was heated at reflux for 16 h. The reaction mixture was cooled to ambient temperature before collecting the precipitate, washing with $Et_2O$ (25 mL), to afford the pyrimidine (91.4 mg, 55%) as an off-white powder. M.P. 298° C. (Decomp.). $^1$H NMR (400 MHz, DMSO) δ 10.31 (s, 2H), 9.74 (s, 2H), 7.94 (s, 2H), 7.48 (d, J=8.6 Hz, 4H), 6.83 (d, J=8.6 Hz, 4H), 6.20 (s, 1H), 5.70 (s, 2H). $^{13}$C (101 MHz, DMSO) δ 162.7, 162.5, 158.3, 140.5, 127.7, 126.3, 115.7, 73.0.

Example 2: Giardia Adherence Assay

Aim.

The aim of this study was to determine the anti-giardial activity of NCL099 and NCL812.

Methods.

Giardia strain WB was grown until confluent (grown and maintained in TYI-S-33 medium with 10% foetal bovine serum). For the assay, media of a confluent culture was replaced with fresh TYI-S-33 medium. Cultures were then cold shocked (on ice) for 40 minutes to detach trophozoites. The cell density of the cultures was adjusted to $1 \times 10^6$ cells/ml and 1 ml was added to each well of a 24 well plate already containing 1 ml of diluted compounds (see below). A coverslip was placed in the bottom of each well and the assay was incubated in an anaerobic environment (candle jar) for 2.5 hours at 37° C. After incubation the coverslips were removed, air-dried and stained with Diff-Quik (a Romanowski stain variant). Coverslips were mounted onto glass slides using polymount. Images at 10× magnification were taken at 5 random locations per coverslip. Dotcount freeware was used to count the number of cells per image and this data was analysed using GraphPad Prism v6. Stock solutions of compounds were prepared in DMSO at 25.6 mg/ml. Compounds were diluted 1:100 in TYI-S-33 medium. A 1:2 serial dilution was then performed in TYI-S-33 medium in 24 well plates.

Results.

Figure 3:
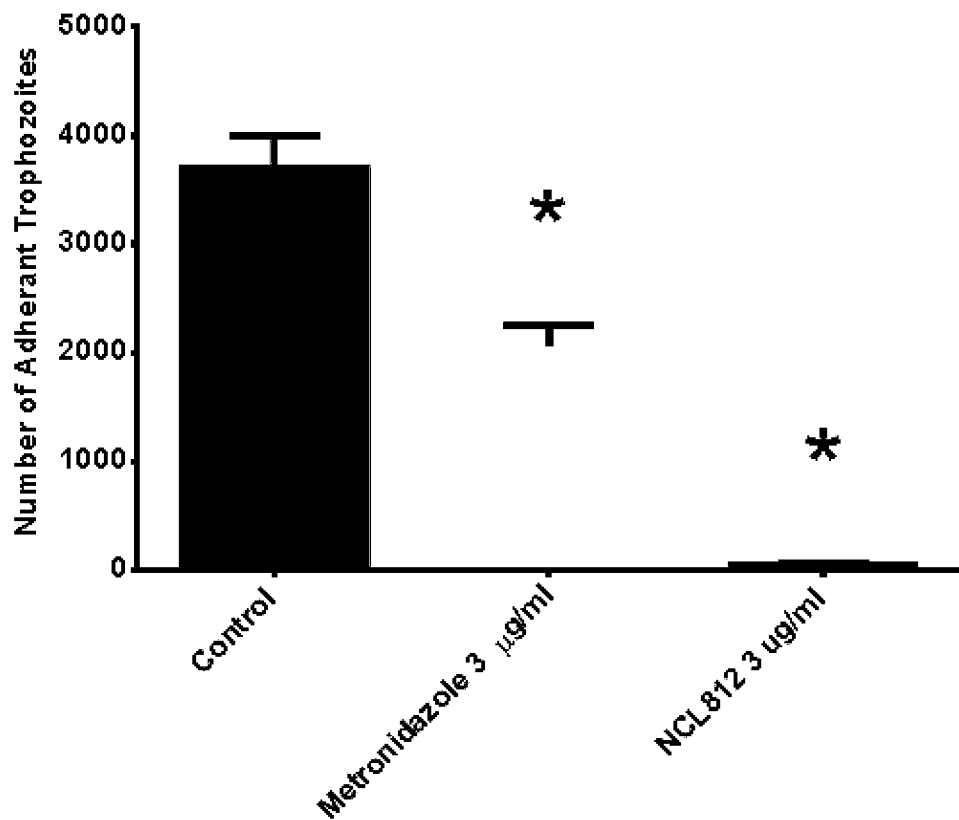
FIG. 3 is a graph illustrating the effect of NCL812 and metronidazole on the adherence of *Giardia duodenalis* trophozoites.

The results of this study are presented in FIGS. 2 to 3. FIG. 2 shows the activity of NCL099 against Giardia duodenalis in vitro. A significant decrease in the number of adherent cells was observed at NCL099 concentrations of 11 μg/ml (P=0.0099), 38 μg/ml (P=0.001) and 128 μg/ml (P=<0.0001) compared to the control (FIG. 2). An increase in activity was seen as the concentration of NCL099 increased. FIG. 3 shows the activity of NCL812 and metronidazole against Giardia duodenalis in vitro. A significant decreases in the number of adherent trophozoites is seen for both metronidazole (P=0.0002) and NCL812 (P=<0.0001). The samples were exposed for 5 hours not 2.5 hours.

Conclusion.

This study demonstrates that NCL099 and NCL812 inhibit the ability of Giardia cells to adhere to a surface therefore limiting the ability of this pathogen to cause disease (as adherence is necessary to cause disease).

Example 3: Resazurin Reduction Assay

Aim.

To determine the activity of NCL812 and NCL062 against Giardia duodenalis in vitro Methods.

Giardia trophozoites were grown until confluent. The media was replaced with fresh media and they were cold shocked for 40 minutes (as above). Cells were diluted to a concentration of ~500 000 cells/ml and 100 μl were added to each well of the assay plate (except media only control). The assay was incubated in an anaerobic environment (candle jar) for 42 hours at 37° C. Alamarblue™ was added to a concentration of 10% and the samples incubated in an anaerobic environment for a further 6 hours. After incubation the absorbance of each sample was read at 570 and 630 nm. The percent reduction of resazurin (Alamarblue™) was calculated and data was analysed with GraphPad Prism v6 software. Assay set-up: the assay was performed in 96 well plates in a total volume of 200 µl. 100 µl of NCL812 or NCL062 (concentration of 25.6 mg/ml in DMSO) or metronidazole (concentration 5 mg/ml in DMSO) stock was added to 9.9 ml of TYI-S-33 medium, then serially diluted 1:2 in the same medium. Cells were added as above.

Results.

Figure 4:
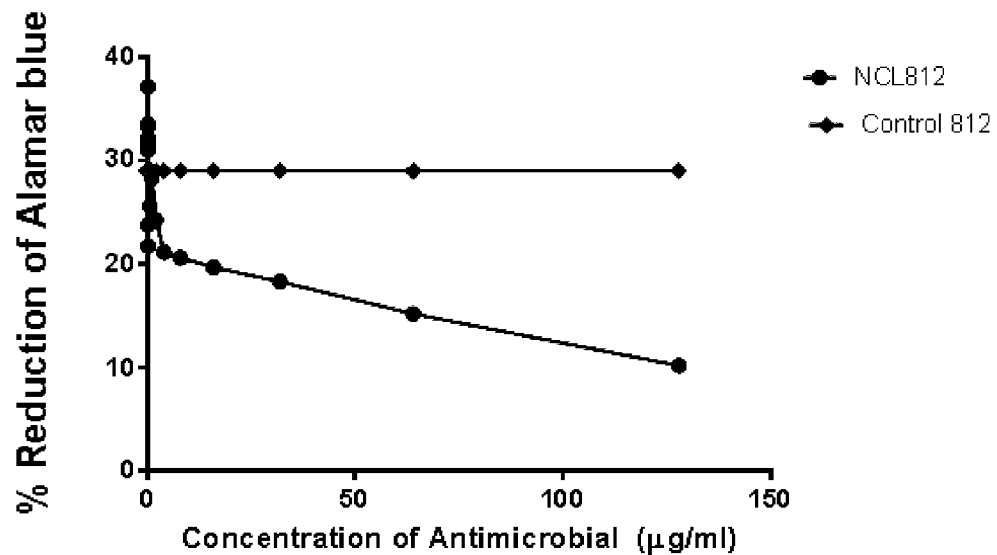
FIG. 4 is a graph illustrating the activity of NCL812 against *Giardia duodenalis*.
Figure 5:
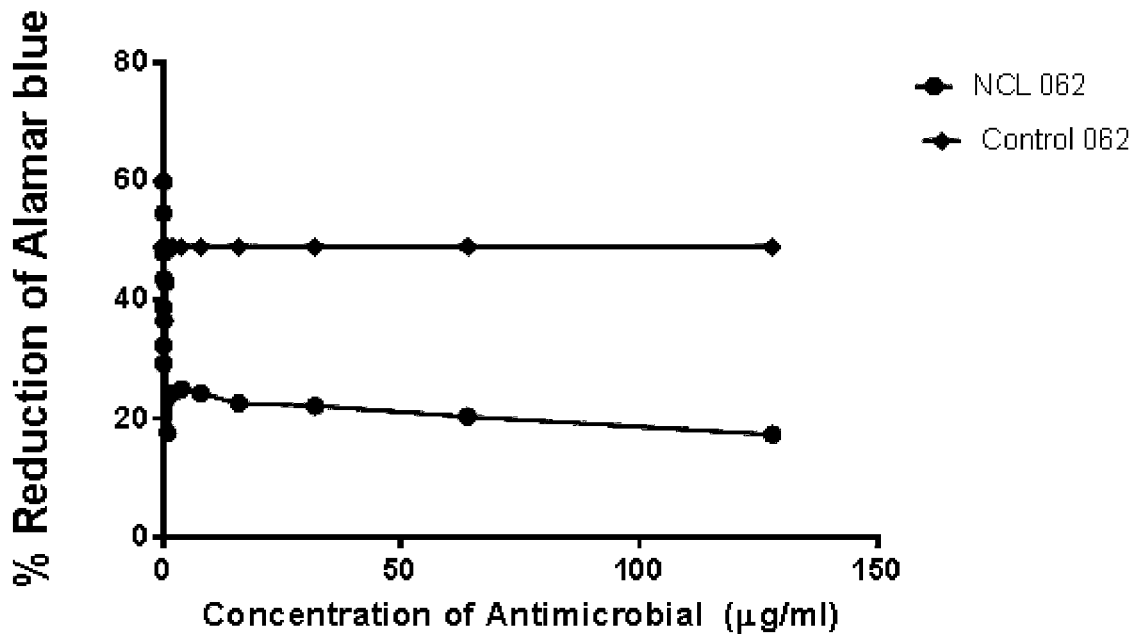
FIG. 5 is a graph illustrating the activity of NCL062 against *Giardia duodenalis*.
Figure 6:
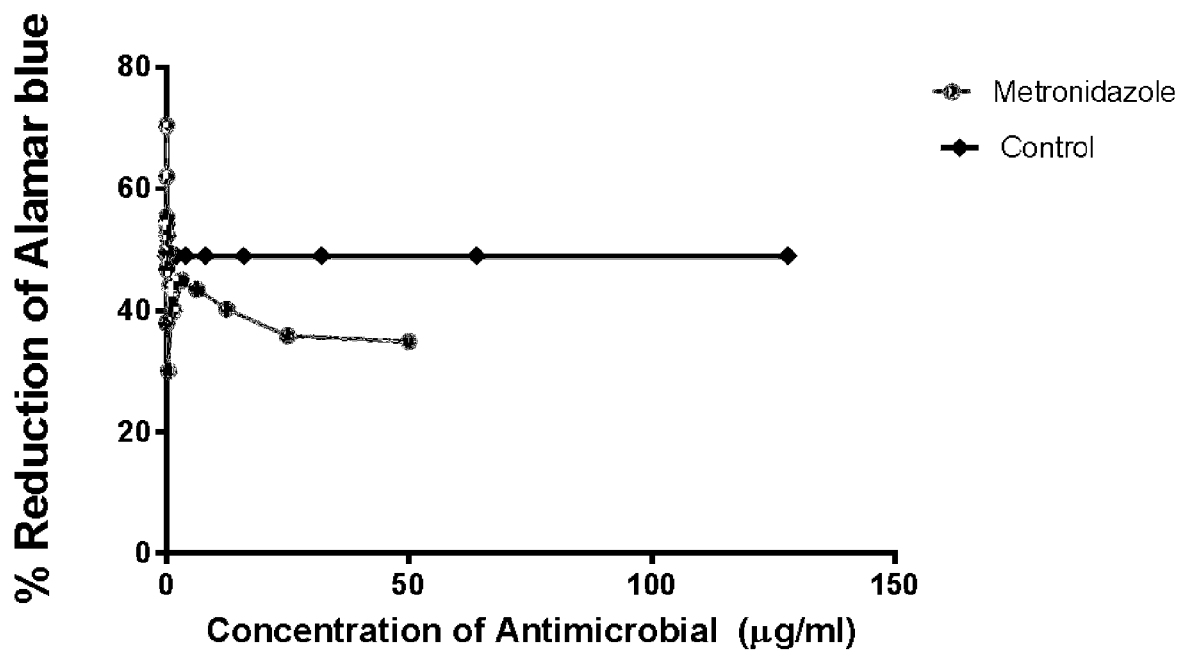
FIG. 6 is a graph illustrating the activity of Metronidazole against *Giardia duodenalis*.

The results are shown in FIGS. 4 to 6. All three compounds tested (NCL812, NCL062 and metronidazole) showed a reduction in the metabolic activity of the trophozoites (indicated by a decreased percentage of reduction of resazurin). Both NCL compounds showed greater activity when compared to metronidazole.

Conclusion.

Both NCL812 and NCL062 show inhibitory activity towards *Giardia duodenalis* trophozoites in vitro.

Example 4: Erythrocyte Haemolysis Assay

Aim.

The aim of this study was to determine the in vitro toxicity of NCL812, NCL099 and NCL062 against mammalian cells.

Methods.

Whole sheep blood was obtained from Thermofisher scientific. The red blood cells were separated from other blood components via centrifugation at 1500 g for 10 minutes and washed with saline 3 times. Erythrocytes were diluted to a concentration of ~1×10$^{10}$ cells/ml in saline. 50 µl of NCL compounds diluted in DMSO (see below) were added to 1.5 ml Eppendorf tubes and 500 µl of diluted red blood cells were added to each tube. Erythrocytes were incubated with compounds for 30 minutes at 37° C. with gentle shaking (75 rpm). After incubation cells were placed on ice for 5 minutes then centrifuged at 1500 rpm for 10 minutes to pellet cells. The supernatant was removed and serially diluted in saline. Absorbance of the supernatant and dilutions were recorded at 550 nm. Sample lysis was compared relative to cells lysed 100% in distilled water and analysed using GraphPad Prism v6 software.

Results.

Figure 7:
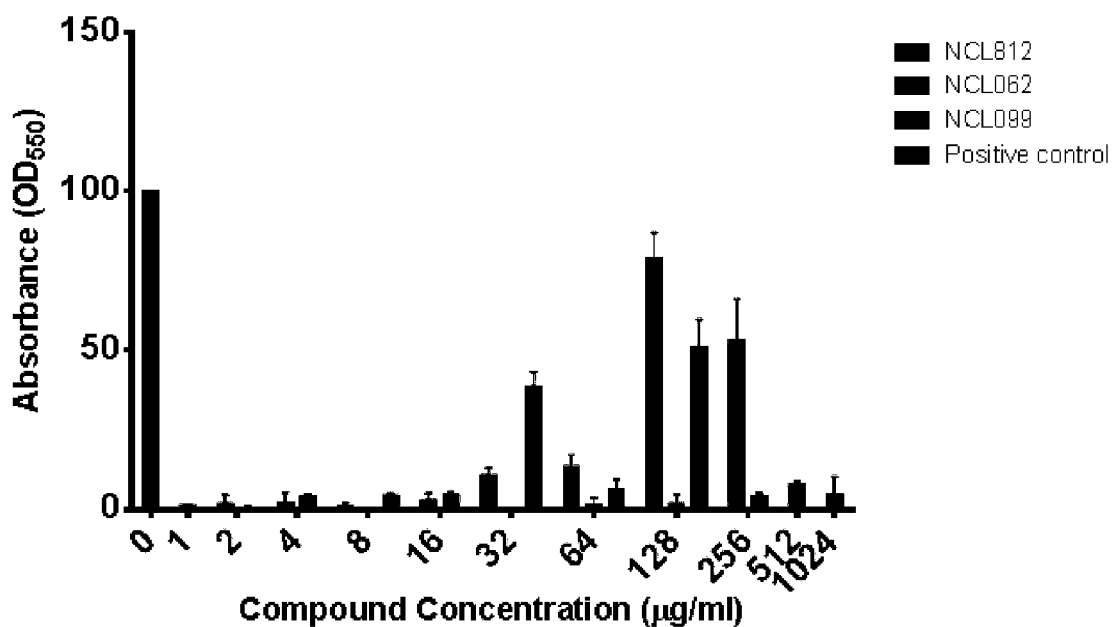
FIG. 7 is a graph illustrating the erythrocyte lysis based on n-fold minimum inhibitory concentration.

The results of this study are presented in FIG. 7 (NCL062 tested from 1 to 128 µg/ml, NCL812 tested from 2 to 256 µg/ml, NCL099 tested from 8 to 1024 µg/ml). FIG. 7 shows the amount of erythrocyte lysis as a percentage of the positive control (100% lysed blood cells in water) at various concentrations.

Conclusion.

This study demonstrates that the concentration required of each compound to cause a toxic effect in mammalian cells (erythrocytes) is much higher than the concentration required to effect protozoal cells (*Giardia*). This study also demonstrates that NCL099 appears to have greater selectivity for bacterial and protozoal cells than mammalian cells when compared to NCL812 and NCL062.

Example 5: Transmission Electron Microscopy Study

Aim.

To determine the effect that NCL812 has on the ultrastructure of *Giardia duodenalis*.

Methods.

*Giardia* WB strain was grown until confluent (same as above) and old media was replaced with fresh media containing 6 µg/ml NCL812, 25 µg/ml metronidazole or 0.1% DMSO (control). Samples were incubated at 37° C. for 1 hour (NCL treated) or 4 hours (Metronidazole and DMSO control) then cold shocked to detach trophozoites. Treated samples were centrifuged at 900×g for 10 minutes and washed twice with cold saline. Final cell pellet was resuspended in pre-cooled fixative (1.25% gluteraldehyde, 4% paraformaldehyde in PBS with 4% sucrose, pH 7.2) and left overnight. Samples were post-fixed in 2% osmium tetroxide solution for 1 hour and dehydrated through a graded ethanol series (70-100%). Samples were embedded in epoxy resin and stained with uranyl acetate and lead citrate before viewing on an FEI Tecnai G2 Spirit Transmission Electron Microscope.

Results.

Figure 8:
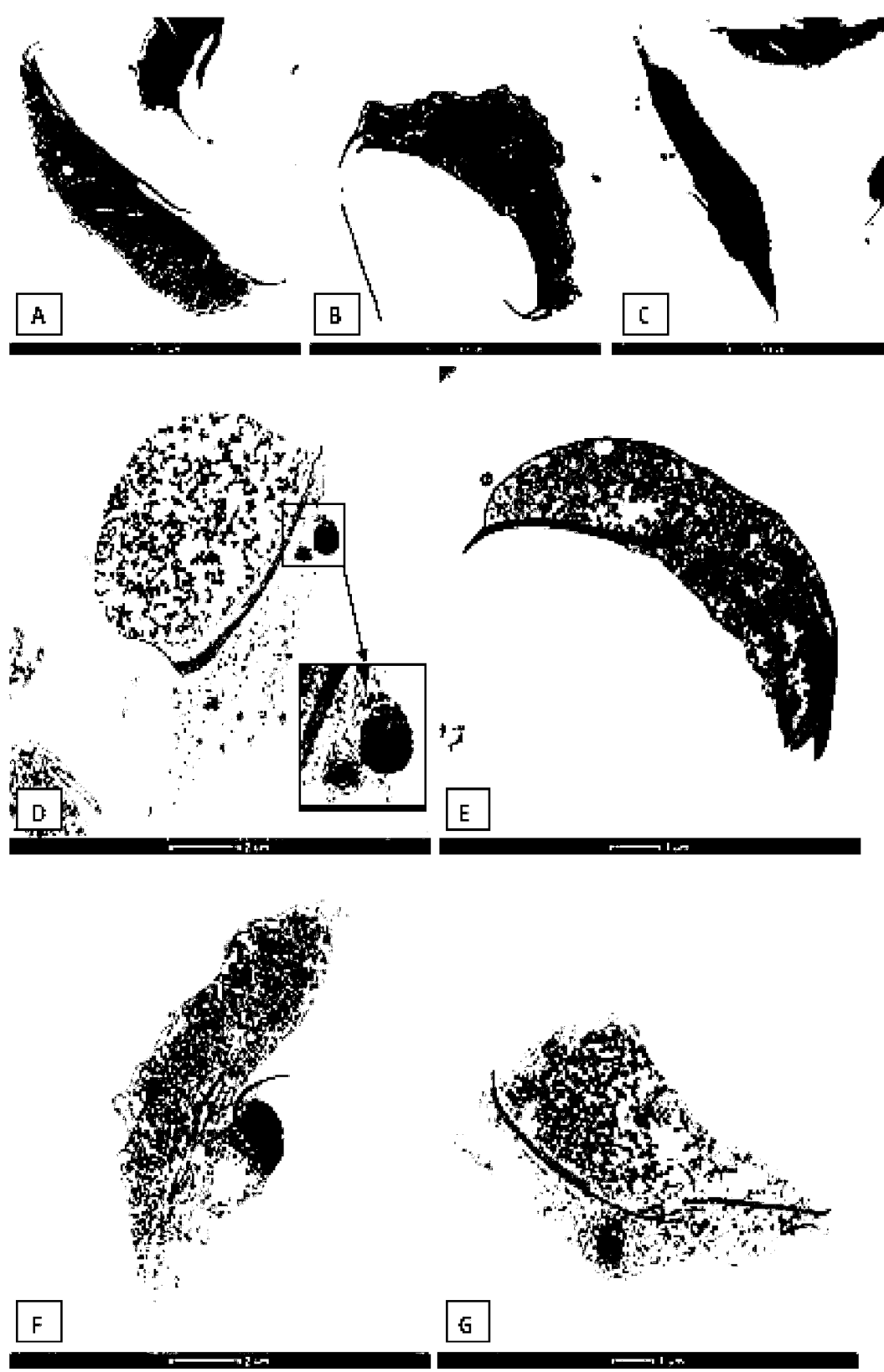
FIG. 8 presents photographs demonstrating changes in the ultrastructure of *Giardia* trophozoites exposed to NCL812. A-B: control 0.1% DMSO, C: metronidzaole control, D-G: NCL812 exposed trophozoites (1 hr)

The results of this study are shown in FIG. 8. This figure shows the severe change in the ultrastructure of the NCL treated trophozoites (D-G) compared to the controls (A-C). Development of vacuoles and disintegration of the cytoplasmic membrane is observed.

Conclusion.

NCL812 causes significant changes in to the ultrastructure of *Giardia duodenalis*.

Example 6: Formulations of Compounds

The following formulations were prepared using standard methods in the art.

Formulation A—Topical Formulation—PEG-Based Gel with Compounds of the Invention 4.0 g PEG 4000;
3.5 g PEG 200;
0.6 g propylene glycol;
1.9 g water; and
0.204 g of Compound (for example, NCL099)

PEG 4000, PEG 200 and propylene glycol were mixed and heated to 150° C. and until all solid crystals were dissolved. Compound was added to water and sonicated for 30 minutes until fully suspended. The Compound solution and gel solutions were mixed and allowed to cool and solidify. Formulation A will likely demonstrate acceptable viscosity, ease of skin application, uniform suspension and consistent and fine texture.

Formulation B—Topical Formulation—PEG-Based Gel with Compounds of the Invention 3.0 g PEG 4000;
1.0 g PEG 8000;
3.0 g PEG 200;
1.0 g propylene glycol;
1.9 g water; and
0.202 g of Compound (for example, NCL099)

PEG 4000, PEG 8000, PEG 200 and propylene glycol were mixed and heated to 150° C. and until all solid crystals were dissolved. Compound (for example, NCL099) was added to water and sonicated for 30 minutes until fully suspended. The Compound solution and gel solutions were mixed and allowed to cool and solidify. Formulation B demonstrated acceptable viscosity, ease of skin application, uniform suspension and consistent and fine texture.

Formulation C—Topical Formulation—PEG-Based Gel with Compound-Soluplus 2.5 g PEG 4000;
4.0 g PEG 200;
2.5 g propylene glycol;
1.0 g water; and
1.8 g solid dispersion of Compound-SoluPlus.

Soluplus was purchased from BASF (www.soluplus.com). Compound-SoluPlus was prepared using standard methods in the art. PEG 4000, PEG 200, Compound- SoluPlus and propylene glycol were mixed and heated to 150° C. and until all solid crystals were dissolve. Water was added and then the solution was sonicated. The solution was allowed to cool and solidify. Formulation C demonstrated acceptable viscosity, ease of skin application, uniform suspension and consistent and fine texture.

Formulation D—Tablet Formulation
  30 mg Calcium hydrogen phosphate dehydrate;
  80 mg Microcrystalline cellulose;
  50 mg Lactose;
  8 mg Hydroxypropyl methyl cellulose
  1.5 mg Talc
  10 mg of compound (for example NCL099)

The excipients were weighed and mixed for 5 minutes. The mixture was fed into a feed hopper of a tablet press machine and the machine was operated according to standard procedures in the art. Formulation D demonstrated acceptable tablet hardness, disintegration and frability.

Formulation E—Oral Suspension
  2.0 ml Glycerol;
  1.5 ml Absolute ethanol;
  600 mg NCL812; and
  To 60 ml Vehicle (Ora Sweet and Ora Plus, 1:1).

NCL 812 powder was sieved through a 75 µm sieve. 600 mg of sieved NCL 812 was mixed with 2.0 ml glycerol and 1.5 ml absolute ethanol. The mixture was placed in a mortar and manually milled until all NCL 812 was suspended uniformly. The suspension was sonicated for 30 minutes. Vehicle (55 ml of Ora Sweet and Ora Plus mixture) was then added to the suspension and milled for another 10 minutes. Volume was made up with the Ora plus and Ora sweet mixture to 60 ml by transferring to a measuring cylinder Formulation E demonstrated acceptable suspension and demonstrated acceptable short term stability.

Formulation F—Intramuscular Injection
  20 mg/ml Polyvinylpyrrolidone K30 (PVPK30);
  0.09 mg/ml NCL812; and
  50 ml water.

Two percent of w/v PVP K30 solution was prepared by the addition of 1.0 g of PVP K30 to 50 ml of MilliQ water. The solution was then placed in a sonicator for 30 minutes to equilibrate and 4.5 mg of NCL 812 was added to the PVP solution and placed on an incubator shaker at a maximum speed of 10 rpm over a period of 24 hours, with controlled temperature of 25±1° C. Solution was transferred to 5 ml vials and checked for clarity, appearance, pH and short-term stability. The pH of solution was 7.25.

Formulation F demonstrated acceptable transparency and short term stability.

Example 7: Release of NCL812 and NCL099 from Formulation B

Aim:

The objective of this study was to measure the release of NCL812 and NCL099 from Formulation B prepared in Example 6.

Method:

Franz diffusion cells were utilized to quantify the release rate of NCL 812 and NCL099 from its topical formulations. Five millilitres of absolute ethanol, which was chosen as the desired release medium, was loaded into the receptor chamber. Temperature of the receptor fluid was kept constant, at 32±1° C. using a water jacket. Acetyl cellulose membranes, with pore size of 0.45 µm (Pall Corporation) was selected and placed between donor and receptor chamber. Followed by that, a number of test samples (Formulation B) was loaded into the donor chamber. One millilitre of receptor fluid was collected at regular time intervals of 0.25, 0.50, 0.75, 1, 2, 3, 4, 5, 6, 7, 8 and 24 hours through the sampling port. One millilitre of fresh absolute ethanol was immediately returned to the receptor chamber. UV-HPLC was utilized to analyse the content of the receptor fluids attained.

Figure 9:
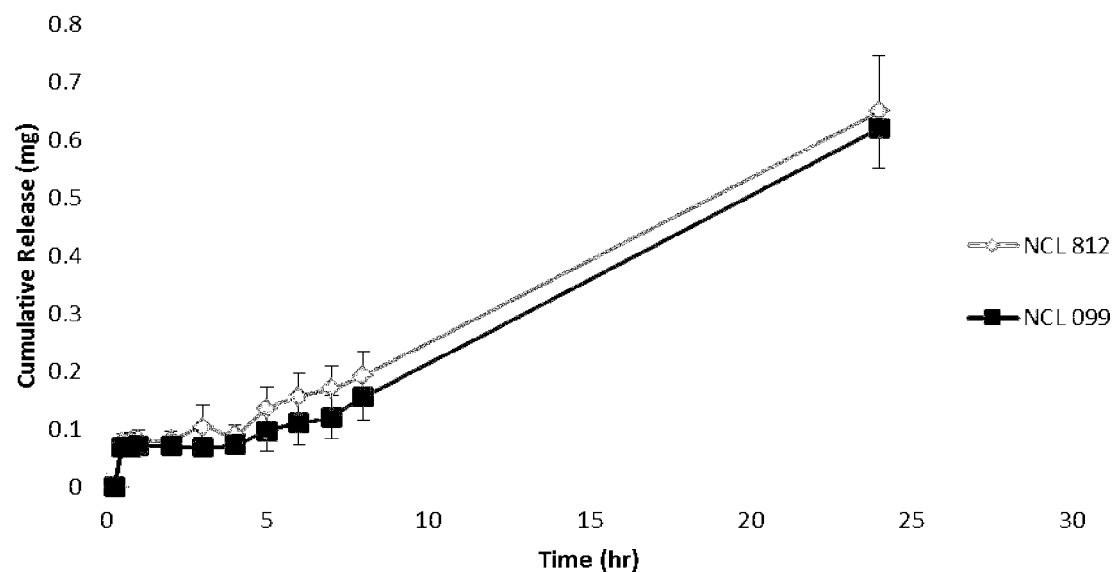
FIG. 9 is a graph illustrating the cumulative release of NCL812 and NCL099 from Formulation B according to example 7.

Results and Conclusion:

FIG. 9 presents the cumulative release of NCL812 and NCL099 over time. This study demonstrates that Formulation B provides an acceptable release profile for NCL812 and NCL099.

Example 8: NMR Specroscopy Lists of Compounds NCL812, NCL001-NCL275

NMR Spectroscopy was performed on compounds NCL812, NCL001-NCL275 using standard methods in the art. The lists of the NMR spectroscopy are presented in Table 3.

TABLE 3

NMR Specroscopy Lists of Compounds NCL812, NCL001-NCL275

| NCL Code | NMR |
|---|---|
| NCL812 | 1H NMR (400 MHz, DMSO) δ 12.04 (br. s, 2H), 8.48 (br. s, 1H), 8.37 (br. s, 2H), 7.97 (d, J = 8.6 Hz, 4H), 7.57 (d, J = 8.6 Hz, 4H) |
| NCL001 | 1H NMR (400 MHz, DMSO) δ 10.84 (br. s, 2H), 8.17 (br. s, 2H), 7.77 (d, J = 8.2 Hz, 4H), 7.50 (d, J = 8.6 Hz, 4H) |
| NCL002 | 1H NMR (400 MHz, DMSO) δ 11.06 (s, 2H), 8.58 (br. s, 2H), 8.17 (br. s, 2H), 7.50-7.52 (m, 2H), 7.41-7.45 (m, 4H) |
| NCL003 | 1H NMR (400 MHz, DMSO) δ 10.71 (s, 2H), 8.17 (br. s, 2H), 7.73-7.88 (m, 4H), 7.28 (t, J = 8.8 Hz, 4H) |
| NCL004 | 1H NMR (400 MHz, DMSO) δ 10.89 (br. s, 2H), 8.19 (br. s, 2H), 7.65 (br. s, 2H), 7.43-7.56 (m, 4H), 7.19-7.27 (m, 2H) |
| NCL005 | 1H NMR (400 MHz, DMSO) δ 10.94 (br. s, 2H), 8.43 (br. s, 2H), 8.10 (br. s, 2H), 7.39-7.52 (m, 2H), 7.21-7.35 (m, 4H) |
| NCL006 | 1H NMR (400 MHz, DMSO) δ 10.50 (s, 2H), 8.11 (br. s, 2H), 7.68 (d, J = 8.6 Hz, 4H), 6.99 (d, J = 8.6 Hz, 4H), 3.80 (s, 6H) |
| NCL007 | 1H NMR (400 MHz, DMSO) δ 11.10 (br. s, 2H), 8.24 (br. s, 2H), 7.81-8.03 (m, 8H) |
| NCL008 | 1H NMR (400 MHz, DMSO) δ 11.24 (br. s, 2H), 8.51 (br. s, 2H), 8.18-8.29 (m, 2H), 7.90 (d, J = 7.4 Hz, 2H), 7.80 (t, J = 7.6 Hz, 2H), 7.59 (t, J = 7.0 Hz, 2H) |
| NCL009 | 1H NMR (400 MHz, DMSO) δ 11.02 (s, 2H), 8.26 (br. s, 4H), 8.07 (d, J = 7.8 Hz, 2H), 7.85 (d, J = 7.8 Hz, 2H), 7.65 (t, J = 7.8 Hz, 2H) |
| NCL010 | 1H NMR (400 MHz, DMSO) δ 10.74 (br. s, 2H), 8.15 (br. s, 2H), 7.25-7.39 (m, 6H), 6.94-7.01 (m, 2H), 3.82 (s, 6H) |
| NCL011 | 1H NMR (400 MHz, DMSO) δ 11.02 (s, 2H), 8.28 (br. s, 2H), 8.13 (s, 2H), 8.04 (d, J = 7.4 Hz, 2H), 7.75 (d, J = 8.0 Hz, 2H), 7.68 (t, J = 8.0 Hz, 2H) |
| NCL012 | 1H NMR (400 MHz, DMSO) δ 11.04 (br. s, 2H), 8.27 (br. s, 2H), 7.97 (d, J = 7.8 Hz, 4H), 7.80 (d, J = 8.2 Hz, 4H) |
| NCL013 | 1H NMR (400 MHz, DMSO) δ 11.22 (br. s, 2H), 8.55 (br. s, 2H), 8.35 (d, J = 7.0 Hz, 2H), 7.73-7.82 (m, 4H), 7.57-7.65 (m, 2H) |
| NCL014 | 1H NMR (400 MHz, DMSO) δ 10.30 (s, 1H), 7.81 (s, 1H), 7.76 (d, J = 8.6 Hz, 2H), 7.43 (d, J = 8.6 Hz, 2H), 6.53 (br. s, 2H) |

TABLE 3-continued

NMR Specroscopy Lists of Compounds NCL812, NCL001-NCL275

| NCL Code | NMR |
|---|---|
| NCL015 | 1H NMR (400 MHz, DMSO) δ 12.02 (br. s, 1H), 8.55 (s, 1H), 8.27-8.33 (m, 1H), 7.79 (br. s, 3H), 7.51-7.56 (m, 1H), 7.39-7.51 (m, 2H) |
| NCL016 | 1H NMR (400 MHz, DMSO) δ 11.98 (br. s, 1H), 8.39 (s, 1H), 8.19-8.26 (m, 1H), 7.80 (br. s, 3H), 7.46-7.58 (m, 1H), 7.20-7.38 (m, 2H) |
| NCL017 | 1H NMR (400 MHz, DMSO) δ 11.79 (br. s, 1H), 8.17 (s, 1H), 7.87 (d, J = 9.8 Hz, 1H), 7.71 (br. s, 3H), 7.62 (d, J = 7.4 Hz, 1H), 7.45-7.54 (m, 1H), 7.25-7.32 (m, 1H) |
| NCL018 | 1H NMR (400 MHz, DMSO) δ 10.66 (s, 2H), 8.47 (br. s, 2H), 7.91-8.00 (m, 2H), 7.19-7.32 (m, 6H), 2.42 (s, 6H) |
| NCL019 | 1H NMR (400 MHz, DMSO) δ 10.68 (br. s, 2H), 8.15 (br. s, 2H), 7.57 (s, 2H), 7.52 (d, J = 7.4 Hz, 2H), 7.32 (t, J = 7.6 Hz, 2H), 7.21 (d, J = 7.4 Hz, 2H), 2.36 (s, 6H) |
| NCL020 | 1H NMR (400 MHz, DMSO) δ 12.37 (br. s, 2H), 8.83 (br. s, 2H), 8.63 (br. s, 2H), 8.39-8.44 (m, 2H), 7.55-7.60 (m, 2H), 7.44-7.55 (m, 4H) |
| NCL021 | 1H NMR (400 MHz, DMSO) δ 12.11 (br. s, 1H), 8.52 (br. s, 2H), 8.40 (br. s, 2H), 8.02 (t, J = 8.6, 4H), 7.35 (t, J = 8.8 Hz, 4H) |
| NCL022 | 1H NMR (400 MHz, DMSO) δ 12.19 (br. s, 2H), 8.65 (br. s, 2H), 8.58 (br. s, 1H), 8.34 (t, J = 7.6 Hz, 2H), 7.51-7.60 (m, 2H), 7.34 (t, J = 8.2 Hz 4H) |
| NCL023 | 1H NMR (400 MHz, DMSO) δ 12.08 (br. s, 2H), 8.38 (br. s, 2H), 7.92-8.00 (m, 2H), 7.65-7.71 (m, 2H), 7.50-7.58 (m, 2H), 7.29-7.37 (m, 2H) |
| NCL024 | 1H NMR (400 MHz, DMSO) δ 12.32 (br. s, 2H), 8.67 (br. s, 2H), 8.44 (br. s, 2H), 8.15 (d, J = 8.6 Hz, 4H), 7.98 (d, J = 8.6 Hz, 4H) |
| NCL025 | 1H NMR (400 MHz, DMSO) δ 8.75 (br. s, 2H), 8.50 (d, J = 8.2 Hz, 2H), 7.97 (d, J = 7.4 Hz, 2H), 7.85 (t, J = 7.6 Hz, 2H), 7.68 (t, J = 7.6 Hz, 2H) |
| NCL026 | 1H NMR (400 MHz, DMSO) δ 12.26 (br. s, 1H), 8.66 (br. s. 1H), 8.55 (s, 2H), 8.43 (br. s, 2H), 8.21 (d, J = 7.8 Hz, 2H), 7.94 (d, J = 7.8 Hz, 2H), 7.71 (t, J = 7.8 Hz, 2H) |
| NCL027 | 1H NMR (400 MHz, DMSO) δ 11.78 (br. s, 2H), 8.31 (br. s, 3H), 7.87(d, J = 8.6 Hz, 4H), 7.04 (d, J = 8.6 Hz, 4H), 3.83 (s, 6H) |
| NCL028 | 1H NMR (400 MHz, DMSO) δ 12.00 (br. s, 2H), 8.75 (br. s, 2H), 8.39 (br. s, 2H), 8.22 (d, J = 6.7 Hz, 2H), 7.44-7.52 (m, 2H), 7.14 (d, J = 8.2 Hz, 2H), 7.05 (t, J = 7.6 Hz, 2H), 3.89 (s, 6H) |
| NCL029 | 1H NMR (400 MHz, DMSO) δ 11.98 (br. s, 2H), 8.48 (br. s, 2H), 8.36 (br. s, 2H), 7.56 (s, 2H), 7.35-7.49 (m, 4H), 7.04-7.10 (m, 2H), 3.84 (s, 6H) |
| NCL030 | 1H NMR (400 MHz, DMSO) δ 11.83 (br. s, 1H), 8.16 (s, 1H), 7.91 (d, J = 8.2 Hz, 2H), 7.75 (br. s, 1H), 7.53 (d, J = 8.2 Hz, 2H) |
| NCL031 | 1H NMR (400 MHz. DMSO) δ 11.91 (br. s, 1H), 8.22 (s, 1H), 8.09 (d, J = 8.2 Hz, 2H), 7.93 (d, J = 8.2 Hz, 2H) |
| NCL032 | 1H NMR (400 MHz, DMSO) δ 12.12 (s, 1H), 8.48 (s, 1H), 8.38 (d, J = 7.8 Hz, 1H), 7.94 (d, J = 7.8 Hz, 1H), 7.86 (br. s, 2H), 7.80 (t, J = 7.8 Hz, 2H), 7.64(t, J = 7.6 Hz, 1H) |
| NCL033 | 1H NMR (400 MHz, DMSO) δ 11.93 (s, 1H), 8.50 (s, 1H), 8.20 (s, 1H), 8.14 (d, J = 7.8 Hz, 1H), 7.90 (d, J = 7.8 Hz, 1H), 7.66 (t, J = 7.8 Hz, 1H) |
| NCL034 | 1H NMR (400 MHz, DMSO) δ 11.87 (br. s, 1H), 8.48 (s, 1H), 8.09 (d, J = 7.8 Hz, 1H), 7.70 (br. s, 2H), 7.38-7.49 (m, 1H), 7.11 (d, J = 8.6 Hz, 1H), 7.01 (t, J = 7.4 Hz, 1H), 3.86 (s, 3H) |
| NCL035 | 1H NMR (400 MHz, DMSO) δ 12.32 (br. s, 2H), 8.69 (br. s, 2H), 8.49 (br. s, 2H), 8.18 (d, J = 7.8 Hz, 4H), 7.86 (d, J = 8.2 Hz, 4H) |
| NCL036 | 1H NMR (400 MHz, DMSO) δ 12.51 (br. s, 1H), 8.80 (br. s, 2H), 8.72 (br. s, 1H), 8.59 (d, J = 7.8 Hz, 2H), 7.78-7.91 (m, 4H), 7.71 (t, J = 8.0 Hz, 2H) |
| NCL037 | 1H NMR (400 MHz, DMSO) δ 12.28 (br. s, 2H), 8.70 (br. s, 2H), 8.50 (br. s, 2H), 8.38 (s, 2H), 8.22 (d, J = 7.8 Hz, 2H), 7.85 (d, J = 7.8 Hz, 2H), 7.74 (t, J = 7.8 Hz, 2H) |
| NCL038 | 1H NMR (400 MHz, DMSO) δ 11.92 (br. s, 2H), 8.41 (br. s, 2H), 8.36 (br. s, 2H), 7.83 (d, J = 8.2 Hz, 4H), 7.31 (d, J = 7.8 Hz, 4H), 2.37 (s, 6H) |
| NCL039 | 1H NMR (400 MHz. DMSO) δ 11.99 (br. s, 2H), 8.73 (br. s, 2H), 8.41 (br. s, 2H), 8.19 (d, J = 7.8 Hz, 2H), 7.37 (t, J = 8.0 Hz, 2H), 7.30 (t, J = 7.8 Hz, 4H), 2.46 (s, 6H) |
| NCL040 | 1H NMR (400 MHz, DMSO) δ 11.97 (br. s, 2H), 8.44 (br. s, 2H), 8.37 (br. s, 2H), 7.76 (s, 2H), 7.71 (d, J = 7.8 Hz, 2H), 7.38 (t, J = 7.8 Hz, 2H), 7.31 (d, J = 7.8 Hz, 2H), 2.38 (s, 6H) |
| NCL041 | 1H NMR (400 MHz, DMSO) δ 11.94 (s, 1H), 8.25 (s, 1H), 8.11 (d, J = 7.8 Hz, 2H), 7.71-7.91 (m, 4H) |
| NCL042 | 1H NMR (400 MHz, DMSO) δ 12.04 (s, 1H), 8.46-8.56 (m, 2H), 7.70-7.93 (m, 5H), 7.66 (t, J = 7.8 Hz, 1H) |
| NCL043 | 1H NMR (400 MHz, DMSO) δ 11.88 (s, 1H), 8.33 (s, 1H), 8.26 (s, 1H), 8.14 (d, J = 7.8 Hz, 1H), 7.80 (d, J = 7.8 Hz, 1H), 7.69 (t, J = 7.8 Hz, 1H) |
| NCL044 | 1H NMR (400 MHz, DMSO) δ 11.71 (br. s, 1H), 8.13 (s, 1H), 7.76 (d, J = 8.2 Hz, 2H), 7.27 (d, J = 7.8 Hz, 2H), 2.35 (s, 3H) |
| NCL045 | 1H NMR (400 MHz, DMSO) δ 11.69 (br. s, 1H), 8.45 (s, 1H), 8.06 (d, J = 7.4 Hz, 1H), 7.67 (br. s, 2H), 7.30-7.39 (m, 1H), 7.20-7.29 (m, 2H), 2.42 (s, 3H) |
| NCL046 | 1H NMR (400 MHz, DMSO) δ 11.64 (br. s, 1H), 8.12 (s, 1H), 7.53-7.77 (m, 4H), 7.34 (t, J = 7.8 Hz, 1H), 7.27 (d, J = 7.8 Hz, 1H), 2.35 (s, 3H) |
| NCL047 | 1H NMR (400 MHz, DMSO) δ 10.47 (s, 1H), 8.23 (s, 1H), 8.16-8.21 (m, 1H), 7.42-7.50 (rn, 1H), 7.30-7.40 (m, 2H), 6.57 (br. s, 2H) |
| NCL048 | 1H NMR (400 MHz, DMSO) δ 10.40 (s, 1H), 8.08-8.15 (m, 1H), 8.05 (s, 1H), 7.34-7.44 (m, 1H), 7.17-7.28 (m, 2H), 6.54 (br. s, 2H) |
| N0L049 | 1H NMR (400 MHz, DMSO) δ 10.51 (s, 1H), 7.93 (d, J = 8.2 Hz, 1H), 7.86 (s, 1H), 7.83 (d, J = 8.2 Hz, 1H), 6.63 (br. s, 2H) |
| NCL050 | 1H NMR (400 MHz, DMSO) δ 10.66 (s, 1H), 8.13 (d, J = 8.0 Hz, 1H), 8.11 (s, 1H), 7.85 (d, J = 7.4 Hz, 1H), 7.71 (t, J = 7.8 Hz, 1H), 7.52 (t, J = 7.0 Hz, 1H), 6.60 (br. s, 2H) |
| NCL051 | 1H NMR (400 MHz, DMSO) δ 10.43 (s, 1H), 8.37 (s, 1H), 7.98 (d, J = 7.8 Hz, 1H), 7.84 (s, 1H), 7.77 (d, J = 7.8 Hz, 1H), 7.57 (t, J = 7.8 Hz, 1H) |
| NCL052 | 1H NMR (400 MHz, DMSO) δ 11.95 (s, 1H), 8.16 (s, 1H), 3.10 (s, 1H), 7.80 (br. s, 2H), 7.76 (d, J = 7.0 Hz, 1H), 7.40-7.55 (m, 2H) |
| NCL053 | 1H NMR (400 MHz, DMSO) δ 11.88 (s, 1H), 8.17 (s, 1H), 7.95 (dd, J = 8.8, 5.7 Hz, 2H), 7.76 (br. s, 1H), 7.30 (t, J = 9.0 Hz, 2H) |
| NCL054 | 1H NMR (400 MHz, DMSO) δ 12.17 (br. s, 2H), 8.61 (br. s, 2H), 8.39 (br. s, 2H), 8.16 (s, 2H), 7.83 (d, J = 7.0 Hz, 2H), 7.45-7.61 (m, 4H) |
| NCL055 | 1H NMR (400 MHz, DMSO) δ 10.34 (s, 1H), 7.93 (s, 1H), 7.80 (s, 1H), 7.54-7.67 (m, 1H), 7.32-7.46 (m, 2H), 6.58 (br. s, 1H) |
| NCL056 | 1H NMR (400 MHz, DMSO) δ 10.23 (s, 1H), 7.82 (s, 1H), 7.78 (dd, J = 8.8, 5.7 Hz, 2H), 7.21 (t, J = 8.8 Hz, 1H), 6.49 (br. s, 2H) |
| NCL057 | 1H NMR (400 MHz, DMSO) δ 10.33 (s, 1H), 7.82 (s, 1H), 7.71 (d, J = 9.8 Hz, 1H), 7.35-7.53 (m, 2H), 7.10-7.23 (m, 1H), 6.57 (br. s, 1H) |
| NCL058 | 1H NMR (400 MHz, DMSO) δ 10.03 (s, 1H), 7.78 (s, 1H), 7.65 (d, J = 9.0 Hz, 2H), 6.94 (d, J = 8.6 Hz, 2H), 6.40 (br. s, 2H), 3.78 (s, 3H) |
| NCL059 | 1H NMR (400 MHz, DMSO) δ 10.23 (s, 1H), 7.80 (s, 1H), 7.34 (s, 1H), 7.29 (t, J = 7.8 Hz, 1H), 7.21 (d, J = 7.8 Hz, 1H), 6.91 (dd, J = 7.8, 2.0 Hz, 1H), 6.51 (br. s, 2H), 3.79 (s, 3H) |
| NCL060 | 1H NMR (400 MHz, DMSO) δ 10.56 (s, 1H), 8.41 (d, J = 7.8 Hz, 1H), 8.19 (br. s, 1H), 7.74 (d, J = 7.8 Hz, 1H), 7.67 (t, J = 7.6 Hz, 1H), 7.54 (t, J = 7.8 Hz, 1H), 6.62 (br. s, 2H) |
| NCL061 | 1H NMR (400 MHz, DMSO) δ 11.71 (br. s, 2H), 8.91 (br. s, 1H), 8.28 (d, J = 7.8 Hz, 4H), 7.82 (d, J = 8.2 Hz, 4H), 2.49 (br. s, 6H) |
| NCL062 | 1H NMR (400 MHz, DMSO) δ 11.68 (br. s, 2H), 8.78 (br. s, 1H), 8.10 (d, J = 8.6 Hz, 4H), 7.52 (d, J = 8.6 Hz, 4H), 2.43 (s, 6H) |
| NCL063 | 1H NMR (400 MHz, DMSO) δ 7.99 (br. s, 4H), 7.83 (d, J = 7.8 Hz, 6H) |

TABLE 3-continued

NMR Specroscopy Lists of Compounds NCL812, NCL001-NCL275

| NCL Code | NMR |
|---|---|
| NCL064 | 1H NMR (400 MHz, DMSO) δ 7.94 (d, J = 7.8 Hz, 4H), 7.84 (t, J = 7.6 Hz, 4H), 7.64 (t, J = 7.6 Hz, 4H) |
| NCL065 | 1H NMR (400 MHz, DMSO) δ 12.20 (br. s, 1H), 11.86 (br. s, 1H), 8.65 (br. s, 1H), 8.50 (br. s, 1H), 8.03-8.27 (m, 3H), 7.90 (d, J = 7.8 Hz, 2H), 7.68 (t, J = 7.6 Hz, 2H) |
| NCL066 | 1H NMR (400 MHz, DMSO) δ 7.43-7.67 (m, 7H), 7.23-7.34 (m, 2H) |
| NCL067 | 1H NMR (400 MHz, DMSO) δ 10.40 (s, 1H), 8.16 (s, 1H), 7.98 (d, J = 7.4 Hz, 1H), 7.90 (s, 1H), 7.67 (d, J = 7.3 Hz, 1H), 7.60 (t, J = 7.4 Hz, 1H) |
| NCL068 | 1H NMR (400 MHz, DMSO) δ 8.47 (br. s, 1H), 8.18 (d, J = 7.8 Hz, 3H), 8.07 (d, J = 8.6 Hz, 2H), 7.85 (d, J = 7.8 Hz, 2H), 7.53 (d, J = 8.6 Hz, 2H), 2.40 (s, 3H) |
| NCL069 | 1H NMR (400 MHz, DMSO) δ 9.44 (br. s, 1H), 8.03 (d, J = 8.2 Hz, 2H), 7.94 (br. s, 2H), 7.48 (d, J = 8.6 Hz, 2H), 2.31 (s, 3H) |
| NCL070 | 1H NMR (400 MHz, DMSO) δ 8.12 (br. s, 1H), 7.71 (br. s, 3H), 7.49 (br. s, 6H) |
| NCL071 | 1H NMR (400 MHz, DMSO) δ 11.43 (s, 1H), 8.40 (s, 1H), 8.16 (br. s, 1H), 8.10 (d, J = 7.4 Hz, 1H), 7.95 (br. s, 1H), 7.37 (t, J = 7.8 Hz, 1H), 7.06 (d, J = 8.2 Hz, 1H), 6.95 (t, J = 7.4 Hz, 1H), 3.82 (s, 3H) |
| NCL072 | 1H NMR (400 MHz, DMSO) δ 7.91 (br. d, J = 8.2 Hz, 3H), 7.52 (d, J = 8.6 Hz, 2H) |
| NCL073 | 1H NMR (400 MHz, DMSO) δ 9.51 (br. s, 1H), 8.22 (d, J = 8.3 Hz, 2H), 8.01 (br. s, 2H), 7.77 (d, J = 8.3 Hz, 2H), 2.36 (s, 3H) |
| NCL074 | 1H NMR (400 MHz, DMSO) δ 12.46 (br. s, 1H), 8.79 (br. s, 1H), 8.66 (br. s, 2H), 8.46 (d, J = 8.2 Hz, 2H), 7.99 (d, J = 7.0 Hz, 2H), 7.77 (br. s, 1H), 7.58 (d, J = 6.7 Hz, 3H) |
| NCL075 | 1H NMR (400 MHz, DMSO) δ 8.48 (br. s, 1H), 8.26 (d, J = 7.4 Hz, 2H), 8.19 (d, J = 7.4 Hz, 2H), 7.75-7.93 (m, 4H), 2.46 (s, 3H) |
| NCL076 | 1H NMR (400 MHz, DMSO) δ 8.53 (br. s, 2H), 6.29-8.46 (m, 2H), 7.99 (d, J = 7.8 Hz, 2H), 7.83 (d, J = 7.8 Hz, 2H), 7.57 (d, J = 7.8 Hz, 2H), 7.31 (d, J = 7.8 Hz, 2H), 2.37 (s, 3H) |
| NCL077 | 1H NMR (400 MHz, DMSO) δ 12.28 (br. s, 1H), 8.67 (br. s, 1H), 8.49 (br. s, 1H), 8.42 (br. s, 1H), 8.18 (d, J = 7.8 Hz, 2H), 8.00 (d, J = 8.2 Hz, 2H), 7.86 (d, J = 8.2 Hz, 2H), 7.58 (d, J = 7.8 Hz, 2H) |
| NCL078 | 1H NMR (400 MHz, DMSO) δ 12.33 (br. s, 1H), 8.74 (br. s, 2H), 8.58 (t, J = 7.6 Hz, 1H), 8.42 (br. s, 1H), 8.00 (d, J = 8.2 Hz, 2H), 7.87 (d, J = 10.2 Hz, 1H), 7.74 (d, J = 8.2 Hz, 1H), 7.58 (d, J = 8.2 Hz, 2H) |
| NCL079 | 1H NMR (400 MHz, DMSO) δ 12.08 (br. s, 1H), 8.54 (br. s, 1H), 8.39 (br. s, 2H), 7.93-8.09 (m, 4H), 7.57 (d, J = 8.2 Hz, 2H), 7.35 (t, J = 8.6 Hz, 2H) |
| NCL080 | 1H NMR (400 MHz, DMSO) δ 12.04 (br. s, 1H), 11.36 (br. s, 1H), 8.40 (br. s, 1H), 8.25 (d, J = 8.2 Hz, 2H), 8.00 (d, J = 7.0 Hz, 2H), 7.82 (d, J = 7.4 Hz, 2H), 7.57 (d, J = 6.7 Hz, 2H), 2.44 (s, 3H) |
| NCL081 | 1H NMR (400 MHz, DMSO) δ 8.39 (br. s, 1H), 8.07 (d, J = 8.6 Hz, 2H), 7.99 (d, J = 8.6 Hz, 2H), 7.57 (d, J = 8.2 Hz, 2H), 7.53 (d, J = 8.6 Hz, 2H), 2.39 (s, 3H) |
| NCL082 | 1H NMR (400 MHz, DMSO) δ 12.40 (br. s, 1H), 8.84 (br. s, 2H), 8.63 (br. s, 2H), 8.42 (br. s, 1H), 7.99 (d, J = 7.8 Hz, 2H), 7.58 (d, J = 8.2 Hz, 3H), 7.43-7.54 (m, 2H) |
| NCL083 | 1H NMR (400 MHz, DMSO) δ 12.30 (br. s, 1H), 8.64 (br. s, 2H), 8.41 (br. s, 2H), 8.17 (s, 1H), 7.99 (d, J = 8.6 Hz, 2H), 7.82 (d, J = 6.7 Hz, 1H), 7.45-7.64 (m, 4H) |
| NCL084 | 1H NMR (400 MHz, DMSO) δ 12.38 (br. s, 1H), 8.64 (br. s, 2H), 8.30-8.50 (m, 2H), 7.99 (d, J = 8.6 Hz, 2H), 7.62 (d, J = 10.4, 1.4 Hz, 1H), 7.57 (d, J = 8.6 Hz, 2H), 7.46 (d, J = 8.6 Hz, 2H) |
| NCL085 | 1H NMR (400 MHz, DMSO) δ 8.77 (br. s, 1H), 8.68 (br. s, 2H), 8.52 (d, J = 8.2 Hz, 1H), 8.46 (br. s, 1H), 7.92-8.06 (m, 3H), 7.84 (t, J = 7.6 Hz, 1H), 7.68 (t, J = 7.6 Hz, 1H), 7.58 (d, J = 8.2 Hz, 2H) |
| NCL086 | 1H NMR (400 MHz, DMSO) δ 12.39 (br. s, 1H), 8.68 (br. s, 2H), 8.57 (s, 1H), 8.43 (br. s, 2H), 8.21 (d, J = 7.4 Hz, 1H), 8.00 (d, J = 8.2 Hz, 2H), 7.94 (d, J = 7.0 Hz, 1H), 7.70 (t, J = 7.2 Hz, 1H), 7.58 (d, J = 7.8 Hz, 2H) |
| NCL087 | 1H NMR (400 MHz, DMSO) δ 8.71 (br. s, 2H), 8.48 (br. s, 1H), 8.43 (br. s, 1H), 8.16 (d, J = 8.2 Hz, 2H), 7.99 (t, J = 8.0 Hz, 4H), 7.58 (d, J = 8.6 Hz, 2H) |
| NCL088 | 1H NMR (400 MHz, DMSO) δ 12.33 (br. s, 1H), 8.68 (br. s, 1H), 8.61 (br. s, 2H), 8.42 (br. s, 1H), 8.35 (t, J = 7.4 Hz, 1H), 7.99 (d, J = 8.2 Hz, 2H), 7.49-7.64 (m, 3H), 7.27-7.41 (m, 2H) |
| NCL089 | 1H NMR (400 MHz, DMSO) δ 11.45 (br. s, 1H), 8.76-8.94 (m, 1H), 8.11 (d, J = 8.0 Hz, 4H), 7.53 (d, J = 8.0 Hz, 4H), 2.42 (br. s, 6H) |
| NCL090 | 1H NMR (400 MHz, DMSO) δ 10.60 (br. s, 1H), 8.68 (s, 1H), 8.09 (br. s, 1H), 7.95 (br. s, 4H), 7.32-7.71 (m, 10H) |
| NCL091 | 1H NMR (400 MHz, DMSO) δ 9.61 (br. s, 1H), 8.19 (d, J = 6.3 Hz, 2H), 7.90 (br. s, 2H), 7.56-7.73 (m, 2H), 7.26-7.40 (m, 2H) |
| NCL092 | 1H NMR (400 MHz, DMSO) δ 12.38 (br. s, 1H), 7.82-7.94 (m, 2H), 7.18-7.63 (m, 7H), 4.39 (br. s, 2H) |
| NCL093 | 1H NMR (300 MHz, DMSO) δ 8.64 (s, 4H), 8.35-8.24 (m, 4H), 8.06-7.93 (m, 6H), 7.64-7.54 (m, 4H). |
| NCL094 | 1H NMR (300 MHz, CDCl3) δ 7.16 (d, J = 4.7 Hz, 2H), 6.10 (br s, 3H), 2.27-2.14 (m, 2H), 1.84-1.61 (m, 10H), 1.37-1.13 (m, 10H). |
| NCL095 | 1H NMR (300 MHz, DMSO) δ 8.39 (s, 2H), 8.36-8.11 (m, 4H), 7.78 (s, 2H), 7.12 (d, J = 1.4 Hz, 2H). |
| NCL096 | 1H NMR (300 MHz, MeOD) δ 8.08 (d, J = 8.2 Hz, 2H), 7.61-7.53 (m, 4H), 7.45-7.30 (m, 6H), 7.17-6.97 (m, 4H). |
| NCL097 | 1H NMR (300 MHz, DMSO) δ 9.06 (br s, 6H), 8.25-8.01 (m, 4H), 6.83 (s, 4H). 13C NMR (75 MHz, DMSO) δ 152.2, 149.7, 146.2, 136.5, 123.7, 107.4. |
| NCL098 | 1H NMR (300 MHz, DMSO) δ 8.65 (s, 2H), 8.53 (s, 2H), 8.40 (s, 2H), 8.24 (d, J = 7.3 Hz, 2H), 8.09-7.98 (m, 2H), 7.62 (t, J = 7.7 Hz, 2H). |
| NCL099 | 1H NMR (300 MHz, DMSO) δ 8.56-8.32 (m, 4H), 7.85 (d, J = 8.3 Hz, 4H), 7.49 (d, J = 8.3 Hz, 4H), 1.31 (s, 18H). 13C NMR (75 MHz, DMSO) δ 153.7, 152.7-148.8, 130.7, 127.8, 125.6, 34.7, 31.0. |
| NCL100 | 1H NMR (300 MHz, DMSO) δ 12.39 (br s, 2H), 8.55 (s, 2H), 8.46 (s, 2H), 8.01-7.88 (m, 4H), 7.55-7.41 (m, 6H). |
| NCL101 | 1H NMR (300 MHz, DMSO) δ 12.06 (br s, 2H), 9.71 (br s, 2H), 9.21 (br s, 2H), 8.70 (s, 2H), 8.30 (s, 2H), 7.50 (d, J = 7.9 Hz, 2H), 6.90 (d, J = 7.7 Hz, 2H), 6.70 (t, J = 7.7 Hz, 2H). |
| NCL102 | 1H NMR (300 MHz, DMSO) δ 12.86 (br s, 2H), 8.89 (s, 2H), 8.77 (s, 2H), 8.52 (d, J = 7.9 Hz, 2H), 8.11 (d, J = 8.1 Hz, 2H), 7.91-7.78 (m, 2H), 7.77-7.65 (m, 2H). |
| NCL103 | 1H NMR (300 MHz, DMSO) δ 11.81 (br s, 2H), 10.32-9.85 (m, 4H), 8.52 (s, 2H), 8.12 (s, 2H), 7.85 (d, J = 8.4 Hz, 2H), 6.43 (s, 2H), 6.33 (d, J = 8.5 Hz, 2H). |
| NCL104 | 1H NMR (300 MHz, DMSO) δ 11.72 (br s, 2H), 9.78 (br s, 2H), 9.45 (s, 2H), 8.48 (s, 2H), 8.34 (br s, 2H), 8.04 (s, 2H), 7.33 (s, 2H), 6.44 (s, 2H). |
| NCL105 | 1H NMR (300 MHz, DMSO) δ 11.75 (br s, 2H), 9.71 (br s, 2H), 9.15 (br s, 2H), 8.86-8.40 (m, 4H), 8.13 (s, 2H), 7.33 (d, J = 8.6 Hz, 2H), 6.42 (d, J = 8.6 Hz, 2H). |
| NCL106 | 1H NMR (300 MHz, DMSO) δ 9.12 (br s, 4H), 8.29 (s, 2H), 8.20 (s, 2H), 7.10 (s, 2H), 6.93 (s, 2H), 3.84 (s, 6H). |
| NCL107 | 1H NMR (300 MHz, DMSO) δ 12.19 (s, 2H), 10.25 (s, 2H), 8.70 (s, 2H), 8.34 (s, 2H), 8.06 (d, J = 7.8 Hz, 2H), 7.35-7.23 (m, 2H), 7.00 (d, J = 8.2 Hz, 2H), 6.87 (t, J = 7.5 Hz, 2H). |
| NCL108 | 1H NMR (300 MHz, DMSO) δ 8.00 (s, 2H), 7.26-7.08 (m, 6H), 6.98-6.43 (m, 4H). |

TABLE 3-continued

NMR Specroscopy Lists of Compounds NCL812, NCL001-NCL275

| NCL Code | NMR |
|---|---|
| NCL109 | 1H NMR (300 MHz, DMSO) δ 8.60 (d, J = 1.2 Hz, 2H), 8.33-8.19 (m, 4H), 8.15 (d, J = 8.0 Hz, 2H), 7.74-7.61 (m, 2H), 7.12 (s, 2H). |
| NCL110 | 1H NMR (300 MHz, DMSO) δ 8.85 (s, 2H), 8.58 (s, 2H), 8.31 (d, J = 8.7 Hz, 4H), 8.23 (d, J = 8.9 Hz, 4H). |
| NCL111 | 1H NMR (300 MHz, DMSO) δ 11.80 (br s, 2H), 10.30-9.80 (m, 4H), 8.52 (s, 2H), 8.12 (s, 2H), 7.84 (d, J = 8.6 Hz, 2H), 6.42 (d, J = 1.8 Hz, 2H), 6.33 (d, J = 8.6 Hz, 2H). |
| NCL112 | 1H NMR (300 MHz, DMSO) δ 12.48 (br s, 2H), 8.62 (s, 2H), 8.51 (s, 2H), 8.04 (d, J = 7.5 Hz, 4H), 7.85-7.69 (m, 8H), 7.54-7.36 (m, 6H). |
| NCL113 | 1H NMR (400 MHz, DMSO) δ 11.92 (br s, 2H), 8.24 (s, 2H), 8.16 (s, 2H), 7.71 (d, J = 8.9 Hz, 4H), 6.74 (d, J = 8.9 Hz, 4H), 2.98 (s, 12H). |
| NCL114 | 1H NMR (400 MHz, DMSO) δ 12.67 (br s, 2H), 8.81 (s, 2H), 8.40 (s, 2H), 8.06 (d, J = 1.8 Hz, 4H), 7.68 (t, J = 1.8 Hz, 2H). |
| NCL115 | 1H NMR (400 MHz, DMSO) δ 12.09 (br s, 2H), 8.44 (s, 2H), 8.34 (s, 2H), 7.63 (d, J = 1.4 Hz, 2H), 7.33 (dd, J = 8.3, 1.6 Hz, 2H), 7.03 (d, J = 8.4 Hz, 2H), 3.86 (s, 6H). |
| NCL116 | 1H NMR (400 MHz, DMSO) δ 12.27 (br s, 2H), 8.49 (s, 2H), 8.44-8.27 (m, 4H), 7.57-7.44 (m, 10H), 7.41-7.33 (m, 6H). |
| NCL117 | 1H NMR (400 MHz, DMSO) δ 9.77 (br s, 2H), 8.36 (s, 2H), 8.29 (s, 2H), 7.58 (d, J = 1.5 Hz, 2H), 7.23 (dd, J = 8.1, 1.2 Hz, 2H), 6.87 (d, J = 8.1 Hz, 2H), 3.86 (s, 6H), 3.81 (s, 6H). |
| NCL118 | 1H NMR (400 MHz, DMSO) δ 12.83 (br s, 2H), 8.76 (s, 2H), 8.69 (s, 2H), 8.31-8.21 (m, 2H), 7.45-7.31 (m, 4H). |
| NCL119 | 1H NMR (400 MHz, DMSO) δ 12.13 (br s, 2H), 10.35 (s, 2H), 8.39 (s, 2H), 8.35 (s, 2H), 7.85 (d, J = 8.7 Hz, 4H), 7.72 (d, J = 8.6 Hz, 4H), 2.08 (s, 6H). |
| NCL120 | 1H NMR (400 MHz, DMSO) δ 8.62-8.29 (m, 4H), 7.85 (d, J = 8.2 Hz, 4H), 7.33 (d, J = 8.2 Hz, 4H), 2.98-2.87 (m, 2H), 1.21 (d, J = 6.9 Hz, 12H). |
| NCL121 | 1H NMR (400 MHz, DMSO) δ 8.60-8.30 (m, 4H), 7.84 (d, J = 8.1 Hz, 4H), 7.28 (d, J = 8.1 Hz, 4H), 2.59 (t, J = 7.5 Hz, 4H), 1.64-1.54 (m, 4H), 0.88 (t, J = 7.3 Hz, 6H). |
| NCL122 | 1H NMR (400 MHz, DMSO) δ 8.56 (s, 2H), 8.42 (d, J = 2.0 Hz, 2H), 8.38 (s, 2H), 8.09 (dd, J = 8.7, 2.0 Hz, 2H), 7.29 (d, J = 8.7 Hz, 2H). |
| NCL123 | 1H NMR (400 MHz, DMSO) δ 8.68 (s, 2H), 8.43 (s, 2H), 8.28-8.16 (m, 2H), 7.77-7.64 (m, 2H), 7.58-7.46 (m, 2H). 13C NMR (101 MHz, DMSO) δ 153.0, 150.8 (dd, J = 250.6, 13.0 Hz), 149.9 (dd, J = 245.9, 13.2 Hz), 146.6, 131.2 (dd, J = 6.4, 3.4 Hz), 126.0 (dd, J = 6.4, 2.8 Hz), 117.8 (d, J = 17.7 Hz), 115.7 (d, J = 18.5 Hz). |
| NCL124 | 1H NMR (400 MHz, DMSO) δ 10.84 (br s, 2H), 9.29 (s, 2H), 8.80 (d, J = 8.6 Hz, 2H), 8.43 (s, 2H), 7.94 (d, J = 9.0 Hz, 2H), 7.87 (d, J = 7.9 Hz, 2H), 7.64-7.56 (m, 2H), 7.43-7.38 (m, 2H), 7.34 (d, J = 8.9 Hz, 2H). |
| NCL125 | 1H NMR (400 MHz, DMSO) δ 9.21 (br s, 2H), 8.42-8.17 (m, 4H), 7.43 (d, J = 1.9 Hz, 2H), 7.25 (dd, J = 8.4, 1.9 Hz, 2H), 6.99 (d, J = 8.4 Hz, 2H), 3.83 (s, 6H). |
| NCL126 | 1H NMR (400 MHz, DMSO) δ 12.27 (br s, 2H), 8.58 (s, 2H), 8.42 (s, 2H), 7.96 (d, J = 8.3 Hz, 4H), 7.58 (d, J = 8.2 Hz, 4H), 4.39 (s, 2H). |
| NCL127 | 1H NMR (400 MHz, DMSO) δ 12.84 (br s, 2H), 8.84 (s, 2H), 8.74 (s, 2H), 8.46 (d, J = 8.6 Hz, 2H), 7.71 (d, J = 1.6 Hz, 2H), 7.54 (dd, J = 8.6, 1.2 Hz, 2H). |
| NCL128 | 1H NMR (400 MHz, DMSO) δ 8.64 (s, 2H), 8.36 (s, 2H). |
| NCL129 | 1H NMR (400 MHz, DMSO) δ 8.84 (s, 2H), 8.69 (s, 2H), 8.41 (dd, J = 7.8, 1.7 Hz, 2H), 7.70 (dd, J = 8.0, 1.0 Hz, 2H), 7.48 (t. J = 7.3 Hz, 2H)*, 7.44-7.37 (m, 2H)*. |
| NCL130 | 1H NMR (400 MHz, DMSO) δ 8.66 (s, 2H), 8.37 (s, 2H), 7.79 (d, J = 1.6 Hz, 2H), 7.68-7.62 (m, 2H), 3.92 (s, 6H), 3.78 (s, 6H). |
| NCL131 | 1H NMR (400 MHz, DMSO) δ 12.45 (br s, 2H), 8.68 (s, 2H), 8.41 (s, 2H), 8.29 (s, 2H), 7.87 (d, J = 7.8 Hz, 2H), 7.70-7.63 (m, 2H), 7.44 (t, J = 7.9 Hz, 2H). |
| NCL132 | 1H NMR (400 MHz, DMSO) δ 12.69 (br s, 2H), 8.61 (s, 4H), 7.34 (dd, J = 9.0, 2.8 Hz, 2H), 7.22 (td, J = 8.6, 2.9 Hz, 2H), 7.03 (dd, = 8.8, 4.6 Hz,2H), 5.29 (s, 4H). |
| NCL133 | 1H NMR (400 MHz, DMSO) δ 12.51 (br s, 2H), 8.49-8.28 (m, 4H), 8.16 (s, 2H), 7.35 (s, 2H). |
| NCL134 | 1H NMR (400 MHz, DMSO) δ 12.42 (br s, 2H), 8.60 (s, 2H), 8.42 (s, 2H), 7.91 (d, J = 8.5 Hz, 4H), 7.69 (d, J = 8.5 Hz, 4H). |
| NCL135 | 1H NMR (400 MHz, DMSO) δ 12.24 (br s, 2H), 8.66 (s, 2H), 8.49 (br s, 2H), 7.79 (s, 2H), 7.24 (s, 2H), 3.88 (s, 6H), 3.85 (s, 6H). |
| NCL136 | 1H NMR (400 MHz, DMSO) δ 12.21 (br s, 2H), 8.44 (s, 2H), 8.39 (s, 2H), 7.83 (d, J = 8.2 Hz, 4H), 7.30 (d, J = 8.2 Hz, 4H), 2.63 (t, J = 7.7 Hz, 4H), 1.61-1.52 (m, 4H), 1.36-1.26 (m, 4H), 0.90 (t, J = 7.3 Hz, 6H). |
| NCL137 | 1H NMR (400 MHz, DMSO) δ 12.94 (br s, 2H), 8.68 (s, 2H), 8.33 (s, 2H), 7.60 (d, J = 7.9 Hz, 4H)*, 7.49 (dd, J = 8.7, 7.4 Hz, 2H)*. |
| NCL138 | 1H NMR (400 MHz, DMSO) δ 12.12 (br s, 2H), 8.21 (s, 2H), 7.97 (s, 2H), 7.54-7.47 (m, 6H), 7.42-7.36 (m, 6H), 7.31-7.21 (m, 8H), 6.84 (d, J = 9.8 Hz, 2H). |
| NCL139 | 1H NMR (400 MHz, DMSO) δ 12.65 (br s, 2H), 9.63 (d, J = 1.8 Hz, 2H), 8.88-8.58 (m, 6H), 8.13-8.01 (m, 4H), 7.88-7.79 (m, 2H), 7.68 (t, J = 7.4 Hz, 2H). |
| NCL140 | 1H NMR (400 MHz, DMSO) δ 12.17 (br s, 2H), 8.46 (s, 2H), 8.37 (s, 2H), 7.86 (d, J = 8.2 Hz, 4H), 7.34 (d, J = 8.2 Hz, 4H), 2.53 (s, 6H). |
| NCL141 | 1H NMR (400 MHz, DMSO) δ 8.66 (s, 2H), 8.60 (d, J = 1.9 Hz, 2H), 8.52 (br s, 2H), 8.49 (s, 2H), 8.09 (d, J = 8.6 Hz, 2H), 7.50 (dd, J = 8.6, 2.0 Hz, 2H). |
| NCL142 | 1H NMR (400 MHz, DMSO) δ 8.80 (s, 2H), 7.41-7.20 (m, 12H), 5.56 (s, 2H), 3.79 (d, J = 3.4 Hz, 4H). |
| NCL143 | 1H NMR (400 MHz, DMSO) δ 11.91 (br s, 2H), 8.66 (br s, 2H), 8.10-8.00 (m, 4H), 7.51-7.41 (m, 6H), 2.45 (s, 6H). |
| NCL144 | 1H NMR (400 MHz, DMSO) δ 12.36 (br s, 2H), 8.38-8.23 (m, 4H), 7.16 (d, J = 3.5 Hz, 2H), 6.82 (d, J = 3.5 Hz, 2H). |
| NCL145 | 1H NMR (400 MHz, DMSO) δ 12.41 (br s, 2H), 8.41-8.21 (m, 4H), 7.20 (d, J = 3.5 Hz, 2H), 6.73 (d, J = 3.5 Hz, 2H). |
| NCL146 | 1H NMR (400 MHz, DMSO) δ 11.97 (br s, 2H), 11.45 (s, 2H), 8.47 (s, 2H), 8.30 (s, 2H), 8.02 (s, 2H), 7.80 (dd, J = 8.6, 0.9 Hz, 2H), 7.48 (d, J = 8.5 Hz, 2H), 7.45-7.40 (m, 2H), 6.53 (s, 2H). 13C NMR (101 MHz, DMSO) δ 152.4, 150.6, 137.4, 127.6, 126.7, 124.5, 121.8, 120.3, 111.9, 102.0. |
| NCL147 | 1H NMR (400 MHz, DMSO) δ 13.09 (br s, 2H), 9.97 (s, 2H), 9.01 (s, 2H), 8.73 (s, 2H), 8.19-8.09 (m, 4H), 7.95-7.84 (m, 4H). |
| NCL148 | 1H NMR (400 MHz, DMSO) δ 12.44 (s, 4H), 8.60 (s, 2H), 8.44 (s, 2H), 7.99 (d, J = 8.3 Hz, 4H), 7.81 (d, J = 8.3 Hz, 4H), 7.63 (d, J = 16.0 Hz, 2H), 6.66 (d, J = 16.0 Hz, 2H). |
| NCL149 | 1H NMR (400 MHz, DMSO) δ 8.75 (d, J = 6.1 Hz, 4H), 8.68 (s, 2H), 8.47 (s, 2H), 8.07 (d, J = 6.1 Hz, 4H). |
| NCL150 | 1H NMR (400 MHz, DMSO) δ 12.10 (br s, 2H), 8.23-8.07 (m, 4H), 7.55 (d, J = 8.7 Hz, 4H), 7.13 (d, J = 16.0 Hz, 2H), 6.99 (d, J = 8.7 Hz, 4H), 6.81 (dd, J = 16.0, 9.4 Hz, 2H), 3.79 (s, 6H). |
| NCL151 | 1H NMR (400 MHz, DMSO) δ 11.92 (br s, 2H), 10.13 (br s, 2H), 8.28 (s, 4H), 7.75 (d, J = 8.5 Hz, 4H), 6.86 (d, J = 8.5 Hz, 4H). |
| NCL152 | 1H NMR (400 MHz, DMSO) δ 12.08 (br s, 2H), 9.35 (s, 2H), 8.66 (s, 2H), 8.48 (s, 2H), 7.67 (d, J = 7.2 Hz, 2H), 7.25 (d, J = 7.2 Hz, 2H), 6.88 (t, J = 7.6 Hz, 2H), 2.23 (s, 6H). |
| NCL153 | 1H NMR (400 MHz, DMSO) δ 11.68 (s, 2H), 8.78 (s, 2H), 8.09 (d, J = 8.4 Hz, 4H), 7.52 (d, J = 8.6 Hz, 4H), 2.92 (q, J = 7.5 Hz, 4H), 1.12 (t, J =7.4 Hz. 6H). |
| NCL154 | 1H NMR (400 MHz, DMSO) δ 12.09 (s, 2H), 8.69 (s, 2H), 8.07 (d, J = 8.6 Hz, 4H), 7.50 (d, J = 8.6 Hz, 4H), 3.01-2.88 (m, 4H), 1.49-1.39 (m, 8H), 0.88 (t, J = 6.6 Hz, 6H). |

TABLE 3-continued

NMR Specroscopy Lists of Compounds NCL812, NCL001-NCL275

| NCL Code | NMR |
|---|---|
| NCL155 | 1H NMR (400 MHz, DMSO) δ 11.63 (s, 2H), 8.76 (s, 2H), 8.01 (d, J = 8.6 Hz, 4H), 7.65 (d, J = 8.6 Hz, 4H), 2.41 (s, 6H). |
| NCL156 | 1H NMR (400 MHz, DMSO) δ 12.18 (s, 2H), 8.71 (s, 2H), 8.08 (d, J = 8.0 Hz, 4H), 7.50 (d, J = 8.3 Hz, 4H), 3.01-2.87 (m, 4H), 1.58-1.46 (m, 4H), 1.01 (t, J = 7.1 Hz, 6H). |
| NCL157 | 1H NMR (400 MHz, DMSO) δ 11.71 (br s, 2H), 8.40 (s, 2H), 8.37 (s, 2H), 7.29 (d, J = 8.4 Hz, 2H), 6.87 (d, J = 2.0 Hz, 2H), 6.73 (br s, 4H), 6.59 (dd, J = 8.3, 2.0 Hz, 2H).<br>13C NMR (101 MHz, DMSO) δ 152.1, 151.5, 148.9, 136.0, 134.7, 115.1, 114.5, 112.8. |
| NCL158 | 1H NMR (400 MHz, DMSO) δ 13.03 (br s, 1H), 10.49 (br s, 1H), 9.35 (br s, 1H), 7.24 (d, J = 7.6 Hz, 2H), 7.11-6.61 (m, 6H), 2.5 (Contains CH2 groups determined by COSY, however eclipsed by solvent signal), 0.93 (s, 6H).<br>13C NMR (101 MHz, DMSO) δ 157.8, 155.4, 152.9, 134.4, 130.1, 118.7, 115.6, 29.9, 10.8.<br>*COSY was used to determine that the signal due to the methylene protons appears under the DMSO signal. Line broadening is apparent in the 13C-NMR (due to tautomerisation effects) making carbon allocation difficult. |
| NCL159 | 1H NMR (400 MHz, DMSO) δ 12.69 (br s, 1H), 10.44 (br s, 1H), 9.15 (br s, 1H), 7.21 (s, 2H), 7.09-6.60 (m, 6H), 2.98 (p, J = 7.7 Hz, 2H), 1.84-1.01 (nn, 16H). |
| NCL160 | 1H NMR (400 MHz, DMSO) δ 12.49 (br s, 2H), 8.65 (s, 2H), 8.49 (s, 2H), 8.10 (d, J= 8.7 Hz, 4H)*, 7.47 (d, J = 8.3 Hz, 4H)*. |
| NCL161 | 1H NMR (400 MHz, DMSO) δ 7.73 (d, J = 8.8 Hz, 2H), 6.92 (d, J = 8.9 Hz, 2H), 3.22-3.13 (m, 4H), 2.99-2.86 (m, 4H), 2.24 (s, 3H). |
| NCL162 | 1H NMR (400 MHz, CDCl3) δ 7.76-7.70 (m, 2H), 7.35-7.30 (m, 2H), 4.99 (s, 2H), 4.34 (q, J = 7.1 Hz, 2H), 2.39 (s, 3H), 1.35 (t, J = 7.1 Hz, 3H). |
| NCL163 | 1H NMR (400 MHz, DMSO) δ 13.88 (s, 1H), 13.21 (s, 1H), 11.50 (s, 2H), 9.70 (s, 2H), 7.70 (s, 2H), 7.43 (t, J = 7.7 Hz, 2H), 7.14 (t, J = 7.5 Hz, 2H), 7.00 (d, J = 7.8 Hz, 2H). |
| NCL164 | 1H NMR (400 MHz, DMSO) δ 10.85 (s, 2H), 9.38 (s, 2H), 8.64 (s, 3H), 7.90 (s, 3H), 7.34 (d, J = 8.5 Hz, 2H), 7.19 (s, 3H), 6.83 (d, J = 2.1 Hz, 2H), 6.57 (dd, J = 8.5, 2.1 Hz, 2H). |
| NCL165 | 1H NMR (400 MHz, DMSO) δ 10.87 (br s, 1H), 9.53 (br s, 1H), 8.77 (br s, 3H), 7.61-7.44 (m, 8H), 7.40 (br s, 3H), 7.27 (br s, 3H), 4.07 (br s, 2H). |
| NCL166 | 1H NMR (400 MHz, DMSO) δ 12.70 (br s, 2H), 8.75 (br s, 2H), 8.55 (br s, 2H), 8.13 (d, J = 8.2 Hz, 4H), 7.81 (d, J = 8.1 Hz, 4H). |
| NCL167 | 1H NMR (400 MHz, DMSO) δ 14.09 (s, 1H), 8.12 (d, J = 6.9 Hz, 2H), 7.97 (dd, J = 6.4, 3.0 Hz, 2H), 7.56 (ddd, J = 8.2, 6.7, 2.9 Hz, 7H). |
| NCL168 | 1H NMR (400 MHz, DMSO) δ 11.86 br s, 2H), 8.42 (br s, 4H), 7.35 (d, J = 6.8 Hz, 4H), 6.75 (s, 2H), 6.57 (d, J = 7.9 Hz, 2H), 3.44 (d, J = 6.9 Hz, 2H)*, 1.24 (t, J = 5.3 Hz, 6H). *Signal partly eclipsed by H2O in DMSO |
| NCL170 | 1H NMR (400 MHz, DMSO) δ 12.29 (s, 2H), 10.29 (s, 2H), 8.55 (s, 2H), 8.45 (s, 2H), 8.13 (d, J = 8.5 Hz, 2H), 7.71 (s, 2H), 7.35 (dd, J = 8.5, 1.8 Hz, 2H), 2.12 (s, 6H). |
| NCL171 | 1H NMR (400 MHz, DMSO) δ 11.63 (s, 2H), 9.84 (s, 2H), 8.46 (s, 2H), 8.02 (s, 2H), 7.74 (d, J = 8.8 Hz, 2H), 6.30 (d, J = 7.4 Hz*, 2H), 6.17 (s, 2H), 2.94 (s, 12H).<br>*Poorly resolved doublet gives reduced coupling constant. |
| NCL172 | 1H NMR (400 MHz, DMSO) δ 12.00 (s, 2H), 8.92 (s, 2H), 8.64 (dd, J = 4.7, 0.6 Hz, 2H), 8.57 (d, J = 8.1 Hz, 2H), 7.89 (td, J = 8.0, 1.6 Hz, 2H), 7.50-7.41 (m, 2H), 2.52 (s, 6H). |
| NCL173 | 1H NMR (400 MHz, DMSO) δ 11.49 (br s, 2H), 10.62 (br s, 2H), 8.55 (br s, 2H), 7.59 (d, J = 8.3 Hz, 2H), 6.98 (d, J = 1.9 Hz, 2H), 6.92 (dd, J = 8.4, 2.0 Hz, 2H), 2.37 (s, 6H). |
| NCL174 | 1H NMR (400 MHz, DMSO) δ 12.02 (s, 2H), 10.81 (s, 2H), 8.63 (s, 2H), 8.38 (s, 2H), 8.12 (d, J = 8.3 Hz, 2H), 7.13-6.84 (m, 4H). |
| NCL175 | 1H NMR (400 MHz, DMSO) δ 12.63 (br s, 2H), 8.90 (d, J = 2.1 Hz, 2H), 8.74 (s, 2H), 8.56-8.42 (m, 4H), 7.66 (d, J = 8.4 Hz, 2H). |
| NCL176 | 1H NMR (400 MHz, DMSO) δ 11.94 (br s, 2H), 8.44 (s, 2H), 8.36 (s, 2H), 8.07 (dd, J = 4.8, 1.7 Hz, 2H), 7.72 (dd, J = 7.6, 1.4 Hz, 2H), 7.19 (s, 4H), 6.67 (dd, J = 7.5, 4.9 Hz, 2H). |
| NCL177 | 1H NMR (400 MHz, DMSO) δ 8.67 (s, 2H), 7.97 (s, 4H), 7.50 (d, J = 8.6 Hz, 4H), 4.81 (s, 4H). |
| NCL178 | 1H NMR (400 MHz, DMSO) δ 10.17 (s, 2H), 8.24 (s, 1H), 7.83 (d, J = 8.6 Hz, 4H), 7.50 (d, J = 8.6 Hz, 4H), 6.97 (s, 1H), 2.32 (s, 6H). |
| NCL179 | 1H NMR (400 MHz, DMSO) δ 10.70 (s, 2H), 8.02 (s, 2H), 7.67 (d, J = 8.4 Hz, 4H), 7.52 (d, J = 8.4 Hz, 4H), 6.28 (s, 1H), 5.85 (s, 2H).<br>13C NMR (101 MHz, DMSO) δ 162.8, 162.6, 138.8, 134.1, 133.1, 128.9, 127.6, 73.5. |
| NCL180 | 1H NMR (400 MHz, DMSO) δ 10.62 (s, 2H), 8.22 (d, J = 0.9 Hz, 1H), 7.82-7.74 (m, 4H), 7.53-7.47 (m, 4H), 6.93 (d, J = 0.6 Hz, 1H), 5.85 (t, J = 5.3 Hz, 2H), 4.74 (d, J = 5.2 Hz, 4H). |
| NCL181 | 1H NMR (400 MHz, DMSO) δ 11.20 (s, 2H), 8.17 (s, 1H), 8.09 (s, 2H), 7.72 (d, J = 7.4 Hz, 4H), 7.54 (d, J = 7.6 Hz, 4H), 6.83 (s, 1H). |
| NCL182 | 1H NMR (400 MHz, CDCl3) 7.44-7.19 (m, 6H), 5.67 (s, 1H), 5.42 (s, 1H), 5.06 (s, 2H), 4.95-4.63 (m, 1H), 1.52 (d, J = 6.8 Hz, 3H). |
| NCL183 | 1H NMR (400 MHz, CDCl3) δ 8.28 (s, 1H), 7.43-7.13 (m, 10H), 6.19 (s, 1H), 5.94 (s, 1H), 4.95-4.48 (m, 2H), 1.56 (d, J = 6.8 Hz, 4H), 1.50 (d, J = 6.5 Hz, 1H). |
| NCL184 | 1H NMR (400 MHz, MeOD) δ 7.44-7.04 (m, 10H), 5.26-4.53 (m, 7H), 1.51-1.35 (m, 6H). |
| NCL188 | 1H NMR (400 MHz, DMSO) δ 11.54 (s, 1H), 7.99 (d, J = 8.7 Hz, 2H), 7.90 (s, 3H), 7.47 (d, J = 8.6 Hz, 2H), 2.91-2.82 (m, 2H), 1.48-1.32 (m, 4H), 0.89-0.84 (m, 3H).<br>13C NMR (101 MHz, DMSO) δ 156.2, 153.8, 134.8, 134.4, 128.7, 128.4, 28.1, 26.6, 22.0, 13.8. |
| NCL190 | 1H NMR (400 MHz, DMSO) δ 11.42 (s, 1H), 8.06 (d, J = 8.7 Hz, 3H), 8.01-7.71 (m, 5H), 7.53 (d, J = 8.7 Hz, 3H), 4.90 (s, 2H), 3.69 (br s, 3H). |
| NCL191 | 1H NMR (400 MHz, DMSO) δ 11.51 (s, 1H), 8.85 (s, 3H), 7.99 (d, J = 8.6 Hz, 7H), 7.46 (d, J = 8.6 Hz, 4H), 2.35 (s, 3H). |
| NCL192 | 1H NMR (400 MHz, DMSO) δ 11.65 (s, 1H), 8.21 (s, 4H), 7.82 (dd, J = 7.6, 1.9 Hz, 2H), 7.53-7.39 (m, 3H). |
| NCL193 | 1H NMR (400 MHz, DMSO) δ 10.71 (s, 2H), 8.00 (s, 2H), 7.66 (d, J = 8.5 Hz, 4H), 7.60 (d, J = 8.6 Hz, 4H), 6.27 (s, 1H), 5.86 (s, 2H).<br>13C NMR (101 MHz, DMSO) δ 162.7, 162.6, 138.8, 134.5, 131.8, 127.9, 121.7, 73.5. |
| NCL194 | 1H NMR (400 MHz, DMSO) δ 12.01 (br s, 1H), 10.84 (s, 2H), 9.98 (br s, 1H), 9.79 (br s, 1H), 7.96 (br s, 3H), 7.79 (br s, 2H), 7.67-7.37 (m, 6H), 5.37 (br s, 1H). |
| NCL195 | 1H NMR (400 MHz, DMSO) δ 10.51 (s, 2H), 8.00 (s, 2H), 7.54 (d, J = 8.0 Hz, 4H), 7.26 (d, J = 7.9 Hz, 4H), 6.26 (s, 1H), 5.77 (s, 2H), 2.34 (s, 6H).<br>13C NMR (101 MHz, DMSO) δ 162.8, 162.6, 140.1, 138.4, 132.5, 129.4, 126.0, 73.3, 21.0. |
| NCL196 | 1H NMR (400 MHz, CDCl3) 6 10.31 (s, 2H), 9.74 (s, 2H), 7.94(s, 2H), 7.48 (d, J = 8.6 Hz, 4H), 6.83 (d, J = 8.6 Hz, 4H), 6.20 (s, 1H), 5.70 (s, 2H).<br>13C NMR (101 MHz, CDCl3) δ 162.7, 162.5, 158.3, 140.5, 127.7, 126.3, 115.7, 73.0. |
| NCL197 | 1H NMR (400 MHz, DMSO) δ 10.51 (s, 2H), 9.55 (s, 2H), 7.95 (s, 2H), 7.22 (t, J = 7.9 Hz, 2H), 7.11-7.04 (m, 4H), 6.76 (d, J = 8.4 Hz, 2H), 6.23 (s, 1H), 5.80(s, 2H).<br>13C NMR (101 MHz, DMSO) δ 162.8, 162.6, 157.7, 140.4, 136.4, 129.9, 117.4, 116.1, 112.4, 73.3. |

TABLE 3-continued

NMR Specroscopy Lists of Compounds NCL812, NCL001-NCL275

| NCL Code | NMR |
|---|---|
| NCL199 | 1H NMR (400 MHz, DMSO) δ 10.60 (s, 2H), 8.04 (s, 2H), 7.66 (d, J = 7.5 Hz, 4H), 7.45 (t, J = 7.1 Hz, 4H), 7.40-7.34 (m, 2H), 6.30 (s, 1H), 5.82 (s, 2H). 13C NMR (101 MHz, DMSO) δ 163.3, 163.1, 140.5, 135.7, 129.3, 129.2, 126.5, 73.9. |
| NCL200 | 1H NMR (400 MHz, DMSO) δ 10.51 (s, 2H), 8.02 (s, 2H), 7.58 (d, J = 8.3 Hz, 4H), 7.47 (d, J = 8.3 Hz, 4H), 6.25 (s, 1H), 5.77 (s, 2H), 1.31 (s, 18H). |
| NCL201 | 1H NMR (400 MHz, DMSO) δ 10.19 (s, 2H), 7.91 (s, 2H), 7.47 (d, J = 8.8 Hz, 4H), 6.77 (d, J = 8.9 Hz, 4H), 6.16 (s, 1H), 5.63 (s, 2H). |
| NCL202 | 1H NMR (600 MHz, DMSO) δ 13.43 (s, 1H), 11.45 (s, 2H), 10.28 (br. s, 1H), 9.47 (s, 1H), 8.38 (s, 2H), 7.71 (dd, J = 7.7, 1.3 Hz, 1H), 7.67 (br d, J = 7.0 Hz, 2H), 7.53-7.48 (m, 1H), 7.28-7.23 (m, 2H), 7.03-6.98 (m, 4H), 6.56 (br s, 1H). *Due to tautomers and rotamers associated with proximity of the phenol to the hydrazone >17 protons are observed. 13C NMR (151 MHz, DMSO) δ 167.7, 163.2, 162.6, 156.7*, 141.4*, 135.3, 133.9, 131.0, 130.5, 120.7*, 119.95, 119.8, 118.9, 117.6, 116.7, 116.6*. *Line broadening due to tautomers and rotamers made signals difficult to assign. |
| NCL203 | 1H NMR (400 MHz, DMSO) δ 12.60-10.94 (m, 3H), 7.79-7.39 (m, 3H), 2.25 (s, 2H), 1.82-1.59 (m, 10H), 1.35-1.15 (m, 10H). |
| NCL204 | 1H NMR (400 MHz, DMSO) δ 9.58 (d, J = 7.6 Hz, 2H), 7.82 (s, 4H), 7.50 (s, 4H), 6.45 (d, J = 9.6 Hz, 1H), 5.75 (s, 2H), 2.28 (d, J = 9.3 Hz, 6H). 13C NMR (101 MHz, DMSO) δ 163.48, 162.11, 143.34, 137.68, 132.88, 128.34, 127.16, 75.15, 13.01. |
| NCL205 | 1H NMR (600 MHz, DMSO) δ 10.92 (s, 2H), 8.42 (s, 2H), 7.98 (d, J = 7.5 Hz, 2H), 7.50 (d, J = 7.8 Hz, 2H), 7.44 (t, J = 7.4 Hz, 2H), 7.38 (t, J = 7.3 Hz, 2H), 6.35 (s, 1H), 5.95 (s, 2H). 13C NMR (151 MHz, DMSO) δ 162.75, 162.68, 136.0, 132.4, 132.0, 130.1, 129.9, 127.6, 126.2, 73.7. |
| NCL206 | 1H NMR (400 MHz, DMSO) δ 10.75 (s, 2H), 8.09 (s, 2H), 7.52 (d, J = 8.1 Hz, 4H), 7.24 (d, J = 8.0 Hz, 4H), 6.71 (s, 1H), 2.33 (s, 6H). |
| NCL207 | 1H NMR (400 MHz, DMSO) δ 11.43 (s, 2H), 11.05 (s, 2H), 8.31 (s, 2H), 7.42 (s, 2H), 7.29-7.18 (m, 2H), 6.89 (t, J = 7.7 Hz, 4H), 6.74 (s, 2H). |
| NCL208 | 1H NMR (400 MHz, DMSO) δ 9.63 (s, 2H), 7.82 (d, J = 8.5 Hz, 4H), 7.46 (d, J = 8.5 Hz, 4H), 6.73 (s, 2H), 2.29 (s, 6H). |
| NCL209 | 1H NMR (400 MHz, DMSO) δ 10.75 (s, 2H), 9.55 (s, 2H), 8.04 (s, 2H), 7.21 (t, J = 7.8 Hz, 2H), 7.06 (s, 2H), 7.02 (d, J = 7.6 Hz, 2H), 6.84-6.57 (m, 4H). |
| NCL210 | 1H NMR (400 MHz, DMSO) δ 11.16 (s, 2H), 8.22 (s, 2H), 7.85 (d, J = 8.3 Hz, 4H), 7.80 (d, J = 8.5 Hz, 4H), 6.92 (s, 2H). |
| NCL211 | 1H NMR (400 MHz, DMSO) δ 10.56 (s, 2H), 9.78 (s, 2H), 8.02 (s, 2H), 7.45 (d, J = 8.6 Hz, 4H), 6.80 (d, J = 8.6 Hz, 4H), 6.62 (s, 2H). |
| NCL212 | 1H NMR (400 MHz, DMSO) δ 10.94 (s, 2H), 8.10 (s, 2H), 7.67-7.60 (m, 4H), 7.61-7.54 (m, 4H), 6.80 (s, 2H). |
| NCL213 | 1H NMR (400 MHz, DMSO) δ 10.23 (br s, 2H), 7.27 (s, 2H), 2.27-1.98 (m, 2H), 1.78-1.42 (m, 10H), 1.33-1.00 (m, 10H). |
| NCL214 | 1H NMR (400 MHz, DMSO) δ 10.84 (s, 2H), 8.14 (s, 2H), 7.63 (d, J = 7.4 Hz, 4H), 7.46-7.33 (m, 3H), 6.76 (s, 2H). |
| NCL215 | 1H NMR (600 MHz, DMSO) δ 12.06 (s, 2H), 8.72 (s, 2H), 7.97 (t, J = 8.4 Hz, 2H), 7.56 (dd, J = 11.1, 1.9 Hz, 2H), 7.38 (dd, J = 8.5, 1.9 Hz, 2H), 2.42 (d, J = 2.9 Hz, 6H). |
| NCL216 | 1H NMR (400 MHz, DMSO) δ 12.43 (br s, 2H), 8.66 (br s, 2H), 8.62 (br s, 2H), 8.38 (t, J = 8.3 Hz, 2H), 7.61 (dd, J = 10.5, 1.9 Hz, 2H), 7.45 (dd, J = 8.6, 1.6 Hz, 2H). 13C NMR (101 MHz, DMSO) δ 160.7 (d, J = 254.5 Hz), 152.8*, 140.8*, 136.3 (d, J = 10.8 Hz), 128.5, 125.3, 120.2 (d, J = 10.0 Hz), 116.7 (d, J = 24.7 Hz). *Broad signals |
| NCL217 | 1H NMR (400 MHz, DMSO) δ 11.66 (s, 2H), 8.61 (s, 2H), 7.94 (d, J = 8.2 Hz, 4H), 7.25 (d, J = 8.1 Hz, 4H), 2.41 (s, 6H), 2.35 (s, 6H). 13C NMR (101 MHz, DMSO) δ 154.0, 153.3, 139.7, 133.9, 129.0, 127.0, 21.0, 14.9. |
| NCL218 | 1H NMR (400 MHz, DMSO) δ 10.73 (s, 2H), 8.05 (s, 2H), 7.70 (d, J = 8.58 Hz, 4H), 7.31-7.27 (m, 4H), 6.24 (s, 1H), 5.92 (s, 2H), 4.17 (dq, J = 7.06, 8.70 Hz, 8H), 1.28 (td, J = 1.01, 7.05 Hz, 12H). |
| NCL219 | 1H NMR (400 MHz, DMSO) δ 11.74 (s, 2H), 8.60 (s, 2H), 7.95 (d, J = 8.6 Hz, 4H), 7.45 (d, J = 8.6 Hz, 4H), 2.42 (s, 6H), 1.31 (s, 18H). 13C NMR (101 MHz, DMSO) δ 154.1, 153.3, 152.6, 134.0, 126.8, 125.0, 34.5, 31.0, 14.9. |
| NCL220 | 1H NMR (400 MHz, DMSO) δ 10.61 (s, 2H), 8.03 (s, 2H), 7.70 (dd, J = 8.7, 5.6 Hz, 4H), 7.29 (t*, J = 8.9 Hz, 4H), 6.27 (s, 1H), 5.82 (s, 2H). |
| NCL221 | 1H NMR (600 MHz, DMSO) δ 10.89 (s, 2H), 8.11 (s, 2H), 7.86 (d, J = 8.2 Hz, 4H), 7.81 (d, J = 8.4 Hz, 4H), 6.34 (s, 1H), 5.94 (s, 2H). |
| NCL222 | 1H NMR (400 MHz, DMSO) δ 10.76 (s, 2H), 7.99 (s, 2H), 7.70 (td, J = 1.7, 9.2 Hz, 2H), 7.54-7.41 (m, 4H), 6.30 (s, 1H), 5.87 (s, 2H). |
| NCL223 | 1H NMR (400 MHz, DMSO) δ 10.48 (s, 2H), 10.07 (s, 2H), 7.98 (s, 2H), 7.65 (d, J = 8.7 Hz, 4H), 7.58 (d, J = 8.7 Hz, 4H), 6.24 (s, 1H), 5.76 (s, 2H), 2.07 (s, 6H). |
| NCL224 | 1H NMR (400 MHz, DMSO) δ 8.36 (s, 1H), 7.96-7.90 (m, 2H), 7.86 (s, 1H), 7.79-7.73 (m, 2H), 7.54-7.47 (m, 6H), 4.26 (q, J = 7.1 Hz, 2H), 1.27 (t, J = 7.1 Hz, 3H). |
| NCL225 | 1H NMR (400 MHz, DMSO) δ 8.35 (s, 1H), 7.98-7.91 (m, 2H), 7.87 (s, 1H), 7.79-7.74 (m, 2H), 7.51 (dd, J = 2.8, 8.5 Hz, 6H), 3.99 (d, J = 6.5 Hz, 2H), 1.95 (hept, J = 6.7 Hz, 1H), 0.93 (d, J = 6.7 Hz, 6H). |
| NCL226 | 1H NMR (400 MHz, DMSO) δ 10.95 (s, 1H), 9.18 (t, J = 5.6 Hz, 1H), 8.38 (d, J = 10.1 Hz, 2H), 8.32 (s, 1H), 7.99-7.92 (m, 2H), 7.83 (d, J = 8.5 Hz, 2H), 7.57-7.46 (m, 5H), 3.30-3.20 (m, 2H), 1.14 (t, J = 7.2 Hz, 3H). |
| NCL227 | 1H NMR (400 MHz, DMSO) δ 11.00 (s, 1H), 9.68 (s, 1H), 8.52 (s, 1H), 8.41 (s, 1H), 8.32 (s, 1H), 8.01-7.80 (m, 4H), 7.56-7.46 (m, 4H), 7.36 (d, J = 6.00 Hz, 4H), 7.30-7.21 (m, 1H), 4.56-4.33 (m, 2H). |
| NCL228 | 1H NMR (400 MHz, DMSO) δ 10.95 (s, 1H), 9.22 (t, J = 5.6 Hz, 1H), 8.40 (s, 1H), 8.34 (s, 1H), 8.32 (s, 1H), 7.98-7.90 (m, 2H), 7.87-7.80 (m, 2H), 7.55-7.48 (m, 4H), 3.22 (q, J = 6.6 Hz, 2H), 1.56-1.46 (m, 2H), 1.39-1.25 (m, 6H), 0.88 (t, J = 6.6 Hz, 3H). |
| NCL229 | 1H NMR (400 MHz, DMSO) δ 10.98 (s, 1H), 9.60 (s, 1H), 8.54 (s, 1H), 8.40 (s, 1H), 8.30 (s, 1H), 8.01-7.89 (m, 2H), 7.85 (d, J = 8.4 Hz, 2H), 7.64-7.59 (m, 1H), 7.54-7.47 (m, 4H), 6.42 (dd, J = 1.8, 3.3 Hz, 1H), 6.31 (m, 1H), 4.44 (d, J = 5.5 Hz, 2H). |
| NCL230 | 1H NMR (400 MHz, DMSO) δ 10.41 (s, 2H), 7.98 (s, 2H), 7.59 (d, J = 8.9 Hz, 4H), 7.02 (d, J = 8.9 Hz, 4H), 6.23 (s, 1H), 5.73 (s, 2H), 3.80 (s, 6H), |
| NCL231 | 1H NMR (400 MHz, DMSO) δ 7.71 (d, J = 8.3 Hz, 2H), 7.34 (d, J = 8.3 Hz, 2H), 6.07 (s, 2H), 5.78 (s, 2H), 2.22 (s, 3H), 1.28 (s, 9H). 13C NMR (101 MHz, DMSO) δ 159.03, 149.99, 147.94, 137.04, 125.31, 124.70, 34.22, 31.09, 13.59. |
| NCL232 | 1H NMR (400 MHz, DMSO) δ 7.96 (s, 1H), 7.57 (d, J = 7.2 Hz, 2H), 7.34 (d, J = 7.3 Hz, 2H), 5.91 (s, 2H), 5.53 (s, 2H), 1.28 (s, 9H). 13C NMR (101 MHz, DMSO) δ 160.25, 150.33, 143.29, 134.17, 126.01, 125.10, 34.35, 31.08. |
| NCL233 | 1H NMR (400 MHz, DMSO) δ 11.52 (s, 1H), 7.99 (d, J = 8.7 Hz, 2H), 7.89 (s, 4H), 7.46 (d, J = 8.7 Hz, 2H), 2.90-2.78 (m, 2H), 1.53-1.37 (m, 2H), 0.97 (t, J = 7.3 Hz, 3H). 13C NMR (101 MHz, DMSO) δ 156.12, 153.60, 134.76, 134.39, 128.69, 128.38, 28.39, 19.40, 13.60. |

TABLE 3-continued

NMR Specroscopy Lists of Compounds NCL812, NCL001-NCL275

| NCL Code | NMR |
|---|---|
| NCL234 | 1H NMR (400 MHz, DMSO) δ 11.42 (s, 1H), 8.00 (d, J = 8.7 Hz, 2H), 7.86 (s, 4H), 7.48 (d. J = 8.7 Hz, 2H), 2.85 (q, J = 7.6 Hz, 2H), 1.06 (t, J = 7.6 Hz, 3H).<br>13C NMR (101 MHz, DMSO) δ 156.08, 154.70, 134.44, 134.38, 128.64, 128.42, 20.07, 10.69. |
| NCL235 | 1H NMR (400 MHz, DMSO) δ 8.25 (s, 1H), 8.22 (t, J = 8.5 Hz, 1H), 7.50 (d, J = 10.5 Hz, 1H), 7.42 (s, 4H), 7.34 (d, J = 8.4 Hz. 1H),<br>OR<br>1H NMR (400 MHz, DMSO) δ 8.31-8.15 (m, 2H), 7.73-7.14 (m, 6H).<br>13C NMR (101 MHz, DMSO) δ 160.16 (d, J = 253.3 Hz), 157.07, 136.99 (d, J = 4.2 Hz), 134.83 (d, J = 10.7 Hz), 128.07 (d, J = 3.6 Hz), 125.08 (d, J = 3.2 Hz), 121.22 (d, J = 10.0 Hz), 116.45 (d, J = 24.8 Hz). |
| NCL236 | 1H NMR (400 MHz, DMSO) δ 11.36 (s, 1H), 7.95-7.64 (m, 5H), 7.53 (d, J = 10.9 Hz, 1H), 7.35 (d, J = 8.1 Hz, 1H), 2.33 (s, 3H).<br>13C NMR (101 MHz, DMSO) δ 159.90 (d, J = 252.9 Hz), 156.21, 148.64, 134.88 (d, J = 10.8 Hz), 131.48 (d, J = 3.9 Hz), 125.07 (d, J = 11.4 Hz), 124.74 (d, J = 3.3 Hz), 116.79 (d, J = 26.3 Hz), 17.80 (d, J = 6.1 Hz). |
| NCL237 | 1H NMR (400 MHz, DMSO) δ 14.38 (s, 1H), 7.30 (d, J = 8.6 Hz, 2H), 6.73-6.56 (m, 2H), 6.39 (s, 2H), 6.27 (s, 2H), 2.57 (t, J = 7.3 Hz, 2H), 1.63-1.46 (m, 5H), 1.32 (s, 1H), 1.13-0.97 (m, 3H), 0.89-0.77 (m, 2H).<br>13C NMR (101 MHz, DMSO) δ 160.62, 158.15, 152.94, 134.16, 130.52, 124.27, 119.53, 116.22, 44.10, 36.13, 32.45, 25.98, 25.57. |
| NCL238 | 1H NMR (400 MHz, DMSO) δ 10.92 (s, 2H), 8.61 (d, J = 1.7 Hz, 2H), 8.14 (dd, J = 8.3, 2.0 Hz, 2H), 8.05 (s, 2H), 7.59 (d, J = 8.3 Hz, 2H), 6.30 (s, 1H), 5.93 (s, 2H).<br>13C NMR (101 MHz, DMSO) δ 162.67, 162.59, 149.65, 147.85, 135.86, 130.63, 124.61, 73.64. |
| NCL239 | 1H NMR (400 MHz, DMSO) δ 10.82 (s, 2H), 8.80 (d, J = 1.6 Hz, 2H), 8.54 (dd, J = 4.7, 1.5 Hz, 2H), 8.11-8.03 (m, 4H), 7.46 (dd, J = 7.9, 4.8 Hz, 2H), 6.33 (s, 1H), 5.91 (s, 2H).<br>13C NMR (101 MHz, DMSO) δ 162.74, 162.62, 149.41, 147.69, 137.19, 132.57, 131.02, 123.96, 73.55. |
| NCL240 | 1H NMR (600 MHz, DMSO) δ 10.91 (s, 2H), 8.60-8.53 (m, 2H), 8.10 (s, 2H), 7.94 (d, J = 7.7 Hz, 2H), 7.87 (t, J= 7.3 Hz, 2H), 7.38-7.30 (m, 2H), 6.35 (s, 1H), 5.94 (br s, 2H).<br>13C NMR (151 MHz, DMSO) δ 162.7\*, 154.0, 149.4, 140.8, 136.7, 123.2, 119.1, 73.7.\*<br>\*2D NMR analysis suggests that the signals for the two quaternary carbons of the pyrimidine core both occur at 162.7 ppm. |
| NCL241 | 1H NMR (400 MHz, DMSO) δ 11.03 (s, 2H), 8.62 (d, J = 3.3 Hz, 4H), 8.01 (s, 2H), 7.60 (d, J = 3.2 Hz, 4H), 6.38 (s, 1H), 6.00 (s, 2H).<br>13C NMR (101 MHz, DMSO) δ 162.71, 162.69, 150.18, 142.21, 137.53, 120.15, 73.96. |
| NCL242 | 1H NMR (400 MHz, DMSO) δ 10.61 (s, 2H), 10.42 (s, 1H), 9.78 (s, 2H), 9.08 (s, 1H), 8.87 (s, 1H), 8.84 (s, 2H), 8.20 (s, 2H), 7.08 (d, J = 2.5 Hz, 1H), 6.93 (d, J = 2.5 Hz, 2H), 6.89-6.76 (m, 2H), 6.71 (d, J = 8.7 Hz, 2H), 6.64 (dd, J = 8.7, 2.7 Hz, 2H), 5.91 (s, 1H), 5.84 (s, 2H).<br>13C NMR (101 MHz, DMSO) δ 162.66, 152.18, 151.58, 149.94, 149.88, 149.08, 140.17, 120.97, 120.39, 118.32, 117.43, 117.23, 116.73, 115.04, 112.60, 72.69. |
| NCL243 | 1H NMR (400 MHz, DMSO) δ 10.25 (s, 2H), 9.18 (s, 4H), 7.87 (s, 2H), 7.11 (d, J = 1.4 Hz, 2H), 6.90 (dd, J = 8.1, 1.4 Hz, 2H), 6.78 (d, J = 8.1 Hz, 2H), 6.14 (s, 1H), 5.69 (s, 2H).<br>13C NMR (101 MHz, DMSO) δ 163.16, 162.89, 147.24, 146.03, 141.55, 127.12, 119.30, 116.24, 113.09, 73.36. |
| NCL244 | 1H NMR (400 MHz, DMSO) δ 10.71 (s, 3H), 9.95 (s, 3H), 9.30 (s, 3H), 8.96 (s, 1H), 8.26 (s, 2H), 7.13 (d, J = 7.7 Hz, 2H), 7.01 (d, J = 7.4 Hz, 2H), 6.95 (d, J = 7.6 Hz, 1H), 6.86-6.74 (m, 3H), 6.71 (t, J = 7.7 Hz, 1H), 5.95 (s, 1H), 5.85 (s, 2H).<br>13C NMR (101 MHz, DMSO) δ 163.39, 162.70, 162.18, 147.40, 145.67, 145.47, 144.80, 140.68, 121.27, 120.58, 119.43, 119.18, 118.88, 118.44, 117.96, 116.00, 72.75. |
| NCL245 | 1H NMR (400 MHz, DMSO) δ 10.75 (s, 2H), 8.83-8.78 (m, 2H), 8.74 (s, 2H), 8.05-8.00 (m, 2H), 7.98 (d, J = 8.2 Hz, 2H), 7.92 (d, J = 7.0 Hz, 2H), 7.67-7.53 (m, 6H), 6.51 (s, 1H), 5.92 (s, 2H).<br>13C NMR (101 MHz, DMSO) δ 152.94, 162.74, 139.74, 133.69, 130.51, 129.90, 129.25, 128.84, 126.93, 126.11, 125.99, 125.60, 123.98, 73.46. |
| NCL246 | 1H NMR (400 MHz, DMSO) δ 10.55 (s, 2H), 7.87 (d, J = 9.2 Hz, 2H), 7.59 (d, J = 7.4 Hz, 4H), 7.37 (t, J = 7.5 Hz, 4H), 7.29 (t, J = 7.3 Hz, 2H), 7.01 (dd, J = 16.1, 9.3 Hz, 2H), 6.84 (d, J = 16.0 Hz, 2H), 6.13 (s, 1H), 5.78 (s, 2H).<br>13C NMR (101 MHz, DMSO) δ 162.52, 142.73, 136.42, 135.24, 128.76, 128.19, 126.69, 126.04, 73.35. |
| NCL247 | 1H NMR (400 MHz, DMSO) δ 10.20 (s, 2H), 9.00 (s, 4H), 8.43 (s, 2H), 7.80 (s, 2H), 6.59 (s, 4H), 6.07 (s, 1H), 5.67 (s, 2H). |
| NCL248 | 1H NMR (400 MHz, DMSO) δ 8.73 (s, 1H), 8.66 (d, J = 8.2 Hz, 1H), 8.00 (d, J = 7.2 Hz, 1H), 7.93 (d, J = 7.6 Hz, 1H), 7.84 (d, J = 8.1 Hz, 1H), 7.60-7.44 (m, 3H), 5.95 (s, 2H), 5.58 (s, 2H).<br>13C NMR (101 MHz, DMSO) δ 160.68, 142.16, 133.59, 132.18, 130.24, 128.52, 127.94, 126.48, 125.77, 125.58, 125.02, 124,11. |
| NCL249 | 1H NMR (400 MHz, DMSO) δ 7.82 (d, J = 9.5 Hz, 1H), 7.47 (d, J = 7.5 Hz, 2H), 7.33 (t, J = 7.6 Hz, 2H), 7.23 (t, J = 7.3 Hz, 1H), 6.95 (dd, J = 16.0, 9.5 Hz, 1H), 6.72 (d, J = 16.0 Hz, 1H), 4.38 (s, 4H). |
| NCL250 | 1H NMR (400 MHz, DMSO) δ 8.34 (s, 2H), 7.78-7.65 (m, 4H), 7.54-7.43 (m, 4H), 3.87 (s, 4H).<br>13C NMR (101 MHz. DMSO) δ 160.85, 135.20, 134.84, 129.44, 128.77, 60.70. |
| NCL251 | 1H NMR (400 MHz, DMSO) δ 8.35 (s, 2H), 7.79-7.70 (m, 4H), 7.55-7.45 (m, 4H), 3.60 (d, J = 0.9 Hz, 4H), 1.67 (t, J = 2.7 Hz, 4H).<br>13C NMR (101 MHz, DMSO) δ 159.49, 135.06, 134.98, 129.42, 128.74, 60.20, 28.25. |
| NCL252 | 1H NMR (400 MHz, CDCl3) δ 8.26 (s, 2H), 7.71-7.60 (m, 4H), 7.42-7.33 (m, 4H), 3.71 (td, J = 6.8, 1.1 Hz, 4H), 2.10 (p, J = 6.8 Hz, 2H).<br>13C NMR (101 MHz, CDCl3) δ 160.00, 136.54, 134.74, 129.25, 128.90, 59.16, 31.90. |
| NCL253 | 1H NMR (400 MHz, DMSO) δ 7.89 (s, 1H), 7.47 (d, J = 8.7 Hz, 2H), 6.67 (d, J = 8.8 Hz, 2H), 5.71 (s, 2H), 5.25 (s, 2H), 2.91 (s, 6H). |
| NCL254 | 1H NMR (400 MHz, DMSO) δ 11.30 (s, 1H), 7.98 (d, J = 8.7 Hz, 2H), 7.80 (s, 4H), 7.47 (d, J = 8.7 Hz, 2H), 2.99-2.68 (m, 2H), 1.68-1.13 (m, 6H), 0.84 (t, J = 7.2 Hz, 3H).<br>13C NMR (101 MHz, DMSO) δ 156.06, 153.87, 134.79,134.40, 128.68, 128.41, 30.95, 26.63, 25.60, 21.95, 13.86. |
| NCL255 | 1H NMR (400 MHz, DMSO) δ 10.69 (s, 2H), 8.09 (s, 2H), 7.77 (s, 8H), 7.71 (d, J = 7.5 Hz, 4H), 7.47 (t, J = 7.6 Hz, 4H), 7.37 (t, J = 7.3 Hz, 2H), 6.42 (s, 1H), 5.87 (s, 2H).<br>13C NMR (101 MHz, DMSO) δ 162.80, 162.64, 140.22, 139.71, 139.48, 134.31, 128.97, 127.64, 127.05, 126.66, 126.55, 73.49. |
| NCL256 | 1H NMR (400 MHz, DMSO) δ 10.47 (s, 4H), 9.81 (s, 2H), 8.14 (s, 2H), 7.29 (d, J = 8.4 Hz, 2H), 6.40-6.24 (m, 4H), 5.78 (s, 3H). |
| NCL257 | 1H NMR (400 MHz, DMSO) δ 11.73 (s, 1H, Isomer A), 10.65 (s, 1H, Isomer A), 8.99 (s, 1H, Isomer A), 8.75 (d, J = 8.6 Hz, 1H, Isomer A), 7.92 (d, J = 8.9 Hz, 1H, Isomer A masking a signal from Isomer B), 7.85 (d, J = 7.7 Hz, 1H, Isomer A), 7.73-7.50 (m, 5H, Isomers A & B), 7.39 (t, J = 7.6 Hz, 1H, Isomer A masking a signal from Isomer B), 7.24 (d, J = 8.9 Hz, 1H, Isomer A).<br>NMR (400 MHz, DMSO) δ 12.88 (s, 1H, Isomer B), 9.99 (s, 1H, Isomer B), 8.65 (d, J = 8.8 Hz, 1H, Isomer B), 8.07-8.01 (m, 2H, Isomer B), 7.95 (d, J = 9.0 Hz, 1H, Isomer B), 7.47-7.42 (m, 1H), 7.30 (d, J = 8.8 Hz, 1H, Isomer B), 7.29 (d, J = 9.0 Hz, 1H, Isomer B). Masked signals are identified in Isomer A NMR.<br>13C NMR (101 MHz, DMSO) δ 157.22, 154.74, 146.77, 133.32, 131.19, 128.61, 128.20, 128.07, 124.17, 123.58, 118.12, 109.69. |

TABLE 3-continued

NMR Specroscopy Lists of Compounds NCL812, NCL001-NCL275

| NCL Code | NMR |
|---|---|
| NCL258 | 1H NMR (400 MHz, DMSO) δ 7.33 (s, 8H), 3.64 (s, 4H), 2.42 (s, 4H), 1.42 (s, 4H).<br>13C NMR (101 MHz, DMSO) δ 140.20, 130.86, 129.64, 127.95, 52.14, 48.53, 27.32. |
| NCL259 | 1H NMR (400 MHz, DMSO) δ 11.37 (s, 1H), 7.98 (d, J = 8.6 Hz, 2H), 7.84 (s, 4H), 7.46 (d, J = 8.6 Hz, 2H), 2.83 (d, J = 7.1 Hz, 2H), 1.69-1.43 (m, 6H), 1.08 (s, 5H).<br>13C NMR (101 MHz, DMSO) δ 156.02, 153.02, 135.35, 134.32, 128.84, 128.33, 35.79, 33.41, 31.97, 25.65. |
| NCL260 | 1H NMR (400 MHz, CDCl3) δ 7.25 (d, J = 8.3 Hz, 4H), 7.21 (d, J = 8.4 Hz, 4H), 3.70 (s, 4H), 2.70 (s, 4H). |
| NCL261 | 1H NMR (400 MHz, DMSO) δ 12.09 (s, 1H), 8.34 (s, 1H), 8.24-8.17 (m, 2H), 7.96 (dd, J = 8.8, 4.6 Hz, 3H), 7.83 (s, 4H), 7.61-7.54 (m, 2H).<br>13C NMR (101 MHz, DMSO) δ 155.42, 146.87, 133.90, 132.70, 131.23, 129.46, 128.35, 128.31, 127.81, 127.35, 126.82, 123.04. |
| NCL262 | 1H NMR (400 MHz, DMSO) δ 9.98 (s, 2H), 7.42-7.07 (m, 12H), 5.97 (d, J = 25.2 Hz, 1H), 5.59 (s, 2H), 2.79 (t, J = 7.6 Hz, 4H), 2.57-2.44 (m, 4H).<br>13C NMR (101 MHz, DMSO) δ 162.74, 162.47, 143.11, 141.16, 128.40, 128.27, 125.86, 72.62, 33.61, 32.43. |
| NCL263 | 1H NMR (400 MHz, DMSO) δ 12.15 (s, 1H), 8.47 (t, J = 7.6 Hz, 1H), 8.40 (s, 1H), 7.90 (s, 4H), 7.81 (d, J = 10.4 Hz, 1H), 7.68 (d, J = 8.3 Hz, 1H). |
| NCL264 | 1H NMR (400 MHz, DMSO) δ 10.78 (s, 2H), 8.23 (s, 2H), 8.10-7.87 (m, 10H), 7.56 (s, 4H), 6.46 (s, 1H), 5.88 (s, 2H).<br>13C NMR (101 MHz, DMSO) δ 162.83, 162.67, 140.09, 133.19, 133.12, 133.00, 128.45, 128.08, 127.76, 126.96, 126.67, 126.53, 122.37, 73.63. |
| NCL265 | 1H NMR (400 MHz, DMSO) δ 7.78 (d, J = 8.7 Hz, 2H), 7.34 (d, J = 8.7 Hz, 2H), 5.85 (s, 2H), 5.45 (s, 2H), 2.90-2.74 (m, 2H), 1.49-1.33 (m, 2H), 1.33-1.11 (m, 8H), 0.84 (t, J = 6.9 Hz, 3H).<br>13C NMR (101 MHz, DMSO) δ 160.12, 149.95, 138.11, 131.48, 127.92, 127.10, 31.31, 29.43, 28.69, 26.44, 25.86, 22.07, 13.96. |
| NCL266 | 1H NMR (400 MHz, DMSO) δ 7.77 (d, J = 8.7 Hz, 2H), 7.34 (d, J = 8.7 Hz, 2H), 5.85 (s, 2H), 5.43 (s, 2H), 2.90-2.77 (m, 2H), 1.82-1.65 (m, 3H), 1.62-1.28 (m, 6H), 1.21-1.00 (m, 2H).<br>13C NMR (101 MHz, DMSO) δ 160.07, 150.06, 138.09, 131.49, 127.96, 127.08, 39.95, 32.79, 32.22, 25.17, 24.86. |
| NCL267 | 1H NMR (400 MHz, DMSO) δ 11.62 (s, 1H), 8.58 (s, 1H), 8.06 (d, J = 4.7 Hz, 2H), 7.76 (d, J = 8.5 Hz, 2H), 7.48 (d, J = 8.5 Hz, 2H)..<br>13C NMR (101 MHz, DMSO) δ 152.2, 145.5, 141.3. 133.8, 133.4, 132.6, 128.8, 128.2. |
| NCL268 | 1H NMR (400 MHz, DMSO) δ 11.49 (s, 1H), 8.54 (s, 1H), 8.03 (s, 2H), 7.62 (d, J = 7.6 Hz, 2H), 7.24 (d, J = 7.4 Hz, 2H), 2.33 (s, 3H).<br>13C NMR (101 MHz, DMSO) δ 152.4, 145.5, 142.9, 139.2, 132.1, 131.7, 129.4, 128.7, 126.6, 21.0. |
| NCL269 | 1H NMR (400 MHz, DMSO) δ 11.66 (s, 1H), 10.89 (br s, 1H), 8.23 (d, J = 7.8 Hz, 1H), 7.97 (d, J = 2.4 Hz, 1H), 7.51 (br s, 3H), 7.42 (d, J = 8.0 Hz, 1H), 7.22-7.14 (m, 1H), 7.14-7.06 (m, 1H), 2.39 (s, 3H).<br>13C NMR (101 MHz, DMSO) δ 155.6, 151.9, 137.2, 129.5, 124.2, 122.8, 122.3, 120.6, 113.8, 111.7, 15.9. |
| NCL270 | 1H NMR (400 MHz, DMSO) δ 11.71 (s, 2H), 11.33 (br s, 2H), 8.33 (d, J = 7.8 Hz, 2H), 8.05 (d, J = 2.7 Hz, 2H), 7.83 (br s, 2H), 7.45 (d, J = 8.0 Hz, 2H), 7.24-7.18 (m, 2H), 7.18-7.12 (m, 2H), 2.50 (s, 6H, obscured by DMSO-d6).<br>13C NMR (101 MHz, DMSO) δ 153.2, 153.0, 137.2, 129.8, 124.2, 122.8, 122.4, 120.6, 113.7, 111.8, 15.9. |
| NCL271 | 1H NMR (400 MHz, DMSO) δ 12.23 (br s, 2H), 8.68 (br s, 2H), 8.06 (d, J = 8.7 Hz, 4H), 7.50 (d, J = 8.7 Hz, 4H), 3.03-2.86 (m, 4H), 1.52-1.36 (m, 8H), 1.34-1.23 (m, 4H), 0.84 (t, J = 7.3 Hz, 6H).<br>13C NMR (101 MHz, DMSO) δ 155.7, 154.4, 134.6. 134.6, 128.9, 128.4, 30.9, 27.2, 25.8, 22.0, 13.9. |
| NCL272 | 1H NMR (400 MHz, DMSO) δ 12.28 (br s, 2H), 8.68 (br s, 2H), 8.06 (d, J = 8.5 Hz, 4H), 7.50 (d, J = 8.5 Hz, 4H), 3.04-2.86 (m, 4H), 1.53-1.35 (m, 8H), 1.32-1.14 (m, 12H), 0.83 (t, J = 6.7 Hz, 6H).<br>13C NMR (101 MHz, DMSO) δ 155.6, 154.3, 134.6 (2 × C)*, 128.9, 128.4, 31.2, 28.6, 28.5, 27.1, 26.1, 22.0, 13.9.<br>*Determined using 2D NMR analysis. |
| NCL273 | 1H NMR (400 MHz, Acetone) δ 13.20 (br s, 2H), 8.19 (br s, 2H), 7.96 (d, J = 8.6 Hz, 4H), 7.46 (d, J = 8.7 Hz, 4H), 3.14-3.05 (m, 4H), 2.15 (dt, J = 15.5, 7.8 Hz, 2H), 1.88-1.78 (m, 4H), 1.67-1.46 (m, 12H), 1.31-1.17 (m, 4H).<br>13C NMR (101 MHz, Acetone) δ 157.7, 156.6, 136.2, 136.1, 129.5, 129.4, 40.9, 33.3, 33.1, 28.4, 25.8. |
| NCL274 | 1H NMR (400 MHz, DMSO) δ 11.99 (s, 2H), 11.64 (s, 2H), 8.50 (br s, 4H), 8.10 (s, 2H), 8.02 (s, 2H), 7.44 (d, J = 7.3 Hz, 2H), 7.36 (d, J = 7.0 Hz, 2H). |
| NCL275 | 1H NMR (400 MHz, DMSO) δ 11.51 (br s, 2H), 8.77 (br s, 2H), 8.10-7.90 (m, 4H), 7.54 (d, J = 8.3 Hz, 4H), 4.81 (br s, 4H), 3.59 (q, J = 6.8 Hz, 4H), 1.20-1.03 (m, 6H). |

Example 9: Antigiardial Activity of NCL Analogues 231-247 and NCL219

Aim:

The objective of this study was to determine the activity of NCL219, and NCL231-NCL247 against *Giardia duodenalis* in vitro using the Resazurin Reduction Assay.

Methods:

*Giardia* trophozoites were grown until confluent. The media was replaced with fresh media and cold shocked for 40 minutes. Compounds were prepared in DMSO and serially diluted 2-fold in DMSO starting at with a 1/100 dilution of the stock (e.g. 128 mg/ml stock starting dilution would be 128 μg/ml). 2 μl of dilutions were added to the appropriate wells and 198 ul of TYI-S-33 media added to each well. Cells were diluted to a concentration of ~500 000 cells/ml and 100 μl were added to each well of the assay plate (except media only control). The assay was incubated in an anaerobic environment (candle jar) for 5 hours at 37° C. The media was removed and replaced with 100 μl of warm PBS then Alamarblue™ added to a concentration of 10%. The samples were incubated in an anaerobic environment until colour development. After incubation, the absorbance of each sample was read at 570 and 630 nm. The percent reduction of resazurin (Alamarblue™) was calculated (using the formula below) and data was analysed with GraphPad Prism v6 software. The formula used to calculate percent reduction of Alamarblue was $((E_{oxi}630 \times A_{570}) - (E_{oxi}570 \times A_{630}))/((E_{red}570 \times C_{630}) - (E_{red} \times C_{570})) \times 100$, Where: $E_{oxi}630 = 34798$, $E_{oxi}570 = 80586$, $A_{570}$=absorbance at 570 nm, $A_{630}$=absorbance at 630 nm, $E_{red}570 = 155677$, $E_{red}630 = 5494$, $C_{630}$=absorbance of negative control well at 630 nm and $C_{570}$=absorbance of negative control well at 570 nm.

Results and Conclusions:

Three of the compounds tested in this assay showed excellent inhibitory activity towards *Giardia duodenalis* in vitro, NCL245 (9.6 uM), NCL246 (5.4 uM) and NCL219 (1.03 uM). The results are presented in Table 4.

TABLE 4

| NCL code | [Stock] (mg/ml) | S. aureus ATCC 29213 (ug/ml) | Giardia WB (ug/ml) | Giardia WB (uM) |
|---|---|---|---|---|
| NCL231 | 25.6 | 32.00 | 9.6 | 41.24 |
| NCL232 | 12.8 | 64, 32 | 20 | 93.48 |
| NCL233 | 25.6 | 64, 32 | 68 | 247.3 |
| NCL234 | 25.6 | 64.00 | >64* | 0 |
| NCL235 | 25.6 | 128 | >64* | NC |
| NCL236 | 25.6 | 16 | >64* | NC |
| NCL237 | 25.6 | 4, 8 | 22.8^ | NC |
| NCL238 | 6.4 | >64 | >64* | NC |
| NCL239 | 12.8 | 32 | 111 | 334 |
| NCL240 | 25.6 | >128 | ~30 | ~91.73 |
| NCL241 | 25.6 | >128 | ~30 | ~91.29 |
| NCL242 | 25.6 | >128 | 32 | ~60.33 |
| NCL243 | 25.6 | >128 | 639 | 1754 |
| NCL244 | 25.6 | 16 | >64* | NC |
| NCL245 | 25.6 | 8 | 4 | 9.591 |
| NCL246 | 25.6 | 8 | 2 | 5.446 |
| NCL247 | 25.6 | >128 | 40 | 92.87 |
| NCL219 | 10.0 | >100 | 0.4 | 1.030 |

*IC50 could not be calculated
^1 repeat only
IC50 after 5 hours, MIC after 24 hours, NC—not converged

Example 10: Anti-Trypanosomatid Activity of NCL Analogues

Background:

Trypanosomatids cause significant human morbidity and mortality with an estimated 1.3 million new cases per year resulting in ~30 000 deaths occurring due to *Leishmania* sp. alone. In addition to this Trypanosomatids, such as *Trypanosoma brucei* (endemic to Africa), cause significant morbidity and mortality to humans (upto 66 million people affected) as well as significant losses in the livestock industry (known as nagana). Currently the chemotherapy available for these organisms is limited and has unwanted toxic side effects. In this study, we looked at the in vitro efficacy of 20 chemical analogues from the NCL series (see Table 5 for details) against the procyclic stage of *T. brucei* and the promastigote stage of *Leishmania donovani*. Analogues that showed promising in vitro activity against either of the parasites were tested in vitro for selectivity against a mouse macrophage cell line (ATCC RAW 264.7).

Aim:

The objective of this study was to: (1) evaluate the in vitro antiparasitic activity of 20 structurally related aminoguanidines (from the NCL series) against *T. brucei* and *L. donovani*; and (2) determine the selectivity of these compounds for parasites over mammalian cell.

Methods:

Antimicrobial agents (Table 5) were all dissolved in DMSO to a final concentration of 10 mM. Pentamidine (Sigma) was used as a positive control and prepared as the NCL compounds

TABLE 5

Scaffold 1

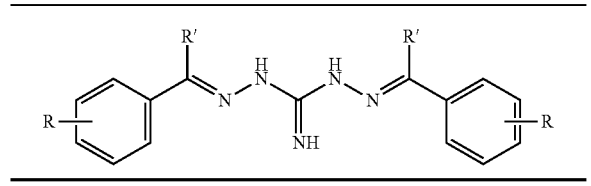

TABLE 5-continued

| Compound | R | R' |
|---|---|---|
| NCL024 | 4-CN | H |
| NCL026 | 3-CN | H |
| NCL028 | 2-OCH$_3$ | H |
| NCL062 | 4-Cl | CH$_3$ |
| NCL099 | 4-C(CH$_3$)$_3$ | H |
| NCL113 | 4-N(CH$_3$)$_2$ | H |
| NCL166 | 4-SCF$_3$ | H |
| NCL171 | 2-OH, 4-N(CH$_3$)$_2$ | H |
| NCL219 | 4-C(CH$_3$)$_3$ | CH$_3$ |
| NCL812 | 4-Cl | H |

Scaffold 2

| Compound | R |
|---|---|
| NCL195 | 4-CH$_3$ |
| NCL197 | 5-OH |
| NCL201 | 4-N(CH$_3$)$_2$ |

Scaffold 3

| Compound | R | R' |
|---|---|---|
| NCL041 | H | 4-CF$_3$ |
| NCL042 | H | 2-CF$_3$ |
| NCL052 | H | 3-Cl |
| NCL191 | CH$_3$ | 4-Cl |
| NCL231 | CH$_3$ | 4-C(CH$_3$)$_3$ |

*L. donovani* Screening. Procyclic promastigotes from exponentially growing cultures maintained in DME-L+ Bob additions were used for all assays. Compounds were initially screened for activity at 10 μM. Compounds were diluted in culture media to a final volume of 10 μM in 96 well plates. Promastigotes were diluted to a density of ~8×10$^5$ cells/ml then added to the assay plate resulting in a final cell density of 4×10$^5$ cells/ml. in 96 well plates. Cells were incubated for 96 hrs at 27° C. before the addition of Alamarblue (thermofisher). Fluorescence was read at excitation 530 nm and Emission 590 nm. Compounds that showed inhibitory activity at 10 μM were further investigated to determine IC$_{50}$ values. Compounds were serially diluted in thirds, in a 96 well plate, in cell growth media so that concentrations ranged from 0.005 to 10 μM and promastigotes added to a final concentration of 1×10$^6$ cells/ml. Cells were incubated at 27° C. for 72 hours before the addition of alamar blue. Fluorescence was measured as above.

*T. brucei* Screening.

Procyclic promastigotes from exponentially growing cells maintained SDM-79 medium were used in all assays. Compounds were initially screened at 10 μM for activity. Compounds were diluted in culture media to a concentration of 20 μM and added to a 96 well plate, after addition of promastigotes (final concentration 4×10$^5$ cells/ml) compound concentration was 10 µM. Cells were incubated for 48 hrs at 27° C. before the addition of alamar blue and fluorescence measurement as described above. Compounds that showed inhibition at 10 µM were further characterised to determine $IC_{50}$ values. Compounds were serially diluted in thirds in culture media resulting in final concentrations ranging from 0.004-10 µM. Promastigotes were added at a final concentration of $4 \times 10^5$ cells/ml. Cells were incubated at 27° C. for 48 hours before addition of alamar blue. In addition promastigotes, at a concentration of $8 \times 10^5$ were exposed to NCL026 for 1.5 hours before removal of the drug via centrifugation at 5000 rpm for 7 minutes and resuspension of cells in culture media. Cells were incubated for 96 hours at 27° C. and observed daily for metabolic activity (alamar blue assay) and morphological changes. A control culture was exposed to DMSO instead of NCL026.

Cell toxicity assays. Mouse macrophages (RAW 264.7) were grown in RPMI1640 media supplemented with L-glutamine and 10% foetal calf serum. Cells were trypsanised when 80% confluent and subcultured every 3-4 days. For cytotoxicity assays cells were diluted to a final cell concentration of $2 \times 10^4$ cells/ml and 198 µl added to each well of a 96 well plate. Cells were incubated in a humidified incubator for 2 hours at 37° C. 5% $CO_2$ before the addition of NCL compounds (2 µl/well, previously diluted in DMSO). Campothecin, triton X and DMSO only were used as controls. Cells were exposed to the compounds for 24 hours. The metabolic activity of the cells was determined using the WST-1 assay system (Roche Life Science). The supernatant was removed, 100 µl of PBS with 10% WST-1 was added to each well and incubated for 1 hr before reading absorbance at 450 nm. The selectivity index of the compounds was determined by dividing the $IC_{50}$ of macrophages by the $IC_{50}$ against parasites. $IC_{50}$ was determined via graphpad prism software.

Figure 10:
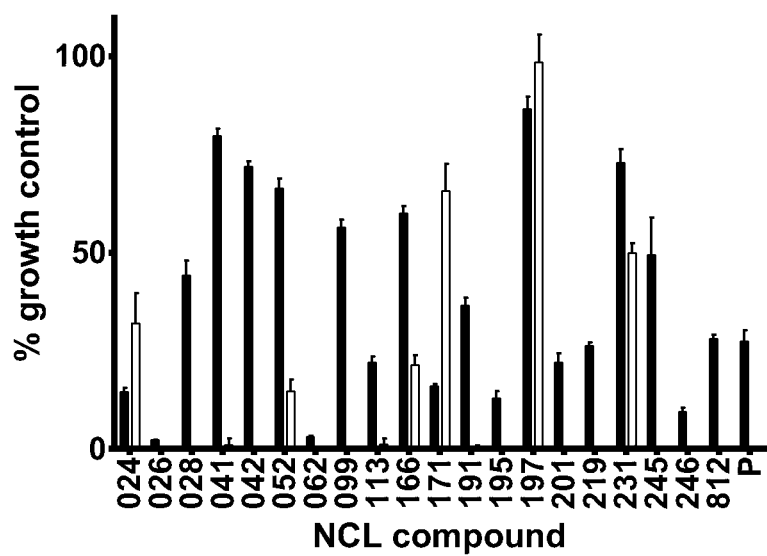
FIG. 10 is a graph illustrating the activity of NCL compounds at 10 μM against *T. brucei* (black) and *L. donovani* (grey)

Results:

Robenidine and 19 structural analogues were screened for activity against the procyclic promastigote stage of L. donovani and T. brucei at 10 µM. Of the compounds tested 70% showed a ≥90% reduction of metabolic activity in L. donovani while 15% showed a similar reduction of metabolic activity in T. brucei (see FIG. 10). The procyclic stage of T. brucei and the promastigote stage of L. donovani were exposed to the compounds for 48 or 96 hrs respectively before the effect was measured using a resazurin dye. Assays were repeated in triplicate. P=pentamidine. Error ±SD.

Of those compounds active against L. donovani NCL026, NCL028, NCL041, NCL042, NCL062, NCL099, NCL195, NCL201, NCL219 and NCL246 had the greatest activity inhibiting the parasite 100%. Against T. brucei NCL026, NCL062, and NCL246 had the greatest inhibitory effect. NCL026, NCL062 and NCL246 were very effective against both species of parasites. Further investigation of a selection of compounds that had activity against the parasites was completed to determine the $IC_{50}$ values. The $IC_{50}$ value was determined for NCL028, NCL099, NCL166, NCL201, NCL245, NCL246 and NCL812 against L. donovani. The $IC_{50}$ ranged from 0.37 µM (NCL028) to 6.48 µM (NCL245 and NCL246). The $IC_{50}$ value was determined against T. brucei with the 6 most effective analogues NCL024, NCL026, NCL062, NCL171, NCL195 and NCL246. Of these analogues NCL026, NCL171 and NCL195 were the most effective with $IC_{50}$ values of 1.7, 1.4 and 1.5 µM respectively. The highest $IC_{50}$ value determined was 4.2 µM for NCL246. A recovery assay to determine the ability of T. brucei to recover after a short exposure to NCL026 was performed. After 1.5 hrs of exposure to the for select periods of time to determine the $GI_{50}$ or $IC_{50}$. The selectivity index (SI) was determined by dividing the $GI_{50}$ of macrophages by the $IC_{50}$ of parasites. An SI≥10 is considered selective for the parasite. Assays were repeated in triplicate. Error ±SD. Based on this assay the selectivity of the compounds ranged from 0.57 to 27.9. It is generally considered that a selectivity index <10 is relatively unselective while a selectivity index>10 is considered selective for the parasite. Based on this convention only one compound (NCL171) could be considered relatively selective for T. brucei while 4 compounds were highly selective for L. donovani in vitro (NCL028, NCL 099, NCL113 and NCL219).

TABLE 6

| Compound | $GI_{50}$ macrophage (µM) | T. brucei $IC_{50}$ (µM) | T. brucei SI | L. donovani $IC_{50}$ (µM) | L. donovani SI |
|---|---|---|---|---|---|
| NCL 024 | 12.74 ± 2.79 | 3.35 ± 0.11 | 3.79 | — | — |
| NCL 026 | 9.60 ± 0.99 | 1.68 ± 0.63 | 5.71 | 2.5 ± 0.13 | 3.84 |
| NCL 028 | 8.10 ± 2.76 | — | — | 0.29 ± 0.05 | 27.9 |
| NCL 062 | 7.15 ± 1.27 | 4.04 ± 0.83 | 1.75 | — | — |
| NCL 099 | 7.66 ± 0.56 | — | — | 0.37 ± 0.04 | 20.7 |
| NCL 113 | 12.90 ± 3.49 | — | — | 0.92 ± 0.06 | 14 |
| NCL 166 | 9.46 ± 0.05 | — | — | 3.23 ± 1.00 | 2.78 |
| NCL 171 | 12.50 ± 3.61 | 1.37 ± 0.03 | 9.14 | — | — |
| NCL 195 | 5.78 ± 0.33 | 1.46 ± 0.76 | 3.79 | — | — |
| NCL 201 | 12.28 ± 2.06 | — | — | 2.92 ± 0.22 | 4.23 |
| NCL 219 | 19.26 ± 3.77 | — | — | 0.80 ± 0.10 | 24.08 |
| NCL 245 | 3.7 ± 0.71 | — | — | 7.17 ± 2.05 | 0.57 |
| NCL 246 | 13.83 ± 0.07 | 4.18 ± 0.37 | 3.31 | 6.72 ± 2.99 | 2.06 |
| NCL 812 | 14.85 ± 1.34 | — | — | 2.9 ± 0.24 | 5.12 |

Conclusion.

This study demonstrated that several of the compounds tested showed high inhibitory activity against either L. donovani or T. brucei in vitro. Based on the in vitro selectivity index, NCL171 appears to be the most promising against T. brucei while NCL028, NCL099 and NCL219 appear to be the most promising against L. donovani.

Example 11: The Physicochemical and Metabolic Properties of NCL026, NCL028, NCL099, NCL171, NCL177, NCL195, NCL217, NCL259 and NCL812

Aim:

The objective of this study was to evaluate the physicochemical and metabolic properties of NCL026, NCL028, NCL099, NCL171, NCL177, NCL195, NCL217, NCL259 and NCL812.

The physicochemical and metabolic characteristics of the nine compounds were assessed using a combination of in silico and experimental techniques and the results have been summarised in FIG. 11.

Calculated physicochemical parameters for each compound were generally within the limits normally associated with compounds having "drug-like" properties. The polar surface area values of NCL026 and NCL171 are however, approaching the upper limit recommended for good membrane permeability, reflecting the relatively high number of heteroatoms within these two structures. All of the compounds demonstrated low kinetic solubilities under neutral pH conditions, except for NCL259 which was more moderate. Most of the compounds showed greater solubility under acidic conditions (pH 2) suggesting an increase in ionisation at low pH. Measured partition coefficient values were relatively high at pH 7.4, with Log $D_{7.4}$ values ranging from 3.6 to >5.3. Log D values were lower under acidic conditions (pH 3), however would still be considered to be moderate to high (2.8 to 4.9). The observed pH dependent solubility and partition coefficient results are consistent with the basic characteristics of the compounds predicted by their structures. The metabolic stability of the nine compounds were evaluated in both human and mouse liver microsomes. Five of the compounds, NCL026, NCL177, NCL195, NCL259 and NCL812, showed low rates of degradation in both species of liver microsomes ($E_H$ values <0.3). NCL099, NCL171 and NCL217 showed intermediate to high rates of degradation ($E_H$ values 0.49 to 0.88) with degradation rates for each compound being broadly comparable between species. NCL028 showed a low rate of degradation in human liver microsomes and a high rate of degradation in mouse liver microsomes which may suggest a significant difference in metabolism between species for this compound. There was no measurable degradation of any of the compounds in control (non-cofactor) incubations in either species suggesting that there was no major cofactor independent metabolism contributing to their overall rates of metabolism.

Experimental Methods

Calculated Physicochemical Parameters Using ChemAxon JChem Software

Theoretical physicochemical values for each compound were calculated using the ChemAxon chemistry cartridge via JChem for Excel software. Parameters calculated and a brief explanation of their relevance is given below.

Molecular Weight (MW): Ideally, MW should be less than 500 for good membrane permeability.

Polar Surface Area (PSA): Calculated using a simplified 2-dimensional modelling approach, which has been validated against a more sophisticated 3-dimensional modelling strategy. The value has been calculated at pH=7.4, which takes ionisation of the molecule into account. It is usually accepted that PSA values of less than approximately 120 $Å^2$ will provide acceptable oral drug absorption and membrane permeability.

Freely Rotating Bonds: Number of single bonds that are not in a ring or constrained system and are not bound to a hydrogen atom. FRB should be less than or equal to 10 for good membrane permeability (See D. Veber et al, J. Med. Chem. 2002, 45, 2615-2623).

H Bond Donor/Acceptors: Number of hydrogen bond donors and acceptors gives an indication of the hydrogen bonding capacity of the molecule which is inversely related to membrane permeability. Ideally, the number of H-Bond donors should be less than 5 and the number of H-Bond acceptors should be less than 10.

pKa: Basic physicochemical measure of the acidity of a compound. In the context of drug development, the values themselves only indicate whether ionisation is likely to be relevant at physiological conditions.

Solubility Estimates Using Nephelometry

Compound in DMSO was spiked into either pH 6.5 phosphate buffer or 0.01 M HCl (approx. pH 2.0) with the final DMSO concentration being 1%. Samples were then analysed via Nephelometry to determine a solubility range. (See C. D. Bevan and R. S. Lloyd, Anal. Chem. 2000, 72, 1781-1787).

Log D Measurement

Partition coefficient values (Log D) of the test compounds were estimated by correlation of their chromatographic retention properties against the characteristics of a series of standard compounds with known partition coefficient values. The method employed is a gradient HPLC based derivation of the method developed by Lombardo (See F. Lombardo et al, J. Med. Chem. 2001, 44, 2490-2497).

Microsomal Stability

Incubation methods: The metabolic stability assay was performed by incubating each test compound (at 1 µM) with human and mouse liver microsomes (Xenotech, Lot #1210057 and 1310211, respectively) at 37° C. and 0.4 mg/mL protein concentration. The metabolic reaction was initiated by the addition of an NADPH-regenerating system (i.e. NADPH is the cofactor required for CYP450-mediated metabolism) and quenched at various time points over a 60 minute incubation period by the addition of acetonitrile containing diazepam as internal standard. Control samples (containing no NADPH) were included (and quenched at 2, 30 and 60 minutes) to monitor for potential degradation in the absence of cofactor. Analytical conditions: Instrument: Waters Micromass Xevo G2 QTOF coupled to a Waters Acquity UPLC; Detection: Positive electrospray ionisation under MSE mode; Cone Voltage 30 V; Column: Ascentis Express Amide column (50×2.1 mm, 2.7 µm); LC conditions: Gradient cycle time: 4 minutes; Injection volume: 5 µL; Flow rate: 0.4 mL/min; Mobile phase: Acetonitrile-water gradient with 0.05% formic acid Metabolite; Identification: A metabolite screen was not included in this study, however, since data was acquired using MSE mode, which allows for the simultaneous acquisition of low and high collision energy MS spectra, a post-hoc metabolite search may be conducted at a later date if warranted.

Calculations: Test compound concentration versus time data were fitted to an exponential decay function to determine the first-order rate constant for substrate depletion. In cases where clear deviation from first-order kinetics was evident, only the initial linear portion of the profile was utilised to determine the degradation rate constant (k). Using standard methods in the art, each substrate depletion rate constant was then used to calculate: [1] a degradation half-life, [2] an in vitro intrinsic clearance value ($CL_{int}$, in vitro); [3] a predicted in vivo hepatic intrinsic clearance value ($CL_{int}$); [4] a predicted in vivo blood clearance value ($CL_{blood}$); and [5] a predicted in vivo hepatic extraction ratio ($E_H$). The following scaling parameters were assumed in the above calculations (Table 7).

TABLE 7

| Species | Liver mass (g liver/kg body weight) | Microsomal protein (mg/g liver mass) | Hepatic blood flow (Q) (mL/minute/ kg body weight) |
|---|---|---|---|
| Human [a] | 25.7 | 32 | 20.7 |
| Mouse [a] | 54.9 | 47 | 120 |

[a] Ring et al. (2011) *Journal of Pharmaceutical Silences*, 100: 4090-4110.

Predictions of in vivo hepatic extraction ratios: The microsome-predicted hepatic extraction ratios (EH) obtained based on the relative rates of test compound degradation in vitro, were used to classify compounds as low (<0.3), intermediate (0.3-0.7), high (0.7-0.95) or very high (>0.95) extraction compounds.

Results:

The physicochemical and metabolic characteristics of the nine compounds were assessed using a combination of in silico and experimental techniques and the results have been summarised in FIG. 11.

Example 12: Exposure of NCL026, NCL195, NCL259 and NCL812 in Male Swiss Outbred Mice Following IV Administration Aim:

The objective of this study was to evaluate the systemic exposure of NCL026, NCL195, NCL259 and NCL812 in male Swiss outbred mice after IV administration at 5 mg/kg.

Methods:

The systemic exposures of NCL026, NCL195, NCL259 and NCL812 were studied in nonfasted male Swiss outbred mice weighing 26.2-32.1 g. Mice had access to food and water ad libitum throughout the pre- and post-dose sampling period. Each compound was administered IV via a bolus injection into the tail vein (vehicle 20% (v/v) DMSO in PEG400, 1 mL/kg dose volume, n=8 mice per compound). Following administration, blood samples were collected at 5, 15, 30, 120, 240 and 480 min postdose (n=2 mice per time point for each compound). A maximum of two samples were obtained from each mouse, with samples being taken either via submandibular bleed (approximately 120 µL; conscious sampling) or terminal cardiac puncture (0.6 mL; while mice were anaesthetised using inhaled Isoflurane). No urine samples were collected as mice were housed in bedded cages during the study. Blood was collected directly into polypropylene Eppendorf tubes containing heparin as anticoagulant, and stabilisation cocktail (containing Complete® (a protease inhibitor cocktail with EDTA) and potassium fluoride) to minimise the potential for ex vivo degradation of the test compounds in blood/plasma samples. Once collected, blood samples were centrifuged immediately, supernatant plasma was removed, and stored at −80° C. until analysis by LC-MS using methods standard in the art.

Each compound was administered in a vehicle composed of 20% (v/v) DMSO in PEG400. Formulations were prepared by dissolving the compounds in DMSO prior to addition of PEG400. Formulations were not filtered prior to dosing and were administered to mice within 2.5 h of preparation. The average measured concentration of each compound in aliquots (n=2) of their respective formulations was 4.58, 4.31, 5.26 and 5.25 mg/mL for NCL026, NCL195, NCL259 and NCL812, respectively. The dose administered to each mouse was calculated on the basis of the measured concentration in the IV formulation, the dose volume and individual mouse body weight. Plasma concentration versus time data were analysed using non-compartmental methods (WinNonlin Version 6.3.0.395). Standard calculations for each pharmacokinetic parameter were calculated using standard methods in the art.

One mouse dosed with NCL812 exhibited abnormal behaviour (frantic, hyperactive) commencing a few minutes after dosing; this mouse was anaesthetised and blood was collected at 15 min post-dose. No other animals in this study appeared to exhibit any adverse reactions or compound-related side effects. There was evidence of haemolysis observed in plasma samples however this is likely to be attributable to the solvents used in the IV formulations (20% (v/v) DMSO in PEG400) which were required because of the limited solubility of the test compounds in aqueous formulation vehicles.

Figure 12:
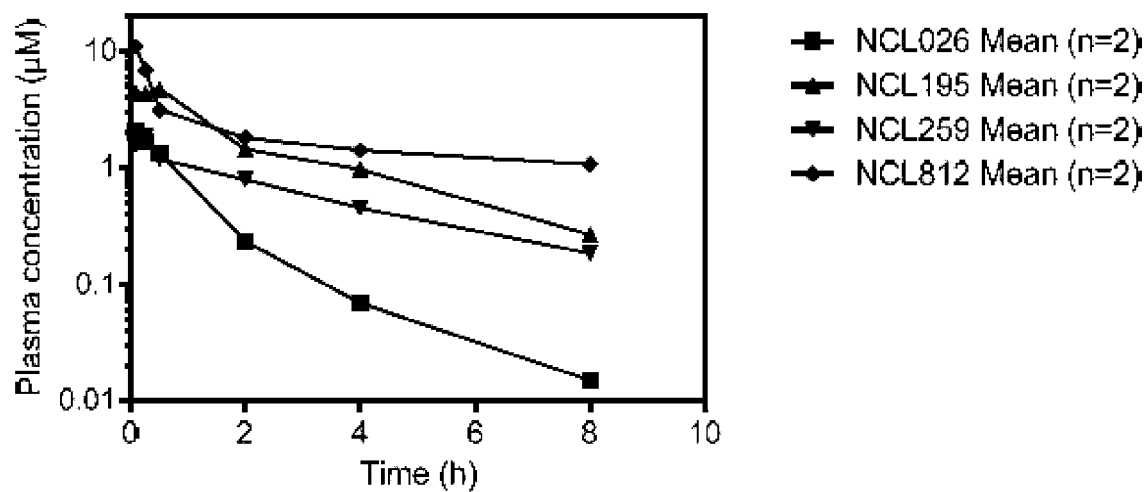
FIG. 12 is a graph illustrating the plasma concentration versus time profiles for NCL026, NCL195, NCL259 and NCL812.

Results:

The plasma concentration versus time profiles for NCL026, NCL195, CL259 and NCL812 are shown in FIG. 12. The pharmacokinetic parameters are presented in Table 8. All compounds exhibited moderate-to-long apparent terminal elimination half-lives.

TABLE 8

|  | NCL026 | NCL195 | NCL259 | NCL812 |
|---|---|---|---|---|
| Measured dose (mg/kg) | 4.8 | 4.4 | 5.4 | 5.3 |
| Apparent $t_{1/2}$ (h) | 1.5 | 2.4 | 2.9 | 8.2[b] |
| Plasma CL (mL/min/kg) | 100.6 | 16.3 | 56.0[a] | 9.5[b] |
| Plasma $V_{ss}$ (L/kg) | 6.9 | 2.6 | 12.8[a] | 5.9[b] |
| $AUC_{0-inf}$ (h * µM) | 2.5 | 12.5 | 5.5[a] | 27.9[b] |

[a]Plasma concentration at time zero could not be determined by log-linear regression of the first two measurements, and was therefore set to the first observed measurement. As such, AUC from 0 to 5 min (and therefore $AUC_{0-inf}$) will be underestimated and parameters calculated based on $AUC_{0-inf}$ are approximations only.
[b]Terminal elimination phase was not well defined, value is an approximation only.

Example 13: Exposure of NCL195 in Male Swiss Outbred Mice Following IP Administration Aim:

The objective of this study was to obtain a preliminary indication of the plasma exposure of NCL195 following IP administration at a target dose of 50 mg/kg.

Methods:

The formulation was prepared by dissolving solid NCL195 in DMSO (to 20% (v/v) of the final volume) before adding PEG400, yielding a clear yellow solution that was dosed to mice within 30 minutes of preparation. The measured concentration of NCL195 in the final formulation was 21.9 mg/mL, resulting in a mean administered dose of 43 mg/kg. Following administration, blood samples were collected up to 24 h post-dose (n=2 mice per time point). A maximum of two samples were obtained from each mouse, with samples being taken either via submandibular bleed (approximately 120 µL; conscious sampling) or terminal cardiac puncture (0.6 mL; while mice were anaesthetised using inhaled Isoflurane). No urine samples were collected as mice were housed in bedded cages during the study. Blood was collected directly into polypropylene Eppendorf tubes containing heparin as anticoagulant and stabilisation cocktail (containing Complete® (a protease inhibitor cocktail), potassium fluoride and EDTA) to minimise the potential for ex vivo degradation of NCL195 in blood/plasma samples. Once collected, blood samples were centrifuged immediately, supernatant plasma was removed, and stored in −20° C. until analysis by LCMS using standard methods in the art.

Figure 13:
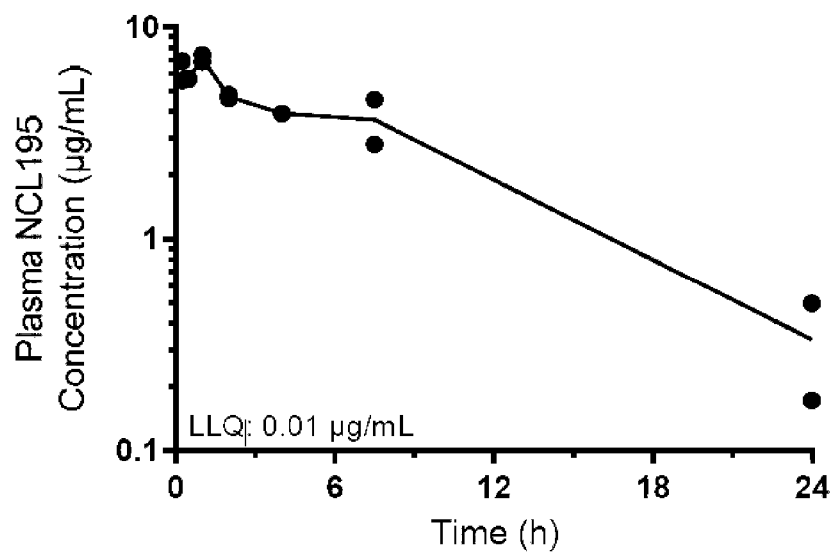
FIG. 13 is a graph illustrating the plasma concentrations of NCL195 in male Swiss outbred mice following IP administration at an average dose of 43 mg/kg.

Results:

No adverse reactions or compound-related side effects were observed in any of the mice following IP administration of NCL195 at a dose of 43 mg/kg. The plasma concentration-time profile (FIG. 13) indicates that NCL195 was rapidly absorbed after dosing. For the duration of the initial 7.5 h post-dose period, plasma concentrations remained above 3-4 µg/mL, however concentrations fell to 0.2-0.5 µg/mL between 7.5 and 24 h post-dose. Assuming that a 2-fold increase in dose would result in a proportional increase in NCL195 exposure, the present data suggests that IP administration of NCL195 at 100 mg/kg (as a solution formulation) would result in at least 7.5 hours of exposure at a plasma concentration >8 µg/mL.

Example 14: Activity of NCL Analogues Against *Trypanosoma cruzi*

Background:

Chagas' disease, also known as American trypanosomiasis, is a potentially life-threatening illness caused by the protozoan parasite *Trypanosoma cruzi* (*T. cruzi*). *T. cruzi* is transmitted when the infected faeces of the triatomine vector are inoculated through a bite site or through an intact mucous membrane of the mammalian host. Vectorborne transmission is limited to areas of North America, Central America, and South America. Both in endemic and in nonendemic areas, other infection routes include transfusion, organ and bone marrow transplantation, and congenital transmission. Outbreaks attributed to contaminated food or drink have been reported in northern South America, where transmission cycles involving wild vector populations and mammalian reservoir hosts are prominent. Infection is lifelong in the absence of effective treatment. The most important consequence of *T. cruzi* infection is cardiomyopathy, which occurs in 20 to 30% of infected persons. The World Health Organisation estimates that in 2015 about 6 million to 7 million people are infected worldwide, mostly in Latin America.

There are only two drugs, the nitrofuran nifurtimox and the nitroimidazole benznidazole, with established efficacy against *T. cruzi* infection. However, each of these agents have significant limitations in effectiveness and safety.

In patients with acute Chagas' disease and in those with early congenital Chagas' disease, both benznidazole and nifurtimox reduce the severity of symptoms, shorten the clinical course of illness, and reduce the duration of parasitaemia; but cure rates in the acute phase are only in the order of 80 to 90%.

Studies of benznidazole involving children with chronic *T. cruzi* infection have revealed cure rates of only around 60%, on the basis of conversion to negative serologic test results 3 to 4 years after treatment.

Nifurtimox use is associated with gastrointestinal side effects (anorexia, weight loss, nausea, and vomiting) in up to 70% of patients. Neurologic toxic effects include irritability, insomnia, disorientation, and tremors. Rare but more serious side effects include paraesthesias, polyneuropathy, and peripheral neuritis.

Benznidazole use is frequently associated with dermatological adverse effects, usually mild rashes that respond to antihistamines. However, severe or exfoliative dermatitis or dermatitis associated with fever and lymphadenopathy prompt immediate interruption of treatment. A dose-dependent peripheral neuropathy occurring late in the course of therapy necessitates immediate cessation of treatment. Although bone marrow suppression is rare its occurrence prompts immediate interruption of treatment.

The absence of safe and effective treatments has led to Chagas' disease being classified as a neglected parasitic infection with major public health implications. The global cost of Chagas' disease has been estimated at more than US$7 billion (Lee, B. Y., K. M. Bacon, M. E. Bottazzi and P. J. Hotez (2013). "Global economic burden of Chagas disease: a computational simulation model." *The Lancet Infectious Diseases* 13(4): 342-348) and there remains a desperate and continuing need to identify and develop improved treatments.

Aim and Methods:

In an endeavour to identify new agents for the treatment of Chagas' disease, the biological activity of robenidine and 79 analogues against *Trypanosoma cruzi* was assessed in an in vitro screening assay according to the methods described by Keenan et al (Keenan, M., M. J. Abbott, P. W. Alexander, T. Armstrong, W. M. Best, B. Berven, A. Botero, J. H. Chaplin, S. A. Charman, E. Chatelain, T. W. von Geldern, M. Kerfoot, A. Khong, T. Nguyen, J. D. McManus, J. Morizzi, E. Ryan, I. Scandale, R. A. Thompson, S. Z. Wang and K. L. White (2012). "Analogues of fenarimol are potent inhibitors of *Trypanosoma cruzi* and are efficacious in a murine model of Chagas disease." *Journal of medicinal chemistry* 55(9): 4189-4204), Buckner and associates (Buckner, F. S., C. L. Verlinde, A. C. La Flamme and W. C. Van Voorhis (1996). "Efficient technique for screening drugs for activity against *Trypanosoma cruzi* using parasites expressing beta-galactosidase." *Antimicrobial Agents and Chemotherapy* 40(11): 2592-2597) and by Van Voorhis and Eisen (Van Voorhis, W. C. and H. Eisen (1989). "FI-160. A surface antigen of *Trypanosoma cruzi* that mimics mammalian nervous tissue." *The Journal of Experimental Medicine* 169(3): 641-652).

In vitro *T. cruzi* Assay for Determination of IC50.

The *T. cruzi* assay uses Tulahuen trypomastigotes expressing the ß-galactosidase gene. The parasites were maintained in vitro by serial passage in L6 cells. Briefly, L6 cells were plated into 96 well, flat-bottom tissue culture plates and incubated at 37° C. in 5% $CO_2$ for 24 h to allow cells to adhere. *T. cruzi* trypomastigotes were then added at a multiplicity of infection of 3, and plates were incubated for a further 48 h to allow infection to establish. All steps were carried out using RPMI media 1640 (without phenol red) supplemented with 10% Foetal Bovine Serum (FBS, Bovogen). Extracellular trypomastigotes were then removed and NCL compounds were added in seven-point serial dilutions performed in triplicate. Benznidazole (Epichem Pty Ltd.) was included as a control. After 96 h of incubation with the compounds, the colorimetric agent, chlorophenol red-fl-D-galactopyranoside (CPRG, Roche) was added with 0.3% v/v Nonidet P-40. After 4-6 h, a colour change following catabolisation of the reagent by viable *T. cruzi* was observed and absorbance was read at 530 nm using a Dynex microplate reader. The % inhibition was calculated by the following equation: % inhibition=100−[(*T. cruzi* with compound−compound only)/(*T. cruzi* only−media only)]×100. For each compound, % inhibition values were used to generate a standard curve from which the $IC_{50}$ was calculated. Each assay was performed at least twice, and the average was used.

Results:

The value of the $IC_{50}$ of 80 NCL compounds is presented in Table 9.

TABLE 9

*Trypanosoma cruzi* activity

| Compound | $IC_{50}$ µM |
|---|---|
| NCL026 | 1.4 |
| NCL041 | 14 |
| NCL086 | 14 |
| NCL052 | 15 |
| NCL075 | 15 |
| NCL021 | 16 |
| NCL037 | 16 |
| NCL038 | 16 |
| NCL040 | 16 |
| NCL043 | 16 |
| NCL083 | 16 |
| NCL087 | 17 |
| NCL030 | 18 |
| NCL023 | 19 |
| NCL029 | 19 |
| NCL054 | 19 |
| NCL076 | 19 |
| NCL088 | 19 |
| NCL025 | 20 |
| NCL035 | 20 |
| NCL081 | 20 |
| NCL085 | 20 |
| NCL015 | 21 |
| NCL082 | 22 |
| NCL084 | 22 |

TABLE 9-continued

_Trypanosoma cruzi activity_

| Compound | IC$_{50}$ μM |
|---|---|
| NCL089 | 3.0 |
| NCL042 | 4.9 |
| NCL080 | 7.8 |
| NCL036 | 8.3 |
| NCL016 | 24 |
| NCL020 | 24 |
| NCL073 | 24 |
| NCL045 | 29 |
| NCL046 | 32 |
| NCL074 | 33 |
| NCL002 | 38 |
| NCL044 | 39 |
| NCL072 | 46 |
| NCL022 | 49 |
| NCL053 | 49 |
| NCL010 | 50 |
| NCL034 | 53 |
| NCL004 | 56 |
| NCL017 | 56 |
| NCL032 | 58 |
| NCL019 | 61 |
| NCL031 | 69 |
| NCL033 | 80 |
| NCL007 | 82 |
| NCL003 | 83 |
| NCL077 | >10 |
| NCL078 | >10 |
| NCL079 | >10 |
| NCL039 | 9.9 |
| NCL024 | 12 |
| NCL028 | 13 |
| NCL027 | 14 |
| NCL812 | >11 |
| NCL011 | >11 |
| NCL005 | >33 |
| NCL018 | >33 |
| NCL001 | >100 |
| NCL006 | >100 |
| NCL008 | >100 |
| NCL009 | >100 |
| NCL012 | >100 |
| NCL013 | >100 |
| NCL014 | >100 |
| NCL047 | >100 |
| NCL048 | >100 |
| NCL049 | >100 |
| NCL050 | >100 |
| NCL051 | >100 |
| NCL055 | >100 |
| NCL056 | >100 |
| NCL057 | >100 |
| NCL058 | >100 |
| NCL059 | >100 |
| NCL060 | >100 |
| NCL071 | >100 |

Conclusion:

Notably, 6 compounds had an IC$_{50}$ of less than 10 μM while 30 compounds had IC$_{50}$ values less than or equal to 20 μM. The NCL series provides a rich source of agents with activity against _Trypanosoma cruzi_.

The invention claimed is:

1. A method of treating or preventing a protozoan colonisation or infection in a subject, the method including the step of administering a therapeutically effective amount of a compound selected from the list comprising:

NCL178 4,6-bis(2-((E)-1-(4-chlorophenyl)ethylidene)hydrazinyl)pyrimidine
NCL179 4,6-bis(2-((E)-4-chlorobenzylidene)hydrazinyl)pyrimidin-2-amine
NCL182 6-chloro-N$^4$-(1-phenylethyl)pyrimidine-2,4-diamine
NCL183 N$^4$,N$^6$-bis(1-phenylethyl)pyrimidine-4,6-diamine
NCL193 4,6-bis(2-((E)-4-bromobenzylidene)hydrazinyl)pyrimidin-2-amine
NCL195 4,6-bis(2-((E)-4-methylbenzylidene)hydrazinyl)pyrimidin-2-amine
NCL198 4,6-bis(2-((E)-4-(tert-butyl)benzylidene)hydrazinyl)pyrimidin-2-amine dihydrochloride
NCL199 4,6-bis(2-((E)-benzylidene)hydrazinyl)pyrimidin-2-amine
NCL200 4,6-bis(2-((E)-4-(tert-butyl)benzylidene)hydrazinyl)pyrimidin-2-amine
NCL201 4,4'-(1E,1'E)-((2-aminopyrimidine-4,6-diyl)bis(hydrazin-2-yl-1-ylidene))bis(methanylylidene))bis(N,N-dimethylaniline)
NCL204 4,6-bis(2-((E)-1-(4-chlorophenyl)ethylidene)hydrazinyl)pyrimidin-2-amine
NCL205 4,6-bis(2-((E)-2-chlorobenzylidene)hydrazinyl)pyrimidin-2-amine
NCL209 3,3'-(1E,1'E)-((6-amino-1,3,5-triazine-2,4-diyl)bis(hydrazin-2-yl-1-ylidene))bis(methanylylidene))diphenol
NCL210 4,6-bis(2-((E)-4-(trifluoromethyl)benzylidene)hydrazinyl)-1,3,5-triazin-2-amine
NCL212 4,6-bis(2-((E)-4-bromobenzylidene)hydrazinyl)-1,3,5-triazin-2-amine
NCL220 4,6-bis(2-((E)-4-fluorobenzylidene)hydrazinyl)pyrimidin-2-amine
NCL221 4,6-bis(2-((E)-4-(trifluoromethyl)benzylidene)hydrazinyl)pyrimidin-2-amine
NCL222 4,6-bis(2-((E)-3,4-difluorobenzylidene)hydrazinyl)pyrimidin-2-amine
NCL230 4,6-bis(2-((E)-4-methoxybenzylidene)hydrazinyl)pyrimidin-2-amine
NCL240 4,6-bis(2-((E)-pyridin-2-ylmethylene)hydrazinyl)pyrimidin-2-amine
NCL245 4,6-bis(2-((E)-naphthalen-1-ylmethylene)hydrazinyl)pyrimidin-2-amine
NCL246 4,6-bis(2-((1E,2E)-3-phenylallylidene)hydrazinyl)pyrimidin-2-amine
NCL264 4,6-bis(2-((E)-naphthalen-2-ylmethylene)hydrazinyl)pyrimidin-2-amine.

2. The method according to claim 1, wherein the compound is a chloride salt.

3. The method according to claim 1, wherein the subject is an animal selected from the group consisting of: human, canine, feline, bovine, ovine, caprine, porcine, avian, piscine and equine species.

4. The method according to claim 1, wherein the compound is administered to the subject in a dose in the range of 0.1 mg/kg to 250 mg/kg bodyweight.

5. The method according to claim 1, wherein the protozoan agent is selected from the group of protozoa genera comprising: _Acanthamoeba, Babesia, Balamuthia, Balantidium, Besnoitia, Blastocystis, Chilomastix, Cochlosoma, Cryptosporidium, Cyclospora, Cystoisospora, Cytauxzoon, Dientamoeba, Eimeria, Endolimax, Entamoeba, Giardia, Haemoproteus, Hammondia Hartmannella, Hepatozoon, Hexamita, Histomonas, Isospora, Leishmania, Leucocytozoon, Naegleria, Neospora, Pentatrichomonas, Plasmodium Sappinia, Sarcocystis, Tetratrichomonas, Theileria, Toxoplasma, Trichomonas, Tritrichomonas, Trypanosoma, Tyzzeria_ and _Wenyonella_.

6. The method according to claim 1, wherein the protozoan infection or colonisation in the subject is a zoonosis.

7. The method according to claim 6, wherein the protozoan infection or colonisation in the subject substantially causes an indication selected from the group comprising: Trypanosomosis; Amoebiasis; Babesiosis; Balantidiosis; Chagas Disease; Cryptosporidiosis; Giardiosis; Leishmaniasis; Malaria; Sarcocystosis; Toxoplasmosis; Cyclosporiasis; Infections caused by free-living Amoebae; Microsporidiosis; Trypanosomiasis; Trichomoniasis; Amoebic dysentery; and Acanthamoebiasis.

8. The method according to claim 1, wherein the compound, is administered to the subject by oral administration, parenteral administration or topical administration.

9. The method according to claim 1, wherein the therapeutically effective amount of the compound is administered to the subject together with an antimicrobial agent selected from the group consisting of: 4-aminoquinoline, 8-aminoquinoline, acetamide, acridine dye, alkylphosphocholine, allylamine, aminoglycosides, aminophenanthridium, aminopyridine antimalarials, pentavalent antimonials, arsenicals, arylaminoalcohol, azo naphthalene dyes, azoles (triazoles and imidazoles), benzamide, benzenediol, benzimidazoles and probenzimidazoles, bicyclohexylammonium, carbamate, cinnamamido adenosine, coumarin, diamidines, dichloroacetamide, dichloroacetamide, difluoromethylornithine, dihydrofolate reductase/thymidyate synthase inhibitors, dihydrooratate dehydrogenase inhibitors, dinitroaniline, dinitrocarbanilide+pyrimidinol, dithiocarbamate, ethoxybenzoic acid, fluoroquinolones, guanidines, halogenated 8-hydroxyquinoline, hydroxyoxo-cyclohexenecarbaldehyde oxime, hydroxyquinolones, imidazolopiperazine, isoquinoline, lincosamides, macrolides, methylquinolinium, miscellaneous, naphthoquinones, naphthyridine, nitrobenzamides, nitrofurans, nitroimidazoles, nitrothiazoles, organometallic antiprotozoal, oxaborole, phenoxyphenol, phenylsulfamide, phosphonic acid derivative, phosphonomethylglycine, phosphoramidothioic acid, polyene, polyether ionophores, polypeptide, polysulfonated naphthylamine, propylphosphonic acid, purinamine, pyrazolopyran, pyrazolopyrimidine, pyridinols, pyrimidine, pyrrolidinediol, quinazolinone, quinoline, quinoxaline, rifamycin, spiroindolone, strobilurin, sulfonamides, sulphone, tetracyclines, tetraoxanes, thiamine analogs, thiophenone, translation elongation factor 2 inhibitor, triazine, triazole, trioxane, trioxolane.

* * * * *